(12) United States Patent
DiMarchi et al.

(10) Patent No.: US 8,946,147 B2
(45) Date of Patent: *Feb. 3, 2015

(54) AMIDE-BASED INSULIN PRODRUGS

(75) Inventors: Richard D. DiMarchi, Carmel, IN (US); Binbin Kou, Bloomington, IN (US); Shujiang Cheng, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/702,197

(22) PCT Filed: Jun. 23, 2011

(86) PCT No.: PCT/US2011/041603
§ 371 (c)(1),
(2), (4) Date: Dec. 5, 2012

(87) PCT Pub. No.: WO2011/163462
PCT Pub. Date: Dec. 29, 2011

(65) Prior Publication Data
US 2013/0123171 A1    May 16, 2013

Related U.S. Application Data

(60) Provisional application No. 61/358,192, filed on Jun. 24, 2010.

(51) Int. Cl.
*C07K 14/00* (2006.01)
*C07K 14/62* (2006.01)
*C07K 14/575* (2006.01)
*A61K 38/28* (2006.01)
*A61K 38/22* (2006.01)
*A61K 38/16* (2006.01)
*A61K 38/00* (2006.01)

(52) U.S. Cl.
CPC *C07K 14/62* (2013.01); *A61K 38/00* (2013.01)
USPC ............... 514/6.2; 514/6.3; 514/6.8; 514/6.9; 530/300; 530/303

(58) Field of Classification Search
CPC .... C07K 14/62; C07K 14/575; C07K 14/435; C07K 14/00; A61K 38/28; A61K 38/22; A61K 38/05; A61K 38/00
See application file for complete search history.

(56) References Cited

U.S. PATENT DOCUMENTS

| | | | |
|---|---|---|---|
| 3,740,385 A | 6/1973 | Ondetti | |
| 4,275,152 A | 6/1981 | Esders et al. | |
| 4,741,897 A | 5/1988 | Andrews et al. | |
| 4,876,242 A | 10/1989 | Applebaum et al. | |
| 4,985,407 A | 1/1991 | Foxton et al. | |
| 5,028,586 A | 7/1991 | Balschmidt et al. | |
| 5,359,030 A | 10/1994 | Ekwuribe | |
| 5,514,646 A | 5/1996 | Chance et al. | |
| 5,545,618 A | 8/1996 | Buckley et al. | |
| 5,759,818 A | 6/1998 | Boime | |
| 5,843,634 A | 12/1998 | Brate et al. | |
| 6,180,767 B1 | 1/2001 | Wickstrom et al. | |
| 6,197,926 B1 | 3/2001 | Gaur et al. | |
| 6,476,290 B1 | 11/2002 | Wright et al. | |
| 6,630,348 B1 | 10/2003 | Lee et al. | |
| 6,746,853 B1 | 6/2004 | Dahiyat et al. | |
| 7,045,337 B2 | 5/2006 | Schultz et al. | |
| 7,326,688 B2 | 2/2008 | O'Harte et al. | |
| 7,521,422 B2 | 4/2009 | Bernard | |
| 8,263,545 B2 | 9/2012 | Levy et al. | |
| 2002/0038026 A1 | 3/2002 | Rao et al. | |
| 2002/0160938 A1 | 10/2002 | Brandenburg et al. | |
| 2003/0195147 A1 | 10/2003 | Pillutla et al. | |
| 2003/0204063 A1 | 10/2003 | Gravel et al. | |
| 2004/0054130 A1 | 3/2004 | Ng et al. | |
| 2004/0121940 A1 | 6/2004 | DeGroot et al. | |
| 2005/0014679 A1* | 1/2005 | Beals et al. ................. 514/3 |
| 2005/0187147 A1 | 8/2005 | Newman et al. | |
| 2006/0171920 A1 | 8/2006 | Shechter et al. | |
| 2006/0210534 A1 | 9/2006 | Lee et al. | |
| 2006/0223753 A1 | 10/2006 | Glass | |
| 2007/0129284 A1 | 6/2007 | Kjeldsen et al. | |
| 2007/0173452 A1 | 7/2007 | DiMarchi et al. | |
| 2007/0203058 A1 | 8/2007 | Lau et al. | |
| 2007/0224119 A1 | 9/2007 | McTavish | |
| 2008/0113411 A1 | 5/2008 | Sheffer | |

(Continued)

FOREIGN PATENT DOCUMENTS

| CN | 1341122 | 3/2002 |
|---|---|---|
| CN | 1511044 | 7/2004 |

(Continued)

OTHER PUBLICATIONS

Suaifan et al., Tetrahedron (2006) 62, 11245-11266.*

(Continued)

*Primary Examiner* — Karlheinz R Skowronek
*Assistant Examiner* — Catherine Mader
(74) *Attorney, Agent, or Firm* — Barnes & Thornburg LLP

(57) ABSTRACT

Prodrug formulations of insulin and insulin analogs are provided wherein the insulin peptide has been modified by an amide bond linkage of a dipeptide prodrug element. The prodrugs disclosed herein have extended half lives of at least 10 hours, and more typically greater than 2 hours, 20 hours and less than 70 hours, and are converted to the active form at physiological conditions through a non-enzymatic reaction driven by chemical instability.

23 Claims, 34 Drawing Sheets

(56) References Cited

U.S. PATENT DOCUMENTS

| | | | |
|---|---|---|---|
| 2008/0113905 | A1 | 5/2008 | DiMarchi et al. |
| 2008/0125574 | A1 | 5/2008 | Sheffer et al. |
| 2008/0214648 | A1 | 9/2008 | De Kock et al. |
| 2009/0054305 | A1 | 2/2009 | Schlein et al. |
| 2009/0176964 | A1 | 7/2009 | Walensky et al. |
| 2009/0186817 | A1 | 7/2009 | Ghosh et al. |
| 2009/0192072 | A1 | 7/2009 | Pillutla et al. |
| 2009/0209453 | A1 | 8/2009 | Moyle |
| 2009/0221037 | A1 | 9/2009 | Lee et al. |
| 2010/0081614 | A1 | 4/2010 | Fares et al. |
| 2010/0190701 | A1 | 7/2010 | Day et al. |
| 2011/0065633 | A1 | 3/2011 | DiMarchi et al. |
| 2011/0257091 | A1 | 10/2011 | DiMarchi et al. |
| 2011/0288003 | A1 | 11/2011 | DiMarchi et al. |
| 2012/0010134 | A1 | 1/2012 | Zion et al. |
| 2012/0184489 | A1 | 7/2012 | Rau et al. |

FOREIGN PATENT DOCUMENTS

| | | |
|---|---|---|
| CN | 1635900 | 7/2005 |
| CN | 1867360 | 11/2006 |
| EP | 0220958 | 5/1987 |
| EP | 741188 | 11/1996 |
| EP | 1161452 | 2/2000 |
| EP | 2036539 A1 | 3/2009 |
| EP | 2036923 A1 | 3/2009 |
| JP | 2003/192698 | 7/2003 |
| WO | 90/12814 | 11/1990 |
| WO | 93/03174 | 2/1993 |
| WO | 96/34882 | 11/1996 |
| WO | 98/11126 | 3/1998 |
| WO | 99/46283 | 9/1999 |
| WO | 9967278 | 12/1999 |
| WO | 00/50456 | 8/2000 |
| WO | 02/10195 | 2/2002 |
| WO | 03/079972 | 3/2004 |
| WO | 2004/067548 | 8/2004 |
| WO | 2004/078777 | 9/2004 |
| WO | 2005/054291 | 6/2005 |
| WO | 2005/025554 | 7/2005 |
| WO | 2006/047214 | 5/2006 |
| WO | 2006/097521 | 9/2006 |
| WO | 2006/009902 | 12/2006 |
| WO | 2007/096332 | 8/2007 |
| WO | 2007030577 | 10/2007 |
| WO | 2008/019368 | 2/2008 |
| WO | 2008/021560 | 2/2008 |
| WO | 2008/025528 | 3/2008 |
| WO | 2008055488 | 5/2008 |
| WO | 2008/081418 | 7/2008 |
| WO | 2008/101017 | 8/2008 |
| WO | WO209034119 A1 | 3/2009 |
| WO | WO2009034118 A1 | 3/2009 |
| WO | 2009/067636 | 5/2009 |
| WO | 2009/095479 | 8/2009 |
| WO | 2009099763 A1 | 8/2009 |
| WO | 2010/011313 | 1/2010 |
| WO | 2010/071807 | 6/2010 |
| WO | 2010/080605 | 7/2010 |
| WO | 2010/080609 | 7/2010 |
| WO | 2011/159895 | 12/2011 |
| WO | 2011/163012 | 12/2011 |
| WO | 2011/163460 | 12/2011 |
| WO | 2011/163462 | 12/2011 |

OTHER PUBLICATIONS

Gershonov et al., J. Med. Chem. (2000) 43, 2530-2537.*
Schechter et al., European Journal of Pharmaceutics and Biopharmaceutics (2008) 70, 19-28.*
Suaifan et al., Tetrahedron (2206) 62, 11245-11266.*
PCT International Search Report and Written Opinion completed by the U.S. Searching Authority on Jan. 11, 2012 and issued in connection with PCT/US2011/041603.
De. Design of Peptide-Based Prodrug Chemistry and its Application to Glucagon-Like Peptide I. Aug. 2007. (Retrieved from the Internet Nov. 7, 2011: <https://scholarworks.iu.edu/dspace/bitstream/handle/2022/3185/Arnab_De)Final)Thesis)Signed.pdf?sequence=1>; p. 5, para 1, Fig. 1, p. 18, Fig. 5B, p. 25, para 1, Fig. 6.
Madsen, et al. "Structure-Activity and Protraction Relationship of Long-Acting Glucagon-Like Peptide-1 Derivatives; Importance of Fatty Acid Length, Polarity and Bulkiness." J. Med Chem 2007, 50:6126-6132; p. 6126, col. 2, para 4, p. 6127, Fig. 1, p. 6128, Table 1, Compound 5.
"Peptides: Frontiers of Peptide Science," Proceedings of the Fifteenth American Peptide Symposium, Jun. 14-19, 1997, Nashville, Tennessee, USA; ed. James P. Tam and Praven T.P. Kaumaya.
De et al., Synthesis and characterization of ester-based prodrugs of glucagon-like peptide 1, *Biopolymers*, 94(4): 448-56 (2010).
Harris, J. Milton, Final Word: PEGylation—A "Sunset" Technology? <http://licence.icopyright.net/user/viewFreeUse.act?fuld=OTU1NjY3OA%3D%3D>, BioPharm International, Jun. 1, 2004.
M.J. Roberts et al., "Chemistry for Peptide and Protein PEGylation," Advance Drug Delivery Reviews, Elsevier BV, Amsterdam, NL, vol. 54, No. 4, Jun. 17, 2002, pp. 459-476.
De, A. and DiMarchi, R. Synthesis & Analysis of Peptide Hormone-based prodrugs, (2009) Proceedings of the 21st American Peptide Society 160-161.
Battersby et al., "Diketopiperazine Formation and N-Terminal Degradation in Recombinant Human Growth Hormone", *International Journal of Peptide & Protein Research* 44: 215-222, (1994).
Eriksson et al., "hPEPT1 Affinity and Translocation of Selected Gln-Sar and Glu-Sar Dipeptide Derivatives", *Molecular Pharmaceutics* vol. 2, No. 3: 242-249 (May 10, 2005).
Garcia-Aparicio et al., "Design and Discovery of a Novel Dipeptidyl-peptidase IV (CD26)-Based Prodrug Approach", *J. Med. Chem.* 49: 5339-5351 (2006).
Goolcharran et al., "Comparison of the Rates of Deamidation, Diketopiperazine Formation, and Oxidation in Recombinant Human Vascular Endothelial Growth Factor and Model Peptides", *AAPS Pharmsci* 2000 2(1) article 5: 1-6 (Mar. 17, 2000).
Santos et al., Cyclization-Activated Prodrugs. Synthesis, Reactivity and Toxicity of Dipeptide Esters of Paracetamol, *Bioorganic & Medicinal Chemistry Letters* 15: 1595-1598 (2005).
Sato, H., "Enzymatic procedure for site-specific pegylation of proteins," Advanced Drug Delivery Reviews 54, pp. 487-504 (2002).
Ward, "Fatty Acid Acylation of Peptides: Developing strategies to enhance medicines for treating metabolic disorders," Jan. 14, 2009.
DiMarchi, "Peptides—Development of Prodrug Chemistry," RBF Symposium Feb. 1-4, 2011 India.
Yang et al., "A Novel Approach to Resin-Based Cysteine Alkylation," American Peptide Society, 2005.
PCT International Search Report for PCT/US2009/068745 completed by the US Searching Authority on Feb. 1, 2010.
PCT International Search Report for PCT/US2009/031593 completed by the US Searching Authority on Jul. 16, 2009.
Schuttler, A. and D. Brandenburg, Preparation and Properties of Covalently Linked Insulin Dimers. Hoppe-Seylers Zeitschrift Fur Physiologische Chemie, 1982. 363(3): p. 317-330.
Tatnell, M.A., et al., Evidence Concerning the Mechanism of Insulin-Receptor Interaction and the Struture of the Insulin-Receptor from Biological Properties of Covalently Linked Insulin Dimers. Biochemical Journal, 1983. 216(3): p. 687-694.
Roth, R.A., et al., Effects of Covalently Linked Insulin Dimers on Receptor Kinase-Activity and Receptor down Regulation. Febs Letters, 1984. 170(2): p. 360-364.
Tatnell, M.A., R.H. Jones, and P.H. Sonksen, Covalently-Linked Insulin Dimers—Their Metabolism and Biological Effects Invivo as Partial Competitive Antagonists of Insulin-Clearance. Diabetologia, 1984. 27(1): p. 27-31.
Joost, H.G., et al., Quantitative Dissociation of Glucose-Transport Stimulation and Insulin-Receptor Tyrosine Kinase Activation in Isolated Adipocytes with a Covalent Insulin Dimer (B29,B29'-Sunberoyl-Insulin). Biochemical Pharmacology, 1989. 38(14): p. 2269-2277.

(56) References Cited

OTHER PUBLICATIONS

Breiner, M., et al., Heterogeneity of Insulin-Receptors in Rat-Tissues as Detected with the Partial Agonist B29,B29'-Suberoyl-Insulin. Molecular Pharmacology, 1993. 44(2): p. 271-276.

Deppe, C., et al., Structure-Activity Relationship of Covalently Dimerized Insulin Derivatives—Correlation of Partial Agonist Efficacy with Cross-Linkage at Lysine B29. Naunyn-Schmiedebergs Archives of Pharmacology, 1994. 350(2): p. 213-217.

Shojaee-Moradie, F., et al., Demonstration of a Relatively Hepatoselective Effect of Covalent Insulin Dimers on Glucose-Metabolism in Dogs. Diabetologia, 1995. 38(9): p. 1007-1013.

Du X et al, Hydroxyl group of insulin a A19Tyris essential for receptor binding: studies on (A9Phe) insulin, BioChem and Mol Biology International, Academic Press, Lindon, GB vol. 45, No. 2, Jun 1, 1998, pp. 255-260. found in extended EP search report 09837982.9 (08055; 216442).

PCT International Search Report for PCT/US2009/068716 completed by the US Searching Authority on May 3, 2010.

European supplemental search report for EP 09837983.7 completed by the EPO on Mar. 15, 2012.

Cheng et al., "The Development of an Insulin-based Prodrug," APS poster presentation, 2011.

Coffman et al., "Insulin-metal ion interactions: the binding of divalent cations to insulin hexamers and tetramers and the assembly of insulin-hexamers," Biochemistry, Aug. 9, 1988, vol. 27, No. 16, pp. 6179-6187.

De, et al., "Investigation of the feasibily of an amide-based prodrug under physiological conditions," Int. J. Pept. Res. Ther., 14, pp. 255-262 (2008).

Du et al., "Biochemistry and Molecular Biology International," vol. 45, No. 2, Jun. 1, 1998, pp. 255-260 XP008147747.

GenBank entry AAH05278, Jul. 15, 2006 [http:www//ncbi.nim.nih.gov/protein/13528972>].

Han et al., "IGF-based Insulin Analogs with an A-Chain Lactam," APS poster presentation, 2011.

Kaur et al., "Novel Single Chain Insulin Analogs Consisting of a Non-Peptide Based Connection," APS poster presentation, May 12, 2011.

Han et al., "Structure-Activity Relationship of Insulin at Position $A^{19}$," APS poster presentation.

Han et al., "Insulin Chemical Synthesis Using a Two-Step Orthogonal Formation of the Disulfides," APS poster presentation.

Kaur et al., "Chemical Synthesis of Insulin and Related Analogs," APS poster presentation.

Kristensen et al., "Alanine Scanning Mutagenesis of Insulin," The Journal of Biological Chemistry, 1997, 272(20):12978-12983.

Mayer et al., Insulin Structure and Function, Peptide Science 2007, 88(5):687-713.

Mroz, Piotr et al., "Bioactivity of Insulin Analogs with Altered B-Chain Secondary Structure," APS poster presentation.

O'Brien, Assay for DPPIV Activity using a Homogenous, Luminescent Method, Cell Notes, 2005, 11:8-11 (http://www.promega.com/resources/articles/pubhub/cellnotes/assay-for-dppiv-activity-using-a-homogeneous-luminescent-method/).

PCT International Search Report for PCT/US2009/068711 completed by the US Searching Authority on Feb. 4, 2010.

PCT International Search Report for PCT/US2009/068712 completed by the US Searching Authority on Mar. 24, 2010.

PCT International Search Report for PCT/US2009/068713, completed May 26, 2010.

PCT International Search Report for PCT/US2011/041601 completed by the US Searching Authority on Nov. 10, 2011.

Phillips et al., "Supramolecular protein engineering: design of zinc-stapled insulin hexamers as a long acting depot," J. Biol. Chem., Apr. 16, 2010, vol. 285, No. 16, pp. 11755-11759.

Schilling et al., "Degradation of Insulin by Trypsin and Alphachymotrypsin," Pharmaceutical Research 1991, 8(6):721-727 (abstract).

Quan et al., "Coordinated Interaction of the Insulin B-chain Helical Domain with the aromatic Active Site," APS poster presentation.

Wang et al., "Identification of Site(s) of Insulin Nitration by Peroxynitrite and Characterization of its Structural Change," Protein & Peptide Letters 2008, 15:1063-1067.

Zhao et al., "Improved Pharmacokinetics through Site-Specific PEGylation of Insulin Analogs," APS poster presentation, 2011.

Evans et al., "Effect of Î-Endorphin C-Terminal Peptides on Glucose Uptake in Isolated Skeletal Muscles of the Mouse", Peptides, vol. 18, No. 1, pp. 165-167, (1997).

Kurapkat et al "Inactive conformation of an insulin despite its wild-type sequence", Protein Science, vol. 6, No. 3, pp. 580-587 (Mar. 1997).

Hamel et al "Cyclosporin a prodrugs: Design, systhesis and biophysical properties", J. Peptide Research, vol. 63 No. 2 pp. 147-154 (Feb. 2004).

Coy et al, J of Medicinal Chemistry, 1973, vol. 16, No. 7, 827-829.

Yang et al, "Relationship between insulin a chain regions and insulin biological activities," World J. of Gastroentero, 2000: 6(3): 371-373 (Jun. 2000).

Hinds et al, Advancec Drug Delivery Reviews 2002, (54) 505-530 (Jun. 17, 2002).

Hua et al, J of Bilogical Chemistry, Mar. 2008, vol. 283, No. 21, 14703-14716 (May 23, 2008).

Weiland et al, "Antagonistic effects of a covalenly dimerized insulin derivatized insulin derivative on insulin receptors in 3T3-L1 adipocytes", PNAS, vol. 87, pp. 1154-1158, Feb. 1990.

Cloutier, et al, "Low-energy (3-24eV) electron damage to the peptide backbone" J Phys Chem B. 111(7), p. 1620-1624, (Feb. 22, 2007).

G. Rajpal et al, "Single Chain Insulins as Receptor Agonists", Molecular Endocrinology, vol. 23, No. 5, Feb. 19, 2009 p. 679-688.

Hiroshi Ogawa et al "N-Methylation of sleeted peptide bonds on the biological activity of insulin", International J of Peptide and Protein Research, vol. 30, No. 4, p. 460-473 (Oct. 1987).

Shechter et al, "Albumin-insulin conjugate releasing insulin slowly under physiologiacal conditions: a new concept for long-acting insulin", Bioconjugate Chemistry vol. 16, No. 4, p. 913-920 (Jul.-Aug. 2005).

Worrall et al "Synthesis of an organoinsulin molecule tha tcan be activated by antibody catalysis", PNAS vol. 98, No. 24, p. 13514-13518 (Nov. 20, 2001).

Zhou et al., "Peptide and protein drugs: I. Therapeutic applications, absorption and parenteral administration," International Journal of Pharmaceutics vol. 75 p. 97-111 (Sep. 20, 1991).

\* cited by examiner

Synthetic "A⁷-B⁷"-derived Insulin Receptor Binding

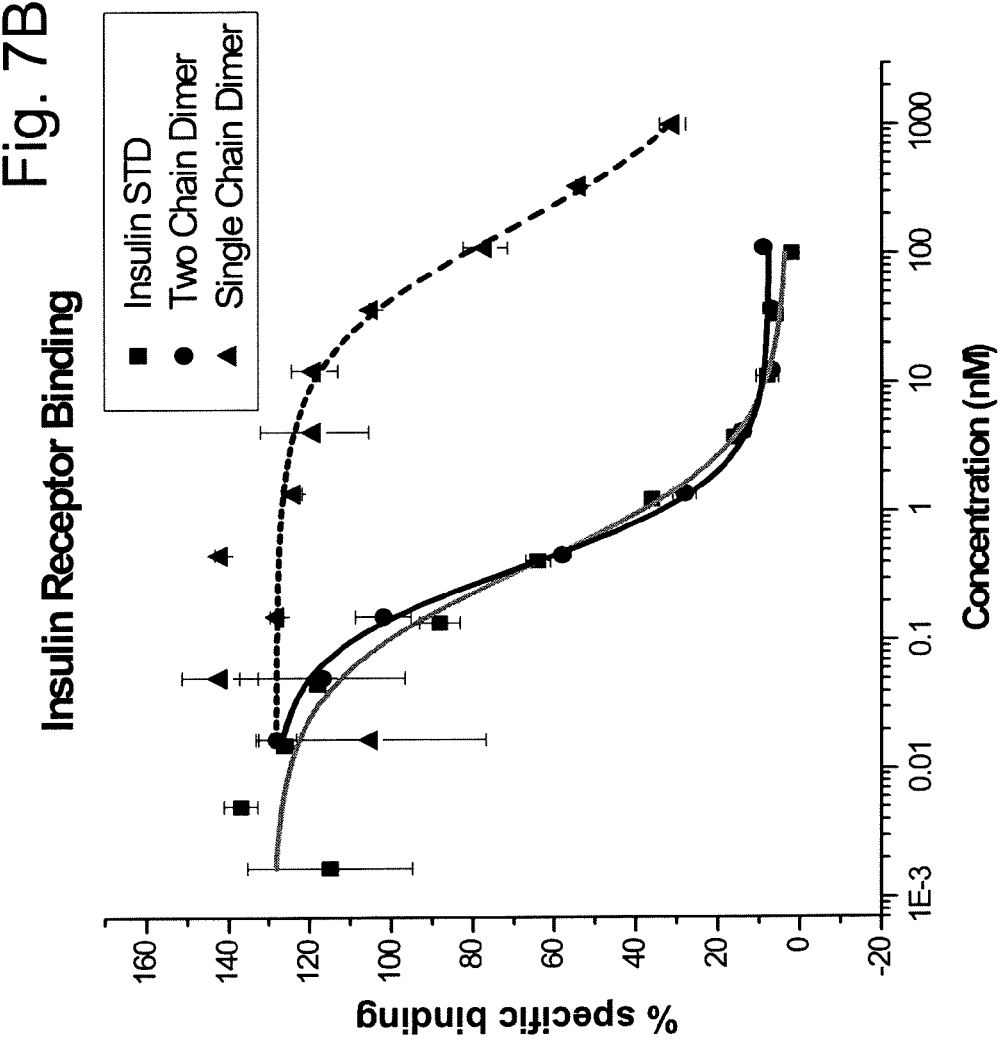

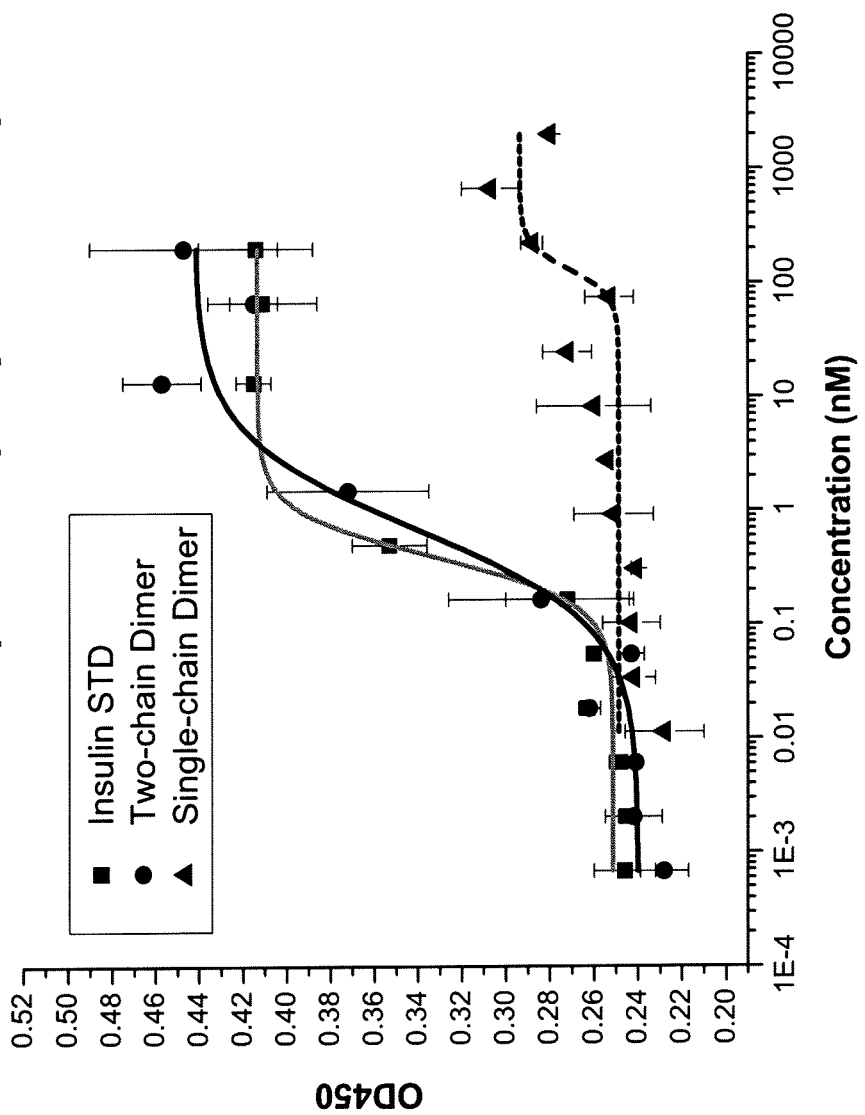

MIU 29: B¹(Y16,L17,Y25)29a : A¹(aF19-dLys(Ac),NLeu)
PBS Incubation

COMPARATIVE INSULIN TOLERANCE TEST FOR MIU 30A,C

Comparative Insulin Tolerance Test for MIU 46 & Detemir

SEQUENCE LISTING

```
<160> NUMBER OF SEQ ID NOS: 71

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

```
<210> SEQ ID NO 3
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine, histidine,
      arginine or lysine
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine, 4-amino phenylalanine or a modified 4-amino
      phenylalanine (having a dipeptide linked via an amide bond at the
      aromatic ring amine)
<220> FEATURE:
<221> NAME/KEY: MISC_FEATURE
<222> LOCATION: (21)..(21)
<223> OTHER INFORMATION: Xaa at position 21 is asparagine, glycine,
      alanine glutamine, glutamate, threonine, or serine

<400> SEQUENCE: 3

Gly Ile Val Glu Gln Cys Cys Xaa Ser Ile Cys Ser Leu Tyr Gln Leu
1               5                   10                  15

Glu Asn Xaa Cys Xaa
            20

<210> SEQ ID NO 4
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine or threonine
<220> FEATURE:
<221> NAME/KEY: MISC_FEATURE
<222> LOCATION: (5)..(5)
<223> OTHER INFORMATION: Xaa at position 5 is alanine, glycine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid

<400> SEQUENCE: 4

Xaa Leu Cys Gly Xaa Xaa Leu Val Glu Ala Leu Tyr Leu Val Cys Gly
1               5                   10                  15

Glu Arg Gly Phe Phe
            20

<210> SEQ ID NO 5
<211> LENGTH: 29
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine.
<220> FEATURE:
<221> NAME/KEY: MISC_FEATURE
<222> LOCATION: (5)..(5)
<223> OTHER INFORMATION: Xaa at position 5 is histidine, threonine or
      serine
```

```
<220> FEATURE:
<221> NAME/KEY: MISC_FEATURE
<222> LOCATION: (9)..(9)
<223> OTHER INFORMATION: Xaa at position 9 is threonine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (16)..(16)
<223> OTHER INFORMATION: Xaa at position 16 is tyrosine or 4-
      hydroxymethyl phenylalanine
<220> FEATURE:
<221> NAME/KEY: MISC_FEATURE
<222> LOCATION: (25)..(25)
<223> OTHER INFORMATION: Xaa at position 25 is tyrosine, phenylalanine
      or 4-hydroxymethyl phenylalanine
<220> FEATURE:
<221> NAME/KEY: MISC_FEATURE
<222> LOCATION: (28)..(28)
<223> OTHER INFORMATION: Xaa at position 28 is aspartate, a lysine-
      proline dipeptide, or a proline-lysine dipeptide
<220> FEATURE:
<221> NAME/KEY: MISC_FEATURE
<222> LOCATION: (29)..(29)
<223> OTHER INFORMATION: Xaa at position 29 is threonine or an arginine-
      arginine dipeptide

<400> SEQUENCE: 5

Xaa Val Asn Gln Xaa Leu Cys Gly Xaa Xaa Leu Val Glu Ala Leu Xaa
1               5                  10                  15

Leu Val Cys Gly Glu Arg Gly Phe Xaa Tyr Thr Xaa Xaa
            20                  25

<210> SEQ ID NO 6
<211> LENGTH: 21
<212> TYPE: PRT
<213> ORGANISM: Artificial Sequence
<220> FEATURE:
<223> OTHER INFORMATION: Analog of insulin a chain
<220> FEATURE:
<221> NAME/KEY: MISC_FEATURE
<222> LOCATION: (19)..(19)
<223> OTHER INFORMATION: Xaa at position 19 is 4-amino phenylalanine

<400> SEQUENCE: 6

Gly Ile Val Glu Gln Cys Cys Thr Ser Ile Cys Ser Leu Tyr Gln Leu
1               5                  10                  15

Glu Asn Xaa Cys Asn
            20

<210> SEQ ID NO 7
<211> LENGTH: 21
<212> TYPE: PRT
<213> ORGANISM: Homo sapiens

<400> SEQUENCE: 7

His Leu Cys Gly Ser His Leu Val Glu Ala Leu Tyr Leu Val Cys Gly
1               5                  10                  15

Glu Arg Gly Phe Phe
            20

<210> SEQ ID NO 8
<211> LENGTH: 30
<212> TYPE: PRT
<213> ORGANISM: Homo sapiens

<400> SEQUENCE: 8
```

```
Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 9
<211> LENGTH: 30
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 10
<211> LENGTH: 32
<212> TYPE: PRT
<213> ORGANISM: Homo sapiens

<400> SEQUENCE: 10

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

<210> SEQ ID NO 11
<211> LENGTH: 4
<212> TYPE: PRT
<213> ORGANISM: Artificial sequence
<220> FEATURE:
<223> OTHER INFORMATION: N-terminus of the B chain of an insulin analog

<400> SEQUENCE: 11

Phe Val Asn Gln
1

<210> SEQ ID NO 12
<211> LENGTH: 30
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine
<220> FEATURE:
<221> NAME/KEY: MISC_FEATURE
<222> LOCATION: (5)..(5)
<223> OTHER INFORMATION: Xaa at position 5 is histidine or threonine
<220> FEATURE:
<221> NAME/KEY: MISC_FEATURE
<222> LOCATION: (9)..(9)
<223> OTHER INFORMATION: Xaa at position 9 is alanine, glucine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 12

Xaa Val Asn Gln Xaa Leu Cys Gly Xaa Xaa Leu Val Glu Ala Leu Tyr
1               5                   10                  15
```

```
Leu Val Cys Gly Glu Arg Gly Phe Phe Tyr Thr Pro Lys Thr
            20                  25                  30
```

<210> SEQ ID NO 13
<211> LENGTH: 30
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine
<220> FEATURE:
<221> NAME/KEY: MISC_FEATURE
<222> LOCATION: (5)..(5)
<223> OTHER INFORMATION: Xaa at position 5 is histidine or threonine
<220> FEATURE:
<221> NAME/KEY: MISC_FEATURE
<222> LOCATION: (9)..(9)
<223> OTHER INFORMATION: Xaa at position 9 is alanine, glycine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid

<400> SEQUENCE: 13

```
Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Lys Pro Thr
            20                  25                  30
```

<210> SEQ ID NO 14
<211> LENGTH: 21
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine, threonine or
      serine
<220> FEATURE:
<221> NAME/KEY: MISC_FEATURE
<222> LOCATION: (5)..(5)
<223> OTHER INFORMATION: Xaa at position 5 is threonine or serine
<220> FEATURE:
<221> NAME/KEY: MISC_FEATURE
<222> LOCATION: (6)..(6)
<223> OTHER INFORMATION: Xaa at position 6 is histidine, aspartic acid,
      glutamic acid, homocysteic acid or cysteic acid
<220> FEATURE:
<221> NAME/KEY: MISC_FEATURE
<222> LOCATION: (12)..(12)
<223> OTHER INFORMATION: Xaa at position 12 is tyrosine, 4-hydroxymethyl
      phenylalanine, 4-amino phenylalanine or a modified 4-amino
      phenylalanine (having a dipeptide linked via an amide bond at the
      aromatic ring amine)
<220> FEATURE:
<221> NAME/KEY: MISC_FEATURE
<222> LOCATION: (21)..(21)
<223> OTHER INFORMATION: Xaa at position 21 is tyrosine, phenylalanine,
      4-hydroxymethyl phenylalanine, 4-amino phenylalanine or a modified
      4-amino phenylalanine (having a dipeptide linked via an amide bond
      at the aromatic ring amine)

<400> SEQUENCE: 14

```
Xaa Leu Cys Gly Xaa Xaa Leu Val Glu Ala Leu Xaa Leu Val Cys Gly
1               5                   10                  15

Glu Arg Gly Phe Xaa
```

```
<210> SEQ ID NO 15
<211> LENGTH: 30
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine
<220> FEATURE:
<221> NAME/KEY: MISC_FEATURE
<222> LOCATION: (5)..(5)
<223> OTHER INFORMATION: Xaa at position 5 is histidine, threonine or
      serine
<220> FEATURE:
<221> NAME/KEY: MISC_FEATURE
<222> LOCATION: (9)..(9)
<223> OTHER INFORMATION: Xaa at position 9 is threonine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (16)..(16)
<223> OTHER INFORMATION: Xaa at position 16 is tyrosine, 4-hydroxymethyl
      phenylalanine, 4-amino phenylalanine or a modified 4-amino
      phenylalanine (having a dipeptide linked via an amide bond at the
      aromatic amine)
<220> FEATURE:
<221> NAME/KEY: MISC_FEATURE
<222> LOCATION: (25)..(25)
<223> OTHER INFORMATION: Xaa at position 25 is tyrosine, phenylalanine,
      4-hydroxymethyl phenylalanine,  4-amino phenylalanine or a modified
      4-amino phenylalanine (having a dipeptide linked via an amide bond
      at the aromatic ring amine)

<400> SEQUENCE: 15

Xaa Val Asn Gln Xaa Leu Cys Gly Xaa Xaa Leu Val Glu Ala Leu Xaa
1               5                   10                  15

Leu Val Cys Gly Glu Arg Gly Phe Xaa Tyr Thr Pro Lys Thr
            20                  25                  30

<210> SEQ ID NO 16
<211> LENGTH: 30
<212> TYPE: PRT
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine
<220> FEATURE:
<221> NAME/KEY: MISC_FEATURE
<222> LOCATION: (5)..(5)
<223> OTHER INFORMATION: Xaa at position 5 is histidine, threonine or
      serine
<220> FEATURE:
<221> NAME/KEY: MISC_FEATURE
<222> LOCATION: (9)..(9)
<223> OTHER INFORMATION: Xaa at position 9 is threonine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
```

```
<222> LOCATION: (16)..(16)
<223> OTHER INFORMATION: Xaa at position 16 is tyrosine,
      4-hydroxymethyl phenylalanine, 4-amino phenyalanine or a modified
      4-amino phenylalanine (having a dipeptide linked via an amide bond
      at the aromatic ring amine)
<220> FEATURE:
<221> NAME/KEY: MISC_FEATURE
<222> LOCATION: (25)..(25)
<223> OTHER INFORMATION: Xaa at position 25 is tyrosine, phenylalanine,
      4-hydroxymethyl phenylalanine, 4-amino phenylalanine or a modified
      4-amino phenylalanine (having a dipeptide linked via an amide bond
      at the aromatic ring amine)

<400> SEQUENCE: 16

Xaa Val Asn Gln Xaa Leu Cys Gly Xaa Xaa Leu Val Glu Ala Leu Xaa
1               5                  10                  15

Leu Val Cys Gly Glu Arg Gly Phe Xaa Tyr Thr Lys Pro Thr
            20                  25                  30

<210> SEQ ID NO 17
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (8)..(8)
<223> OTHER INFORMATION: Xaa at position 8 is threonine, histidine,
      arginine or lysine
<220> FEATURE:
<221> NAME/KEY: MISC_FEATURE
<222> LOCATION: (21)..(21)
<223> OTHER INFORMATION: Xaa at position 21 is asparagine, glycine,
      alanine glutamine, glutamate, threonine, or serine

<400> SEQUENCE: 17

Gly Ile Val Glu Gln Cys Cys Xaa Ser Ile Cys Ser Leu Tyr Gln Leu
1               5                  10                  15

Glu Asn Tyr Cys Xaa
            20

<210> SEQ ID NO 18
<211> LENGTH: 21
<212> TYPE: PRT
<213> ORGANISM: Artificial Sequence
<220> FEATURE:
<223> OTHER INFORMATION: Analog of the insulin A chain
<220> FEATURE:
<221> NAME/KEY: MISC_FEATURE
<222> LOCATION: (19)..(19)
<223> OTHER INFORMATION: Xaa at position 19 is tyrosine, 4-methoxy
      phenylalanine, 4-amino phenylalanine or a modified 4-amino
      phenylalanine (having a dipeptide linked via an amide bond at the
      aromatic ring amine)
<220> FEATURE:
<221> NAME/KEY: MISC_FEATURE
<222> LOCATION: (21)..(21)
<223> OTHER INFORMATION: Xaa at position 21 is asparagine, glycine,
      alanine glutamine, glutamate, threonine, or serine

<400> SEQUENCE: 18

Gly Ile Val Glu Gln Cys Cys Thr Ser Ile Cys Ser Leu Tyr Gln Leu
1               5                  10                  15

Glu Asn Xaa Cys Xaa
            20

<210> SEQ ID NO 19
<211> LENGTH: 21
<212> TYPE: PRT
```

```
<213> ORGANISM: Artificial Sequence
<220> FEATURE:
<223> OTHER INFORMATION: Analog of the insulin B chain
<220> FEATURE:
<221> NAME/KEY: MISC_FEATURE
<222> LOCATION: (1)..(1)
<223> OTHER INFORMATION: Xaa at position 1 is histidine, threonine or
      serine

<400> SEQUENCE: 19

Xaa Leu Cys Gly Ser His Leu Val Glu Ala Leu Tyr Leu Val Cys Gly
1               5                   10                  15

Glu Arg Gly Phe Phe
            20

<210> SEQ ID NO 20
<211> LENGTH: 29
<212> TYPE: PRT
<213> ORGANISM: Artificial Sequence
<220> FEATURE:
<223> OTHER INFORMATION: Analog of insulin B chain
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine.
<220> FEATURE:
<221> NAME/KEY: MISC_FEATURE
<222> LOCATION: (5)..(5)
<223> OTHER INFORMATION: Xaa at position 5 is histidine, threonine or
      serine
<220> FEATURE:
<221> NAME/KEY: MISC_FEATURE
<222> LOCATION: (9)..(9)
<223> OTHER INFORMATION: Xaa at position 9 is threonine or serine
<220> FEATURE:
<221> NAME/KEY: MISC_FEATURE
<222> LOCATION: (10)..(10)
<223> OTHER INFORMATION: Xaa at position 10 is histidine, aspartic acid,
      glutamic acid, homocysteic acid or cysteic acid
<220> FEATURE:
<221> NAME/KEY: MISC_FEATURE
<222> LOCATION: (16)..(16)
<223> OTHER INFORMATION: Xaa at position 16 is tyrosine or 4-
      hydroxymethyl phenylalanine
<220> FEATURE:
<221> NAME/KEY: MISC_FEATURE
<222> LOCATION: (25)..(25)
<223> OTHER INFORMATION: Xaa at position 25 is tyrosine, phenylalanine
      or 4-hydroxymethyl phenylalanine
<220> FEATURE:
<221> NAME/KEY: MISC_FEATURE
<222> LOCATION: (28)..(28)
<223> OTHER INFORMATION: Xaa at position 28 is aspartate, a lysine-
      proline dipeptide, or a proline-lysine dipeptide
<220> FEATURE:
<221> NAME/KEY: MISC_FEATURE
<222> LOCATION: (29)..(29)
<223> OTHER INFORMATION: Xaa at position 29 is threonine or an arginine-
      arginine dipeptide

<400> SEQUENCE: 20

Xaa Val Asn Gln Xaa Leu Cys Gly Xaa Xaa Leu Val Glu Ala Leu Tyr
1               5                   10                  15

Leu Val Cys Gly Glu Arg Gly Phe Phe Tyr Thr Xaa Xaa
            20                  25

<210> SEQ ID NO 21
<211> LENGTH: 4
<212> TYPE: PRT
<213> ORGANISM: Artificial sequence
<220> FEATURE:
<223> OTHER INFORMATION: N-terminus of the B chain of an insulin analog
```

```
<220> FEATURE:
<221> NAME/KEY: MISC_FEATURE
<222> LOCATION: (1)..(1)
<223> OTHER INFORMATION: Xaa at position 1 is phenylalanine or desamino-
      phenylalanine.

<400> SEQUENCE: 21

Xaa Val Asn Gln
1

<210> SEQ ID NO 22
<211> LENGTH: 7
<212> TYPE: PRT
<213> ORGANISM: Artificial Sequence
<220> FEATURE:
<223> OTHER INFORMATION: peptide linker

<400> SEQUENCE: 22

Gly Gly Gly Pro Gly Lys Arg
1               5

<210> SEQ ID NO 23
<211> LENGTH: 12
<212> TYPE: PRT
<213> ORGANISM: Artificial Sequence
<220> FEATURE:
<223> OTHER INFORMATION: peptide linker

<400> SEQUENCE: 23

Gly Tyr Gly Ser Ser Ser Arg Arg Ala Pro Gln Thr
1               5                   10

<210> SEQ ID NO 24
<211> LENGTH: 7
<212> TYPE: PRT
<213> ORGANISM: Artificial Sequence
<220> FEATURE:
<223> OTHER INFORMATION: peptide linker

<400> SEQUENCE: 24

Gly Gly Gly Gly Gly Lys Arg
1               5

<210> SEQ ID NO 25
<211> LENGTH: 7
<212> TYPE: PRT
<213> ORGANISM: Artificial Sequence
<220> FEATURE:
<223> OTHER INFORMATION: peptide linker

<400> SEQUENCE: 25

Arg Arg Gly Gly Gly Gly Gly
1               5

<210> SEQ ID NO 26
<211> LENGTH: 9
<212> TYPE: PRT
<213> ORGANISM: Artificial Sequence
<220> FEATURE:
<223> OTHER INFORMATION: peptide linker

<400> SEQUENCE: 26

Gly Gly Ala Pro Gly Asp Val Lys Arg
1               5

<210> SEQ ID NO 27
<211> LENGTH: 9
```

```
<212> TYPE: PRT
<213> ORGANISM: Artificial Sequence
<220> FEATURE:
<223> OTHER INFORMATION: peptide linker

<400> SEQUENCE: 27

Arg Arg Ala Pro Gly Asp Val Gly Gly
1               5

<210> SEQ ID NO 28
<211> LENGTH: 9
<212> TYPE: PRT
<213> ORGANISM: Artificial Sequence
<220> FEATURE:
<223> OTHER INFORMATION: peptide linker

<400> SEQUENCE: 28

Gly Gly Tyr Pro Gly Asp Val Lys Arg
1               5

<210> SEQ ID NO 29
<211> LENGTH: 9
<212> TYPE: PRT
<213> ORGANISM: Artificial Sequence
<220> FEATURE:
<223> OTHER INFORMATION: peptide linker

<400> SEQUENCE: 29

Arg Arg Tyr Pro Gly Asp Val Gly Gly
1               5

<210> SEQ ID NO 30
<211> LENGTH: 9
<212> TYPE: PRT
<213> ORGANISM: Artificial Sequence
<220> FEATURE:
<223> OTHER INFORMATION: peptide linker

<400> SEQUENCE: 30

Gly Gly His Pro Gly Asp Val Lys Arg
1               5

<210> SEQ ID NO 31
<211> LENGTH: 9
<212> TYPE: PRT
<213> ORGANISM: Artificial Sequence
<220> FEATURE:
<223> OTHER INFORMATION: peptide linker

<400> SEQUENCE: 31

Arg Arg His Pro Gly Asp Val Gly Gly
1               5

<210> SEQ ID NO 32
<211> LENGTH: 7
<212> TYPE: PRT
<213> ORGANISM: Artificial Sequence
<220> FEATURE:
<223> OTHER INFORMATION: peptide linker

<400> SEQUENCE: 32

Arg Arg Gly Pro Gly Gly Gly
1               5

<210> SEQ ID NO 33
<211> LENGTH: 51
<212> TYPE: PRT
```

<213> ORGANISM: Artificial Sequence
<220> FEATURE:
<223> OTHER INFORMATION: single chain human insulin analog
<220> FEATURE:
<221> NAME/KEY: MISC_FEATURE
<222> LOCATION: (49)..(49)
<223> OTHER INFORMATION: Xaa at position 49 is 4-amino phenylalanine or a
      modified 4-amino phenylalanine (having a dipeptide linked via an
      amide bond at the aromatic ring amine)

<400> SEQUENCE: 33

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gly Ile
            20                  25                  30

Val Glu Gln Cys Cys Thr Ser Ile Cys Ser Leu Tyr Gln Leu Glu Asn
        35                  40                  45

Xaa Cys Asn
    50

<210> SEQ ID NO 34
<211> LENGTH: 63
<212> TYPE: PRT
<213> ORGANISM: Artificial Sequence
<220> FEATURE:
<223> OTHER INFORMATION: single-chain human insulin analog
<220> FEATURE:
<221> NAME/KEY: MISC_FEATURE
<222> LOCATION: (61)..(61)
<223> OTHER INFORMATION: Xaa at position 61 is 4-amino phenylalanine or a
      modified 4-amino phenylalanine (having a dipeptide linked via an
      amide bond at the aromatic ring amine)

<400> SEQUENCE: 34

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Gln Pro
            20                  25                  30

Leu Ala Leu Glu Gly Ser Leu Gln Lys Arg Gly Ile Val Glu Gln Cys
        35                  40                  45

Cys Thr Ser Ile Cys Ser Leu Tyr Gln Leu Glu Asn Xaa Cys Asn
    50                  55                  60

<210> SEQ ID NO 35
<211> LENGTH: 7
<212> TYPE: PRT
<213> ORGANISM: Artificial Sequence
<220> FEATURE:
<223> OTHER INFORMATION: peptide linker

<400> SEQUENCE: 35

Ala Gly Arg Gly Ser Gly Lys
1               5

<210> SEQ ID NO 36
<211> LENGTH: 7
<212> TYPE: PRT
<213> ORGANISM: Artificial Sequence
<220> FEATURE:
<223> OTHER INFORMATION: peptide linker

<400> SEQUENCE: 36

Ala Gly Leu Gly Ser Gly Lys
1               5

```
<210> SEQ ID NO 37
<211> LENGTH: 7
<212> TYPE: PRT
<213> ORGANISM: Artificial Sequence
<220> FEATURE:
<223> OTHER INFORMATION: peptide linker

<400> SEQUENCE: 37

Ala Gly Met Gly Ser Gly Lys
1               5

<210> SEQ ID NO 38
<211> LENGTH: 7
<212> TYPE: PRT
<213> ORGANISM: Artificial Sequence
<220> FEATURE:
<223> OTHER INFORMATION: peptide linker

<400> SEQUENCE: 38

Ala Ser Trp Gly Ser Gly Lys
1               5

<210> SEQ ID NO 39
<211> LENGTH: 7
<212> TYPE: PRT
<213> ORGANISM: Artificial Sequence
<220> FEATURE:
<223> OTHER INFORMATION: peptide linker

<400> SEQUENCE: 39

Thr Gly Leu Gly Ser Gly Gln
1               5

<210> SEQ ID NO 40
<211> LENGTH: 7
<212> TYPE: PRT
<213> ORGANISM: Artificial Sequence
<220> FEATURE:
<223> OTHER INFORMATION: peptide linker

<400> SEQUENCE: 40

Thr Gly Leu Gly Arg Gly Lys
1               5

<210> SEQ ID NO 41
<211> LENGTH: 7
<212> TYPE: PRT
<213> ORGANISM: Artificial Sequence
<220> FEATURE:
<223> OTHER INFORMATION: peptide linker

<400> SEQUENCE: 41

Thr Gly Leu Gly Ser Gly Lys
1               5

<210> SEQ ID NO 42
<211> LENGTH: 7
<212> TYPE: PRT
<213> ORGANISM: Artificial Sequence
<220> FEATURE:
<223> OTHER INFORMATION: peptide linker

<400> SEQUENCE: 42

His Gly Leu Tyr Ser Gly Lys
1               5

<210> SEQ ID NO 43
```

```
<211> LENGTH: 7
<212> TYPE: PRT
<213> ORGANISM: Artificial Sequence
<220> FEATURE:
<223> OTHER INFORMATION: peptide linker

<400> SEQUENCE: 43

Lys Gly Leu Gly Ser Gly Gln
1               5

<210> SEQ ID NO 44
<211> LENGTH: 7
<212> TYPE: PRT
<213> ORGANISM: Artificial Sequence
<220> FEATURE:
<223> OTHER INFORMATION: peptide linker

<400> SEQUENCE: 44

Val Gly Leu Met Ser Gly Lys
1               5

<210> SEQ ID NO 45
<211> LENGTH: 7
<212> TYPE: PRT
<213> ORGANISM: Artificial Sequence
<220> FEATURE:
<223> OTHER INFORMATION: peptide linker

<400> SEQUENCE: 45

Val Gly Leu Ser Ser Gly Gln
1               5

<210> SEQ ID NO 46
<211> LENGTH: 7
<212> TYPE: PRT
<213> ORGANISM: Artificial Sequence
<220> FEATURE:
<223> OTHER INFORMATION: peptide linker

<400> SEQUENCE: 46

Val Gly Leu Tyr Ser Gly Lys
1               5

<210> SEQ ID NO 47
<211> LENGTH: 7
<212> TYPE: PRT
<213> ORGANISM: Artificial Sequence
<220> FEATURE:
<223> OTHER INFORMATION: peptide linker

<400> SEQUENCE: 47

Val Gly Leu Ser Ser Gly Lys
1               5

<210> SEQ ID NO 48
<211> LENGTH: 7
<212> TYPE: PRT
<213> ORGANISM: Artificial Sequence
<220> FEATURE:
<223> OTHER INFORMATION: peptide linker

<400> SEQUENCE: 48

Val Gly Met Ser Ser Gly Lys
1               5

<210> SEQ ID NO 49
<211> LENGTH: 7
```

```
<212> TYPE: PRT
<213> ORGANISM: Artificial Sequence
<220> FEATURE:
<223> OTHER INFORMATION: peptide linker

<400> SEQUENCE: 49

Val Trp Ser Ser Ser Gly Lys
1               5

<210> SEQ ID NO 50
<211> LENGTH: 7
<212> TYPE: PRT
<213> ORGANISM: Artificial Sequence
<220> FEATURE:
<223> OTHER INFORMATION: peptide linker

<400> SEQUENCE: 50

Val Gly Ser Ser Ser Gly Lys
1               5

<210> SEQ ID NO 51
<211> LENGTH: 7
<212> TYPE: PRT
<213> ORGANISM: Artificial Sequence
<220> FEATURE:
<223> OTHER INFORMATION: peptide linker

<400> SEQUENCE: 51

Val Gly Met Ser Ser Gly Lys
1               5

<210> SEQ ID NO 52
<211> LENGTH: 7
<212> TYPE: PRT
<213> ORGANISM: Artificial Sequence
<220> FEATURE:
<223> OTHER INFORMATION: peptide linker

<400> SEQUENCE: 52

Thr Gly Leu Gly Ser Gly Arg
1               5

<210> SEQ ID NO 53
<211> LENGTH: 7
<212> TYPE: PRT
<213> ORGANISM: Artificial Sequence
<220> FEATURE:
<223> OTHER INFORMATION: peptide linker

<400> SEQUENCE: 53

Thr Gly Leu Gly Lys Gly Gln
1               5

<210> SEQ ID NO 54
<211> LENGTH: 7
<212> TYPE: PRT
<213> ORGANISM: Artificial Sequence
<220> FEATURE:
<223> OTHER INFORMATION: peptide linker

<400> SEQUENCE: 54

Lys Gly Leu Ser Ser Gly Gln
1               5

<210> SEQ ID NO 55
<211> LENGTH: 7
<212> TYPE: PRT
```

```
<213> ORGANISM: Artificial Sequence
<220> FEATURE:
<223> OTHER INFORMATION: peptide linker

<400> SEQUENCE: 55

Val Lys Leu Ser Ser Gly Gln
1               5

<210> SEQ ID NO 56
<211> LENGTH: 7
<212> TYPE: PRT
<213> ORGANISM: Artificial Sequence
<220> FEATURE:
<223> OTHER INFORMATION: peptide linker

<400> SEQUENCE: 56

Val Gly Leu Lys Ser Gly Gln
1               5

<210> SEQ ID NO 57
<211> LENGTH: 7
<212> TYPE: PRT
<213> ORGANISM: Artificial Sequence
<220> FEATURE:
<223> OTHER INFORMATION: peptide linker

<400> SEQUENCE: 57

Thr Gly Leu Gly Lys Gly Gln
1               5

<210> SEQ ID NO 58
<211> LENGTH: 7
<212> TYPE: PRT
<213> ORGANISM: Artificial Sequence
<220> FEATURE:
<223> OTHER INFORMATION: peptide linker

<400> SEQUENCE: 58

Val Gly Leu Ser Lys Gly Gln
1               5

<210> SEQ ID NO 59
<211> LENGTH: 6
<212> TYPE: PRT
<213> ORGANISM: Artificial Sequence
<220> FEATURE:
<223> OTHER INFORMATION: synthetic peptide for testing cleavage of
      dipeptide prodrug element

<400> SEQUENCE: 59

His Ser Arg Gly Thr Phe
1               5

<210> SEQ ID NO 60
<211> LENGTH: 8
<212> TYPE: PRT
<213> ORGANISM: Artificial Sequence
<220> FEATURE:
<223> OTHER INFORMATION: synthetic peptide for testing cleavage of
      dipeptide prodrug element
<220> FEATURE:
<221> NAME/KEY: MISC_FEATURE
<222> LOCATION: (2)..(2)
<223> OTHER INFORMATION: Xaa at position 2 is Sarcosine

<400> SEQUENCE: 60

Lys Xaa His Ser Arg Gly Thr Phe
1               5
```

<210> SEQ ID NO 61
<211> LENGTH: 21
<212> TYPE: PRT
<213> ORGANISM: Homo sapiens

<400> SEQUENCE: 61

Gly Ile Val Asp Glu Cys Cys Phe Arg Ser Cys Asp Leu Arg Arg Leu
1               5                   10                  15

Glu Met Tyr Cys Ala
            20

<210> SEQ ID NO 62
<211> LENGTH: 29
<212> TYPE: PRT
<213> ORGANISM: Homo sapiens

<400> SEQUENCE: 62

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr
            20                  25

<210> SEQ ID NO 63
<211> LENGTH: 6
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: d-histidine
<220> FEATURE:
<221> NAME/KEY: MOD_RES
<222> LOCATION: (2)..(2)
<223> OTHER INFORMATION: d-threonine
<220> FEATURE:
<221> NAME/KEY: MOD_RES
<222> LOCATION: (3)..(3)
<223> OTHER INFORMATION: d-arginine
<220> FEATURE:
<221> NAME/KEY: MOD_RES
<222> LOCATION: (5)..(5)
<223> OTHER INFORMATION: d-threonine
<220> FEATURE:
<221> NAME/KEY: MOD_RES
<222> LOCATION: (6)..(6)
<223> OTHER INFORMATION: d-phenylalanine

<400> SEQUENCE: 63

Xaa Xaa Xaa Gly Xaa Xaa
1               5

<210> SEQ ID NO 64
<211> LENGTH: 8
<212> TYPE: PRT
<213> ORGANISM: Artificial Sequence
<220> FEATURE:
<223> OTHER INFORMATION: glucagon analogue
<220> FEATURE:
<221> NAME/KEY: MOD_RES
<222> LOCATION: (1)..(1)
<223> OTHER INFORMATION: d-lysine
<220> FEATURE:
<221> NAME/KEY: MOD_RES
<222> LOCATION: (2)..(2)
<223> OTHER INFORMATION: d-sarcosine
<220> FEATURE:
<221> NAME/KEY: MOD_RES

```
<222> LOCATION: (3)..(3)
<223> OTHER INFORMATION: d-histidine
<220> FEATURE:
<221> NAME/KEY: MOD_RES
<222> LOCATION: (4)..(4)
<223> OTHER INFORMATION: d-threonine
<220> FEATURE:
<221> NAME/KEY: MOD_RES
<222> LOCATION: (5)..(5)
<223> OTHER INFORMATION: d-arginine
<220> FEATURE:
<221> NAME/KEY: MOD_RES
<222> LOCATION: (7)..(7)
<223> OTHER INFORMATION: d-threonine
<220> FEATURE:
<221> NAME/KEY: MOD_RES
<222> LOCATION: (8)..(8)
<223> OTHER INFORMATION: d-phenylalanine

<400> SEQUENCE: 64

Xaa Xaa Xaa Xaa Xaa Gly Xaa Xaa
1               5

<210> SEQ ID NO 65
<211> LENGTH: 8
<212> TYPE: PRT
<213> ORGANISM: Homo sapiens

<400> SEQUENCE: 65

Ser Arg Val Ser Arg Arg Ser Arg
1               5

<210> SEQ ID NO 66
<211> LENGTH: 8
<212> TYPE: PRT
<213> ORGANISM: Homo sapiens

<400> SEQUENCE: 66

Gly Tyr Gly Ser Ser Ser Arg Arg
1               5

<210> SEQ ID NO 67
<211> LENGTH: 8
<212> TYPE: PRT
<213> ORGANISM: Homo sapiens

<400> SEQUENCE: 67

Gly Ser Ser Ser Arg Arg Ala Pro
1               5

<210> SEQ ID NO 68
<211> LENGTH: 48
<212> TYPE: PRT
<213> ORGANISM: Artificial Sequence
<220> FEATURE:
<223> OTHER INFORMATION: IGF1 B and A chain analogs
<220> FEATURE:
<221> NAME/KEY: MISC_FEATURE
<222> LOCATION: (22)..(22)
<223> OTHER INFORMATION: Xaa at position 22 is ornithine
<220> FEATURE:
<221> NAME/KEY: MISC_FEATURE
<222> LOCATION: (36)..(36)
<223> OTHER INFORMATION: Xaa at position 36 is ornithine
<220> FEATURE:
<221> NAME/KEY: MISC_FEATURE
<222> LOCATION: (41)..(41)
<223> OTHER INFORMATION: Xaa at position 41 is ornithine
<220> FEATURE:
<221> NAME/KEY: MISC_FEATURE
<222> LOCATION: (42)..(42)
```

```
<223> OTHER INFORMATION: Xaa at position 42 is ornithine

<400> SEQUENCE: 68

Cys Gly Pro Glu His Leu Cys Gly Ala Glu Leu Val Asp Ala Leu Tyr
1               5                   10                  15

Leu Val Cys Gly Asp Xaa Gly Phe Tyr Phe Asn Gly Ile Val Asp Glu
            20                  25                  30

Cys Cys Phe Xaa Ser Cys Asp Leu Xaa Xaa Leu Glu Asn Tyr Cys Asn
            35                  40                  45

<210> SEQ ID NO 69
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (7)..(7)
<223> OTHER INFORMATION: The Xaa at position 7 is ornithine

<400> SEQUENCE: 69

Gly Tyr Gly Ser Ser Ser Xaa Arg
1               5

<210> SEQ ID NO 70
<211> LENGTH: 12
<212> TYPE: PRT
<213> ORGANISM: Homo sapiens

<400> SEQUENCE: 70

Gly Ala Gly Ser Ser Ser Arg Arg Ala Pro Gln Thr
1               5                   10

<210> SEQ ID NO 71
<211> LENGTH: 8
<212> TYPE: PRT
<213> ORGANISM: Artificial Sequence
<220> FEATURE:
<223> OTHER INFORMATION: peptide linker
<220> FEATURE:
<221> NAME/KEY: MISC_FEATURE
<222> LOCATION: (7)..(7)
<223> OTHER INFORMATION: The Xaa at position 7 is ornithine, arginine or
      lysine
<220> FEATURE:
<221> NAME/KEY: MISC_FEATURE
<222> LOCATION: (8)..(8)
<223> OTHER INFORMATION: The Xaa at position 8 is ornithine, arginine or
      lysine

<400> SEQUENCE: 71

Gly Tyr Gly Ser Ser Ser Xaa Xaa
1               5
```

US 8,946,147 B2

AMIDE-BASED INSULIN PRODRUGS

CROSS REFERENCE TO RELATED APPLICATIONS

This application is a U.S. national counterpart application of International Application No. PCT/US2011/041603 filed Jun. 23, 2011, which claims priority to U.S. Provisional Patent Application No. 61/358,192, filed Jun. 24, 2010. The entire disclosures of PCT/US2011/041603 and U.S. Ser. No. 61/358,192 are hereby incorporated by reference.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: One 27 KB ACII (Text) file named "IN216461" created on Jun. 23, 2011.

BACKGROUND

Insulin is a peptide hormone comprised of a two chain heterodimer that is biosynthetically derived from a low potency single chain proinsulin precursor through enzymatic processing. Human insulin is comprised of two peptide chains (an "A chain" (SEQ ID NO: 1) and "B chain" (SEQ ID NO: 2)) bound together by disulfide bonds and having a total of 51 amino acids. The C-terminal region of the B-chain and the two terminal regions of the A-chain associate in a three-dimensional structure to assemble a site for high affinity binding to the insulin receptor.

Insulin demonstrates unparalleled ability to lower glucose in virtually all forms of diabetes. Unfortunately, its pharmacology is not glucose sensitive and as such it is capable of excessive action that can lead to life-threatening hypoglycemia. Inconsistent pharmacology is a hallmark of insulin therapy such that it is extremely difficult to normalize blood glucose without occurrence of hypoglycemia. Furthermore, native insulin is of short duration of action and requires modification to render it suitable for use in control of basal glucose. Established approaches to delay the onset of insulin action include reduction in solubility, and albumin binding.

For example, two commercially available insulin derivatives have been prepared to provide a longer action profile. More particularly, the insulin derivative [GlyA21, ArgB31, ArgB32] insulin was prepared to shift insulin's pI from 5.4 to 6.7 resulting in the peptide being precipitated at physiological pH and thus delaying adsoption and time of action (see Bolli et al., Diabetologia 1999, 42, 1151-1167). However, this insulin derivative has enhanced IGF-1 affinity, leading to increased proliferative actions and the possibility of tumorigenesis. Another commercially available insulin derivative is [LysB29-tetradecanoyl, des(B30)] insulin, wherein LysB29 has been acylated with a $C_{14}$ fatty acid (Mayer et al., Peptide Science, 88, 5, 687-713). The presence of the fatty acid chain enhances binding of the peptide to serum albumin, resulting in increased plasma half life. However, this derivative suffers the disadvantage of having reduced potency in vivo. In addition, both insulin derivatives exhibit variability in biological action from one patient to the next.

Prodrug chemistry offers the opportunity to precisely control the onset and duration of insulin action after clearance from the site of administration and equilibration in the plasma at a highly defined concentration. The central virtue of such an approach, relative to current long-acting insulin analogs and formulations, is that the insulin reservoir is not the subcutaneous fatty tissue where injection occurs, but rather the blood compartment. This removes the variability in absorption encountered with prior art delayed onset insulin derivatives. It also enables administration of the peptide hormone by routes other than a subcutaneous injection.

Binding of insulin to its receptor will result in biological stimulation, but will also initiate the subsequent deactivation of insulin induced pharmacology through the enzymatic degradation of the insulin peptide. An added advantage of using a prodrug derivative of insulin is that such an approach also extends insulin's biological half life based on a strategy of inhibiting recognition of the prodrug by the corresponding receptor. In spite of these advantages associated with prodrug derivatives, the complex nature of preparing such prodrugs has, until now, prevented the preparation of an efficacious prodrug derivative of insulin. To build a successful prodrug-hormone, an active site structural address is needed that can form the basis for the reversible attachment of a prodrug structural element. The structural address needs to offer two key features; (1) the potential for selective chemical modification and (2) the ability to provide a high degree of activity in the native form upon removal of the prodrug structural element. The insulin prodrugs disclosed herein are chemically converted to structures that can be recognized by the receptor, wherein the speed of this chemical conversion will determine the time of onset and duration of in vivo biological action. The prodrug chemistry disclosed in this application relies upon an intramolecular chemical reaction that is not dependent upon additional chemical additives, or enzymes or enzyme inhibitors.

The ideal prodrug should be soluble in water at physiological conditions (for example, a pH of 7.2 and 37° C.), and it should be stable in the powder form for long term storage. It should also be immunologically silent and exhibit a low activity relative to the parent drug. Typically the prodrug will exhibit no more than 10% of the activity of the parent drug, in one embodiment the prodrug exhibits less than 10%, less than 5%, about 1%, or less than 1% activity relative to the parent drug. Furthermore, the prodrug, when injected in the body, should be quantitatively converted to the active drug within a defined period of time. Applicants are the first to disclose insulin prodrug analogs that meet each of these objectives.

SUMMARY

Peptide-based drugs are highly effective medicines with relatively short duration of action and variable therapeutic index. The present disclosure is directed to insulin prodrugs wherein the prodrug derivative is designed to delay onset of action and extend the half life of the drug. The delayed onset of action is advantageous in that it allows systemic distribution of the prodrug prior to its activation. Accordingly, the administration of prodrugs eliminates complications caused by peak activities upon administration and increases the therapeutic index of the parent drug.

In accordance with one embodiment, a prodrug derivative of insulin is prepared by covalently linking a dipeptide to an active site of the insulin peptide via an amide linkage. In one embodiment the dipeptide is covalently bound to the insulin peptide at a position that interferes with insulin's ability to interact with the insulin and IGF-1 receptors. Subsequent removal of the dipeptide via an intramolecular reaction, resulting in diketopiperazine or diketomorpholine formation, under physiological conditions and in the absence of enzymatic activity, restores full activity to the polypeptide.

In one embodiment an insulin prodrug is provided having the general structure of U-O-insulin, wherein U is an amino acid or a hydroxyl acid and O is an N-alkylated amino acid linked to the insulin peptide through formation of an amide bond between U-O and an amine of an insulin peptide. In one embodiment the U-O dipeptide is bound at the N-terminus, or at the side chain of an amino acid corresponding to positions A19, B16 or B25, of the respective A chain or B chain via an amide bond. The structure of U-O is selected, in one embodiment wherein chemical cleavage of U-O from the insulin peptide is at least about 90% complete within about 1 to about 720 hours in PBS under physiological conditions. In one embodiment the chemical cleavage half-life ($t_{1/2}$) of U-O from the insulin peptide is at least about 1 hour to about 1 week in PBS under physiological conditions.

In one embodiment U and O are selected to inhibit enzymatic cleavage of the U-O dipeptide from an insulin peptide by enzymes found in mammalian serum. In one embodiment U and/or O are selected such that the cleavage half-life of U-O from the insulin peptide, in PBS under physiological conditions, is not more than two fold the cleavage half-life of U-O from the insulin peptide in a solution comprising a DPP-IV protease (i.e., cleavage of U-O from the insulin prodrug does not occur at a rate more than 2× faster in the presence of DPP-IV protease and physiological conditions relative to identical conditions in the absence of the enzyme). In one embodiment U, O, or the amino acid of the insulin peptide to which U-O is linked is a non-coded amino acid. In one embodiment U and/or O is an amino acid in the D stereoisomer configuration. In some exemplary embodiments, U is an amino acid in the D stereoisomer configuration and O is an amino acid in the L stereoisomer configuration. In some exemplary embodiments, U is an amino acid in the L stereoisomer configuration and O is an amino acid in the D stereoisomer configuration. In some exemplary embodiments, U is an amino acid in the D stereoisomer configuration and O is an amino acid in the D stereoisomer configuration. In one embodiment O is an N-alkylated amino acid but is not proline.

In one embodiment the dipeptide prodrug element comprises a compound having the general structure of Formula I:

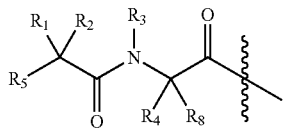

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH.

In one embodiment the dipeptide prodrug element comprises a compound having the general structure of Formula I:

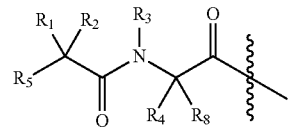

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In one embodiment the dipeptide extension comprises a compound of the general structure:

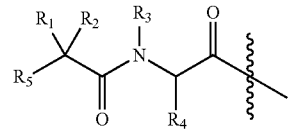

wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring; and
$R_7$ is selected from the group consisting of H and OH. In one embodiment $R_3$ is $C_1$-$C_8$ alkyl and $R_4$ is selected from the group consisting of H, $C_1$-$C_8$ alkyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$) NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl) or $R_4$ and $R_3$ together with the atoms to which they are attached form a 5 or 6 member heterocyclic ring.

In accordance with one embodiment an insulin prodrug analog is provided comprising an A chain and a B chain, wherein the A chain comprises the sequence Z-GIVEQCCX$_1$SICSLYQLENX$_2$CX$_3$ (SEQ ID NO: 3) and the B chain comprises the sequence of J-X$_{14}$-X$_4$LCGX$_5$X$_6$LVEALX$_7$LVCG ERGFX$_8$ (SEQ ID NO: 14). The Z and J designations of the A and B chain formulas are independently H (forming an N-terminal amine) or a dipeptide comprising the general structure:

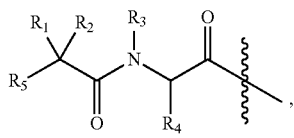

wherein $X_{14}$ is either a bond joining the "J" element to the N-terminus of the X$_4$LCGX$_5$X$_6$LVEALX$_7$LVCG ERGFX$_8$ (SEQ ID NO: 14) sequence or X$_{14}$ represents a 1 to 4 amino acid sequence selected from the group consisting of a FVNQ (SEQ ID NO: 11), VNQ, NQ and Q that joins the "J" element to the N-terminus of the X$_4$LCGX$_5$X$_6$LVEALX$_7$LVCG ERGFX$_8$ (SEQ ID NO: 14) sequence.

$X_1$ is selected from the group consisting of threonine and histidine;

$X_2$ is an amino acid of the general structure

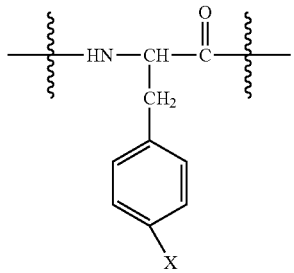

wherein X is selected from the group consisting of OH, NH$_2$, NHR$_{10}$ and OCH$_3$, wherein R$_{10}$ is a dipeptide comprising the general structure:

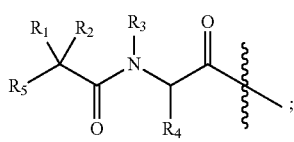

$X_3$ is selected from the group consisting of asparagine, ornithine, glycine, alanine, threonine, and serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is an amino acid of the general structure

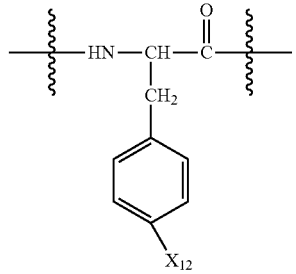

wherein $X_{12}$ is selected from the group consisting of OH, NH$_2$, NHR$_{11}$ and OCH$_3$, wherein R$_{11}$ is a dipeptide comprising the general structure:

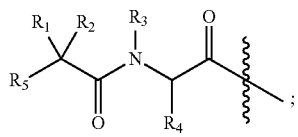

$X_8$ is histidine, asparagine or an amino acid of the general structure

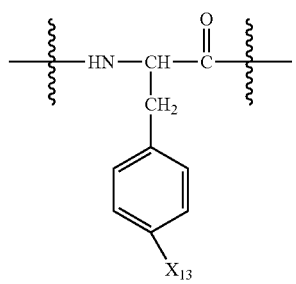

wherein $X_{13}$ is selected from the group consisting of H, OH, NH$_2$, NHR$_{12}$ and OCH$_3$, wherein R$_{12}$ is a dipeptide comprising the general structure:

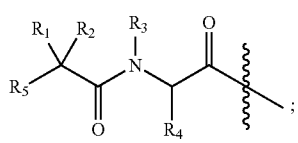

wherein $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-

$C_4$ alkyl)NHC(NH$_2^+$)NH$_2$, (C$_0$-C$_4$ alkyl)(C$_3$-C$_6$ cycloalkyl), (C$_0$-C$_4$ alkyl)(C$_6$-C$_{10}$ aryl)R$_7$, and CH$_2$(C$_5$-C$_9$ heteroaryl);

R$_3$ is selected from the group consisting of C$_1$-C$_8$ alkyl, (C$_1$-C$_4$ alkyl)OH, (C$_1$-C$_4$ alkyl)SH, (C$_3$-C$_6$)cycloalkyl or R$_4$ and R$_3$ together with the atoms to which they are attached form a 5 or 6 member heterocyclic ring;

R$_5$ is NHR$_6$ or OH;

R$_6$ is H, or R$_6$ and R$_2$ together with the atoms to which they are attached form a 5 or 6 member heterocyclic ring; and R$_7$ is selected from the group consisting of H and OH, with the proviso that one and only one of X, X$_{12}$, X$_{13}$, J and Z comprises a dipeptide of the general structure:

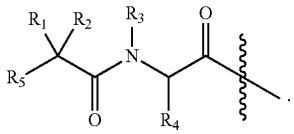

In one embodiment the insulin analog comprises the sequence identified immediately above with the exception that X$_8$ is histidine or asparagine. In one embodiment when J or Z comprise the dipeptide of Formula I, and R$_4$ and R$_3$ together with the atoms to which they are attached form a 4, 5 or 6 member heterocyclic ring, then both R$_1$ and R$_2$ are not hydrogen In accordance with one embodiment the dipeptide present at Z, J, R$_{10}$, R$_{11}$ or R$_{12}$ comprises a compound having the general structure of Formula I:

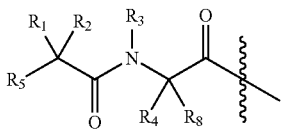

wherein

R$_1$, R$_2$, R$_4$ and R$_8$ are independently selected from the group consisting of H, C$_1$-C$_{18}$ alkyl, C$_2$-C$_{18}$ alkenyl, (C$_1$-C$_{18}$ alkyl)OH, (C$_1$-C$_{18}$ alkyl)SH, (C$_2$-C$_3$ alkyl)SCH$_3$, (C$_1$-C$_4$ alkyl)CONH$_2$, (C$_1$-C$_4$ alkyl)COOH, (C$_1$-C$_4$ alkyl)NH$_2$, (C$_1$-C$_4$ alkyl)NHC(NH$_2^+$)NH$_2$, (C$_0$-C$_4$ alkyl)(C$_3$-C$_6$ cycloalkyl), (C$_0$-C$_4$ alkyl)(C$_2$-C$_5$ heterocyclic), (C$_0$-C$_4$ alkyl)(C$_6$-C$_{10}$ aryl)R$_7$, (C$_1$-C$_4$ alkyl)(C$_3$-C$_9$ heteroaryl), and C$_1$-C$_{12}$ alkyl (W$_1$)C$_1$-C$_{12}$ alkyl, wherein W$_1$ is a heteroatom selected from the group consisting of N, S and O, or R$_1$ and R$_2$ together with the atoms to which they are attached form a C$_3$-C$_{12}$ cycloalkyl; or R$_4$ and R$_8$ together with the atoms to which they are attached form a C$_3$-C$_6$ cycloalkyl;

R$_3$ is selected from the group consisting of C$_1$-C$_{18}$ alkyl, (C$_1$-C$_{18}$ alkyl)OH, (C$_1$-C$_{18}$ alkyl)NH$_2$, (C$_1$-C$_{18}$ alkyl)SH, (C$_0$-C$_4$ alkyl)(C$_3$-C$_6$)cycloalkyl, (C$_0$-C$_4$ alkyl)(C$_2$-C$_5$ heterocyclic), (C$_0$-C$_4$ alkyl)(C$_6$-C$_{10}$ aryl)R$_7$, and (C$_1$-C$_4$ alkyl)(C$_3$-C$_9$ heteroaryl) or R$_4$ and R$_3$ together with the atoms to which they are attached form a 4, 5 or 6 member heterocyclic ring;

R$_5$ is NHR$_6$ or OH;

R$_6$ is H, C$_1$-C$_8$ alkyl or R$_6$ and R$_1$ together with the atoms to which they are attached form a 4, 5 or 6 member heterocyclic ring; and R$_7$ is selected from the group consisting of hydrogen, C$_1$-C$_{18}$ alkyl, C$_2$-C$_{18}$ alkenyl, (C$_0$-C$_4$ alkyl)CONH$_2$, (C$_0$-C$_4$ alkyl)COOH, (C$_0$-C$_4$ alkyl)NH$_2$, (C$_0$-C$_4$ alkyl)OH, and halo.

In accordance with one embodiment the dipeptide present at Z, J, R$_{10}$, R$_{11}$ or R$_{12}$ comprises a compound having the general structure of Formula I:

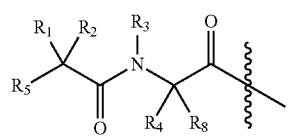

wherein

R$_1$ and R$_8$ are independently H or C$_1$-C$_8$ alkyl;

R$_2$ and R$_4$ are independently selected from the group consisting of H, C$_1$-C$_8$ alkyl, C$_2$-C$_8$ alkenyl, (C$_1$-C$_4$ alkyl)OH, (C$_1$-C$_4$ alkyl)SH, (C$_2$-C$_3$ alkyl)SCH$_3$, (C$_1$-C$_4$ alkyl)CONH$_2$, (C$_1$-C$_4$ alkyl)COOH, (C$_1$-C$_4$ alkyl)NH$_2$, (C$_1$-C$_4$ alkyl)NHC(NH$_2^+$)NH$_2$, (C$_0$-C$_4$ alkyl)(C$_3$-C$_6$ cycloalkyl), (C$_0$-C$_4$ alkyl)(C$_2$-C$_5$ heterocyclic), (C$_0$-C$_4$ alkyl)(C$_6$-C$_{10}$ aryl)R$_7$, and CH$_2$(C$_3$-C$_9$ heteroaryl), or R$_1$ and R$_2$ together with the atoms to which they are attached form a C$_3$-C$_{12}$ cycloalkyl;

R$_3$ is C$_1$-C$_{18}$ alkyl;

R$_5$ is NHR$_6$;

R$_6$ is H or C$_1$-C$_8$ alkyl; and

R$_7$ is selected from the group consisting of hydrogen, C$_1$-C$_{18}$ alkyl, C$_2$-C$_{18}$ alkenyl, (C$_0$-C$_4$ alkyl)CONH$_2$, (C$_0$-C$_4$ alkyl)COOH, (C$_0$-C$_4$ alkyl)NH$_2$, (C$_0$-C$_4$ alkyl)OH, and halo.

In accordance with one embodiment an insulin analog is provided wherein the A chain of the insulin peptide comprises the sequence Z-GIVEQCCTSICSLYQLENX$_2$CN (SEQ ID NO: 6) and the B chain comprising a sequence selected from the group consisting of HLCGSHLVEALYLVCGERGFF (SEQ ID NO: 7), FVNQHLCGSHLVEALYLVCGERG-FFYTPKT (SEQ ID NO: 8) and FVNQHLCG-SHLVEALYLVCGERGFFYTKPT (SEQ ID NO: 9) wherein Z is H or a dipeptide comprising the general structure:

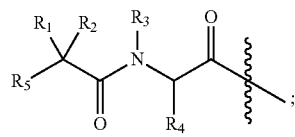

X$_2$ is an amino acid of the general structure

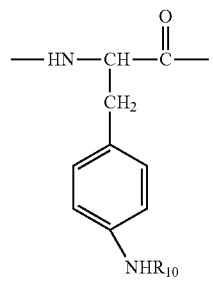

wherein R$_{10}$ is H or a dipeptide comprising the general structure:

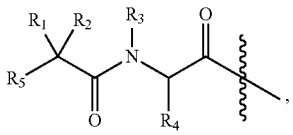

with the proviso that Z and $R_{10}$ are not both H and are not both a dipeptide comprising the general structure:

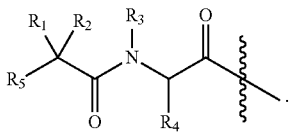

In accordance with one embodiment single-chain insulin prodrug analogs are provided. In this embodiment the carboxy terminus of the human insulin B chain, or a functional analog thereof, is covalently linked to the N-terminus of the human insulin A chain, or functional analog thereof, wherein a dipeptide prodrug moiety having the general structure:

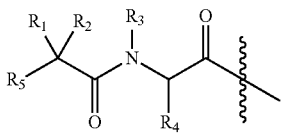

is covalently bound at the N-terminus of the peptide or at the side chain of an amino acid corresponding to positions A19, B16 or B25 of the respective A chain or B chain via an amide bond. In one embodiment the B chain is linked to the A chain via peptide linker of 4-12 or 4-8 amino acids.

In another embodiment the solubility of the insulin prodrug analogs is enhanced by the covalent linkage of a hydrophilic moiety to the peptide. In one embodiment the hydrophilic moiety is linked to the insulin analog via a linker. In one embodiment the hydrophilic moiety is linked (directly or indirectly through a linker) to either the N-terminal alpha amine of the B chain or to the side chain of an amino acid at position 28 of SEQ ID NO: 9 or the amino acid at position 29 of SEQ ID NO: 8. In one embodiment the hydrophilic moiety is a polyethylene glycol (PEG) chain, having a molecular weight selected from the range of about 500 to about 40,000 Daltons. In one embodiment the polyethylene glycol chain has a molecular weight selected from the range of about 500 to about 5,000 Daltons. In another embodiment the polyethylene glycol chain has a molecular weight of about 10,000 to about 20,000 Daltons.

Acylation or alkylation can increase the half-life of the insulin peptides in circulation. Acylation or alkylation can advantageously delay the onset of action and/or extend the duration of action at the insulin receptors upon activation of the prodrug. The insulin analogs may be acylated or alkylated at the same amino acid position where a hydrophilic moiety is linked, or at a different amino acid position.

In accordance with one embodiment a pharmaceutical composition is provided comprising any of the novel insulin prodrug analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In accordance with one embodiment an improved method of regulating blood glucose levels in insulin dependent patients is provided. The method comprises the steps of administering an insulin prodrug analog of the present disclosure in an amount therapeutically effective for the control of diabetes. In one embodiment the insulin prodrug analog is pegylated with a PEG chain having a molecular weight selected from the range of about 5,000 to about 40,000 Daltons

BRIEF DESCRIPTION OF THE DRAWINGS

FIG. 7A-7C provides the activity of a dimer prepared in accordance with the present disclosure. FIG. 7A shows the structure of an IGF-1 single chain dimer that comprises two single chain IGF$^{B16B17}$ derivative peptides (IGF-1B chain [$C^0H^5Y^{16}L^{17}O^{22}$]-A chain[$O^{9,14,15}N^{18,21}$]; SEQ ID NO: 68) linked together by a disulfide bond between the side chains of the amino terminus of the B chains. FIG. 7B is a graph demonstrating the relative insulin receptor binding of insulin, IGF-1, a single chain IGF$^{B16B17}$ derivative peptide dimer and a two chain IGF$^{B16B17}$ derivative peptide dimer. FIG. 7C is a graph demonstrating the relative activity of insulin, IGF-1, and a two chain IGF$^{B16B17}$ derivative peptide dimer to induce insulin receptor phosphorylation.

FIG. 9A is a graph comparing relative insulin receptor binding of native insulin (measured at 1 hour at 4° C.) and the A19 IGF prodrug analog (Aib,dPro-IGF1YL) over time (0 hours, 2.5 hours and 10.6 hours) incubated in PBS. FIG. 9B is a graph comparing relative insulin receptor binding of native insulin (measured at 1.5 hour at 4° C.) and the A19 IGF prodrug analog (Aib,dPro-IGF1YL) over time (0 hours, 1.5 hours and 24.8 hours) incubated in 20% plasma/PBS. As indicated by the data presented in the graph, increased activity is recovered form the A19 IGF prodrug analog sample as the prodrug form is converted to the active IGF1YL peptide.

FIG. 10A is a graph comparing relative insulin receptor binding of native insulin (measured at 1 hour at 4° C.) and the A19 IGF prodrug analog (IGF1YL: dK,(N-isobutylG) over time (0 hours, 5 hours and 52 hours) incubated in PBS. FIG. 10B is a graph comparing relative insulin receptor binding of native insulin (measured at 1.5 hour at 4° C.) and the A19 IGF prodrug analog (IGF1YL: dK,(N-isobutylG) over time (0 hours, 3.6 hours and 24.8 hours) incubated in 20% plasma/PBS. As indicated by the data presented in the graph, increased activity is recovered form the A19 IGF prodrug analog sample as the prodrug form is converted to the active IGF1YL peptide.

FIG. 11A is a graph comparing relative insulin receptor binding of native insulin (measured at 1 hour at 4° C.) and the A19 IGF prodrug analog (IGF1YL: dK(e-acetyl),Sar) over time (0 hours, 7.2 hours and 91.6 hours) incubated in PBS. FIG. 11B is a graph comparing relative insulin receptor binding of native insulin (measured at 1.5 hour at 4° C.) and the A19 IGF prodrug analog (IGF1YL: dK(e-acetyl),Sar) over time (0 hours, 9 hours and 95 hours) incubated in 20% plasma/PBS. As indicated by the data presented in the graph, increased activity is recovered from the A19 IGF prodrug analog sample as the prodrug form is converted to the active IGF1YL peptide.

FIG. 19A shows that in vitro insulin receptor binding increase with time MIU-29 is incubated ex vivo in PBS buffer at 37° C. and exhibiting a half life of about 4.4 hours. FIG. 19B is a graph showing the results of a comparative insulin tolerance test conducted in normal mice for a prodrug two chain insulin analog acylated at the dipeptide prodrug element (MIU-29: [$B^1$(Y16,L17,Y25)29a: $A^1$(aF19-dLys(Ac),NLeu)] relative to its parent insulin analog (MIU-27: [B1(Y16,L17,Y25)29a: $A^1$(aF19-NH2)]. The prodrug derivative MIU-29 comprises a 4-amino-phenylalanine substitution at position A19 wherein a dipeptide dLys(Ac),NLeu has been covalently linked at the 4-amino position of the A19 residue and the side chain of the lysine of the dipeptide element has been acylated with a C14 fatty acid. This dipeptide will auto-cleave under physiological conditions with a half life of approximately 4.4 hours. After incubating MIU-29 for 24 hours ex vivo, the resultant compound (designated "MIU-29c") was administered to mice and its ability to lower blood glucose was compared to parent compound. As shown in FIG. 12 the two compounds performed almost identically.

(wherein the acylated dipeptide dLys(Ac),Sar is linked via an amide bond to the insulin analog through the A19 4-aminoPhe). The half life of the prodrug is estimated to be approximately 20 hours. The data shown in FIG. 20A reveals that the parent compound has low potency, but after incubation in 20% plasma for 48 hours (generating "MIU-30c") potency is increased. ●=vehicle control, ▼=MIU 30a, 90 nm/kg; ▽=MIU 30c, 90 nm/kg; ◆=MIU 30a, 270 nm/kg; ◇=MIU 30c, 270 nm/kg. Similarly, FIG. 20B represents blood glucose AUC after 8 hours in C57/Blk mice indicating that the potency of the compounds increases with time incubated in vitro prior to administration.

As shown in FIGS. 23A-23D acylated analog MIU-46 is not very potent relative to Detemir.

DETAILED DESCRIPTION

Definitions

Figure 1:
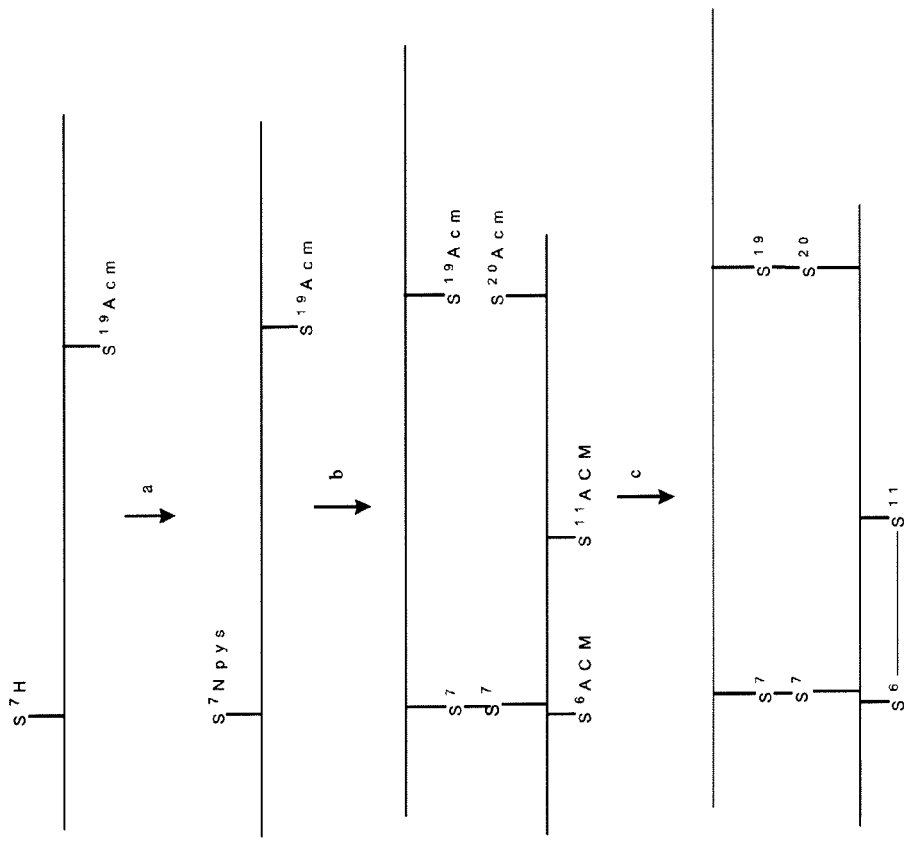
FIG. 1. is a schematic overview of the two step synthetic strategy for preparing human insulin. Details of the procedure are provided in Example 1.

In describing and claiming the invention, the following terminology will be used in accordance with the definitions set forth below.

As used herein, the term "prodrug" is defined as any compound that undergoes chemical modification before exhibiting its pharmacological effects.

A "bioactive polypeptide" refers to polypeptides which are capable of exerting a biological effect in vitro and/or in vivo.

As used herein the term "amino acid" encompasses any molecule containing both amino and carboxyl functional groups, wherein the amino and carboxylate groups are attached to the same carbon (the alpha carbon). The alpha carbon optionally may have one or two further organic substituents. Designation of an amino acid without specifying its stereochemistry is intended to encompass either the L or D form of the amino acid or a racemic mixture. However, in the instance where an amino acid is designated by its three letter code and includes a superscript number, the D form of the amino acid is specified by inclusion of a lower case d before the three letter code and superscript number (e.g., dLys$^{-1}$), wherein the designation lacking the lower case d (e.g., Lys$^{-1}$) is intended to specify the native L form of the amino acid. In this nomenclature, the inclusion of the superscript number designates the position of the amino acid in the IGF peptide sequence, wherein amino acids that are located within the IGF sequence are designated by positive superscript numbers numbered consecutively from the N-terminus. Additional amino acids linked to the IGF peptide either at the N-terminus or through a side chain are numbered starting with 0 and increasing in negative integer value as they are further removed from the IGF sequence. For example, the position of an amino acid within a dipeptide prodrug linked to the N-terminus of IGF is designated aa$^{-1}$-aa$^0$-IGF wherein aa$^0$ represents the carboxy terminal amino acid of the dipeptide and aa$^{-1}$ designates the amino terminal amino acid of the dipeptide.

As used herein the term "hydroxyl acid" refers to amino acids that have been modified to replace the alpha carbon amino group with a hydroxyl group.

As used herein the term "non-coded amino acid" encompasses any amino acid that is not an L-isomer of any of the following 20 amino acids: Ala, Cys, Asp, Glu, Phe, Gly, His, Ile, Lys, Leu, Met, Asn, Pro, Gln, Arg, Ser, Thr, Val, Trp, Tyr.

A "dipeptide" is a compound formed by linkage of an alpha amino acid or an alpha hydroxyl acid to another amino acid, through a peptide bond.

As used herein the term "chemical cleavage" absent any further designation encompasses a non-enzymatic reaction that results in the breakage of a covalent chemical bond.

A "bioactive polypeptide" refers to polypeptides which are capable of exerting a biological effect in vitro and/or in vivo.

As used herein a general reference to a peptide is intended to encompass peptides that have modified amino and carboxy termini. For example, an amino acid sequence designating the standard amino acids is intended to encompass standard amino acids at the N- and C-terminus as well as a corresponding hydroxyl acid at the N-terminus and/or a corresponding C-terminal amino acid modified to comprise an amide group in place of the terminal carboxylic acid.

As used herein an "acylated" amino acid is an amino acid comprising an acyl group which is non-native to a naturally-occurring amino acid, regardless by the means by which it is produced. Exemplary methods of producing acylated amino acids and acylated peptides are known in the art and include acylating an amino acid before inclusion in the peptide or peptide synthesis followed by chemical acylation of the peptide. In one embodiment, the acyl group causes the peptide to have one or more of (i) a prolonged half-life in circulation, (ii) a delayed onset of action, (iii) an extended duration of action, (iv) an improved resistance to proteases, such as DPP-IV, and (v) increased potency at the insulin peptide receptor.

As used herein, an "alkylated" amino acid is an amino acid comprising an alkyl group which is non-native to a naturally-occurring amino acid, regardless of the means by which it is produced. Exemplary methods of producing alkylated amino acids and alkylated peptides are known in the art and including alkylating an amino acid before inclusion in the peptide or peptide synthesis followed by chemical alkylation of the peptide. Without being held to any particular theory, it is believed that alkylation of peptides will achieve similar, if not the same, effects as acylation of the peptides, e.g., a prolonged half-life in circulation, a delayed onset of action, an extended duration of action, an improved resistance to proteases, such as DPP-IV, and increased potency at the insulin peptide receptor.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, the term "treating" includes prophylaxis of the specific disorder or condition, or alleviation of the symptoms associated with a specific disorder or condition and/or preventing or eliminating said symptoms. For example, as used herein the term "treating diabetes" will refer in general to maintaining glucose blood levels near normal levels and may include increasing or decreasing blood glucose levels depending on a given situation.

As used herein an "effective" amount or a "therapeutically effective amount" of a prodrug refers to a nontoxic but sufficient amount of the prodrug to provide the desired effect. For example one desired effect would be the prevention or treatment of hyperglycemia. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as intranasal, inhalation, subcutaneous, intramuscular, intraspinal, or intravenous.

As used herein the term "native insulin peptide" is intended to designate the 51 amino acid heterodimer comprising the A chain of SEQ ID NO: 1 and the B chain of SEQ ID NO: 2, as well as single-chain insulin analogs that comprise SEQ ID NOS: 1 and 2. The term "insulin peptide" as used herein, absent further descriptive language is intended to encompass the 51 amino acid heterodimer comprising the A chain of SEQ ID NO: 1 and the B chain of SEQ ID NO: 2, as well as single-chain insulin analogs thereof (including for example those disclosed in published international application WO96/34882 and U.S. Pat. No. 6,630,348, the disclosures of which are incorporated herein by reference), and includes heterodimers and single-chain analogs that comprise modified derivatives of the native A chain and/or B chain, including modification of the amino acid at position A19, B16 or B25 to a 4-amino phenylalanine or one or more amino acid substitutions at positions selected from A5, A8, A9, A10, A12, A14, A15, A17, A18, A21, B1, B2, B3, B4, B5, B9, B10, B13, B14, B17, B20, B21, B22, B23, B26, B27, B28, B29 and B30 or deletions of any or all of positions B1-4 and B26-30. An "insulin prodrug analog" as used herein refers to an insulin peptide (or an IGF1-based insulin analog as disclosed in Example 9) that has been modified by the covalent attachment of a dipeptide, via an amide linkage, at a location that interferes with insulin's or IGF1-based insulin analog's activity (e.g., the ability to interact with the insulin and IGF-1 receptors).

As used herein, the term "single-chain insulin analog" encompasses a group of structurally-related proteins wherein the insulin A and B chains are covalently linked.

As used herein an amino acid "modification" refers to a substitution, addition or deletion of an amino acid, or the derivation of an amino acid by the addition and/or removal of chemical groups to/from the amino acid, and includes substitution with or addition of any of the 20 amino acids commonly found in human proteins, as well as atypical or non-naturally occurring amino acids. Commercial sources of atypical amino acids include Sigma-Aldrich (Milwaukee, Wis.), ChemPep Inc. (Miami, Fla.), and Genzyme Pharmaceuticals (Cambridge, Mass.). Atypical amino acids may be purchased from commercial suppliers, synthesized de novo, or chemically modified or derivatized from naturally occurring amino acids.

As used herein an amino acid "substitution" refers to the replacement of one amino acid residue by a different amino acid residue. Throughout the application, all references to a particular amino acid position by letter and number (e.g. position A5) refer to the amino acid at that position of either the A chain (e.g. position A5) or the B chain (e.g. position B5) in the respective native human insulin A chain (SEQ ID NO: 1) or B chain (SEQ ID NO: 2), or the corresponding amino acid position in any analogs thereof. For example, a reference herein to "position B28" absent any further elaboration would mean the corresponding position B27 of the B chain of an insulin analog in which the first amino acid of SEQ ID NO: 2 has been deleted.

As used herein, the term "conservative amino acid substitution" is defined herein as exchanges within one of the following five groups:

I. Small aliphatic, nonpolar or slightly polar residues:
Ala, Ser, Thr, Pro, Gly;
II. Polar, negatively charged residues and their amides:
Asp, Asn, Glu, Gln;
III. Polar, positively charged residues:
His, Arg, Lys; Ornithine (Orn)
IV. Large, aliphatic, nonpolar residues:
Met, Leu, Ile, Val, Cys, Norleucine (Nle), homocysteine
V. Large, aromatic residues:
Phe, Tyr, Trp, acetyl phenylalanine As used herein the general term "polyethylene glycol chain" or "PEG chain", refers to mixtures of condensation polymers of ethylene oxide and water, in a branched or straight chain, represented by the general formula $H(OCH_2CH_2)_nOH$, wherein n is at least 9. Absent any further characterization, the term is intended to include polymers of ethylene glycol with an average total molecular weight selected from the range of 500 to 80,000 Daltons. "Polyethylene glycol chain" or "PEG chain" is used in combination with a numeric suffix to indicate the approximate average molecular weight thereof. For example, PEG-5,000 refers to polyethylene glycol chain having a total molecular weight average of about 5,000 Daltons.

As used herein the term "pegylated" and like terms refers to a compound that has been modified from its native state by linking a polyethylene glycol chain to the compound. A "pegylated polypeptide" is a polypeptide that has a PEG chain covalently bound to the polypeptide.

As used herein a "linker" is a bond, molecule or group of molecules that binds two separate entities to one another. Linkers may provide for optimal spacing of the two entities or may further supply a labile linkage that allows the two entities to be separated from each other. Labile linkages include photocleavable groups, acid-labile moieties, base-labile moieties and enzyme-cleavable groups.

As used herein an "insulin dimer" is a complex comprising two insulin peptides covalently bound to one another via a linker. The term insulin dimer, when used absent any qualifying language, encompasses both insulin homodimers and insulin heterodimers. An insulin homodimer comprises two identical subunits (each comprising an A and B chain), whereas an insulin heterodimer comprises two subunits that differ, although the two subunits are substantially similar to one another.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_n$ alkyl)($C_5$-$C_6$ heteroaryl)" refers to a 5 or 6 membered heteroaryl that is attached to a parent moiety via a one to "n" membered alkyl chain.

The term "$C_3$-$C_n$ cycloalkyl" refers to a non-aromatic, monocyclic or polycyclic ring comprising carbon and hydrogen atoms with the subscript number indicating the number of carbon atoms present. For example the term $C_3$-$C_8$ cycloalkyl represents the compounds cyclopropyl, cyclobutyl, cyclopentyl, cyclohexyl, cycloheptyl, and cyclooctyl.

The term "$C_3$-$C_n$ heterocyclic" refers to a cycloalkyl ring system containing from one to "n−1" heteroatoms wherein the heteroatoms are selected from the group consisting of oxygen, sulfur, and nitrogen. For example the phrase "5-membered heterocycle" or "$C_5$ heterocycle" includes, but is not limited to, 5-membered heterocycles having one hetero atom (e.g. thiophenes, pyrroles, furans); 5-membered heterocycles having two heteroatoms in 1,2 or 1,3 positions (e.g. oxazoles, pyrazoles, imidazoles, thiazoles, purines); 5-membered heterocycles having three heteroatoms (e.g. triazoles, thiadiazoles).

The term "$C_3$-$C_n$ membered ring" as used herein refers to a saturated or unsaturated hydrocarbon ring structure comprising a total of three to "n" number of elements linked to one another to form a ring, wherein the ring elements are selected from the group consisting of C, O, S and N. The term is intended to encompass cycloalkyls, heterocycles, aryls and heteroaryls.

As used herein, the term "halo" refers to one or more members of the group consisting of fluorine, chlorine, bromine, and iodine.

As used herein the term "patient" without further designation is intended to encompass any warm blooded vertebrate domesticated animal (including for example, but not limited to livestock, horses, cats, dogs and other pets) and humans.

EMBODIMENTS

The present disclosure provides insulin prodrug derivatives that are formulated to delay onset of action and enhance the half life of the insulin peptide, thus improving the therapeutic index of the underlying insulin peptide. The insulin prodrug chemistry disclosed herein allows for activation of the prodrug via a non-enzymatic degradation mechanism. The disclosed prodrug chemistry can be chemically conjugated to active site amines to form amides that revert to the parent amine upon diketopiperazine formation and release of the prodrug element. This novel biologically friendly prodrug chemistry spontaneously degrades under physiological conditions (e.g. pH of about 7, at 37° C. in an aqueous environment) and is not reliant on enzymatic degradation. The duration of the prodrug derivative is determined by the selection of the dipeptide prodrug sequence, and thus allows for flexibility in prodrug formulation.

In one embodiment a prodrug is provided having a non-enzymatic activation half time (t½) of between 1-100 hrs under physiological conditions. Physiological conditions as disclosed herein are intended to include a temperature of about 35 to 40° C. and a pH of about 7.0 to about 7.4 and more typically include a pH of 7.2 to 7.4 and a temperature of 36 to 38° C. in an aqueous environment. In one embodiment a dipeptide, capable of undergoing diketopiperazine formation under physiological conditions, is covalently linked through an amide linkage to the insulin peptide.

Advantageously, the rate of cleavage, and thus activation of the prodrug, depends on the structure and stereochemistry of the dipeptide pro-moiety and also on the strength of the nucleophile. The prodrugs disclosed herein will ultimately be chemically converted to structures that can be recognized by the native receptor of the drug, wherein the speed of this chemical conversion will determine the time of onset and duration of in vivo biological action. The prodrug chemistry disclosed in this application relies upon an intramolecular chemical reaction that is not dependent upon additional chemical additives, or enzymes. The speed of conversion is controlled by the chemical nature of the dipeptide substituent and its cleavage under physiological conditions. Since physiological pH and temperature are tightly regulated within a highly defined range, the speed of conversion from prodrug to drug will exhibit high intra and interpatient reproducibility.

As disclosed herein prodrugs are provided wherein the bioactive polypeptides have extended half lives of at least 1 hour, and more typically greater than 20 hours but less than 100 hours, and are converted to the active form at physiological conditions through a non-enzymatic reaction driven by inherent chemical instability. In one embodiment the a non-enzymatic activation t½ time of the prodrug is between 1-100 hrs, and more typically between 12 and 72 hours, and in one embodiment the t½ is between 24-48 hrs as measured by incubating the prodrug in a phosphate buffer solution (e.g., PBS) at 37° C. and pH of 7.2. The half lives of the various prodrugs are calculated by using the formula $t_{1/2}=0.693/k$, where 'k' is the first order rate constant for the degradation of the prodrug. In one embodiment, activation of the prodrug occurs after cleavage of an amide bond linked dipeptide, and formation of a diketopiperazine or diketomorpholine, and the active insulin peptide.

Specific dipeptides composed of natural or synthetic amino acids have been identified that facilitate intramolecular decomposition under physiological conditions to release active insulin peptides. The dipeptide can be linked (via an amide bond) to an amino group present on native insulin, or an amino group introduced into the insulin peptide by modification of the native insulin peptide. In one embodiment the dipeptide structure is selected to resist cleavage by peptidases present in mammalian sera, including for example dipeptidyl peptidase IV (DPP-IV). Accordingly, in one embodiment the rate of cleavage of the dipeptide prodrug element from the bioactive peptide (e.g., insulin peptide (Q)) is not substantially enhanced (e.g., greater than 2×) when the reaction is conducted using physiological conditions in the presence of serum proteases, relative to conducting the reaction in the absence of the proteases. Thus the cleavage half-life of the dipeptide prodrug element from the insulin peptide (in PBS under physiological conditions) is not more than two, three, four or five fold the cleavage half-life of the dipeptide prodrug element from the insulin peptide in a solution comprising a DPP-IV protease. In one embodiment the solution comprising a DPP-IV protease is serum, more particularly mammalian serum, including human serum.

In accordance with one embodiment the dipeptide prodrug element comprises the structure U-O, wherein U is an amino acid or a hydroxyl acid and O is an N-alkylated amino acid. In one embodiment U, O, or the amino acid of the insulin peptide to which U-O is linked is a non-coded amino acid. In one embodiment U and/or O is an amino acid in the D stereoisomer configuration. In some exemplary embodiments, U is an amino acid in the D stereoisomer configuration and O is an amino acid in the L stereoisomer configuration. In some exemplary embodiments, U is an amino acid in the L stereoisomer configuration and O is an amino acid in the D stereoisomer configuration. In some exemplary embodiments, U is an amino acid in the D stereoisomer configuration and O is an amino acid in the D stereoisomer configuration. In one embodiment O is an N-alkylated amino acid but is not proline. In one embodiment the N-alkylated group of amino acid O is a $C_1$-$C_{18}$ alkyl, and in one embodiment N-alkylated group is $C_1$-$C_6$ alkyl. In one embodiment U-O is a dipeptide comprising the structure of Formula I as defined herein.

In one embodiment the dipeptide is linked to the insulin peptide at an amino group selected from the N-terminal amino group of the A or B chain, or the side chain amino group of an amino acid present at an active site of the insulin peptide. In accordance with one embodiment the dipeptide extension is covalently linked to an insulin peptide through the side chain amine of a lysine residue that resides at or near the active site. In one embodiment the dipeptide extension is attached through a synthetic amino acid or a modified amino acid, wherein the synthetic amino acid or modified amino acid exhibits a functional group suitable for covalent attachment of the dipeptide extension (e.g., the aromatic amine of amino-phenylalanine). In accordance with one embodiment the dipeptide is linked to the insulin peptide at an amino group selected from the N-terminal amino group of the A or B chain, or the side chain amino group of an aromatic amine (e.g., a 4-amino-phenylalanine residue) present at position A19, B16 or B25. In one embodiment the U-O dipeptide is bound at position A19 through a 4-amino phenylalanine present at position A19.

The dipeptide prodrug element is designed to spontaneously cleave its amide linkage to the insulin analog under physiological conditions and in the absence of enzymatic activity. In one embodiment the N-terminal amino acid of the dipeptide extension comprises a C-alkylated amino acid (e.g. amino isobutyric acid). In one embodiment the C-terminal amino acid of the dipeptide comprises an N-alkylated amino acid (e.g., proline or N-methyl glycine). In one embodiment the dipeptide comprises the sequence of an N-terminal C-alkylated amino acid followed by an N-alkylated amino acid.

Figure 3:
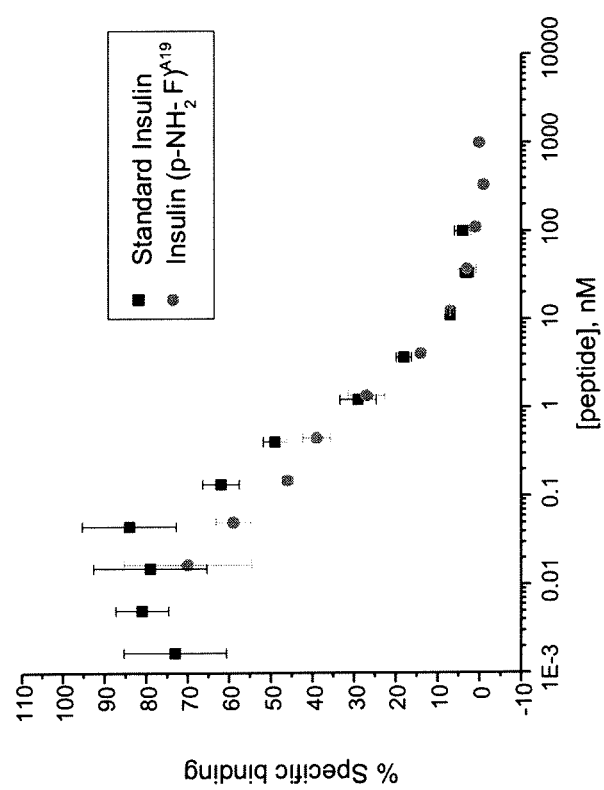
FIG. 3 is a graph comparing relative insulin receptor binding of native insulin and the A19 insulin analog (Insulin(p-$NH_2$—F)$^{19}$). As indicated by the data presented in the graph, the two molecules have similar binding activities.

Applicants have discovered that the selective insertion of a 4-amino phenyl amino acid moiety for the native tyrosine at position 19 of the A chain can be accommodated without loss in potency of the insulin peptide (see FIG. 3). Subsequent chemical amidation of this active site amino group with the dipeptide prodrug moiety disclosed herein dramatically lessens insulin receptor binding activity and thus provides a suitable prodrug of insulin (see FIG. 6, data provided for the IGF1$Y^{16}L^{17}$ (p-NH$_2$—F)$^{A19}$ analog which has been demonstrated to have comparable activity as insulin (p-NH$_2$—F)$^{A19}$, see FIG. 4). Accordingly, in one embodiment the dipeptide prodrug element is linked to the aromatic ring of an A19

4-aminophenylalanine via an amide bond, wherein the C-terminal amino acid of the dipeptide comprises an N-alkylated amino acid and the N-terminal amino acid of the dipeptide is any amino acid.

The dipeptide prodrug moiety can also be attached to additional sites of an insulin peptide to prepare a prodrug or depot analog of insulin. In accordance with one embodiment an insulin prodrug/depot analog is provided comprising an A chain, a B chain, and a dipeptide linked via an amide bond to one or more sites selected from the group consisting of the N-terminal amino group of the A chain or B chain, or the side chain amino group of an internal amino acid including for example, linked to the aromatic amine of a 4-amino-phenylalanine residue present at position A19, B16 or B25. In one embodiment the insulin peptide comprises two dipeptide elements, wherein the dipeptide elements are optionally pegylated, alkylated, acylated or linked to a depot polymer. In one embodiment the dipeptide comprises an N-terminal C-alkylated amino acid followed by an N-alkylated amino acid.

The A chain and B chain comprising the insulin prodrug analog may comprise the native sequence of the respective peptides (i.e., SEQ ID NO: 1 and SEQ ID NO: 2) or may comprise a derivative of SEQ ID NO: 1 and/or SEQ ID NO: 2 wherein the derivative includes modification of the amino acid at position A19, B16 or B25 to a 4-amino phenylalanine and/or one or more amino acid substitutions at positions selected from A5, A8, A9, A10, A14, A15, A17, A18, A19 and A21, B1, B2, B3, B4, B5, B9, B10, B13, B14, B17, B20, B22, B23, B26, B27, B28, B29 and B30 or deletions of any or all of positions B1-4 and B26-30. In one embodiment the dipeptide prodrug element is linked to an N-terminal amino group of the A or B chain, wherein the C-terminal amino acid of the dipeptide prodrug element comprises an N-alkylated amino acid and the N-terminal amino acid of the dipeptide prodrug element is any amino acid, with the proviso that when the C-terminal amino acid of the dipeptide is proline, the N-terminal amino acid of the dipeptide comprises a C-alkylated amino acid.

In one embodiment the dipeptide prodrug element comprises the general structure of Formula I:

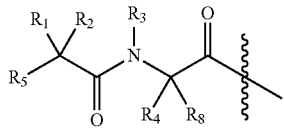

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH, with the proviso that when $R_4$ and $R_3$ together with the atoms to which they are attached form a 4, 5 or 6 member heterocyclic ring, both $R_1$ and $R_2$ are other than H.

In another embodiment the dipeptide prodrug element comprises the general structure:

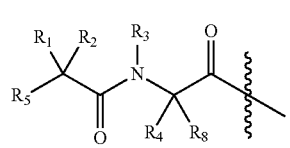

wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, and CH$_2$($C_3$-$C_9$ heteroaryl), or $R_1$ and $R_2$ together with the atoms to which they are attached form a $C_3$-$C_{12}$ cycloalkyl;

$R_3$ is selected from the group consisting of $C_1$-$C_8$ alkyl, ($C_1$-$C_4$ alkyl)OH, ($C_1$-$C_4$ alkyl)NH$_2$, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, $C_1$-$C_8$ alkyl, or $R_6$ and $R_2$ together with the atoms to which they are attached form a 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH and halo, provided that when the dipeptide of Formula I is linked through the N-terminal amine of a peptide and $R_4$ and $R_3$ together with the atoms to which they are attached form a 5 or 6 member heterocyclic ring, both $R_1$ and $R_2$ are not H. In one embodiment either the first amino acid and/or the second amino acid of the dipeptide prodrug element is an amino acid in the D stereoisomer configuration.

In one embodiment the prodrug element of Formula I is provided wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)R$_7$, and CH$_2$($C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring;

$R_7$ is selected from the group consisting of H and OH and $R_8$ is H. In one embodiment $R_3$ is $C_1$-$C_8$ alkyl and $R_4$ is selected from the group consisting of H, $C_1$-$C_6$ alkyl, $CH_2OH$, $(C_0$-$C_4$ alkyl$)(C_6$-$C_{10}$ aryl$)R_7$, and $CH_2(C_5$-$C_9$ heteroaryl) or $R_4$ and $R_3$ together with the atoms to which they are attached form a 5 or 6 member heterocyclic ring. In a further embodiment $R_5$ is $NHR_6$ and $R_8$ is H.

In a further embodiment the prodrug element of Formula I is provided wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, $(C_1$-$C_4$ alkyl)OH, $(C_1$-$C_4$ alkyl)SH, $(C_2$-$C_3$ alkyl)$SCH_3$, $(C_1$-$C_4$ alkyl)$CONH_2$, $(C_1$-$C_4$ alkyl)COOH, $(C_1$-$C_4$ alkyl)$NH_2$, $(C_1$-$C_4$ alkyl)$NHC(NH_2^+)NH_2$, $(C_0$-$C_4$ alkyl)$(C_3$-$C_6$ cycloalkyl), $(C_0$-$C_4$ alkyl)$(C_6$-$C_{10}$ aryl)$R_7$, and $CH_2(C_5$-$C_9$ heteroaryl), or $R_1$ and $R_2$ together with the atoms to which they are attached form a $C_3$-$C_8$ cycloalkyl ring;

$R_3$ is selected from the group consisting of $C_1$-$C_8$ alkyl, $(C_1$-$C_4$ alkyl)OH, $(C_1$-$C_4$ alkyl)SH, $(C_1$-$C_4$ alkyl)$NH_2$, $(C_3$-$C_6)$cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring;

$R_7$ is selected from the group consisting of hydrogen, $C_1$-$C_{18}$ alkyl, $C_2$-$C_{18}$ alkenyl, $(C_0$-$C_4$ alkyl)$CONH_2$, $(C_0$-$C_4$ alkyl)COOH, $(C_0$-$C_4$ alkyl)$NH_2$, $(C_0$-$C_4$ alkyl)OH and halo; and $R_8$ is H, provided that when $R_4$ and $R_3$ together with the atoms to which they are attached form a 5 or 6 member heterocyclic ring, both $R_1$ and $R_2$ are not H. In one embodiment either the first amino acid and/or the second amino acid of the dipeptide prodrug element is a non-coded amino acid and in one embodiment is an amino acid in the D stereoisomer configuration.

In other embodiments the dipeptide prodrug element has the structure of Formula I, wherein $R_1$ and $R_8$ are independently H or $C_1$-$C_8$ alkyl;

$R_2$ and $R_4$ are independently selected from the group consisting of H, $C_1$-$C_8$ alkyl, $C_2$-$C_8$ alkenyl, $(C_1$-$C_4$ alkyl)OH, $(C_1$-$C_4$ alkyl)SH, $(C_2$-$C_3$ alkyl)$SCH_3$, $(C_1$-$C_4$ alkyl)$CONH_2$, $(C_1$-$C_4$ alkyl)COOH, $(C_1$-$C_4$ alkyl)$NH_2$, $(C_1$-$C_4$ alkyl)$NHC(NH_2^+)NH_2$, $(C_0$-$C_4$ alkyl)$(C_3$-$C_6$ cycloalkyl), $(C_0$-$C_4$ alkyl)$(C_2$-$C_5$ heterocyclic), $(C_0$-$C_4$ alkyl)$(C_6$-$C_{10}$ aryl)$R_7$, and $CH_2(C_3$-$C_9$ heteroaryl), or $R_1$ and $R_2$ together with the atoms to which they are attached form a $C_3$-$C_{12}$ cycloalkyl;

$R_3$ is $C_1$-$C_{18}$ alkyl;

$R_5$ is $NHR_6$;

$R_6$ is H or $C_1$-$C_8$ alkyl;

$R_7$ is selected from the group consisting of hydrogen, $C_1$-$C_{18}$ alkyl, $C_2$-$C_{18}$ alkenyl, $(C_0$-$C_4$ alkyl)$CONH_2$, $(C_0$-$C_4$ alkyl)COOH, $(C_0$-$C_4$ alkyl)$NH_2$, $(C_0$-$C_4$ alkyl)OH, and halo and $R_8$ is H.

In a further embodiment the dipeptide prodrug element has the structure of Formula I, wherein $R_1$ and $R_2$ are independently $C_1$-$C_{18}$ alkyl or $(C_0$-$C_4$ alkyl)$(C_6$-$C_{10}$ aryl)$R_7$; or $R_1$ and $R_2$ are linked through $-(CH_2)_p$-, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_{18}$ alkyl, $C_2$-$C_{18}$ alkenyl, $(C_0$-$C_4$ alkyl)$CONH_2$, $(C_0$-$C_4$ alkyl)COOH, $(C_0$-$C_4$ alkyl)$NH_2$, $(C_0$-$C_4$ alkyl)OH, and halo.

In a further embodiment the dipeptide prodrug element has the structure of Formula I, wherein $R_1$ and $R_2$ are independently selected from the group consisting of hydrogen, $C_1$-$C_{18}$ alkyl, $(C_1$-$C_{18}$ alkyl)OH, $(C_1$-$C_4$ alkyl)$NH_2$, and $(C_0$-$C_4$ alkyl)$(C_6$-$C_{10}$ aryl)$R_7$, or $R_1$ and $R_2$ are linked through $(CH_2)_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and $(C_0$-$C_4$ alkyl)$(C_6$-$C_{10}$ aryl)$R_7$;

$R_5$ is $NH_2$; and $R_7$ is selected from the group consisting of H, $C_1$-$C_{18}$ alkyl, $C_2$-$C_{18}$ alkenyl, $(C_0$-$C_4$ alkyl)$CONH_2$, $(C_0$-$C_4$ alkyl)COOH, $(C_0$-$C_4$ alkyl)$NH_2$, $(C_0$-$C_4$ alkyl)OH, and halo, with the proviso that both $R_1$ and $R_2$ are not hydrogen and provided that at least one of $R_4$ or $R_8$ is hydrogen.

In another embodiment the dipeptide prodrug element has the structure of Formula I, wherein $R_1$ and $R_2$ are independently selected from the group consisting of hydrogen, $C_1$-$C_8$ alkyl and $(C_1$-$C_4$ alkyl)$NH_2$, or $R_1$ and $R_2$ are linked through $(CH_2)_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl;

$R_8$ is hydrogen; and $R_5$ is $NH_2$, with the proviso that both $R_1$ and $R_2$ are not hydrogen.

In a further embodiment the dipeptide prodrug element has the structure of Formula I, wherein $R_1$ and $R_2$ are independently selected from the group consisting of hydrogen, $C_1$-$C_8$ alkyl and $(C_1$-$C_4$ alkyl)$NH_2$;

$R_3$ is $C_1$-$C_6$ alkyl;

$R_4$ and $R_8$ are each hydrogen; and $R_5$ is $NH_2$, with the proviso that both $R_1$ and $R_2$ are not hydrogen.

In another embodiment the dipeptide prodrug element has the structure of Formula I, wherein $R_1$ and $R_2$ are independently selected from the group consisting of hydrogen and $C_1$-$C_8$ alkyl, $(C_1$-$C_4$ alkyl)$NH_2$, or $R_1$ and $R_2$ are linked through $(CH_2)_p$, wherein p is 2-9;

$R_3$ is $C_1$-$C_8$ alkyl;

$R_4$ is $(C_0$-$C_4$ alkyl)$(C_6$-$C_{10}$ aryl)$R_7$;

$R_5$ is $NH_2$;

$R_7$ is selected from the group consisting of hydrogen, $C_1$-$C_8$ alkyl and $(C_0$-$C_4$ alkyl)OH; and $R_8$ is hydrogen, with the proviso that both $R_1$ and $R_2$ are not hydrogen.

In another embodiment the dipeptide prodrug element has the structure of Formula I, wherein $R_1$ is selected from the group consisting of hydrogen, $C_1$-$C_8$ alkyl and $(C_0$-$C_4$ alkyl)$(C_6$-$C_{10}$ aryl)$R_7$;

$R_2$ is hydrogen;

$R_3$ is $C_1$-$C_{18}$ alkyl;

$R_4$ and $R_8$ are each hydrogen;

$R_5$ is $NHR_6$ or OH;

R$_6$ is H, C$_1$-C$_8$ alkyl, or R$_6$ and R$_1$ together with the atoms to which they are attached form a 4, 5 or 6 member heterocyclic ring; and R$_7$ is selected from the group consisting of hydrogen, C$_1$-C$_{18}$ alkyl, C$_2$-C$_{18}$ alkenyl, (C$_0$-C$_4$ alkyl)CONH$_2$, (C$_0$-C$_4$ alkyl)COOH, (C$_0$-C$_4$ alkyl)NH$_2$, (C$_0$-C$_4$ alkyl)OH, and halo, with the proviso that, if R$_1$ is alkyl or (C$_0$-C$_4$ alkyl)(C$_6$-C$_{10}$ aryl)R$_7$, then R$_1$ and R$_5$ together with the atoms to which they are attached form a 4-11 heterocyclic ring.

In accordance with one embodiment an insulin prodrug analog is provided comprising an insulin peptide and an amide linked dipeptide. More particularly, the insulin prodrug analog comprises an A chain sequence and a B chain sequence wherein the A chain comprises the sequence Z-GIVEQCCX$_1$SICSLYQLENX$_2$CX$_3$-R$_{13}$ (SEQ ID NO: 3), or an analog thereof comprising a sequence that differs from SEQ ID NO: 3 by 1 to 9, 1 to 5 or 1 to 3 amino acid modifications, selected from positions A5, A8, A9, A10, A14, A15, A17, A18 (relative to the native insulin A chain), and the B chain sequence comprises the sequence of J-X$_{14}$-X$_4$LCGX$_5$X$_6$LVEALX$_7$LVCGERGFX$_8$ (SEQ ID NO: 14), or an analog thereof comprising a sequence that differs from SEQ ID NO: 14 sequence by 1 to 10, 1 to 5 or 1 to 3 amino acid modifications, selected from positions B1, B2, B3, B4, B5, B13, B14, B17, B20, B22, B23, B26, B27, B28, B29 and B30 (relative to the native insulin B chain; i.e., amino acid X$_4$ of SEQ ID NO: 14 corresponds to position B5 in native insulin). Z and J are independently H or a dipeptide comprising the general structure of Formula I:

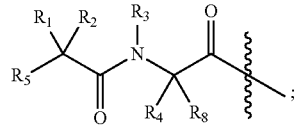

I

X$_{14}$ is either a bond joining the "J" element to the X$_4$LCGX$_5$X$_6$LVEALX$_7$LVCG ERGFX$_8$ (SEQ ID NO: 14) sequence or X$_{14}$ represents a 1 to 4 amino acid sequence selected from the group consisting of a X$_9$VNQ (SEQ ID NO: 21), VNQ, NQ and Q that joins the "J" element to the X$_4$LCGX$_5$X$_6$LVEALX$_7$LVCG ERGFX$_8$ (SEQ ID NO: 14) sequence.

X$_1$ is selected from the group consisting of threonine and histidine;

X$_2$ is an amino acid of the general structure

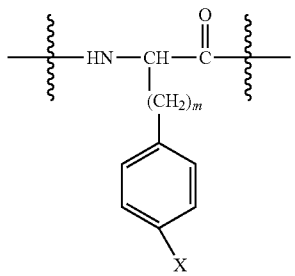

wherein m is an integer selected from 0-3 and X is selected from the group consisting of OH, NH$_2$, NHR$_{10}$ and OCH$_3$, wherein R$_{10}$ is H or a dipeptide comprising the general structure of Formula I:

X$_3$ is selected from the group consisting of asparagine, glycine, alanine, threonine and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_7$ is an amino acid of the general structure

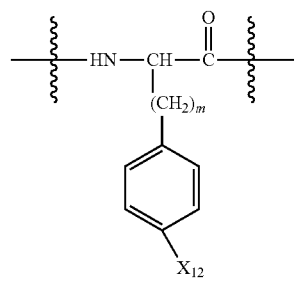

wherein m is an integer selected from 0-3 and X$_{12}$ is selected from the group consisting of OH, NH$_2$, NHR$_{11}$ and OCH$_3$, wherein R$_{11}$ is H or a dipeptide comprising the general structure of Formula I:

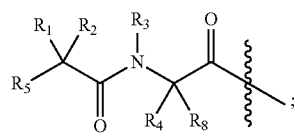

I

X$_8$ is histidine, arginine or an amino acid of the general structure

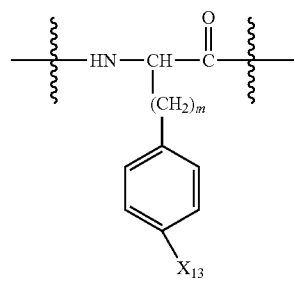

wherein m is an integer selected from 0-3 and X$_{13}$ is selected from the group consisting of H, OH, NH$_2$, NHR$_{12}$ and OCH$_3$, wherein R$_{12}$ is H or a dipeptide comprising the general structure of Formula I:

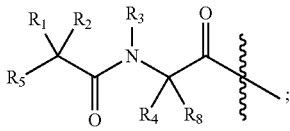

$X_9$ is selected from the group consisting of phenylalanine and desamino-phenylalanine; wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2$$^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl (W)$C_1$-$C_{12}$ alkyl, wherein W is a heteroatom selected from the group consisting of N, S and O, or $R_1$ and $R_2$ together with the atoms to which they are attached form a $C_3$-$C_{12}$ cycloalkyl or aryl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_2$ together with the atoms to which they are attached form a 4, 5 or 6 member heterocyclic ring; and $R_7$ is selected from the group consisting of H and OH; and $R_{13}$ is COOH or CONH$_2$. In one embodiment $X_8$ is histidine, arginine or tyrosine. In another embodiment $X_8$ is an amino acid of the general structure

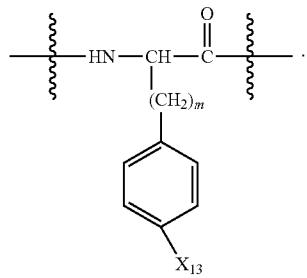

In one embodiment $R_{13}$ is COOH and the carboxy terminal amino acid of the B chain has an amide (CONH$_2$) in place of the natural alpha carbon carboxy group. In one embodiment one or more of X, $X_{12}$, $X_{13}$, J and Z is a dipeptide comprising the general structure of Formula I:

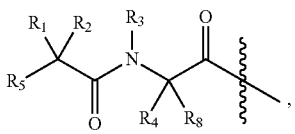

and in one embodiment two of X, $X_{12}$, $X_{13}$, J and Z comprise a dipeptide of the general structure of Formula I:

In accordance with one embodiment at least one of X, $X_{12}$, $X_{13}$, J and Z is a dipeptide comprising the general structure of Formula I:

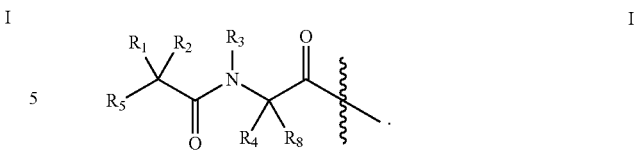

and in one embodiment one and only one of X, $X_{12}$, $X_{13}$, J and Z comprises a dipeptide of the general structure of Formula I:

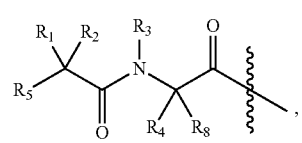

(i.e., only one dipeptide prodrug element is attached to the insulin peptide). Furthermore, when the dipeptide prodrug element is linked to the N-terminus of the A or B chain (i.e., either J or Z comprise the dipeptide) and $R_4$ and $R_3$ together with the atoms to which they are attached form a 4, 5 or 6 member heterocyclic ring, then at least one of $R_1$ and $R_2$ are other than H, and in one embodiment both $R_1$ and $R_2$ are other than H. In one embodiment J and Z are both H, $X_{12}$ is OH, $X_{13}$ is H or OH, and X is NHR$_{10}$ wherein $R_{10}$ a dipeptide comprising the general structure of Formula I. In a further embodiment, the A chain comprises the sequence GIVEQCCX$_1$SICSLYQLENX$_2$CX$_3$-$R_{13}$ (SEQ ID NO: 3), the B chain sequence comprises the sequence of $X_{14}$-X$_4$LCGX$_5$X$_6$LVEALX$_7$LVCGERGFX$_8$ (SEQ ID NO: 14), m is 1, $X_{12}$ is OH, $X_{13}$ is H or OH, X is NHR$_{10}$, wherein $R_{10}$ a dipeptide comprising the general structure of Formula I, $R_{13}$ is COOH and the carboxy terminal amino acid of the B chain has an amide (CONH$_2$) in place of the natural alpha carbon carboxy group, with the remaining designations defined as immediately above.

In one embodiment the dipeptide present at X, $X_{12}$, $X_{13}$, J and Z is a dipeptide comprising the general structure of Formula I:

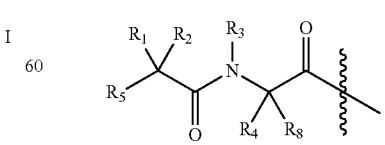

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)$NHC(NH_2^+)NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)$NH_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is $NHR_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo provided that when $R_4$ and $R_3$ together with the atoms to which they are attached form a 5 or 6 member heterocyclic ring, both $R_1$ and $R_2$ are not H. Those skilled in the art appreciate that when $W_1$ is N, under physiological conditions the nitrogen atom is also linked to H. In one embodiment when J or Z comprise the dipeptide of Formula I, and $R_4$ and $R_3$ together with the atoms to which they are attached form a 4, 5 or 6 member heterocyclic ring, then both $R_1$ and $R_2$ are not hydrogen.

In one embodiment $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl) OH, ($C_1$-$C_4$ alkyl)SH, ($C_2$-$C_3$ alkyl)$SCH_3$, ($C_1$-$C_4$ alkyl) $CONH_2$, ($C_1$-$C_4$ alkyl)COOH, ($C_1$-$C_4$ alkyl)$NH_2$, ($C_1$-$C_4$ alkyl)$NHC(NH_2^+)NH_2$, ($C_0$-$C_4$ alkyl)($C_3$-$C_6$ cycloalkyl), ($C_0$-$C_4$ alkyl)($C_6$-$C_{10}$ aryl)$R_7$, and $CH_2$($C_5$-$C_9$ heteroaryl);

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)$NH_2$, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring;

$R_7$ is selected from the group consisting of H and OH and $R_8$ is H. In accordance with another embodiment, m is 1, $R_8$ is H, $R_3$ is $C_1$-$C_6$ alkyl and $R_4$ is selected from the group consisting of H, $C_1$-$C_4$ alkyl, ($C_3$-$C_6$)cycloalkyl, ($C_1$-$C_4$ alkyl)OH, ($C_1$-$C_4$ alkyl)SH and ($C_0$-$C_4$ alkyl)($C_6$ aryl)$R_7$, or $R_3$ and $R_4$ together with the atoms to which they are attached form a 5 member heterocyclic ring. In one embodiment, m is 1, $R_8$ is H, $R_3$ is $C_1$-$C_6$ alkyl and $R_4$ is selected from the group consisting of H, $C_1$-$C_4$ alkyl or $R_3$ and $R_4$ together with the atoms to which they are attached form a 5 member heterocyclic ring. In a further embodiment $X_9$ is phenylalanine and a single dipeptide extension is linked to the insulin peptide through an amide bond to the N-terminus of the A chain or the B chain. In an alternative embodiment the insulin peptide comprises a 4 amino phenylalanine substitution at position 19 of the A chain and a single dipeptide extension is linked to the insulin peptide through an amide bond formed at the aromatic amine of the 4 amino phenylalanine. In one embodiment insulin analogs disclosed herein comprise a C-terminal amide or ester in place of a C-terminal carboxylate on the A chain and/or B chain.

In accordance with one embodiment the dipeptide of Formula I is further modified to comprise a large polymer that interferes with the insulin analog's ability to interact with the insulin or IGF-1 receptor. Subsequent cleavage of the dipeptide releases the insulin analog from the dipeptide complex wherein the released insulin analog is fully active. In accordance with one embodiment J comprises the dipeptide of Formula I, wherein the dipeptide of Formula I is further modified to comprises a large polymer that interferes with the bound insulin analog's ability to interact with the insulin or IGF-1 receptor. In accordance with one embodiment one of X, $X_{12}$, $X_{13}$, J and Z comprises a dipeptide of the general structure of Formula I:

I

, wherein the dipeptide of Formula I is pegylated, alkylated or acylated. In one embodiment either J, Z or X comprises an acylated or pegylated dipeptide of Formula I, and in one embodiment J comprises an acylated or pegylated dipeptide of Formula I.

In one embodiment, the dipeptide prodrug element is covalently bound to the insulin peptide via an amide linkage at the N-terminus of the A chain or the B chain, or attached to an amine bearing side chain of an internal amino acid, wherein the dipeptide further comprises a depot polymer linked to dipeptide. In one embodiment a native amino acid of the insulin peptide is substituted with an amino acid suitable for forming an amide bond with the dipeptide of Formula I. In one embodiment a depot bearing dipeptide is linked at a position selected from A14, A19, B16, B28 and B29. In one embodiment two or more depot polymers are linked to a single dipeptide element. The depot polymer is selected to be biocompatible and of sufficient size that the insulin peptide modified by covalent attachment of the dipeptide remains sequestered at an injection site and/or incapable of interacting with its corresponding receptor upon administration to a patient. Subsequent cleavage of the dipeptide releases the insulin peptide to interact with its intended target.

In accordance with one embodiment the depot polymer is selected from biocompatible polymers known to those skilled in the art. The depot polymers typically have a size selected from a range of about 20,000 to 120,000 Daltons. In one embodiment the depot polymer has a size selected from a range of about 40,000 to 100,000 or about 40,000 to 80,000 Daltons. In one embodiment the depot polymer has a size of about 40,000, 50,000, 60,000, 70,000 or 80,000 Daltons. Suitable depot polymers include but are not limited to dextrans, polylactides, polyglycolides, caprolactone-based polymers, poly(caprolactone), polyanhydrides, polyamines, polyesteramides, polyorthoesters, polydioxanones, polyacetals, polyketals, polycarbonates, polyphosphoesters, polyesters, polybutylene terephthalate, polyorthocarbonates, polyphosphazenes, succinates, poly(malic acid), poly(amino acids), polyvinylpyrrolidone, polyethylene glycol, polyhydroxycellulose, polysaccharides, chitin, chitosan, hyaluronic acid, and copolymers, terpolymers and mixtures thereof, and biodegradable polymers and their copolymers including caprolactone-based polymers, polycaprolactones and copolymers which include polybutylene terephthalate. In one embodiment the depot polymer is selected from the group consisting of polyethylene glycol, dextran, polylactic acid, polyglycolic acid and a copolymer of lactic acid and glycolic acid, and in one specific embodiment the depot polymer is polyethylene glycol. In one embodiment the depot polymer is polyethylene glycol and the combined molecular weight of depot polymer(s) linked to the dipeptide element is about 40,000 to 80,000 Daltons.

In accordance with one embodiment the dipeptide of Formula I further comprises a polyethylene oxide, alkyl or acyl group. In one embodiment one or more polyethylene oxide chains are linked to the dipeptide of Formula I wherein the combined molecular weight of the polyethylene oxide chains ranges from about 20,000 to about 80,000 Daltons, or 40,000 to 80,000 Daltons or 40,000 to 60,000 Daltons. In one embodiment the polyethylene oxide is polyethylene glycol. In one embodiment at least one polyethylene glycol chain having a molecular weight of about 40,000 Daltons or about 20,000 Daltons is linked to the dipeptide of Formula either directly or through a linker/spacer. In another embodiment the dipeptide of Formula I is acylated with an acyl group of sufficient size to bind serum albumin, and thus inactivate the insulin analog upon administration. The acyl group can be linear or branched, and in one embodiment is a C16 to C30 fatty acid. For example, the acyl group can be any of a C16 fatty acid, C18 fatty acid, C20 fatty acid, C22 fatty acid, C24 fatty acid, C26 fatty acid, C28 fatty acid, or a C30 fatty acid. In one embodiment, the acyl group is a C16 to C20 fatty acid, e.g., a C18 fatty acid or a C20 fatty acid.

In accordance with one embodiment an insulin prodrug analog is provided comprising an A chain sequence and a B chain sequence wherein the A chain comprises the sequence GIVEQCCX$_1$SICSLYQLENX$_2$CX$_3$-R$_{13}$ (SEQ ID NO: 3), and the B chain sequence comprises the sequence of X$_{14}$-X$_4$LCGX$_5$X$_6$LVEALX$_7$LVCGERGFX$_8$ (SEQ ID NO: 14), wherein X$_{14}$ is selected from the group consisting of an N-terminal amine, X$_9$VNQ (SEQ ID NO: 21), VNQ, NQ and Q that joins the "J" element to the X$_4$LCGX$_5$X$_6$LVEALX$_7$LVCG ERGFX$_8$-R$_{14}$ (SEQ ID NO: 14) sequence.

X$_1$ is selected from the group consisting of threonine and histidine;

X$_2$ is an amino acid of the general structure

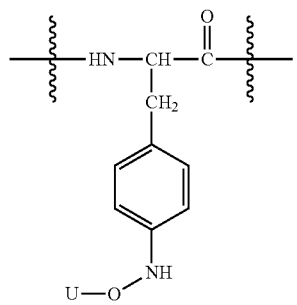

wherein U is an amino acid or a hydroxyl acid and O is an N-alkylated amino acid linked through an amide bond;

X$_3$ is selected from the group consisting of asparagine, ornithine, glycine, alanine, threonine and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_7$ is an amino acid of the general structure

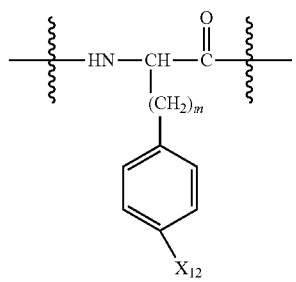

wherein m is an integer selected from 0-3 and X$_{12}$ is selected from the group consisting of OH, NH$_2$ and OCH$_3$;

X$_8$ is an amino acid of the general structure

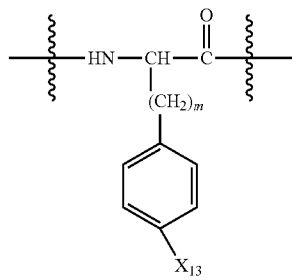

wherein m is an integer selected from 0-3 and X$_{13}$ is selected from the group consisting of H, OH, NH$_2$ and OCH$_3$;

X$_9$ is selected from the group consisting of phenylalanine and desamino-phenylalanine; and R$_{13}$ and R$_{14}$ are independently COOH or CONH$_2$. In one embodiment, X$_7$ and X$_8$ are both tyrosine, R$_{13}$ is COOH and the carboxy terminal amino acid of the B chain has an amide (CONH$_2$) in place of the natural alpha carbon carboxy group.

In accordance with one embodiment a compound comprising the sequence Z-GIVEQCCX$_1$SICSLYQLENX$_2$CX$_3$ (SEQ ID NO: 3), or an analog thereof comprising a sequence that differs from SEQ ID NO: 3 by 1 to 3 amino acid modifications, selected from positions A5, A8, A9, A10, A14, A15, A17, A18 (relative to the native insulin A chain sequence) is provided. In this embodiment X$_1$ is selected from the group consisting of threonine and histidine;

$X_2$ is an amino acid of the general structure

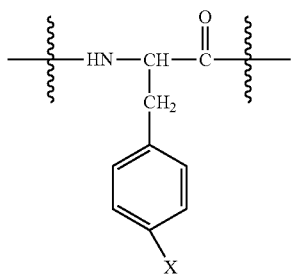

wherein X is selected from the group consisting of OH, $NH_2$, $NHR_{10}$ and $OCH_3$, further wherein $R_{10}$ and Z are independently H or a dipeptide of the structure U-O, wherein U is an amino acid or a hydroxyl acid and O is an N-alkylated amino acid, wherein O is linked to the peptide of SEQ ID NO: 3 through formation of an amide bond, with the proviso that $R_{10}$ and Z are not the same and that U, O or the amino acid of SEQ ID NO: 3 to which U-O is linked is a non-coded amino acid. In one embodiment the chemical cleavage of the dipeptide from SEQ ID NO: 3 is at least about 90% complete within about 1 to about 720 hours in PBS under physiological conditions. In another embodiment the chemical cleavage half-life ($t_{1/2}$) of U-O from SEQ ID NO: 3 is at least about 1 hour to about 1 week in PBS under physiological conditions. The compound in one embodiment further comprises an insulin B chain linked to the A chain of SEQ ID NO: 3 either through intermolecular disulfide linkages or as a recombinant single chain polypeptide.

Selection of the substituents on the dipeptide element and the attachment site of the dipeptide prodrug element can impact the rate of chemical cleavage of the dipeptide prodrug element from the insulin peptide. In one embodiment an insulin prodrug is provided comprising an A chain sequence and a B chain sequence, wherein the A chain comprises the sequence GIVEQCCX$_1$SICSLYQLENX$_2$CX$_3$ (SEQ ID NO: 3) and the B chain sequence comprises the sequence of X$_{14}$-X$_4$LCGX$_5$X$_6$LVEALYLVCGERGFF (SEQ ID NO: 4) wherein $X_1$ is selected from the group consisting of threonine and histidine;

$X_2$ is an amino acid of the general structure

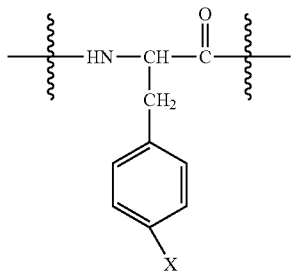

wherein X is selected from the group consisting of OH, $NH_2$, and $OCH_3$;

$X_3$ is selected from the group consisting of asparagine, glycine, alanine, threonine and serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid; and $X_{14}$ is selected from the group consisting of a bond, $X_9$VNQ (SEQ ID NO: 21), VNQ, NQ and Q, and $X_9$ is selected from the group consisting of phenylalanine and desamino-phenylalanine, further wherein a dipeptide prodrug element comprises the structure:

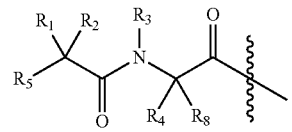

I is linked to the alpha amino group of the N-terminal amino acid of the peptide of SEQ ID NO: 3 or SEQ ID NO: 4 with the proviso that when $R_4$ and $R_3$ together with the atoms to which they are attached form a 4, 5 or 6 member heterocyclic ring, then both $R_1$ and $R_2$ are not hydrogen. In this embodiment, compounds having a $t_{1/2}$ of about 1 hour in PBS under physiological conditions are provided wherein $R_1$ and $R_2$ are independently $C_1$-$C_{18}$ alkyl or aryl; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen; and $R_5$ is an amine.

In other embodiments, prodrugs having the prodrug element linked at the N-terminus and having a $t_{1/2}$ of, e.g., about 1 hour comprise a dipeptide prodrug element with the structure:

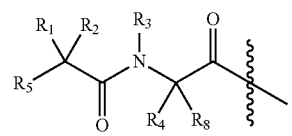

wherein $R_1$ and $R_2$ are independently $C_1$-$C_{18}$ alkyl or $(C_0$-$C_4$ alkyl$)(C_6$-$C_{10}$ aryl$)R_7$; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_{18}$ alkyl, $C_2$-$C_{18}$ alkenyl, $(C_0$-$C_4$ alkyl$)CONH_2$, $(C_0$-$C_4$ alkyl$)COOH$, $(C_0$-$C_4$ alkyl$)NH_2$, $(C_0$-$C_4$ alkyl$)OH$, and halo.

Alternatively, an insulin prodrug is provided comprising an A chain sequence of GIVEQCCX$_1$SICSLYQLENX$_2$CX$_3$ (SEQ ID NO: 3) and a B chain sequence of X$_{14}$-X$_4$LCGX$_5$X$_6$LVEALX$_7$LVCGERGFX$_8$ (SEQ ID NO: 14) wherein the dipeptide prodrug element is linked to the alpha amino group of the N-terminal amino acid of the peptide of SEQ ID NO: 3 or SEQ ID NO: 14 and exhibits a $t_{1/2}$ between about 6 to about 24 hours in PBS under physiological conditions. In one embodiment such compounds comprise a prodrug element of Formula I, wherein $R_1$ and $R_2$ are independently selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and aryl; and $R_5$ is an amine, with the proviso that both $R_1$ and $R_2$ are not hydrogen and provided that one of $R_4$ or $R_8$ is hydrogen.

In a further embodiment an insulin prodrug is provided comprising an A chain sequence of GIVEQCCX$_1$SICSLYQLENX$_2$CX$_3$ (SEQ ID NO: 3) and a B chain sequence of X$_{14}$-X$_4$LCGX$_5$X$_6$LVEALX$_7$LVCGERGFX$_8$ (SEQ ID NO: 14) wherein the dipeptide prodrug element is linked to the alpha amino group of the N-terminal amino acid of the peptide of SEQ ID NO: 3 or SEQ ID NO: 14 and exhibits a $t_{1/2}$ of about 72 to about 168 hours in PBS under physiological conditions. In one embodiment such compounds comprise a prodrug element of Formula I, wherein $R_1$ is selected from the group consisting of hydrogen, $C_1$-$C_8$ alkyl and aryl;

$R_2$ is H;

$R_3$ is $C_1$-$C_{18}$ alkyl;

$R_4$ and $R_8$ are each hydrogen; and $R_5$ is an amine or N-substituted amine or a hydroxyl;

with the proviso that, if $R_1$ is alkyl or aryl, then $R_1$ and $R_5$ together with the atoms to which they are attached form a 4-11 heterocyclic ring.

In one embodiment, prodrugs having the dipeptide prodrug element linked to the N-terminal alpha amino acid of the insulin A or B chain peptide and having a $t_{1/2}$, e.g., between about 12 to about 72 hours, or in one embodiment between about 12 to about 48 hours, comprise a dipeptide prodrug element with the structure:

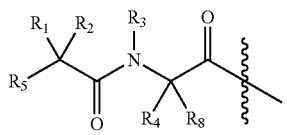

I wherein $R_1$ and $R_2$ are independently selected from the group consisting of hydrogen, $C_1$-$C_{18}$ alkyl, ($C_1$-$C_{18}$ alkyl)OH, ($C_1$-$C_4$ alkyl)NH$_2$, and ($C_0$-$C_4$ alkyl)($C_6$-$C_{10}$ aryl)$R_7$, or $R_1$ and $R_2$ are linked through (CH$_2$)$_p$, wherein p is 2-9;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_8$ alkyl and ($C_0$-$C_4$ alkyl)($C_6$-$C_{10}$ aryl)$R_7$;

$R_5$ is NH$_2$; and $R_7$ is selected from the group consisting of H, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo; with the proviso that both $R_1$ and $R_2$ are not hydrogen and provided that at least one of $R_4$ or $R_8$ is hydrogen.

In one embodiment, prodrugs having the dipeptide prodrug element linked to the N-terminal amino acid of the insulin A or B chain peptide and having a $t_{1/2}$, e.g., between about 12 to about 72 hours, or in one embodiment between about 12 to about 48 hours, comprise a dipeptide prodrug element with the structure:

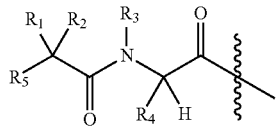

I wherein $R_1$ and $R_2$ are independently selected from the group consisting of hydrogen, $C_1$-$C_8$ alkyl and ($C_1$-$C_4$ alkyl)NH$_2$, or $R_1$ and $R_2$ are linked through (CH$_2$)$_p$, wherein p is 2-9;

$R_3$ is $C_1$-$C_8$ alkyl or $R_3$ and $R_4$ together with the atoms to which they are attached form a 4-6 heterocyclic ring;

$R_4$ is selected from the group consisting of hydrogen and $C_1$-$C_8$ alkyl; and $R_5$ is NH$_2$. with the proviso that both $R_1$ and $R_2$ are not hydrogen.

In other embodiments, prodrugs having the dipeptide prodrug element linked to the N-terminal amino acid of the insulin A or B chain peptide and having a $t_{1/2}$, e.g., between about 12 to about 72 hours, or in one embodiment between about 12 to about 48 hours, comprise a dipeptide prodrug element with the structure:

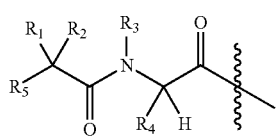

I wherein $R_1$ and $R_2$ are independently selected from the group consisting of hydrogen, $C_1$-$C_8$ alkyl and ($C_1$-$C_4$ alkyl)NH$_2$;

$R_3$ is $C_1$-$C_6$ alkyl;

$R_4$ is hydrogen; and $R_5$ is NH$_2$. with the proviso that both $R_1$ and $R_2$ are not hydrogen.

In one embodiment, prodrugs having the dipeptide prodrug element linked to the N-terminal amino acid of the insulin A or B chain peptide and having a $t_{1/2}$, e.g., between about 12 to about 72 hours, or in one embodiment between about 12 to about 48 hours, comprise a dipeptide prodrug element with the structure:

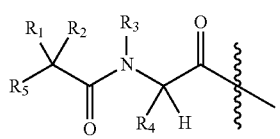

I wherein $R_1$ and $R_2$ are independently selected from the group consisting of hydrogen and $C_1$-$C_8$ alkyl, ($C_1$-$C_4$ alkyl)NH$_2$, or $R_1$ and $R_2$ are linked through (CH$_2$)$_p$, wherein p is 2-9;

$R_3$ is $C_1$-$C_8$ alkyl;

$R_4$ is ($C_0$-$C_4$ alkyl)($C_6$-$C_{10}$ aryl)$R_7$;

$R_5$ is NH$_2$; and $R_7$ is selected from the group consisting of hydrogen, $C_1$-$C_8$ alkyl and ($C_0$-$C_4$ alkyl)OH. with the proviso that both $R_1$ and $R_2$ are not hydrogen.

In addition a prodrug having the dipeptide prodrug element linked to the N-terminal alpha amino acid of the insulin A or B chain peptide and having a $t_{1/2}$, e.g., of about 72 to about 168 hours is provided wherein the dipeptide prodrug element has the structure:

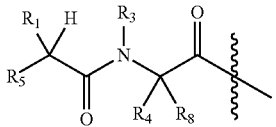

wherein $R_1$ is selected from the group consisting of hydrogen, $C_1$-$C_8$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is $NHR_6$ or OH;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo. with the proviso that, if $R_1$ is alkyl or ($C_0$-$C_4$ alkyl)($C_6$-$C_{10}$ aryl)$R_7$, then $R_1$ and $R_5$ together with the atoms to which they are attached form a 4-11 heterocyclic ring.

In one embodiment the dipeptide prodrug element is linked to a side chain amine of an internal amino acid of the insulin peptide. In this embodiment prodrugs having a $t_{1/2}$, e.g., of about 1 hour have the structure:

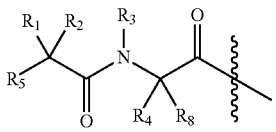

wherein $R_1$ and $R_2$ are independently $C_1$-$C_8$ alkyl or ($C_0$-$C_4$ alkyl)($C_6$-$C_{10}$ aryl)$R_7$; or $R_1$ and $R_2$ are linked through —$(CH_2)_p$—, wherein p is 2-9;

$R_3$ is $C_1$-$C_{18}$ alkyl;

$R_4$ and $R_8$ are each hydrogen;

$R_5$ is $NH_2$; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

Furthermore, prodrugs having a $t_{1/2}$, e.g., between about 6 to about 24 hours and having the dipeptide prodrug element linked to an internal amino acid side chain comprise a dipeptide prodrug element with the structure:

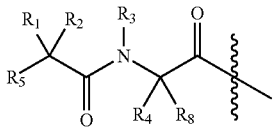

wherein $R_1$ and $R_2$ are independently selected from the group consisting of hydrogen, $C_1$-$C_8$ alkyl, and ($C_0$-$C_4$ alkyl)($C_6$-$C_{10}$ aryl)$R_7$, or $R_1$ and $R_2$ are linked through —$(CH_2)_p$—, wherein p is 2-9;

$R_3$ is $C_1$-$C_8$ alkyl or $R_3$ and $R_4$ together with the atoms to which they are attached form a 4-12 heterocyclic ring;

$R_4$ and $R_8$ are independently hydrogen, $C_1$-$C_{18}$ alkyl or ($C_0$-$C_4$ alkyl)($C_6$-$C_{10}$ aryl)$R_7$;

$R_5$ is $NHR_6$;

$R_6$ is H or $C_1$-$C_8$ alkyl, or $R_6$ and $R_2$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo, with the proviso that both $R_1$ and $R_2$ are not hydrogen and provided that at least one of $R_4$ or $R_8$ is hydrogen.

In addition a prodrug having a $t_{1/2}$, e.g., of about 72 to about 168 hours and having the dipeptide prodrug element linked to an internal amino acid side chain of the insulin peptide is provided wherein the dipeptide prodrug element has the structure:

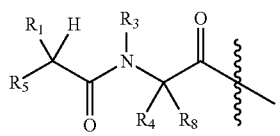

wherein $R_1$ is selected from the group consisting of hydrogen, $C_1$-$C_{18}$ alkyl and ($C_0$-$C_4$ alkyl)($C_6$-$C_{10}$ aryl)$R_7$;

$R_3$ is $C_1$-$C_{18}$ alkyl;

$R_4$ and $R_8$ are each hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl) COOH, ($C_0$-$C_4$ alkyl)$NH_2$, ($C_0$-$C_4$ alkyl)OH, and halo; with the proviso that, if $R_1$ and $R_2$ are both independently an alkyl or ($C_0$-$C_4$ alkyl)($C_6$-$C_{10}$ aryl)$R_7$, either $R_1$ or $R_2$ is linked through $(CH_2)_p$ to $R_5$, wherein p is 2-9.

In one embodiment the dipeptide prodrug element is linked to a side chain amine of an internal amino acid of the insulin peptide wherein the internal amino acid comprises the structure of Formula IV:

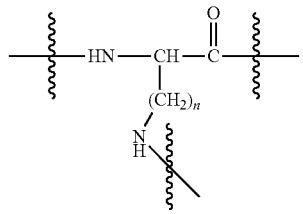

wherein n is an integer selected from 1 to 4. In one embodiment n is 3 or 4 and in one embodiment the internal amino acid is lysine. In one embodiment the dipeptide prodrug element is linked to a primary amine on a side chain of an amino acid located at position 28, or 29 of the B-chain of the insulin peptide.

In one embodiment an insulin prodrug is provided comprising an A chain sequence and a B chain sequence, wherein the A chain comprises the sequence GIVEQCCX$_1$SICSLYQLENX$_2$CX$_3$ (SEQ ID NO: 3) and the B chain sequence comprises the sequence of X$_{14}$-X$_4$LCGX$_5$X$_6$LVEALX$_7$LVCGERGFX$_8$ (SEQ ID NO: 14) wherein X$_1$ is selected from the group consisting of threonine and histidine;

X$_2$ is an amino acid of the general structure

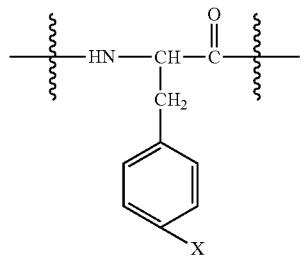

wherein X is selected from the group consisting of OH, NH$_2$, NHR$_{10}$ and OCH$_3$, wherein R$_{10}$ is H or a dipeptide comprising the general structure:

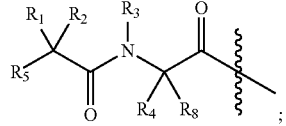

wherein

R$_1$ and R$_2$ are independently selected from the group consisting of hydrogen, C$_1$-C$_8$ alkyl, and (C$_0$-C$_4$ alkyl)(C$_6$-C$_{10}$ aryl)R$_7$, or R$_1$ and R$_2$ are linked through —(CH$_2$)$_p$—, wherein p is 2-9;

R$_3$ is C$_1$-C$_{18}$ alkyl or R$_3$ and R$_4$ together with the atoms to which they are attached form a 4-12 heterocyclic ring;

R$_4$ and R$_8$ are independently hydrogen, C$_1$-C$_{18}$ alkyl or (C$_0$-C$_1$ alkyl)(C$_6$-C$_{10}$ aryl)R$_7$;

R$_5$ is NHR$_6$;

R$_6$ is H or C$_1$-C$_8$ alkyl, or R$_6$ and R$_2$ together with the atoms to which they are attached form a 4, 5 or 6 member heterocyclic ring; and R$_7$ is selected from the group consisting of hydrogen, C$_1$-C$_{18}$ alkyl, C$_2$-C$_{18}$ alkenyl, (C$_0$-C$_4$ alkyl)CONH$_2$, (C$_0$-C$_4$ alkyl)COOH, (C$_0$-C$_4$ alkyl)NH$_2$, (C$_0$-C$_4$ alkyl)OH, and halo;

X$_3$ is selected from the group consisting of asparagine, glycine, alanine, threonine and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_7$ is an amino acid of the general structure

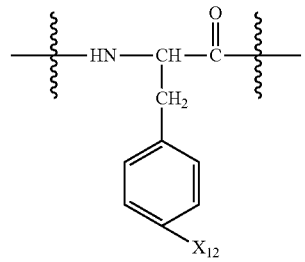

wherein X$_{12}$ is selected from the group consisting of OH, NH$_2$, NHR$_{11}$ and OCH$_3$, wherein R$_{11}$ is H or a dipeptide comprising the general structure:

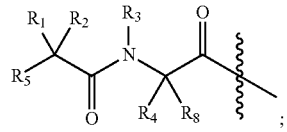

X$_8$ is an amino acid of the general structure

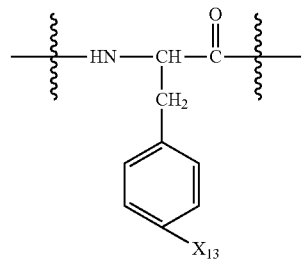

wherein X$_{13}$ is selected from the group consisting of H, OH, NH$_2$, NHR$_{12}$ and OCH$_3$, wherein R$_{12}$ is H or a dipeptide comprising the general structure:

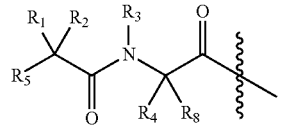

X$_{14}$ is selected from the group consisting of a Hydrogen (forming an N-terminal amine), X$_9$VNQ (SEQ ID NO: 21), VNQ, NQ and Q, and X$_9$ is selected from the group consisting of phenylalanine and desamino-phenylalanine, with the proviso that one and only one of R$_{10}$, R$_{11}$ and R$_{12}$ is a dipeptide comprising the general structure:

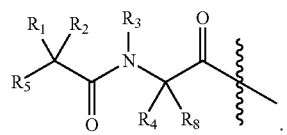

In accordance with one embodiment wherein the dipeptide prodrug element is linked to an amino substituent of an aryl group of an aromatic amino acid, prodrug formulations can be provided having the desired time of activation. For example, an insulin prodrug comprising the structure of Formula III:

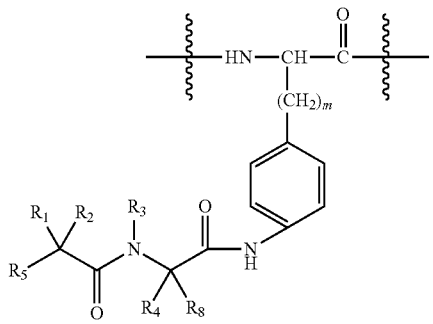

wherein m is an integer from 0 to 3 and having a t1/2 of about 1 hour in PBS under physiological conditions is provided. In one embodiment where an insulin prodrug comprises the structure of formula III and exhibits such a half life, $R_1$ and $R_2$ are independently $C_1$-$C_{18}$ alkyl or aryl;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and aryl; and $R_5$ is an amine or a hydroxyl. In one embodiment m is 1.

In one embodiment, the dipeptide prodrug element is linked to the insulin peptide via an amine present on an aryl group of an aromatic amino acid of the insulin peptide, wherein prodrugs having a $t_{1/2}$, e.g., of about 1 hour have a dipeptide structure of:

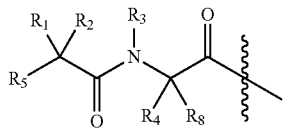

wherein $R_1$ and $R_2$ are independently $C_1$-$C_{18}$ alkyl or ($C_0$-$C_4$ alkyl)($C_6$-$C_{10}$ aryl)$R_7$;

$R_3$ is $C_1$-$C_{18}$ alkyl or $R_3$ and $R_4$ together with the atoms to which they are attached form a 4-12 heterocyclic ring;

$R_4$ and $R_8$ are independently selected from the group consisting of hydrogen, $C_1$-$C_{18}$ alkyl and ($C_0$-$C_4$ alkyl)($C_6$-$C_{10}$ aryl)$R_7$;

$R_5$ is $NH_2$ or OH; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In another embodiment an insulin prodrug comprising the structure of Formula III, wherein m is an integer from 0 to 3 and has a t1/2 of about 6 to about 24 hours in PBS under physiological conditions, is provided. In one embodiment where an insulin prodrug comprises the structure of Formula III and exhibits such a half life, $R_1$ and $R_2$ are independently selected from the group consisting of hydrogen, $C_1$-$C_{18}$ alkyl and aryl, or $R_1$ and $R_2$ are linked through —$(CH_2)_p$—, wherein p is 2-9;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and aryl; and $R_5$ is an amine or N-substituted amine. In one embodiment m is 1.

In one embodiment, prodrugs having the dipeptide prodrug element linked via an amine present on an aryl group of an aromatic amino acid and having a $t_{1/2}$, e.g., of about 6 to about 24 hours are provided wherein the dipeptide comprises a structure of:

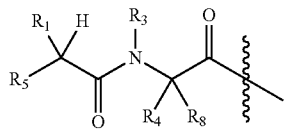

wherein $R_1$ is selected from the group consisting of hydrogen, $C_1$-$C_{18}$ alkyl, ($C_1$-$C_{18}$ alkyl)OH, ($C_1$-$C_4$ alkyl)$NH_2$, and ($C_0$-$C_4$ alkyl)($C_6$-$C_{10}$ aryl)$R_7$;

$R_3$ is $C_1$-$C_{18}$ alkyl or $R_3$ and $R_4$ together with the atoms to which they are attached form a 4-6 heterocyclic ring;

$R_4$ and $R_8$ are independently selected from the group consisting of hydrogen, $C_1$-$C_{18}$ alkyl and ($C_0$-$C_4$ alkyl)($C_6$-$C_{10}$ aryl)$R_7$;

$R_5$ is $NHR_6$;

$R_6$ is H, $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)$CONH_2$, ($C_0$-$C_4$ alkyl)COOH, ($C_0$-$C_4$ alkyl)$NH_2$, ($C_0$-$C_4$ alkyl)OH, and halo.

In another embodiment an insulin prodrug comprising the structure of Formula III, wherein m is an integer from 0 to 3 and has a t1/2 of about 72 to about 168 hours in PBS under physiological conditions, is provided. In one embodiment where an insulin prodrug comprises the structure of formula III and exhibits such a half life, $R_1$ and $R_2$ are independently selected from the group consisting of hydrogen, $C_1$-$C_8$ alkyl and aryl;

$R_3$ is $C_1$-$C_{18}$ alkyl or $R_3$ and $R_4$ together with the atoms to which they are attached form a 4-6 heterocyclic ring;

$R_4$ and $R_8$ are each hydrogen; and $R_5$ is selected from the group consisting of amine, N-substituted amine and hydroxyl. In one embodiment m is 1.

In one embodiment, prodrugs having the dipeptide prodrug element linked via an aromatic amino acid and having a $t_{1/2}$, e.g., of about 72 to about 168 hours are provided wherein the dipeptide comprises a structure of:

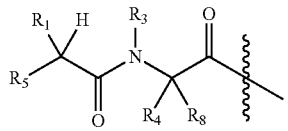

wherein $R_1$ is selected from the group consisting of hydrogen, $C_1$-$C_8$ alkyl, ($C_1$-$C_4$ alkyl)COOH, and ($C_0$-$C_4$ alkyl)($C_6$-$C_{10}$ aryl)$R_7$, or $R_1$ and $R_5$ together with the atoms to which they are attached form a 4-11 heterocyclic ring;

$R_3$ is $C_1$-$C_{18}$ alkyl or $R_3$ and $R_4$ together with the atoms to which they are attached form a 4-6 heterocyclic ring;

$R_4$ is hydrogen or forms a 4-6 heterocyclic ring with $R_3$;

$R_8$ is hydrogen;

$R_5$ is $NHR_6$ or OH;

$R_6$ is H or $C_1$-$C_8$ alkyl, or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In one embodiment the insulin prodrug analog comprises an A chain sequence of GIVEQCCX$_1$SICSLYQLENX$_2$CX$_3$-R$_{13}$ (SEQ ID NO: 3) and a B chain sequence of X$_{14}$-X$_4$LCGX$_5$X$_6$LVEALX$_7$LVCGERGFX$_8$ (SEQ ID NO: 14) wherein $X_1$ is selected from the group consisting of threonine, histidine, arginine and lysine;

$X_2$ is an amino acid of the general structure

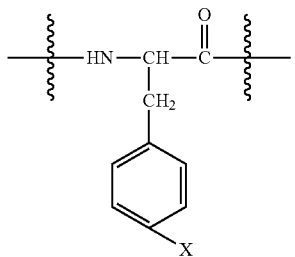

wherein X is selected from the group consisting of OH, NH$_2$, and OCH$_3$;

$X_3$ is asparagine, glycine, alanine, threonine, or serine.

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is tyrosine;

$X_8$ is tyrosine or phenylalanine;

$X_9$ is selected from the group consisting of phenylalanine and desamino-phenylalanine;

$X_{10}$ is aspartate-lysine dipeptide, a lysine-proline dipeptide, or a proline-lysine dipeptide;

$X_{11}$ is threonine, alanine, or a threonine-arginine-arginine tripeptide; further wherein the B chain comprises a carboxy terminus extension of 1 to 4 amino acids wherein said carboxy terminal extension comprises an amino acid having the structure of

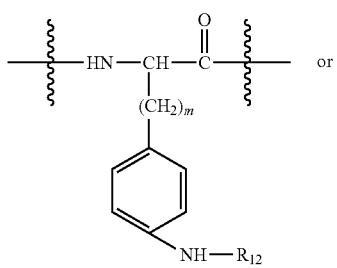 or

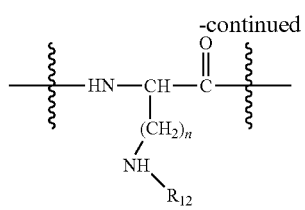

wherein m is an integer from 0-3;
n is an integer from 1-4;
$R_{12}$ is a dipeptide comprising the general structure:

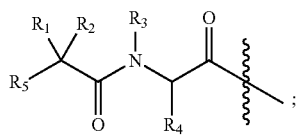

$R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)R$_7$, and CH$_2$($C_5$-$C_9$ heteroaryl);

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring;

$R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo; and $R_{13}$ is COOH or CONH$_2$, In one embodiment the insulin prodrug analog comprises an A chain sequence that includes the sequence GIVEQCCX$_1$SICSLYQLENX$_2$CX$_3$-R$_{13}$ (SEQ ID NO: 3) and a B chain sequence that includes the sequence of J-X$_{14}$-X$_4$LCGX$_5$X$_6$LVEALX$_7$LVCGERGFX$_8$ (SEQ ID NO: 14) or J-X$_9$VNQX$_4$LCGX$_5$X$_6$LVEALX$_7$LVCGERGFX$_8$YTX$_{10}$X$_{11}$-R$_{14}$ (SEQ ID NO: 5) wherein J is H (forming an N-terminal amine) or a dipeptide comprising the general structure:

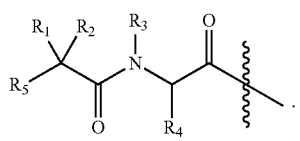

wherein X$_{14}$ is either a bond joining the "J" element to SEQ ID NO: 14 or X$_{14}$ represents a 1 to 4 amino acid sequence selected from the group consisting of a FVNQ (SEQ ID NO: 11), VNQ, NQ and Q that joins the "J" element to SEQ ID NO: 14;

$X_1$ is selected from the group consisting of threonine, histidine, arginine and lysine;

$X_2$ is an amino acid of the general structure

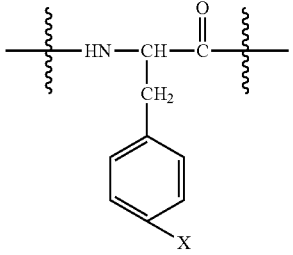

wherein X is selected from the group consisting of OH, $NH_2$, and $OCH_3$;

$X_3$ is asparagine, glycine, alanine, threonine, or serine.

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is an amino acid of the general structure

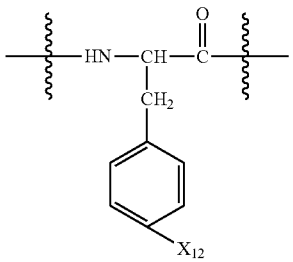

wherein $X_{12}$ is selected from the group consisting of OH, $OCH_3$, $NH_2$ and $NHR_{11}$, wherein $R_{11}$ is a dipeptide comprising the general structure:

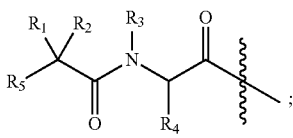

$X_8$ is an amino acid of the general structure

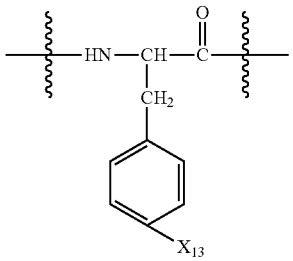

wherein $X_{13}$ is selected from the group consisting of H, OH, $OCH_3$, $NH_2$, and $NHR_{12}$, wherein $R_{12}$ is a dipeptide comprising the general structure:

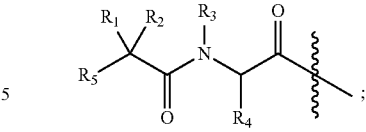

$X_9$ is selected from the group consisting of phenylalanine and desamino-phenylalanine;

$X_{10}$ is aspartate-lysine dipeptide, a lysine-proline dipeptide, or a proline-lysine dipeptide;

$X_{11}$ is threonine, alanine, or a threonine-arginine-arginine tripeptide;

wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_6$-$C_{10}$ aryl)$R_7$, and $CH_2$($C_5$-$C_9$ heteroaryl);

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)$NH_2$, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring;

$R_7$ is selected from the group consisting of H and OH; and $R_{13}$ and $R_{14}$ are independently COOH or $CONH_2$, with the proviso that one and only one of $X_{12}$, $X_{13}$, or J is a dipeptide comprising the general structure:

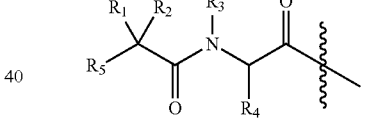

(i.e., only one dipeptide prodrug element is attached to the insulin peptide). In one embodiment J is a dipeptide comprising the general structure:

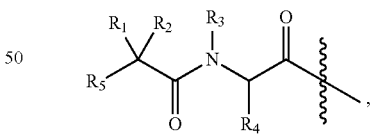

and X and $X_{12}$ are each OH and $X_{13}$ is H, with the further proviso that when $R_4$ and $R_3$ together with the atoms to which they are attached form a 5 member heterocyclic ring, both $R_1$ and $R_2$ are other than H. In an alternative embodiment $X_{12}$ is $NHR_{11}$, J and $X_{13}$ are each H and X is OH. In another alternative embodiment $X_{13}$ is $NHR_{12}$, X and $X_{12}$ are each OH and J is H. In one embodiment the B chain comprises the sequence J-$X_9$VNQ$X_4$LCG$X_5$$X_6$LVEAL$X_7$LVCGERGF$X_8$YTPKT (SEQ ID NO: 15) or J-$X_9$VNQ$X_4$LCG$X_5$$X_6$LVEAL$X_7$LVCGERGF$X_8$YTKPT (SEQ ID NO: 16), wherein J, $X_4$, $X_5$, $X_6$, $X_7$, $X_8$ and $X_9$ are defined as immediately above. In a further embodiment $R_3$ is $C_1$-$C_6$ alkyl and $R_4$ is selected from the group consisting of H, $C_1$-$C_4$ alkyl, or $R_3$ and $R_4$ together with the atoms to which they are attached form a 5 member heterocyclic ring. In another further embodiment $X_4$ is histidine, $X_5$ is serine and $X_6$ is histidine.

In another embodiment an insulin prodrug analog is provided comprising an A chain sequence of Z-GIVEQCCX$_1$SICSLYQLENX$_2$CX$_3$ (SEQ ID NO: 3) and a B chain sequence comprising a sequence of X$_4$LCGX$_5$X$_6$LVEALYLVCGERGFF (SEQ ID NO: 4) wherein Z is H or a dipeptide comprising the general structure:

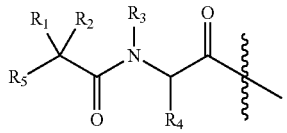

$X_1$ is selected from the group consisting of threonine and histidine;

$X_2$ is an amino acid of the general structure

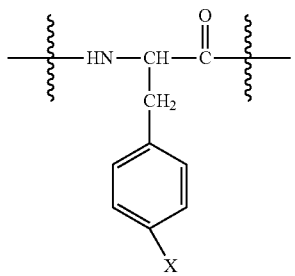

wherein X is selected from the group consisting of OH, $NH_2$, $NHR_{10}$ and $OCH_3$, wherein $R_{10}$ is a dipeptide comprising the general structure:

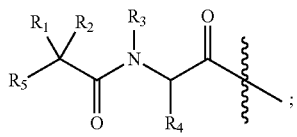

$X_3$ is selected from the group consisting of asparagine, glycine, alanine, threonine, or serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

wherein $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)R$_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring; and $R_7$ is selected from the group consisting of H and OH, with the proviso that X and Z are not both dipeptides and Z is not H when X is OH. In one embodiment when Z is a dipeptide comprising the general structure:

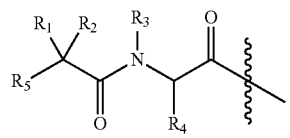

and $R_4$ and $R_3$ together with the atoms to which they are attached form a 5 member heterocyclic ring, then at least one of $R_1$ and $R_2$ are other than H. In one embodiment the A chain comprises a sequence of Z-GIVEQCCX$_1$SICSLYQLENYCX$_3$ (SEQ ID NO: 17) and the B chain sequence comprises the sequence X$_9$VNQX$_4$LCGX$_5$X$_6$LVEALYLVCGERGFFYTPKT (SEQ ID NO: 12) or X$_9$VNQX$_4$LCGX$_5$X$_6$LVEALYLVCGERGFFYTKPT (SEQ ID NO: 13).

In an alternative embodiment an insulin prodrug analog is provided comprising an A chain sequence of GIVEQCCX$_1$SICSLYQLENX$_2$CX$_3$ (SEQ ID NO: 3) and a B chain sequence comprising the sequence X$_9$VNQX$_4$LCGX$_5$X$_6$LVEALYLVCGERGFFYTPKT (SEQ ID NO: 12) or X$_9$VNQX$_4$LCGX$_5$X$_6$LVEALYLVCGERGFFYTKPT (SEQ ID NO: 13), wherein $X_1$ is selected from the group consisting of threonine and histidine;

$X_2$ is an amino acid of the general structure

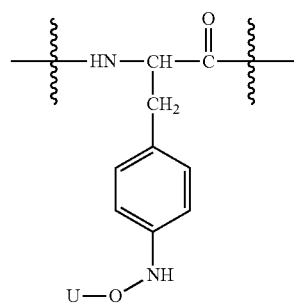

wherein U is an amino acid or a hydroxyl acid and O is an N-alkylated amino acid;

$X_3$ is asparagine, glycine, alanine, threonine, or serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_9$ is selected from the group consisting of phenylalanine and desamino-phenylalanine. In one embodiment U-O represent a dipeptide of the general structure;

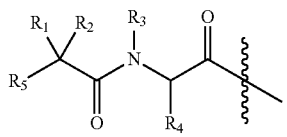

wherein $R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring; and $R_7$ is selected from the group consisting of H and OH. In a further embodiment $X_7$ is tyrosine, $X_8$ is phenylalanine and $X_9$ is phenylalanine, and in an additional further embodiment $X_4$ is histidine, $X_5$ is serine and $X_6$ is histidine. In a further embodiment U-O represent a dipeptide of the general structure;

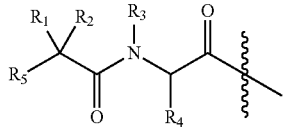

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a 4, 5 or 6 member heterocyclic ring;

$R_5$ is NHR$_6$ or OH;

$R_6$ is H, $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

In another embodiment an insulin prodrug analog is provided comprising an A chain sequence of Z-GIVEQCCTSICSLYQLENX$_2$CX$_3$-R$_{13}$ (SEQ ID NO: 18) and a B chain sequence comprising a sequence of X$_4$LCGSHLVEALYLVCGERGFF-R$_{14}$ (SEQ ID NO: 19) wherein Z is H or an amide linked dipeptide comprising the general structure:

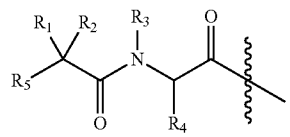

$X_2$ is an amino acid of the general structure

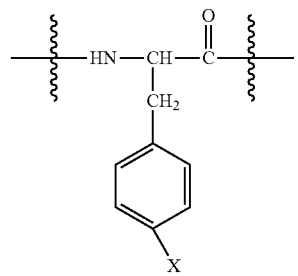

wherein X is selected from the group consisting of OH and NHR$_{10}$;

wherein R$_{10}$ is a dipeptide comprising the general structure:

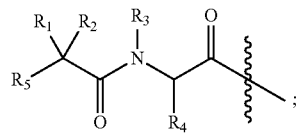

$X_3$ is serine, asparagine or glycine;

$X_4$ is selected from the group consisting of histidine and threonine;

$R_1$ is selected from the group consisting of H and $C_1$-$C_8$ alkyl;

$R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring;

$R_7$ is selected from the group consisting of H and OH; and $R_{13}$ and $R_{14}$ are independently COOH or CONH$_2$; with the proviso that when Z is H, X is not OH and when X is OH, Z is not H. In one embodiment $R_{13}$ is COOH and $R_{14}$ is CONH$_2$. In a further embodiment $X_2$ is an amino acid of the general structure of Formula III:

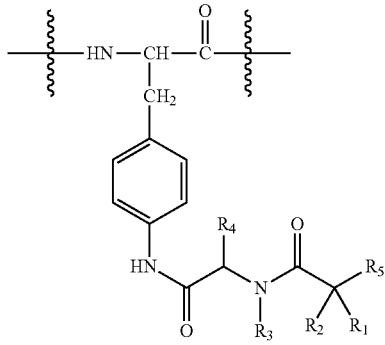

Z is H, $X_3$ is serine, $X_4$ is histidine, $R_{13}$ is COOH and $R_{14}$ is CONH$_2$. In an additional further embodiment $R_1$ is selected from the group consisting of H and $C_1$-$C_4$ alkyl;

$R_2$ is selected from the group consisting of H, $C_1$-$C_6$ alkyl, $C_2$-$C_8$ alkenyl, ($C_1$-$C_4$ alkyl)OH, ($C_1$-$C_4$ alkyl)NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl) or $R_2$ and $R_6$ together with the atoms to which they are attached form a 5 member heterocyclic ring;

$R_3$ is $C_1$-$C_6$ alkyl;

$R_4$ is selected from the group consisting of H and $C_1$-$C_4$ alkyl or $R_3$ and $R_4$ together with the atoms to which they are attached form a 5 member heterocyclic ring. In a further embodiment $R_3$ is CH$_3$, $R_4$ is H and $R_5$ is NH$_2$, or alternatively, $R_5$ is NH$_2$ and $R_3$ and $R_4$ together with the atoms to which they are attached form a 5 member heterocyclic ring. In accordance with one embodiment the B chain of the insulin prodrug analog comprises the sequence FVNQHLCG-SHLVEALYLVCGERGFFYTPKT-$R_{14}$ (SEQ ID NO: 8), FVNQHLCGSHLVEALYLVCGERGFFYTKPT-$R_{14}$ (SEQ ID NO: 9) or FVNQHLCGSHLVEALYLVCGERGFFYTP-KTRR-$R_{14}$ (SEQ ID NO: 10), wherein $R_{14}$ is COOH or CONH$_2$, and in one embodiment $R_{14}$ is CONH$_2$.

In one embodiment an insulin prodrug analog is provided comprising a polypeptide of the sequence Z-GIVEQCCX$_1$SICSLYQLENX$_2$CX$_3$ (SEQ ID NO: 3), wherein Z is a dipeptide comprising the general structure:

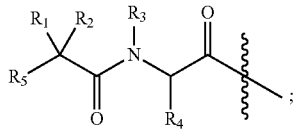

$X_1$ is selected from the group consisting of threonine and histidine;

$X_2$ is an amino acid of the general structure

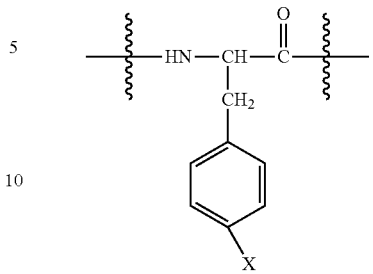

wherein X is selected from the group consisting of OH, NH$_2$, and OCH$_3$;

$X_3$ is asparagine, glycine, alanine, threonine, or serine;

$R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring; and $R_7$ is selected from the group consisting of H and OH. In one embodiment $X_1$ is threonine and $X_3$ is asparagine or glycine and in a further embodiment $R_3$ is $C_1$-$C_6$ alkyl and $R_4$ is selected from the group consisting of H, $C_1$-$C_4$ alkyl, ($C_3$-$C_6$)cycloalkyl, ($C_1$-$C_4$ alkyl)OH, ($C_1$-$C_4$ alkyl)SH and ($C_0$-$C_4$ alkyl)($C_6$ aryl)$R_7$, or $R_3$ and $R_4$ together with the atoms to which they are attached form a 5 member heterocyclic ring, with the proviso that when $R_4$ and $R_3$ together with the atoms to which they are attached form a 5 or 6 member heterocyclic ring, both $R_1$ and $R_2$ are both other than H.

In one embodiment an insulin prodrug analog is provided comprising a polypeptide of the sequence GIVEQCCX$_1$SICSLYQLENX$_2$CX$_3$ (SEQ ID NO: 3), wherein $X_1$ is selected from the group consisting of threonine and histidine;

$X_2$ is an amino acid of the general structure

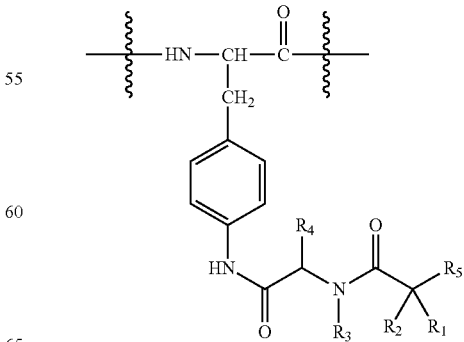

$X_3$ is asparagine, glycine, alanine, threonine, or serine;

$R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)$R_7$, CH$_2$($C_5$-$C_9$ heteroaryl), or $R_1$ and $R_2$ together with the atoms to which they are attached form a $C_3$-$C_6$ cycloalkyl;

$R_3$ is selected from the group consisting of $C_1$-$C_8$ alkyl, ($C_1$-$C_4$ alkyl)OH, ($C_1$-$C_4$ alkyl)SH, ($C_3$-$C_6$)cycloalkyl or $R_4$ and $R_3$ together with the atoms to which they are attached form a 5 or 6 member heterocyclic ring;

$R_5$ is NHR$_6$ or OH;

$R_6$ is H, or $R_6$ and $R_2$ together with the atoms to which they are attached form a 5 or 6 member heterocyclic ring; and $R_7$ is selected from the group consisting of H and OH. In one embodiment the A chain of GIVEQCCX$_1$SICSLYQLENX$_2$CX$_3$ (SEQ ID NO: 3) as defined immediately above is linked, either by disulfide bonds or as a single chain polypeptide, to a B chain comprising the sequence $X_{14}$-X$_4$LCGX$_5$X

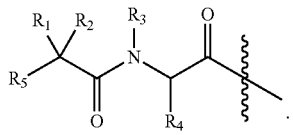

wherein $X_{14}$ is either a bond or a 1 to 4 amino acid sequence selected from the group consisting of a FVNQ (SEQ ID NO: 11), VNQ, NQ and Q.

$X_1$ is selected from the group consisting of threonine and histidine;

$X_2$ is an amino acid of the general structure

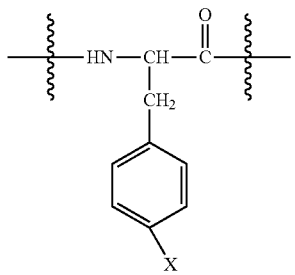

wherein X is selected from the group consisting of OH, $NHR_{10}$ and $OCH_3$; wherein $R_{10}$ is H or a dipeptide comprising the general structure:

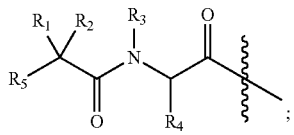

$X_3$ is asparagine, glycine, alanine, threonine, or serine.

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is an amino acid of the general structure

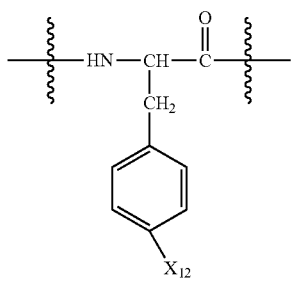

wherein $X_{12}$ is selected from the group consisting of OH, $OCH_3$ and $NHR_{11}$, wherein $R_{11}$ is H or a dipeptide comprising the general structure:

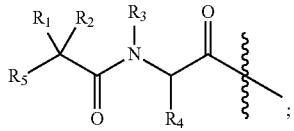

$X_8$ is an amino acid of the general structure

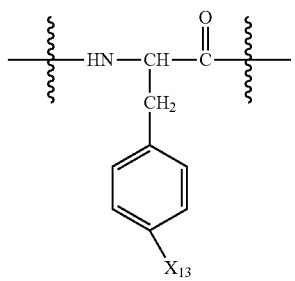

wherein $X_{13}$ is selected from the group consisting of H, OH, $OCH_3$ and $NHR_{12}$, wherein $R_{12}$ is H or a dipeptide comprising the general structure:

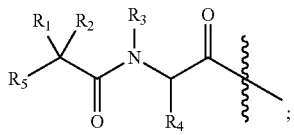

wherein $R_1$ is selected from the group consisting of H and $C_1$-$C_8$ alkyl; and $R_2$ and $R_4$ are independently selected from the group consisting of H, $C_1$-$C_8$ alkyl, $C_2$-$C_8$ alkenyl, ($C_1$-$C_4$ alkyl)OH, ($C_1$-$C_4$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_6$-$C_{10}$ aryl)R$_7$, and CH$_2$($C_5$-$C_9$ heteroaryl);

$R_3$ is selected from the group consisting of $C_1$-$C_8$ alkyl, ($C_1$-$C_4$ alkyl)OH, ($C_1$-$C_4$ alkyl)SH, ($C_1$-$C_4$ alkyl)NH$_2$, ($C_3$-$C_6$)cycloalkyl or $R_4$ and $R_3$ together with the atoms to which they are attached form a 5 or 6 member heterocyclic ring;

$R_5$ is $NHR_6$ or OH;

$R_6$ is H, or $R_6$ and $R_2$ together with the atoms to which they are attached form a 5 or 6 member heterocyclic ring; and $R_7$ is selected from the group consisting of H and OH, with the proviso that one and only one of Z, J, $R_{10}$, $R_{11}$ or $R_{12}$ is a dipeptide comprising the general structure:

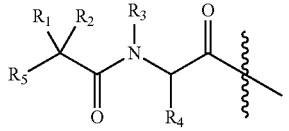

(i.e., only one dipeptide prodrug element is attached to the insulin peptide).

In one embodiment J is a dipeptide comprising the general structure:

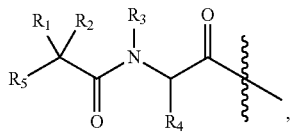

and X and $X_{12}$ are each OH and $X_{13}$ is H, with the proviso that when $R_4$ and $R_3$ together with the atoms to which they are attached form a 5 member heterocyclic ring, both $R_1$ and $R_2$ are other than H. In an alternative embodiment $X_{12}$ comprises the dipeptide of Formula I, J and $X_{13}$ are each H and X is OH. In another alternative embodiment $X_{13}$ is comprises the dipeptide of Formula I, X and $X_{12}$ are each OH and J is H. In another embodiment X comprises the dipeptide of Formula I, J and $X_{13}$ are each H and $X_{12}$ is OH. In one embodiment the B chain comprises the sequence J-$X_9$VNQ$X_4$LCG$X_5$$X_6$LVEAL$X_7$LVCGERGF$X_8$YTPKT (SEQ ID NO: 15) or J-$X_9$VNQ$X_4$LCG$X_5$$X_6$LVEAL$X_7$LVCGERGF$X_8$YTKPT (SEQ ID NO: 16), wherein J, $X_4$, $X_5$, $X_6$, $X_7$, $X_8$ and $X_9$ are defined as immediately above. In a further embodiment $R_3$ is $C_1$-$C_6$ alkyl and $R_4$ is selected from the group consisting of H, $C_1$-$C_4$ alkyl, or $R_3$ and $R_4$ together with the atoms to which they are attached form a 5 member heterocyclic ring. In another further embodiment $X_4$ is histidine, $X_5$ is serine and $X_6$ is histidine.

In one embodiment the single chain insulin analog comprises a compound of the formula: B-P-A, wherein:

B represents a B chain sequence comprising a sequence of $X_4$LCG$X_5$$X_6$LVEALYLVCG ERGFF (SEQ ID NO: 4) or a functional analog thereof, A represents an A chain sequence comprising a sequence of GIVEQCC$X_1$SICSLYQLEN$X_2$C$X_3$ (SEQ ID NO: 3) or a functional analog thereof and "P" represents a linker including for example an 8-12 amino acid linker, wherein $X_1$ is selected from the group consisting of threonine and histidine;

$X_2$ is an amino acid of the general structure

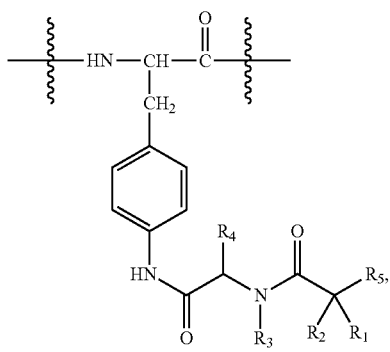

$X_3$ is asparagine or glycine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid.

P represents a linker, including a peptide linker, that covalently joins the amino-terminus of the A chain to the carboxy-terminus of the B chain. In an alternative embodiment the single-chain insulin analog comprises a compound of the formula: A-P-B, wherein: A represents a human insulin A chain, or a functional analog thereof, B represents a human insulin B chain, or a functional analog thereof, and P represents a linker, including a peptide linker, that covalently joins the amino-terminus of the B chain to the carboxy-terminus of the A chain. In one embodiment the peptide linker comprises 4 to 8 amino acids.

In accordance with one embodiment the peptide linker is 5 to 18 amino acids in length and comprises a sequence selected from the group consisting of: Gly-Gly-Gly-Pro-Gly-Lys-Arg (SEQ ID NO: 22), Gly-Tyr-Gly-Ser-Ser-Ser-Arg-Arg-Ala-Pro-Gln-Thr (SEQ ID NO: 23), Arg-Arg-Gly-Pro-Gly-Gly-Gly (SEQ ID NO: 32), Gly-Gly-Gly-Gly-Gly-Lys-Arg (SEQ ID NO: 24), Arg-Arg-Gly-Gly-Gly-Gly-Gly (SEQ ID NO: 25), Gly-Gly-Ala-Pro-Gly-Asp-Val-Lys-Arg (SEQ ID NO: 26), Arg-Arg-Ala-Pro-Gly-Asp-Val-Gly-Gly (SEQ ID NO: 27), Gly-Gly-Tyr-Pro-Gly-Asp-Val-Lys-Arg (SEQ ID NO: 28), Arg-Arg-Tyr-Pro-Gly-Asp-Val-Gly-Gly (SEQ ID NO: 29), Gly-Gly-His-Pro-Gly-Asp-Val-Lys-Arg (SEQ ID NO: 30) and Arg-Arg-His-Pro-Gly-Asp-Val-Gly-Gly (SEQ ID NO: 31). In one embodiment the peptide linker is 7 to 12 amino acids in length and comprises the sequence Gly-Gly-Gly-Pro-Gly-Lys-Arg (SEQ ID NO: 22) or Gly-Tyr-Gly-Ser-Ser-Ser-Arg-Arg-Ala-Pro-Gln-Thr (SEQ ID NO: 23).

In a further embodiment the peptide linker comprises a sequence selected from the group consisting of AGRGSGK (SEQ ID NO: 35), AGLGSGK (SEQ ID NO: 36), AGMGSGK (SEQ ID NO: 37), ASWGSGK (SEQ ID NO: 38), TGLGSGQ (SEQ ID NO: 39), TGLGRGK (SEQ ID NO: 40), TGLGSGK (SEQ ID NO: 41), HGLYSGK (SEQ ID NO: 42), KGLGSGQ (SEQ ID NO: 43), VGLMSGK (SEQ ID NO: 44), VGLSSGQ (SEQ ID NO: 45), VGLYSGK (SEQ ID NO: 46), VGLSSGK (SEQ ID NO: 47), VGMSSGK (SEQ ID NO: 48), VWSSSGK (SEQ ID NO: 49), VGSSSGK (SEQ ID NO: 50), VGMSSGK (SEQ ID NO: 51), TGLGSGR (SEQ ID NO: 52), TGLGKGQ (SEQ ID NO: 53), KGLSSGQ (SEQ ID NO: 54), VKLSSGQ (SEQ ID NO: 55), VGLKSGQ (SEQ ID NO: 56), TGLGKGQ (SEQ ID NO: 57) SRVSRRSR (SEQ ID NO: 65), GYGSSSRRAPQT (SEQ ID NO: 23) and VGL-SKGQ (SEQ ID NO: 58). In one embodiment the linker comprises GSSSRRAP (SEQ ID NO: 67) or SRVSRRSR (SEQ ID NO: 65).

In one embodiment the single-chain insulin analog has the amino acid sequence: Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Gly-Ile-Val-Glu-Gln-Cys-Cys-Thr-Ser-Ile-Cys-Ser-Leu-Tyr-Gln-Leu-Glu-Asn-Xaa-Cys-Asn (SEQ ID NO: 33) or Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr-Gln-Pro-Leu-Ala-Leu-Glu-Gly-Ser-Leu-Gln-Lys-Arg-Gly-Ile-Val-Glu-Gln-Cys-Cys-Thr-Ser-Ile-Cys-Ser-Leu-Tyr-Gln-Leu-Glu-Asn-Xaa-Cys-Asn (SEQ ID NO: 34) wherein Xaa is an amino acid of the general structure

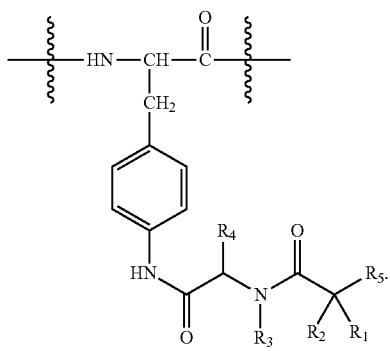

The insulin peptides disclosed herein may be part of a dimer, trimer or higher order multimer comprising at least two, three, or more peptides bound via a linker, wherein at least one or both peptides comprises a dipeptide prodrug element linked to the insulin peptide. The dimer may be a homodimer or heterodimer, comprising peptides selected from the group consisting of native insulin, native IGF-1, native IGF-II and insulin analog peptides as disclosed herein. In one embodiment, the linker is selected from the group consisting of a bifunctional thiol crosslinker and a bifunctional amine crosslinker. In certain embodiments, the linker is PEG, e.g., a 5 kDa PEG, 20 kDa PEG. In some embodiments, the linker is a disulfide bond.

For example, each monomer of the dimer may comprise a Cys residue (e.g., a terminal or internally positioned Cys) and the sulfur atom of each Cys residue participates in the formation of the disulfide bond. Each monomer of the dimer represents a heterodimer of an A and B chain. The A and B chain are either linked via disulfide bonds or are prepared as single chain peptides. In some aspects of the invention, the monomers are connected via terminal amino acids (e.g., N-terminal or C-terminal), via internal amino acids, or via a terminal amino acid of at least one monomer and an internal amino acid of at least one other monomer. In specific aspects, the monomers are not connected via an N-terminal amino acid. In some aspects, the monomers of the multimer are attached together in a "tail-to-tail" orientation in which the C-terminal amino acids of each monomer are attached together. A conjugate moiety may be covalently linked to any of the insulin peptides described herein, including a dimer, trimer or higher order multimer.

The prodrugs disclosed herein can be further modified to improve the peptide's solubility in aqueous solutions at physiological pH, while enhancing the effective duration of the peptide by preventing renal clearance of the peptide. Peptides are easily cleared because of their relatively small molecular size when compared to plasma proteins. Increasing the molecular weight of a peptide above 40 kDa exceeds the renal threshold and significantly extends duration in the plasma. Accordingly, in one embodiment the peptide prodrugs are further modified to comprise a covalently linked hydrophilic moiety. In one embodiment the hydrophilic moiety is a plasma protein polyethylene oxide chain or the Fc portion of an immunoglobin. Therefore, in one embodiment the presently disclosed prodrugs are further modified to comprise one or more hydrophilic groups covalently linked to the side chains of amino acids.

In accordance with one embodiment the insulin prodrugs disclosed herein are further modified by linking a hydrophilic moiety to either the N-terminal amino acid of the B chain or to the side chain of a lysine amino acid located at the carboxy terminus of the B chain, including for example, at position 28 of SEQ ID NO: 9/SEQ ID NO: 13 or at position 29 of SEQ ID NO: 8/SEQ ID NO: 12. In one embodiment a single-chain insulin prodrug analog is provided wherein one of the amino acids of the peptide linker is modified by linking a hydrophilic moiety to the side chain of the peptide linker. In one embodiment the modified amino acid is cysteine, lysine or acetyl phenylalanine. In one embodiment the peptide linker is selected from the group consisting of TGLGSGQ (SEQ ID NO: 39), VGLSSGQ (SEQ ID NO: 45), VGLSSGK (SEQ ID NO: 47), TGLGSGR (SEQ ID NO: 52), TGLGKGQ (SEQ ID NO: 53), KGLSSGQ (SEQ ID NO: 54), VKLSSGQ (SEQ ID NO: 55), VGLKSGQ (SEQ ID NO: 56), TGLGKGQ (SEQ ID NO: 57) and VGLSKGQ (SEQ ID NO: 58) and the hydrophilic moiety (e.g., polyethylene glycol) is linked to the lysine side chain of the peptide linker.

In another embodiment the insulin prodrug analogs disclosed herein are further modified by the addition of a modified amino acid to the carboxy terminus of the B chain of the insulin prodrug, wherein the C-terminally added amino acid is modified to comprise a hydrophilic moiety linked to the amino acid. In one embodiment the amino acid added to the C-terminus is a modified cysteine, lysine or acetyl phenylalanine. In one embodiment the hydrophilic moiety is selected from the group consisting of a plasma protein, polyethylene oxide chain and an Fc portion of an immunoglobin.

In one embodiment the hydrophilic group is a polyethylene oxide chain, and in one embodiment two or more polyethylene oxide chains are covalently attached to two or more amino acid side chains of the insulin prodrug analog. In accordance with one embodiment the hydrophilic moiety is covalently attached to an amino acid side chain of an insulin prodrug analog disclosed herein at a position selected from the group consisting of A9, A14, A15, B22, B28, B29 and the C-terminus or N-terminus of the B chain. For insulin prodrug analogs having multiple polyethylene oxide chains, the polyethylene oxide chains can be attached at the N-terminal amino acid of the B chain or to the side chain of a lysine amino acid located at the carboxy terminus of the B chain, or by the addition of a single amino acid at the C-terminus of the peptide wherein the added amino acid has a polyethylene oxide chain linked to its side chain. In accordance with one embodiment the polyethylene oxide chain or other hydrophilic moiety is linked to the side chain of one of the two amino acids comprising the dipeptide prodrug element. In one embodiment the dipeptide prodrug element comprises a lysine (in the D or L configuration) with a polyethylene oxide chain attached to the side chain amine of the lysine.

Linkage of Hydrophilic Moieties

In another embodiment the solubility of the insulin analogs disclosed herein are enhanced by the covalent linkage of a hydrophilic moiety to the peptide. Hydrophilic moieties can be attached to the insulin analogs under any suitable conditions used to react a protein with an activated polymer molecule. Any means known in the art can be used, including via acylation, reductive alkylation, Michael addition, thiol alkylation or other chemoselective conjugation/ligation methods through a reactive group on the PEG moiety (e.g., an aldehyde, amino, ester, thiol, α-haloacetyl, maleimido or hydrazino group) to a reactive group on the target compound (e.g., an aldehyde, amino, ester, thiol, α-haloacetyl, maleimido or hydrazino group). Activating groups which can be used to link the water soluble polymer to one or more proteins include without limitation sulfone, maleimide, sulfhydryl, thiol, triflate, tresylate, azidirine, oxirane and 5-pyridyl. If attached to the peptide by reductive alkylation, the polymer selected should have a single reactive aldehyde so that the degree of polymerization is controlled. See, for example, Kinstler et al., *Adv. Drug. Delivery Rev.* 54: 477-485 (2002); Roberts et al., *Adv. Drug Delivery Rev.* 54: 459-476 (2002); and Zalipsky et al., *Adv. Drug Delivery Rev.* 16: 157-182 (1995).

Suitable hydrophilic moieties include polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10)alkoxy- or aryloxy-polyethylene glycol, carboxymethylcellulose, polyacetals, polyvinyl alcohol (PVA), polyvinyl pyrrolidone, poly-1,3-dioxolane, poly-1,3,6-trioxane, ethylene/maleic anhydride copolymer, poly(.beta.-amino acids) (either homopolymers or random copolymers), poly(n-vinyl pyrrolidone)polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof.

The hydrophilic moiety, e.g., polyethylene glycol chain in accordance with one embodiment has a molecular weight selected from the range of about 500 to about 40,000 Daltons. In one embodiment the hydrophilic moiety, e.g. PEG, has a molecular weight selected from the range of about 500 to about 5,000 Daltons, or about 1,000 to about 5,000 Daltons. In another embodiment the hydrophilic moiety, e.g., PEG, has a molecular weight of about 10,000 to about 20,000 Daltons. In yet other exemplary embodiments the hydrophilic moiety, e.g., PEG, has a molecular weight of about 20,000 to about 40,000 Daltons.

In one embodiment dextrans are used as the hydrophilic moiety. Dextrans are polysaccharide polymers of glucose subunits, predominantly linked by α1-6 linkages. Dextran is available in many molecular weight ranges, e.g., about 1 kDa to about 100 kDa, or from about 5, 10, 15 or 20 kDa to about 20, 30, 40, 50, 60, 70, 80 or 90 kDa.

Linear or branched polymers are contemplated. Resulting preparations of conjugates may be essentially monodisperse or polydisperse, and may have about 0.5, 0.7, 1, 1.2, 1.5 or 2 polymer moieties per peptide.

In accordance with one embodiment, the insulin prodrug analogs disclosed herein are further modified by amino acid substitutions, wherein the substituting amino acid comprises a side chain suitable for crosslinking with hydrophilic moieties, including for example, polyethylene glycol. In one embodiment the amino acid at the position of the insulin prodrug analog where the hydrophilic moiety is to be linked is substituted (or added at the C-terminus) with a natural or synthetic amino acid to introduce, or allow for ease in attaching, the hydrophilic moiety. For example, in one embodiment a native amino acid at position selected from A5, A8, A9, A10, A12, A14, A15, A17, A18, B1, B2, B3, B4, B5, B13, B14, B17, B21, B22, B26, B27, B28, B29 and B30 is substituted with a lysine, cysteine or acetyl phenylalanine residue (or a lysine, cysteine or acetyl phenylalanine residue is added to the C-terminus) to allow for the covalent attachment of a polyethylene glycol chain.

In one embodiment the insulin prodrug analog has a single cysteine residue added to the carboxy terminus of the B chain, or the insulin prodrug analog is substituted with at least one cysteine residue, wherein the side chain of the cysteine residue is further modified with a thiol reactive reagent, including for example, maleimido, vinyl sulfone, 2-pyridylthio, haloalkyl, and haloacyl. These thiol reactive reagents may contain carboxy, keto, hydroxyl, and ether groups as well as other hydrophilic moieties such as polyethylene glycol units. In an alternative embodiment, the insulin prodrug analog has a single lysine residue added to the carboxy terminus of the B chain, or the insulin prodrug analog is substituted with lysine, and the side chain of the substituting lysine residue is further modified using amine reactive reagents such as active esters (succinimido, anhydride, etc) of carboxylic acids or aldehydes of hydrophilic moieties such as polyethylene glycol.

In those embodiments wherein the insulin prodrug analog comprises a polyethylene glycol chain, the polyethylene glycol chain may be in the form of a straight chain or it may be branched. In accordance with one embodiment the polyethylene glycol chain has an average molecular weight selected from the range of about 20,000 to about 60,000 Daltons. Multiple polyethylene glycol chains can be linked to the insulin prodrug analog to provide an insulin prodrug analog with optimal solubility and blood clearance properties. In one embodiment the insulin prodrug analog is linked to a single polyethylene glycol chain that has an average molecular weight selected from the range of about 20,000 to about 60,000 Daltons. In another embodiment the insulin prodrug analog is linked to two polyethylene glycol chains wherein the combined average molecular weight of the two chains is selected from the range of about 40,000 to about 80,000 Daltons. In one embodiment a single polyethylene glycol chain having an average molecular weight of 20,000 or 60,000 Daltons is linked to the insulin prodrug analog. In another embodiment a single polyethylene glycol chain is linked to the insulin prodrug analog and has an average molecular weight selected from the range of about 40,000 to about 50,000 Daltons. In one embodiment two polyethylene glycol chains are linked to the insulin prodrug analog wherein the first and second polyethylene glycol chains each have an average molecular weight of 20,000 Daltons. In another embodiment two polyethylene glycol chains are linked to the insulin prodrug analog wherein the first and second polyethylene glycol chains each have an average molecular weight of 40,000 Daltons.

In a further embodiment an insulin prodrug analog comprising two or more polyethylene glycol chains covalently bound to the peptide is provided, wherein the total molecular weight of the polyethylene glycol chains is about 40,000 to about 60,000 Daltons. In one embodiment the pegylated insulin prodrug analog comprises a polyethylene glycol chain linked to one or more amino acids selected from the N-terminus of the B chain and/or position 28 of SEQ ID NO: 9 or at position 29 of SEQ ID NO: 8, wherein the combined molecular weight of the PEG chain(s) is about 40,000 to about 80,000 Daltons.

In accordance with one embodiment, an insulin peptide, or prodrug/depot derivative thereof, is fused to an accessory peptide which is capable of forming an extended conformation similar to chemical PEG (e.g., a recombinant PEG (rPEG) molecule), such as those described in International Patent Application Publication No. WO2009/023270 and U.S. Patent Application Publication No. US2008/0286808. The rPEG molecule is not polyethylene glycol. The rPEG molecule in some aspects is a polypeptide comprising one or more of glycine, serine, glutamic acid, aspartic acid, alanine, or proline. In some aspects, the rPEG is a homopolymer, e.g., poly-glycine, poly-serine, poly-glutamic acid, poly-aspartic acid, poly-alanine, or poly-proline. In other embodiments, the rPEG comprises two types of amino acids repeated, e.g., poly(Gly-Ser), poly(Gly-Glu), poly(Gly-Ala), poly(Gly-Asp), poly(Gly-Pro), poly(Ser-Glu), etc. In some aspects, the rPEG comprises three different types of amino acids, e.g., poly(Gly-Ser-Glu). In specific aspects, the rPEG increases the half-life of the insulin peptide. In some aspects, the rPEG comprises a net positive or net negative charge. The rPEG in some aspects lacks secondary structure. In one embodiment, the rPEG is greater than or equal to 10 amino acids in length, and in one embodiment is about 40 to about 50 amino acids in length. The accessory peptide in some aspects is fused to the N- or C-terminus of the peptide of the invention through a peptide bond or a proteinase cleavage site, or is inserted into the loops of the peptide of the invention. The rPEG in some aspects comprises an affinity tag or is linked to a PEG that is greater than 5 kDa. In one embodiment, the rPEG confers the peptide of the invention with an increased hydrodynamic radius, serum half-life, protease resistance, or solubility and in some aspects confers the peptide with decreased immunogenicity.

In accordance with one embodiment, an insulin prodrug analog is provided wherein a plasma protein has been covalently linked to an amino acid side chain of the peptide to improve the solubility, stability and/or pharmacokinetics of the insulin prodrug analog. For example, serum albumin can be covalently bound to the insulin prodrug analogs presented herein. In one embodiment the plasma protein is covalently bound to the N-terminus of the B chain and/or to an amino acid corresponding to position 28 of SEQ ID NO: 9 or at position 29 of SEQ ID NO: 8.

In accordance with one embodiment, an insulin prodrug analog is provided wherein a linear amino acid sequence representing the Fc portion of an immunoglobin molecule has been covalently linked to an amino acid side chain of an insulin prodrug analog disclosed herein to improve the solubility, stability and/or pharmacokinetics of the insulin prodrug analog. For example, the amino acid sequence representing the Fc portion of an immunoglobin molecule can be covalently bound to the N-terminus of the B chain or the C-terminus of the A or B chain, or the C-terminus of an A or B chain that has been terminally extended. For example, the amino acid sequence representing the Fc portion of an immunoglobin molecule can be covalently bound to the C-terminus of the B chain, including for example linkage to an amino acid corresponding to position 28 of SEQ ID NO: 9 or at position 29 of SEQ ID NO: 8. The Fc portion is typically one isolated from IgG, but the Fc peptide fragment from any immunoglobin should function equivalently.

In a specific aspect of the invention, the insulin prodrug analog is modified to comprise an alkyl or acyl group by direct alkylation or acylation of an amine, hydroxyl, or thiol of a side chain of an amino acid of the insulin prodrug analog. In one embodiment, the insulin prodrug analog is directly acylated through the side chain amine, hydroxyl, or thiol of an amino acid. In one embodiment, acylation is at one or more positions selected from A9, A14, A15, B22, B28 or B29. In this regard, the acylated insulin prodrug analog can comprise an A chain amino acid sequence of SEQ ID NO: 3 and a B chain of SEQ ID NO: 5, or a modified amino acid sequence of SEQ ID NO: 3 and/or SEQ ID NO: 5 with at least one of the amino acids at positions A9, A14, A15, B22, B28 or B29 modified to any amino acid comprising a side chain amine, hydroxyl, or thiol. In some specific embodiments, the direct acylation of the insulin prodrug analog occurs through the side chain amine, hydroxyl, or thiol of the amino acid at position B28 or B29. In one further embodiment the insulin prodrug analog comprises an acyl group of a carboxylic acid with 1-24 carbon atoms bound to the epsilon-amino group of a Lys present at position B28 or B29. In one embodiment a single-chain insulin prodrug analog is provided wherein one of the amino acids of the peptide linker is modified to comprise an acyl group by direct acylation of an amine, hydroxyl, or thiol of a side chain of an amino acid of the peptide linker. In accordance with one embodiment the peptide linker of the single-chain insulin analog is selected from the group consisting of AGRGSGK (SEQ ID NO: 35), AGLGSGK (SEQ ID NO: 36), AGMGSGK (SEQ ID NO: 37), ASWGSGK (SEQ ID NO: 38), TGLGSGQ (SEQ NO: 39), TGLGRGK (SEQ ID NO: 40), TGLGSGK (SEQ NO: 41), HGLYSGK (SEQ ID NO: 42), KGLGSGQ (SEQ ID NO: 43), VGLMSGK (SEQ ID NO: 44), VGLSSGQ (SEQ ID NO: 45), VGLYSGK (SEQ ID NO: 46), VGLSSGK (SEQ ID NO: 47), VGMSSGK (SEQ ID NO: 48), VWSSSGK (SEQ ID NO: 49), VGSSSGK (SEQ ID NO: 50), VGMSSGK (SEQ ID NO: 51), TGLGSGR (SEQ ID NO: 52), TGLGKGQ (SEQ ID NO: 53), KGLSSGQ (SEQ ID NO: 54), VKLSSGQ (SEQ ID NO: 55), VGLKSGQ (SEQ ID NO: 56), TGLGKGQ (SEQ ID NO: 57) and VGLSKGQ (SEQ ID NO: 58) wherein at least one lysine residue in the A-chain, in the B-chain or in the connecting peptide has been chemically modified by acylation. In one embodiment the acylating group comprises a 1-5, 10-12 or 12-24 carbon chain.

In accordance with one embodiment the insulin prodrug analogs as disclosed herein are further modified to link an additional compound to the prodrug dipeptide moiety of the analog. In one embodiment the side chain of an amino acid comprising the dipeptide prodrug element is pegylated, acylated or alkylated. In one embodiment the dipeptide is acylated with a group comprising a 1-5, 10-12 or 12-24 carbon chain. In one embodiment the dipeptide is pegylated with a 40-80 KDa polyethylene glycol chain. In one embodiment the dipeptide prodrug element is pegylated and the insulin peptide linked to the dipeptide is acylated, including, for example, acylation at the C-terminal lysine of the B chain. In accordance with one embodiment a hydrophilic moiety or a sequestering macromolecule is covalently linked to the $R_2$ side chain of the dipeptide comprising the general structure:

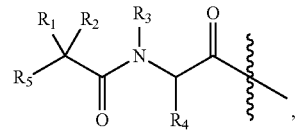

wherein $R_2$ is selected from the group consisting of $(C_1$-$C_4$ alkyl)OH, $(C_1$-$C_4$ alkyl)SH, and $(C_1$-$C_4$ alkyl)NH$_2$. In one embodiment $R_2$ is $(C_3$-$C_4$ alkyl)NH$_2$. Sequestering macromolecules are known to those skilled in the art and include dextrans and large molecular weight polyethylene glycol (i.e., greater than or equal to 80 KDa) By linking the sequestering macromolecule to the dipeptide moiety, the prodrug will remain sequestered, while the active insulin peptide is slowly released based on the kinetics of the cleavage of the dipeptide amide bond.

The present disclosure also encompasses other conjugates in which insulin prodrug analogs of the invention are linked, optionally via covalent bonding, and optionally via a linker, to a conjugate. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

Exemplary conjugates include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising an insulin prodrug analog of the present disclosure and a plasma protein, wherein the plasma protein is selected from the group consisting of albumin, transferin and fibrinogen. In one embodiment the plasma protein moiety of the conjugate is albumin or transferin. In one embodiment, the linker comprises a chain of atoms from 1 to about 60, or 1 to 30 atoms or longer, 2 to 5 atoms, 2 to 10 atoms, 5 to 10 atoms, or 10 to 20 atoms long. In one embodiment, the chain atoms are all carbon atoms. In one embodiment, the chain atoms in the backbone of the linker are selected from the group consisting of C, O, N, and S. Chain atoms and linkers may be selected according to their expected solubility (hydrophilicity) so as to provide a more soluble conjugate. In one embodiment, the linker provides a functional group that is subject to cleavage by an enzyme or other catalyst or hydrolytic conditions found in the target tissue or organ or cell. In one embodiment, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

Conjugates and Fusions

The present disclosure also encompasses other conjugates in which the insulin analogs disclosed herein are linked, optionally via covalent bonding and optionally via a linker, to a conjugate moiety. Linkage can be accomplished by covalent chemical bonds, physical forces such electrostatic, hydrogen, ionic, van der Waals, or hydrophobic or hydrophilic interactions. A variety of non-covalent coupling systems may be used, including biotin-avidin, ligand/receptor, enzyme/substrate, nucleic acid/nucleic acid binding protein, lipid/lipid binding protein, cellular adhesion molecule partners; or any binding partners or fragments thereof which have affinity for each other.

The peptide can be linked to conjugate moieties via direct covalent linkage by reacting targeted amino acid residues of the peptide with an organic derivatizing agent that is capable of reacting with selected side chains or the N- or C-terminal residues of these targeted amino acids. Reactive groups on the peptide or conjugate include, e.g., an aldehyde, amino, ester, thiol, α-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, the conjugate moieties can be linked to the peptide indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, 0-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N=C=N—R'), where R and R' are different alkyl groups, such as 1-cyclohexyl-3-(2-morpholinyl-4-ethyl)carbodiimide or 1-ethyl-3-(4-azonia-4,4-dimethylpentyl)carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagines or glutamine, acetylation of the N-terminal amine, and/or amidation or esterification of the C-terminal carboxylic acid group.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO87/05330 published 11 Sep. 1987, and in Aplin and Wriston, CRC Crit. Rev. Biochem., pp. 259-306 (1981).

Exemplary conjugate moieties that can be linked to any of the insulin analogs described herein include but are not limited to a heterologous peptide or polypeptide (including for example, a plasma protein), a targeting agent, an immunoglobulin or portion thereof (e.g. variable region, CDR, or Fc region), a diagnostic label such as a radioisotope, fluorophore or enzymatic label, a polymer including water soluble polymers, or other therapeutic or diagnostic agents. In one embodiment a conjugate is provided comprising an insulin analog disclosed herein and a plasma protein, wherein the plasma protein is selected form the group consisting of albumin, transferin, fibrinogen and globulins.

In one embodiment, the linker comprises a chain of atoms from 1 to about 60, or 1 to 30 atoms or longer, 2 to 5 atoms, 2 to 10 atoms, 5 to 10 atoms, or 10 to 20 atoms long. In one embodiment, the chain atoms are all carbon atoms. In one embodiment, the chain atoms in the backbone of the linker are selected from the group consisting of C, O, N, and S. Chain atoms and linkers may be selected according to their expected solubility (hydrophilicity) so as to provide a more soluble conjugate. In one embodiment, the linker provides a functional group that is subject to cleavage by an enzyme or other catalyst or hydrolytic conditions found in the target tissue or organ or cell. In one embodiment, the length of the linker is long enough to reduce the potential for steric hindrance. If the linker is a covalent bond or a peptidyl bond and the conjugate is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may alternatively be produced by recombinant genetic engineering methods known to one of ordinary skill in the art.

As noted above, in one embodiment, the insulin analogs are conjugated, e.g., fused to an immunoglobulin or portion thereof (e.g. variable region, CDR, or Fc region). Known types of immunoglobulins (Ig) include IgG, IgA, IgE, IgD or IgM. The Fc region is a C-terminal region of an Ig heavy chain, which is responsible for binding to Fc receptors that carry out activities such as recycling (which results in prolonged half-life), antibody dependent cell-mediated cytotoxicity (ADCC), and complement dependent cytotoxicity (CDC).

For example, according to some definitions the human IgG heavy chain Fc region stretches from Cys226 to the C-terminus of the heavy chain. The "hinge region" generally extends from Glu216 to Pro230 of human IgG1 (hinge regions by other IgG isotypes may be aligned with the IgG1 sequence by aligning the cysteines involved in cysteine bonding). The Fc region of an IgG includes two constant domains, CH2 and CH3. The CH2 domain of a human IgG Fc region usually extends from amino acids 231 to amino acid 341. The CH3 domain of a human IgG Fc region usually extends from amino acids 342 to 447. References made to amino acid numbering of immunoglobulins or immunoglobulin fragments, or regions, are all based on Kabat et al. 1991, Sequences of Proteins of Immunological Interest, U.S. Department of Public Health, Bethesda, Md. In a related embodiments, the Fc region may comprise one or more native or modified constant regions from an immunoglobulin heavy chain, other than CH1, for example, the CH2 and CH3 regions of IgG and IgA, or the CH3 and CH4 regions of IgE.

Suitable conjugate moieties include portions of immunoglobulin sequence that include the FcRn binding site. FcRn, a salvage receptor, is responsible for recycling immunoglobulins and returning them to circulation in blood. The region of the Fc portion of IgG that binds to the FcRn receptor has been described based on X-ray crystallography (Burmeister et al. 1994, Nature 372:379). The major contact area of the Fc with the FcRn is near the junction of the CH2 and CH3 domains. Fc-FcRn contacts are all within a single Ig heavy chain. The major contact sites include amino acid residues 248, 250-257, 272, 285, 288, 290-291, 308-311, and 314 of the CH2 domain and amino acid residues 385-387, 428, and 433-436 of the CH3 domain.

Some conjugate moieties may or may not include FcγR binding site(s). FcγR are responsible for ADCC and CDC. Examples of positions within the Fc region that make a direct contact with FcγR are amino acids 234-239 (lower hinge region), amino acids 265-269 (B/C loop), amino acids 297-299 (C'/E loop), and amino acids 327-332 (F/G) loop (Sondermann et al., Nature 406: 267-273, 2000). The lower hinge region of IgE has also been implicated in the FcRI binding (Henry, et al., Biochemistry 36, 15568-15578, 1997). Residues involved in IgA receptor binding are described in Lewis et al., (J. Immunol. 175:6694-701, 2005). Amino acid residues involved in IgE receptor binding are described in Sayers et al. (J Biol. Chem. 279(34):35320-5, 2004).

Amino acid modifications may be made to the Fc region of an immunoglobulin. Such variant Fc regions comprise at least one amino acid modification in the CH3 domain of the Fc region (residues 342-447) and/or at least one amino acid modification in the CH2 domain of the Fc region (residues 231-341). Mutations believed to impart an increased affinity for FcRn include T256A, T307A, E380A, and N434A (Shields et al. 2001, J. Biol. Chem. 276:6591). Other mutations may reduce binding of the Fc region to FcγRI, FcγRIIA, FcγRIIB, and/or FcγRIIIA without significantly reducing affinity for FcRn. For example, substitution of the Asn at position 297 of the Fc region with Ala or another amino acid removes a highly conserved N-glycosylation site and may result in reduced immunogenicity with concomitant prolonged half-life of the Fc region, as well as reduced binding to FcγRs (Routledge et al. 1995, Transplantation 60:847; Friend et al. 1999, Transplantation 68:1632; Shields et al. 1995, J. Biol. Chem. 276:6591). Amino acid modifications at positions 233-236 of IgG1 have been made that reduce binding to FcγRs (Ward and Ghetie 1995, Therapeutic Immunology 2:77 and Armour et al. 1999, Eur. J. Immunol. 29:2613). Some exemplary amino acid substitutions are described in U.S. Pat. Nos. 7,355,008 and 7,381,408, each incorporated by reference herein in its entirety.

Acylation and Alkylation

In accordance with one embodiment, the insulin analogs disclosed herein are modified to comprise an acyl group or alkyl group. Acylation or alkylation can increase the half-life of the insulin analogs in circulation. Acylation or alkylation can advantageously delay the onset of action and/or extend the duration of action at the insulin and/or IGF-1 receptors and/or improve resistance to proteases such as DPP-IV and/or improve solubility. Insulin analogs may be acylated or alkylated at the same amino acid position where a hydrophilic moiety is linked, or at a different amino acid position.

In one embodiment, the invention provides an insulin analog modified to comprise an acyl group or alkyl group covalently linked to the amino acid at a position corresponding to A10, B28, B29 of native insulin, or at the C-terminus or N-terminus of the A or B chain. The Insulin analog may further comprise a spacer between the Insulin analog amino acid and the acyl group or alkyl group. In one embodiment, the acyl group is a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The spacer is any moiety with suitable reactive groups for attaching acyl or alkyl groups. In exemplary embodiments, the spacer comprises an amino acid, a dipeptide, or a tripeptide, or a hydrophilic bifunctional spacer. In one embodiment, the spacer is selected from the group consisting of: Trp, Glu, Asp, Cys and a spacer comprising NH₂(CH₂CH₂O)n(CH₂)mCOOH, wherein m is any integer from 1 to 6 and n is any integer from 2 to 12. Such acylated or alkylated insulin peptides may also further comprise a hydrophilic moiety, optionally a polyethylene glycol. Any of the foregoing insulin analogs may comprise two acyl groups or two alkyl groups, or a combination thereof.

Acylation can be carried out at any positions within the insulin analog, provided that insulin analog insulin agonist activity is retained. The acyl group can be covalently linked directly to an amino acid of the insulin analog, or indirectly to an amino acid of the insulin analog via a spacer, wherein the spacer is positioned between the amino acid of the insulin peptide and the acyl group. In a specific aspect of the invention, the insulin analog is modified to comprise an acyl group by direct acylation of an amine, hydroxyl, or thiol of a side chain of an amino acid of the insulin peptide. In one embodiment, the insulin analog is directly acylated through the side chain amine, hydroxyl, or thiol of an amino acid. In one embodiment, acylation is at a position corresponding to A10, B28, B29 of native insulin, or at the C-terminus or N-terminus of the A or B chain. In this regard, the acylated insulin analog can comprise the amino acid sequence of SEQ ID NO: 9 and SEQ ID NO: 10, or a modified amino acid sequence thereof comprising one or more of the amino acid modifications described herein, with at least one of the amino acids at a position corresponding to A10, B28, B29 of native insulin, or at the C-terminus or N-terminus of the A or B chain modified to any amino acid comprising a side chain amine, hydroxyl, or thiol. In some specific embodiments, the direct acylation of the insulin peptide occurs through the side chain amine, hydroxyl, or thiol of the amino acid at a position corresponding to A10, B28, B29 of native insulin. In accordance with one embodiment one of the amino acid side chains of the dipeptide element is acylated.

In one embodiment, the amino acid to be acylated is an amino acid of Formula IV:

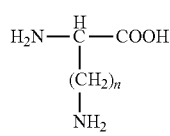

[Formula IV]

wherein n = 1 to 4

In some exemplary embodiments, the amino acid of Formula IV, is the amino acid wherein n is 4 (Lys) or n is 3 (Orn).

In other embodiments, the amino acid comprising a side chain hydroxyl is an amino acid of Formula V:

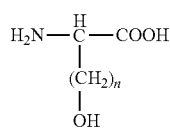

[Formula V]

wherein n = 1 to 4

In some exemplary embodiments, the amino acid of Formula V is the amino acid wherein n is 1 (Ser).

In yet other embodiments, the amino acid comprising a side chain thiol is an amino acid of Formula VI:

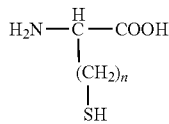

[Formula VI]

wherein n = 1 to 4

In some exemplary embodiments, the amino acid of Formula VI is the amino acid wherein n is 1 (Cys).

In some exemplary embodiments, the insulin analog is modified to comprise an acyl group by acylation of an amine, hydroxyl, or thiol of a spacer, which spacer is attached to a side chain of an amino acid at position A10, B28 or B29 (according to the amino acid numbering of wild type insulin). The amino acid to which the spacer is attached can be any amino acid comprising a moiety which permits linkage to the spacer. For example, an amino acid comprising a side chain NH2, —OH, or —COOH (e.g., Lys, Orn, Ser, Asp, or Glu) is suitable. In one embodiment, the spacer is an amino acid comprising a side chain amine, hydroxyl, or thiol, or a dipeptide or tripeptide comprising an amino acid comprising a side chain amine, hydroxyl, or thiol.

When acylation occurs through an amine group of a spacer the acylation can occur through the alpha amine of the amino acid or a side chain amine. In the instance in which the alpha amine is acylated, the spacer amino acid can be any amino acid. For example, the spacer amino acid can be a hydrophobic amino acid, e.g., Gly, Ala, Val, Leu, Ile, Trp, Met, Phe, Tyr. Alternatively, the spacer amino acid can be an acidic residue, e.g., Asp and Glu. In the instance in which the side chain amine of the spacer amino acid is acylated, the spacer amino acid is an amino acid comprising a side chain amine, e.g., an amino acid of Formula I (e.g., Lys or Orn). In this instance, it is possible for both the alpha amine and the side chain amine of the spacer amino acid to be acylated, such that the insulin peptide is diacylated. The present disclosure further contemplates diacylated insulin analogs.

When acylation occurs through a hydroxyl group of a spacer, the amino acid or one of the amino acids of the dipeptide or tripeptide can be an amino acid of Formula II. In a specific exemplary embodiment, the amino acid is Ser.

When acylation occurs through a thiol group of a spacer, the amino acid or one of the amino acids of the dipeptide or tripeptide can be an amino acid of Formula III. In a specific exemplary embodiment, the amino acid is Cys.

In one embodiment, the spacer comprises a hydrophilic bifunctional spacer. In a specific embodiment, the spacer comprises an amino poly(alkyloxy)carboxylate. In this regard, the spacer can comprise, for example, NH₂(CH₂CH₂O)ₙ(CH₂)ₘCOOH, wherein m is any integer from 1 to 6 and n is any integer from 2 to 12, such as, e.g., 8-amino-3,6-dioxaoctanoic acid, which is commercially available from Peptides International, Inc. (Louisville, Ky.).

Suitable methods of peptide acylation via amines, hydroxyls, and thiols are known in the art. See, for example, Miller, *Biochem Biophys Res Commun* 218: 377-382 (1996); Shimohigashi and Stammer, *Int J Pept Protein Res* 19: 54-62 (1982); and Previero et al., *Biochim Biophys Acta* 263: 7-13 (1972) (for methods of acylating through a hydroxyl); and San and Silvius, *J Pept Res* 66: 169-180 (2005) (for methods of acylating through a thiol); *Bioconjugate Chem*. "Chemical Modifications of Proteins: History and Applications" pages 1, 2-12 (1990); Hashimoto et al., *Pharmacuetical Res*. "Synthesis of Palmitoyl Derivatives of Insulin and their Biological Activity" Vol. 6, No: 2 pp. 171-176 (1989).

The acyl group of the acylated insulin peptide can be of any size, e.g., any length carbon chain, and can be linear or branched. In some specific embodiments of the invention, the acyl group is a C4 to C30 fatty acid. For example, the acyl group can be any of a C4 fatty acid, C6 fatty acid, C8 fatty acid, C10 fatty acid, C12 fatty acid, C14 fatty acid, C16 fatty acid, C18 fatty acid, C20 fatty acid, C22 fatty acid, C24 fatty acid, C26 fatty acid, C28 fatty acid, or a C30 fatty acid. In one embodiment, the acyl group is a C8 to C20 fatty acid, e.g., a C14 fatty acid or a C16 fatty acid.

In an alternative embodiment, the acyl group is a bile acid. The bile acid can be any suitable bile acid, including, but not limited to, cholic acid, chenodeoxycholic acid, deoxycholic acid, lithocholic acid, taurocholic acid, glycocholic acid, and cholesterol acid.

In a specific embodiment, the insulin analog comprises a cholesterol acid, which is linked to a Lys residue of the insulin analog through an alkylated des-amino Cys spacer, i.e., an alkylated 3-mercaptopropionic acid spacer. The alkylated des-amino Cys spacer can be, for example, a des-amino-Cys spacer comprising a dodecaethylene glycol moiety. In one embodiment, the insulin analog comprises the structure:

suitable spacers include a spacer comprising one or more amino acids selected from the group consisting of Cys, Lys, Orn, homo-Cys, and Ac-Phe.

In accordance with one embodiment, the insulin analog is modified to comprise an alkyl group which is attached to the insulin analog via an ester, ether, thioether, amide, or alkyl amine linkage for purposes of prolonging half-life in circulation and/or delaying the onset of and/or extending the duration of action and/or improving resistance to proteases such as DPP-IV.

The alkyl group of the alkylated insulin peptide can be of any size, e.g., any length carbon chain, and can be linear or branched. In one embodiment of the invention, the alkyl group is a C1 to C30 alkyl. For example, the alkyl group can be any of a C1 alkyl, C2 alkyl, C3 alkyl, C4 alkyl, C6 alkyl, C8 alkyl, C10 alkyl, C12 alkyl, C14 alkyl, C16 alkyl, C18 alkyl, C20 alkyl, C22 alkyl, C24 alkyl, C26 alkyl, C28 alkyl, or a C30 alkyl. In one embodiment, the alkyl group is a C8 to C20 alkyl, e.g., a C14 alkyl or a C16 alkyl.

In some specific embodiments, the alkyl group comprises a steroid moiety of a bile acid, e.g., cholic acid, chenodeoxycholic acid, deoxycholic acid, lithocholic acid, taurocholic acid, glycocholic acid, and cholesterol acid.

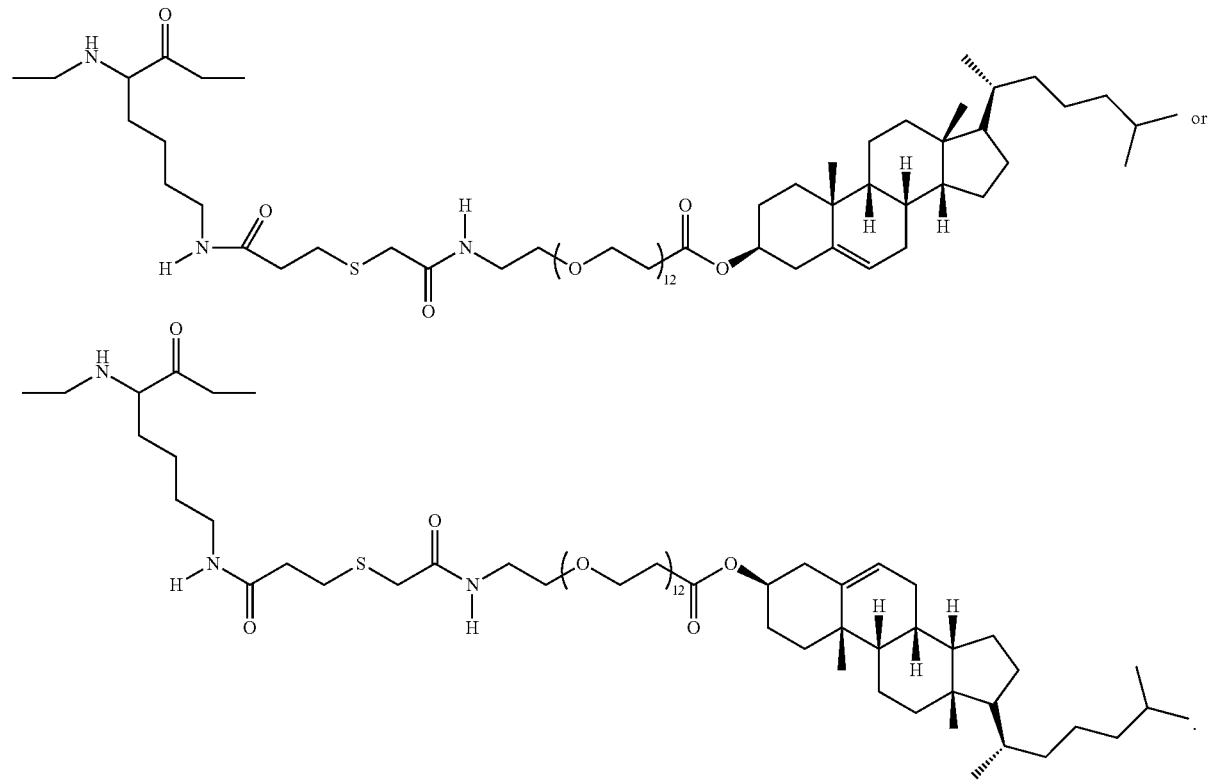

The acylated insulin analogs described herein can be further modified to comprise a hydrophilic moiety. In some specific embodiments the hydrophilic moiety can comprise a polyethylene glycol (PEG) chain. The incorporation of a hydrophilic moiety can be accomplished through any suitable means, such as any of the methods described herein.

Alternatively, the acylated insulin peptide can comprise a spacer, wherein the spacer is both acylated and modified to comprise the hydrophilic moiety. Nonlimiting examples of In accordance with some embodiments the dipeptide prodrug element can be further modified to comprise a hydrophilic moiety. In some embodiments the hydrophilic moiety is a polyethylene glycol chain. In accordance with some embodiments a polyethylene glycol chain of 40 k or higher is covalently bound to the side chain of the A or B amino acid of the dipeptide prodrug element. In another embodiment the dipeptide prodrug element is additionally or alternatively acylated or alkylated with a fatty acid or bile acid, or salt thereof, e.g. a C4 to C30 fatty acid, a C8 to C24 fatty acid, cholic acid, a C4 to C30 alkyl, a C8 to C24 alkyl, or an alkyl comprising a steroid moiety of a bile acid. The 'A' amino acid of the dipeptide prodrug element can include, for example, d-lysine covalently bound to an acyl or alkyl group through its side chain amino group, or d-cysteine covalently bound to a PEG molecule through its side chain sulfhydryl group. The dipeptide prodrug element can be directly bound to the hydrophilic moiety, acyl group, or alkyl group, or bound to the hydrophilic moiety, acyl group, or alkyl group through a spacer, as described herein. Alternatively, the dipeptide prodrug element can be linked to a depot protein such as dextran or a large PEG molecule (greater or equal to 80,000 daltons) that serves to sequester the prodrug at an injection site until cleavage of the dipeptide releases the active insulin peptide (Q).

Effect of Dipeptide Prodrug Element Structure on Cleavage Rate

As previously described herein, the rate of cleavage of the dipeptide prodrug element A-B from the bioactive peptide (e.g., insulin peptide (Q)), and thus activation of the prodrug, depends on the structure (including N-alkylation, number of substituents, length or bulkiness), and stereochemistry of the amino acids of the dipeptide prodrug element. The rate of cleavage of the dipeptide prodrug element A-B from the (e.g., insulin peptide (Q)) also depends on the steric hindrance, nucleophilicity, and stability of the leaving group of Q during diketopiperazine formation. Some of these structural features are described in Category I, Category II, and Category III below, which form part of the invention. Explicitly excluded from any of these categories are peptide sequences disclosed in Int'l Application No. PCT/US2009/68745, filed Dec. 18, 2009 or its sequence listing, and sub-categories of (1) dipeptide prodrug elements, (2) A amino acids, and/or (3) B amino acids disclosed in Int'l Application No. PCT/US2009/68745, filed Dec. 18, 2009, to the extent they fall completely within and/or overlap with a portion of any of the sub-categories described herein, and only to the extent necessary to confer novelty on claimed subject matter.

In accordance with one embodiment a auto-cleaving dipeptide element (A-B) is covalently linked to the insulin peptide (Q) through an amide bond between A-B and an aliphatic amino group of Q. For example, the aliphatic amino group A-B is linked to can be the alpha amino group on the N-terminal amino acid of the A chain or the B chain. Alternatively, the aliphatic amino group A-B is linked to can be an aliphatic amino group on a side chain of Q. In one embodiment A-B is linked to the side chain amine of a lysine, including for example at position B29 of the b chain sequence FVNQHLCGSHLVEALYLVCGERGFFYTPKT (SEQ ID NO: 8) or at position B28 of the B chain sequence FVNQHLCGSHLVEALYLVCGERGFFYTKPT (SEQ ID NO: 9).

In one embodiment Q is an insulin peptide comprising an A chain and a B chain wherein the A chain comprises the sequence GIVEQCCX$_1$SICSLYQLENX$_2$CX$_3$ (SEQ ID NO: 3) and the B chain comprises the sequence of X$_{14}$-X$_4$LCGX$_5$X$_6$LVEALX$_7$LVCG ERGFX$_8$ (SEQ ID NO: 14), wherein X$_{14}$ is a bond, or a 1 to 4 amino acid sequence selected from the group consisting of a FVNQ (SEQ ID NO: 11), VNQ, NQ and Q;

X$_1$ is selected from the group consisting of threonine and histidine;

X$_2$ is an amino acid of the general structure

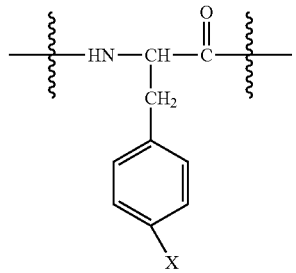

wherein X is selected from the group consisting of OH, NH$_2$ and OCH$_3$;

X$_3$ is selected from the group consisting of asparagine, ornithine, glycine, alanine, threonine, and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

X$_7$ is tyrosine;

X$_8$ is histidine, asparagine or tyrosine, wherein A-B is linked to Q through an amide bond between A-B and an aliphatic amino group of Q.

In one embodiment Q is an insulin peptide comprising an A chain and a B chain wherein Q is an insulin peptide comprising an A chain and a B chain wherein the A chain comprises the sequence GIVEQCCX$_1$SICSLYQLENX$_2$CX$_3$ (SEQ ID NO: 3) and the B chain comprises the sequence of X$_{14}$-X$_4$LCGX$_5$X$_6$LVEALX$_7$LVCG ERGFX$_8$ (SEQ ID NO: 14), wherein X$_{14}$ is a bond, or a 1 to 4 amino acid sequence selected from the group consisting of a FVNQ (SEQ ID NO: 11), VNQ, NQ and Q;

X$_1$ is selected from the group consisting of threonine and histidine;

X$_2$ is an amino acid of the general structure

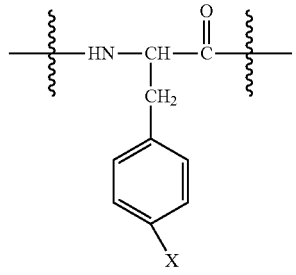

wherein X is selected from the group consisting of OH, NH$_2$, NHR$_{10}$ and OCH$_3$, wherein R$_{10}$ is a dipeptide of the general structure A-B;

X$_3$ is selected from the group consisting of asparagine, ornithine, glycine, alanine, threonine, and serine;

X$_4$ is selected from the group consisting of histidine and threonine;

X$_5$ is selected from the group consisting of alanine, glycine and serine;

X$_6$ is selected from the group consisting of histidine, aspartic acid, glutamic acid, homocysteic acid and cysteic acid;

$X_7$ is an amino acid of the general structure

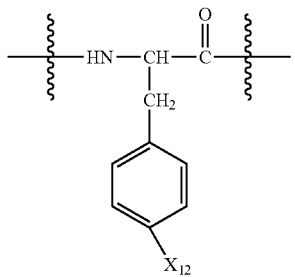

wherein $X_{12}$ is selected from the group consisting of OH, $NH_2$, $NHR_{11}$ and $OCH_3$, wherein $R_{11}$ is a dipeptide of the general structure A-B;

$X_8$ is histidine, asparagine or an amino acid of the general structure

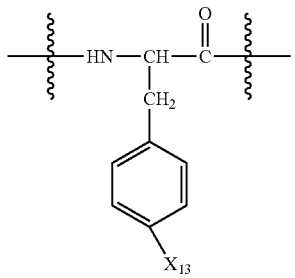

wherein $X_{13}$ is selected from the group consisting of H, OH, $NH_2$, $NHR_{12}$ and $OCH_3$, wherein $R_{12}$ is a dipeptide of the general structure A-B, wherein A-B is linked to Q through an amide bond between A-B and an aromatic amino group on an amino acid side chain of Q.

Category I: Composition of Amino Acid B of the Dipeptide Prodrug Element

In some embodiments, the half-life of the prodrug, e.g., the chemical cleavage half-life ($t_{1/2}$) of A-B from Q of at least about 1 hour to about 1 week in PBS, under physiological conditions, is dependent on the presence and length of the N-alkyl substituent on the B amino acid. For example, a prodrug that has a shorter N-alkyl substituent on the B amino acid (e.g. Gly(N-methyl)), will undergo a slower rate of cleavage of A-B, and have a longer half-life, than a prodrug that has a longer N-alkyl substituent on the B amino acid (e.g., Gly(N-hexyl)).

In some embodiments, the half-life of the prodrug is dependent on the presence or absence of an alkyl side chain, and the degree of substitution at the beta position of the alkyl side chain, of the B amino acid of the dipeptide prodrug element. For example, a prodrug that has an N-alkylated B amino acid that is disubstituted at the beta position (e.g., N-alkylated isoleucine) will undergo slower cleavage of A-B, and have a longer half-life, than a prodrug that has an N-alkylated B amino acid that is monosubstituted at the beta position (e.g., N-alkylated leucine). Further, a prodrug that has an N-alkylated B amino acid that is monosubstituted at the beta position (e.g., N-alkylated leucine) will undergo slower cleavage of A-B, and have a longer half-life, than a prodrug that has an N-alkylated B amino acid that is unsubstituted at the beta position (e.g., N-alkylated alanine). Further still, a prodrug with an N-alkylated B amino acid that has an unsubstituted beta position (e.g., N-alkylated alanine) will undergo slower cleavage of A-B, and have a longer half-life, than a prodrug that has glycine or N-alkylated glycine as the B amino acid.

In some embodiments, the half-life of the prodrug is dependent on the bulkiness of the side chain of the B amino acid. For example, a prodrug that has a bulkier side chain on the B amino acid (e.g., N-alkylated phenylalanine), will undergo slower cleavage of A-B, and have a longer half-life, than a prodrug that has a less bulky side chain on the B amino acid (e.g., N-alkylated alanine). Cleavage rates of dipeptides can be further differentiated by the amine of the drug (e.g., insulin) to which they are attached. More particularly the same dipeptide will cleave at a faster rate when linked to an aromatic amine relative to an N-terminal amine, where the dipeptide linked to an N-terminal amine will cleave at a faster rate relative to when the dipeptide is linked to the side chain amine of a lysine residue.

The composition of the B amino acid of the dipeptide prodrug element can be classified into the below sub-categories IA, IB, and IC. Generally, the dipeptide prodrug elements in sub-category IA undergo cleavage the fastest and the dipeptide prodrug elements in sub-category IC undergo cleavage the slowest.

Sub-Category IA: Amino Acid B of the Dipeptide Prodrug Element is N-Alkylated Glycine In some embodiments, the prodrug comprises the structure:

A-B-Q;

wherein Q is a bioactive peptide (e.g., an insulin peptide); wherein A-B comprises the structure:

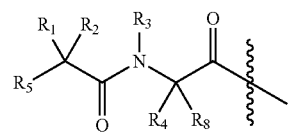

I wherein $R_1$ and $R_2$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl;

$R_3$ is $C_1$-$C_{18}$ alkyl;

$R_4$ and $R_8$ are each H;

$R_5$ is $NHR_6$;

$R_6$ is H or $C_1$-$C_4$ alkyl, or $R_5$ and $R_2$ together with the atoms to which they are attached form a 4, 5 or 6 member heterocyclic ring; and, $R_7$ is selected from the group consisting of H and OH.

In some embodiments, the B amino acid is selected from the group consisting of glycine(N-methyl), glycine(N-ethyl), glycine(N-propyl), glycine(N-butyl), glycine(N-pentyl), glycine(N-hexyl), glycine(N-heptyl), and glycine(N-octyl). For example, the B amino acid can be glycine(N-methyl) or glycine(N-hexyl).

In some embodiments when $R_1$ and $R_2$ are both hydrogen, $R_3$ is $C_1$-$C_4$ alkyl. In some embodiments when one of $R_1$ or $R_2$ is other than hydrogen, $R_3$ is $C_1$-$C_4$ alkyl.

Sub-Category IB: Amino Acid B of the Dipeptide Prodrug Element is Unsubstituted or Monosubstituted at the Beta Position In some embodiments, the prodrug comprises the structure:

A-B-Q;

wherein Q is a bioactive peptide (e.g., an insulin peptide); wherein A-B comprises the structure:

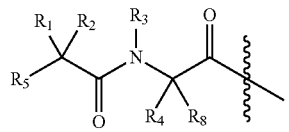

I wherein $R_1$ and $R_2$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl;

$R_3$ is $C_1$-$C_{18}$ alkyl;

$R_4$ is selected from the group consisting of CH$_3$, CH$_2$($C_1$-$C_{10}$ alkyl), CH$_2$($C_2$-$C_{10}$ alkenyl), CH$_2$($C_0$-$C_{10}$ alkyl)OH, CH$_2$($C_0$-$C_{10}$ alkyl)SH, CH$_2$($C_0$-$C_3$ alkyl)SCH$_3$, CH$_2$($C_0$-$C_3$ alkyl)CONH$_2$, CH$_2$($C_0$-$C_3$ alkyl)COOH, CH$_2$($C_0$-$C_3$ alkyl)NH$_2$, CH$_2$($C_0$-$C_3$ alkyl)NHC(NH$_2^+$)NH$_2$, CH$_2$($C_0$-$C_3$ alkyl)($C_3$-$C_6$ cycloalkyl), CH$_2$($C_0$-$C_3$ alkyl)($C_2$-$C_5$ heterocyclic), CH$_2$($C_0$-$C_3$ alkyl)($C_6$-$C_{10}$ aryl)$R_7$, CH$_2$($C_1$-$C_3$ alkyl)($C_3$-$C_9$ heteroaryl), and CH$_2$($C_0$-$C_{12}$ alkyl)($W_1$)$C_1$-$C_{12}$ alkyl, wherein $W_1$ is a heteroatom selected from the group consisting of N, S and O; or $R_4$ and $R_3$ together with the atoms to which they are attached form a 4, 5 or 6 member heterocyclic ring;

$R_8$ is H;

$R_5$ is NHR$_6$, or $R_5$ and $R_2$ together with the atoms to which they are attached form a 4, 5 or 6 member heterocyclic ring;

$R_6$ is H or $C_1$-$C_4$ alkyl; and, $R_7$ is selected from the group consisting of H and OH.

In some embodiments, $R_4$ is selected from the group consisting of CH$_3$, CH$_2$($C_1$-$C_4$ alkyl), CH$_2$($C_1$-$C_4$)alkenyl, CH$_2$($C_0$-$C_4$ alkyl)OH, CH$_2$($C_0$-$C_4$ alkyl)SH, CH$_2$($C_0$-$C_3$ alkyl)SCH$_3$, CH$_2$($C_0$-$C_3$ alkyl)CONH$_2$, CH$_2$($C_0$-$C_3$ alkyl)COOH, CH$_2$($C_0$-$C_4$ alkyl)NH$_2$, and CH$_2$($C_0$-$C_3$ alkyl)NHC(NH$_2^+$)NH$_2$.

Nonlimiting examples of the B amino acid in these embodiments include alanine(N—$C_1$-$C_{10}$alkyl), leucine(N—$C_1$-$C_{10}$alkyl), methionine(N—$C_1$-$C_{10}$alkyl), asparagine(N—$C_1$-$C_{10}$alkyl), glutamic acid(N—$C_1$-$C_{10}$alkyl), aspartic acid(N—$C_1$-$C_{10}$alkyl), glutamine(N—$C_1$-$C_{10}$alkyl), histidine(N—$C_1$-$C_{10}$ alkyl), lysine(N—$C_1$-$C_{10}$alkyl), arginine(N—$C_1$-$C_{10}$alkyl), serine(N—$C_1$-$C_{10}$alkyl), and cysteine(N—$C_1$-$C_{10}$alkyl).

In some embodiments, the B amino acid is selected from the group consisting of alanine(N—$C_1$-$C_6$alkyl), leucine(N—$C_1$-$C_6$alkyl), methionine(N—$C_1$-$C_6$alkyl), asparagine(N—$C_1$-$C_6$alkyl), glutamic acid(N—$C_1$-$C_6$alkyl), aspartic acid(N—$C_1$-$C_6$alkyl), glutamine(N—$C_1$-$C_6$alkyl), histidine(N—$C_1$-$C_6$alkyl), lysine(N—$C_1$-$C_6$alkyl), arginine(N—$C_1$-$C_6$alkyl), serine(N—$C_1$-$C_6$alkyl), and cysteine(N—$C_1$-$C_6$alkyl).

For example, the B amino acid can include alanine(N-methyl), leucine(N-methyl), methionine(N-methyl), asparagine(N-methyl), glutamic acid(N-methyl), aspartic acid(N-methyl), glutamine(N-methyl), histidine(N-methyl), lysine(N-methyl), arginine(N-methyl), serine(N-methyl), and cysteine(N-methyl).

In some embodiments, $R_4$ is selected from the group consisting of CH$_2$($C_0$-$C_3$ alkyl)($C_3$-$C_6$ cycloalkyl), CH$_2$($C_0$-$C_3$ alkyl)($C_2$-$C_5$ heterocyclic), CH$_2$($C_0$-$C_3$ alkyl)($C_6$-$C_{10}$ aryl)$R_7$, CH$_2$($C_1$-$C_3$ alkyl)($C_3$-$C_9$ heteroaryl), and CH$_2$($C_0$-$C_{12}$ alkyl)($W_1$)$C_1$-$C_{12}$ alkyl, wherein $W_1$ is a heteroatom selected from the group consisting of N, S and O, and wherein $R_7$ is selected from the group consisting of H and OH.

Nonlimiting examples of the B amino acid in these embodiments include phenylalanine(N—$C_1$-$C_{10}$alkyl), tyrosine(N—$C_1$-$C_{10}$alkyl), and tryptophan(N—$C_1$-$C_{10}$alkyl). In some embodiments, the B amino acid is selected from the group consisting of phenylalanine(N—$C_1$-$C_6$alkyl), tyrosine(N—$C_1$-$C_6$alkyl), and tryptophan(N—$C_1$-$C_6$alkyl). For example, the B amino acid can include phenylalanine(N-methyl), tyrosine(N-methyl), and tryptophan(N-methyl).

In some embodiments, the B amino acid is proline. In some embodiments, proline is excluded from Sub-Category IB.

Sub-Category IC: Amino Acid B of the Dipeptide Prodrug Element Disubstituted at the Beta Position In some embodiments, the prodrug comprises the structure:

A-B-Q;

wherein Q is a bioactive peptide (e.g., an insulin peptide); wherein A-B comprises the structure:

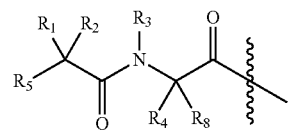

I wherein $R_1$ and $R_2$ are independently selected from the group consisting of H, $C_1$-$C_{1s}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl; or $R_1$ and $R_2$ together with the atoms to which they are attached form a $C_3$-$C_{12}$ cycloalkyl;

$R_3$ is $C_1$-$C_{18}$ alkyl;

$R_4$ is independently selected from the group consisting of CH($C_1$-$C_8$ alkyl)$_2$, CH($C_2$-$C_8$ alkenyl)$_2$, CH($C_1$-$C_8$ alkyl)(OH), CH($C_1$-$C_8$ alkyl)(($C_1$-$C_8$ alkyl)SH), CH($C_1$-$C_3$ alkyl)(($C_1$-$C_8$ alkyl)(NH$_2$));

$R_8$ is H;

$R_5$ is NHR$_6$, or $R_5$ and $R_2$ together with the atoms to which they are attached form a 4, 5 or 6 member heterocyclic ring;

$R_6$ is H or $C_1$-$C_4$ alkyl; and, $R_7$ is selected from the group consisting of H and OH.

In some embodiments, $R_4$ is $CH(C_1$-$C_8$ alkyl$)_2$ or $CH(C_1$-$C_8$ alkyl)OH. Nonlimiting examples of the B amino acid include isoleucine(N—$C_1$-$C_{10}$alkyl), valine(N—$C_1$-$C_{10}$alkyl), and threonine(N—$C_1$-$C_{10}$alkyl). In some embodiments, the B amino acid is selected from the group consisting of isoleucine(N—$C_1$-$C_6$alkyl), valine(N—$C_1$-$C_6$alkyl), and threonine(N—$C_1$-$C_6$alkyl). For example, the B amino acid can include isoleucine(N-methyl), valine(N-methyl), and threonine(N-methyl).

Category II: Composition of Amino Acid A of the Dipeptide Prodrug Element

In some embodiments, the half-life of the prodrug is dependent on the number of substituents at the alpha position of the A amino acid. For example, a prodrug comprising an A amino acid that is an α-monosubstituted amino acid (e.g., Ala) will undergo cleavage more slowly, and have a longer half-life than, a prodrug comprising an A amino acid that is an α,α-disubstituted amino acid (e.g., Aib).

In some embodiments, the half-life of the prodrug is dependent on the degree of alkylation on the alpha amino group of the A amino acid. Generally, the greater the degree of alkylation, the slower the rate of cleavage and the longer the half-life of the prodrug. For example, a dipeptide prodrug element having N-alkylated Ala will cleave at a slower rate, and have a longer half-life, than Ala.

The composition of the A amino acid of the dipeptide prodrug element can be classified into the below sub-categories IIA and IIB. Generally, the dipeptide prodrug elements in sub-category IIA cleave faster than dipeptide prodrug elements in sub-category IIB.

Sub-Category IIA: Amino Acid A of the Dipeptide Prodrug Element is Disubstituted at the Alpha Position In some embodiments, the A amino acid of the dipeptide prodrug element is disubstituted at the alpha position. In these embodiments, $R_1$ and $R_2$ of the structures described in sub-categories IA, IB, and IC are independently selected from the group consisting of $C_1$-$C_{10}$ alkyl, $C_2$-$C_{10}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl ($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl, and wherein $R_7$ is selected from the group consisting of H and OH.

For example, the A amino acid can include aminoisobutyric acid (Aib).

Sub-Category IIB: Amino Acid A of the Dipeptide Prodrug Element is Unsubstituted or Monosubstituted at the Alpha Position In some embodiments, the A amino acid of the dipeptide prodrug element is unsubstituted or monosubstituted at the alpha position. In these embodiments, $R_1$ of the structures described in sub-categories IA, IB, and IC is H, and $R_2$ of the structures described in sub-categories IA, IB, and IC is selected from the group consisting of H, $C_1$-$C_{10}$ alkyl, $C_2$-$C_{10}$ alkenyl, ($C_1$-$C_{10}$ alkyl)OH, ($C_1$-$C_{10}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $R_7$ is selected from the group consisting of H and OH, wherein $W_1$ is a heteroatom selected from the group consisting of N, S and O, or $R_1$ and $R_2$ together with the atoms to which they are attached form a $C_3$-$C_{12}$ cycloalkyl, or $R_2$ and $R_5$ together with the atoms to which they are attached form a 4, 5 or 6 member heterocyclic ring.

In some embodiments, the A amino acid of the dipeptide prodrug element has 'd' stereochemistry. Nonlimiting examples of the A amino acid in these embodiments include lysine, cysteine, and alanine. For example, d-lysine, d-cysteine, and d-alanine. In some embodiments, d-stereochemistry may enhance half-life through reducing proteolytic degradation of the prodrug peptide.

In some embodiments, the A amino acid is N-alkylated with a group that has 1 to 4 carbon atoms such as Ala(N—$C_1$-$C_4$alkyl), Lys(N—$C_1$-$C_4$alkyl), and Cys(N—$C_1$-$C_4$alkyl). For example, the A amino acid can be Ala(N-methyl), Lys(N-methyl), and Cys(N-methyl). N-alkylation of the A amino acid decreases the rate of cleavage of the dipeptide prodrug element from Q and provides a longer half-life.

Category III: Conjugation Site of the Dipeptide Prodrug Element (A-B) to the Peptide Drug (Q)

In some embodiments, the half-life of the prodrug depends on the steric hindrance, nucleophilicity, and stability of the leaving group on Q during diketopiperazine formation. The less sterically hindered the leaving group, the less nucleophilic the leaving group, or the more stable the leaving group after cleavage, the shorter the half life of the prodrug. The type of leaving group on Q can be determined by the type of the linkage between A-B and an amino group of Q, as described in sub-categories IIIA and IIIB below. Generally, dipeptide prodrug elements in sub-category IIIB cleave faster from Q and have a shorter half-life than dipeptide prodrug elements in subcategory IIIA.

Sub-Category IIIA: A-B Linked to an Aliphatic Amino Group of Q

In some embodiments, A-B is linked to Q through an amide bond between A-B and an aliphatic amino group of Q to result in a prodrug with a chemical cleavage half-life ($t_{1/2}$) of A-B from Q of at least about 1 hour to about 1 week in PBS, under physiological conditions, as previously described herein.

In some embodiments, A-B is linked to Q through an amide bond between A-B and the alpha amino group of the N-terminal amino acid of Q. For example, a dipeptide prodrug element having a B amino acid from any of sub-categories IA, IB, and IC and an A amino acid from any of sub-categories IIA and IIB can be linked to the N-terminal amino acid of Q to result in a prodrug with a chemical cleavage half-life ($t_{1/2}$) of A-B from Q of at least about 1 hour to about 1 week in PBS, under physiological conditions.

In some embodiments, A-B is linked to Q through an amide bond between A-B and an aliphatic amino group on a side chain of an amino acid of Q. For example, a dipeptide prodrug element having a B amino acid from any of sub-categories IA, IB, and IC and an A amino acid from any of sub-categories IIA and IIB can be linked to an aliphatic amino group of a side chain of an amino acid of Q to result in a prodrug with a chemical cleavage half-life ($t_{1/2}$) of A-B from Q of at least about 1 hour to about 1 week in PBS, under physiological conditions.

In some embodiments, when A-B is linked to Q through an amide bond between A-B and an aliphatic amino group of Q, either A should be an α,α-disubstituted amino acid (Sub-category IIA) or B should be N-alkylated (any of Sub-categories IA, IB or IC), or both. For example, when A is an α-monosubstituted amino acid (e.g., Ala), B is not N-alkylated, and A-B is attached to Q through an aliphatic amino group of Q, then there will not be significant cleavage of A-B.

In other embodiments, when A-B is linked to Q through an amide bond between A-B and an aliphatic amino group of Q, and A is an amino acid that is unsubstituted at the alpha position (e.g. glycine) and B is an amino acid from Sub-category IA (N-alkylated glycine), the N-alkyl substituent of the B amino acid has a length of at least five carbon atoms (for example, N—$C_5$-$C_8$alkyl).

In yet other embodiments, when A-B is linked to Q through an amide bond between A-B and an aliphatic amino group of Q, and the A amino acid is unsubstituted or monosubstituted at the alpha position (Sub-category IIB), the B amino acid is not proline.

Sub-Category IIIB: A-B Linked to an Aromatic Amino Group of Q

In some embodiments, A-B is linked to Q through an amide bond between A-B and an aromatic amino group of a side chain of an amino acid of Q to result in a prodrug with a chemical cleavage half-life ($t_{1/2}$) of A-B from Q of at least about 1 hour to about 1 week in PBS, under physiological conditions, as previously described herein. For example, a dipeptide prodrug element having a B amino acid from any of sub-categories IA, IB, and IC and an A amino acid from any of sub-categories IIA and IIB can be linked to an aromatic amino group of a side chain of an amino acid of Q to result in a prodrug with a chemical cleavage half-life ($t_{1/2}$) of A-B from Q of at least about 1 hour to about 1 week in PBS, under physiological conditions.

Any of the B amino acids defined by Category I can be combined with any of the A amino acids defined by Category II to form a dipeptide prodrug element. This dipeptide prodrug element can be linked to any of the positions described in Category III. The half life of the prodrug can be tuned through the selection of:
(i) the number of substituents on the alpha position of the A amino acid;
(ii) the degree of N-alkylation of the A and the B amino acids;
(iii) the number of substituents on the beta position of the B amino acid;
(iv) the bulkiness of the side chain of the B amino acid; and,
(iii) the steric hindrance, nucleophilicity, and stability of the leaving group on Q during diketopiperazine formation.

Modification of Dipeptide Prodrug Element A-B

The dipeptide prodrug elements described above can be further modified to comprise a hydrophilic moiety, an acyl group, or an alkyl group, as previously described herein. In some embodiments, the dipeptide prodrug element includes lysine that is conjugated to an acyl group or an alkyl group through its side chain amino group. In some embodiments, the dipeptide prodrug element includes cysteine that is conjugated to a hydrophilic moiety (e.g., 40 kD PEG) through the side chain sulfhydryl group. The hydrophilic moiety, acyl group, or alkyl group can be conjugated directly to the dipeptide prodrug element or through a spacer. In some exemplary embodiments, the hydrophilic group, the alkyl group and/or the acyl group are conjugated to the A amino acid of the dipeptide prodrug element.

In some embodiments, the following dipeptide prodrug elements are PEGylated: dCys-Gly(N-Hexyl) dCys-Gly(N-Methyl), and dCys-Phe(N-Methyl). In some embodiments, the following dipeptide prodrug elements include an acyl group: dLys-Gly(N-Hexyl), dLys-Gly(N-Methyl), and dLys-Phe(N-Methyl). In some embodiments, the following dipeptide prodrug elements include an alkyl group: dLys-Gly(N-Hexyl), dLys-Gly(N-Methyl), and dLys-Phe(N-Methyl).

Exemplary Embodiments

The dipeptide prodrug element of the invention can include combinations of any of the B amino acids from Category I with any of the A amino acids from Category II. Nonlimiting examples of amino acids suitable for the A amino acid and for the B amino acid of the dipeptide prodrug element are listed in the below Table.

| Amino Acid # | Amino Acid 'A' | Amino Acid 'B' |
|---|---|---|
| 1 | Aib | Gly(N-$C_1$-$C_8$alkyl) |
| 2 | Gly | Ala(N-$C_1$-$C_8$alkyl) |
| 3 | Ala | Leu(N-$C_1$-$C_8$alkyl) |
| 4 | Leu | Met(N-$C_1$-$C_8$alkyl) |
| 5 | Met | Asn(N-$C_1$-$C_8$alkyl) |
| 6 | Asn | Glu(N-$C_1$-$C_8$alkyl) |
| 7 | Glu | Asp(N-$C_1$-$C_8$alkyl) |
| 8 | Asp | Gln(N-$C_1$-$C_8$alkyl) |
| 9 | Gln | His(N-$C_1$-$C_8$alkyl) |
| 10 | His | Lys(N-$C_1$-$C_8$alkyl) |
| 11 | Lys | Arg(N-$C_1$-$C_8$alkyl) |
| 12 | Arg | Ser(N-$C_1$-$C_8$alkyl) |
| 13 | Ser | Cys(N-$C_1$-$C_8$alkyl) |
| 14 | Cys | Pro |
| 15 | Pro | Phe(N-$C_1$-$C_8$alkyl) |
| 16 | Phe | Tyr(N-$C_1$-$C_8$alkyl) |
| 17 | Tyr | Trp(N-$C_1$-$C_8$alkyl) |
| 18 | Trp | Ile(N-$C_1$-$C_8$alkyl) |
| 19 | Ile | Val(N-$C_1$-$C_8$alkyl) |
| 20 | Val | Thr(N-$C_1$-$C_8$alkyl) |
| 21 | Thr | d-Ala(N-$C_1$-$C_8$alkyl) |
| 22 | d-Ala | d-Leu(N-$C_1$-$C_8$alkyl) |
| 23 | d-Leu | d-Met(N-$C_1$-$C_8$alkyl) |
| 24 | d-Met | d-Asn(N-$C_1$-$C_8$alkyl) |
| 25 | d-Asn | d-Glu(N-$C_1$-$C_8$alkyl) |
| 26 | d-Glu | d-Asp(N-$C_1$-$C_8$alkyl) |
| 27 | d-Asp | d-Gln(N-$C_1$-$C_8$alkyl) |
| 28 | d-Gln | d-His(N-$C_1$-$C_8$alkyl) |
| 29 | d-His | d-Lys(N-$C_1$-$C_8$alkyl) |
| 30 | d-Lys | d-Arg(N-$C_1$-$C_8$alkyl) |
| 31 | d-Arg | d-Ser(N-$C_1$-$C_8$alkyl) |
| 32 | d-Ser | d-Cys(N-$C_1$-$C_8$alkyl) |
| 33 | d-Cys | d-Pro |
| 34 | d-Pro | d-Phe(N-$C_1$-$C_8$alkyl) |
| 35 | d-Phe | d-Tyr(N-$C_1$-$C_8$alkyl) |
| 36 | d-Tyr | d-Trp(N-$C_1$-$C_8$alkyl) |
| 37 | d-Trp | d-Ile(N-$C_1$-$C_8$alkyl) |
| 38 | d-Ile | d-Val(N-$C_1$-$C_8$alkyl) |
| 39 | d-Val | d-Thr(N-$C_1$-$C_8$alkyl) |
| 40 | d-Thr | Gly(N-methyl) |
| 41 | Gly(N-methyl) | Ala(N-methyl) |
| 42 | Ala(N-methyl) | Leu(N-methyl) |
| 43 | Leu(N-methyl) | Met(N-methyl) |
| 44 | Met(N-methyl) | Asn(N-methyl) |
| 45 | Asn(N-methyl) | Glu(N-methyl) |
| 46 | Glu(N-methyl) | Asp(N-methyl) |
| 47 | Asp(N-methyl) | Gln(N-methyl) |
| 48 | Gln(N-methyl) | His(N-methyl) |
| 49 | His(N-methyl) | Lys(N-methyl) |
| 50 | Lys(N-methyl) | Arg(N-methyl) |
| 51 | Arg(N-methyl) | Ser(N-methyl) |
| 52 | Ser(N-methyl) | Cys(N-methyl) |
| 53 | Cys(N-methyl) | Phe(N-methyl) |
| 54 | Phe(N-methyl) | Tyr(N-methyl) |
| 55 | Tyr(N-methyl) | Trp(N-methyl) |
| 56 | Trp(N-methyl) | Ile(N-methyl) |
| 57 | Ile(N-methyl) | Val(N-methyl) |
| 58 | Val(N-methyl) | Thr(N-methyl) |
| 59 | Thr(N-methyl) | d-Ala(N-methyl) |
| 60 | d-Ala(N-methyl) | d-Leu(N-methyl) |
| 61 | d-Leu(N-methyl) | d-Met(N-methyl) |
| 62 | d-Met(N-methyl) | d-Asn(N-methyl) |
| 63 | d-Asn(N-methyl) | d-Glu(N-methyl) |
| 64 | d-Glu(N-methyl) | d-Asp(N-methyl) |
| 65 | d-Asp(N-methyl) | d-Gln(N-methyl) |
| 66 | d-Gln(N-methyl) | d-His(N-methyl) |
| 67 | d-His(N-methyl) | d-Lys(N-methyl) |
| 68 | d-Lys (N-methyl) | d-Arg(N-methyl) |
| 69 | d-Arg(N-methyl) | d-Ser(N-methyl) |
| 70 | d-Ser(N-methyl) | d-Cys(N-methyl) |
| 71 | d-Cys(N-methyl) | d-Phe(N-methyl) |
| 72 | d-Phe(N-methyl) | d-Tyr(N-methyl) |

| Amino Acid # | Amino Acid 'A' | Amino Acid 'B' |
|---|---|---|
| 73 | d-Tyr(N-methyl) | d-Trp(N-methyl) |
| 74 | d-Trp(N-methyl) | d-Ile(N-methyl) |
| 75 | d-Ile(N-methyl) | d-Val(N-methyl) |
| 76 | d-Val(N-methyl) | d-Thr(N-methyl) |
| 77 | d-Thr(N-methyl) | Gly(N-hexyl) |
| 78 | | Ala(N-hexyl) |
| 79 | | Leu(N-hexyl) |
| 80 | | Met(N-hexyl) |
| 81 | | Asn(N-hexyl) |
| 82 | | Glu(N-hexyl) |
| 83 | | Asp(N-hexyl) |
| 84 | | Gln(N-hexyl) |
| 85 | | His(N-hexyl) |
| 86 | | Lys(N-hexyl) |
| 87 | | Arg(N-hexyl) |
| 88 | | Ser(N-hexyl) |
| 89 | | Cys(N-hexyl) |
| 90 | | Phe(N-hexyl) |
| 91 | | Tyr(N-hexyl) |
| 92 | | Trp(N-hexyl) |
| 93 | | Ile(N-hexyl) |
| 94 | | Val(N-hexyl) |
| 95 | | Thr(N-hexyl) |
| 96 | | d-Ala(N-hexyl) |
| 97 | | d-Leu(N-hexyl) |
| 98 | | d-Met(N-hexyl) |
| 99 | | d-Asn(N-hexyl) |
| 100 | | d-Glu(N-hexyl) |
| 101 | | d-Asp(N-hexyl) |
| 102 | | d-Gln(N-hexyl) |
| 103 | | d-His(N-hexyl) |
| 104 | | d-Lys(N-hexyl) |
| 105 | | d-Arg(N-hexyl) |
| 106 | | d-Ser(N-hexyl) |
| 107 | | d-Cys(N-hexyl) |
| 108 | | d-Phe(N-hexyl) |
| 109 | | d-Tyr(N-hexyl) |
| 110 | | d-Trp(N-hexyl) |
| 111 | | d-Ile(N-hexyl) |
| 112 | | d-Val(N-hexyl) |
| 113 | | d-Thr(N-hexyl) |

In some embodiments, the dipeptide prodrug element includes the combination of any one of A1-A77 with any one of B1-B113. For example, combinations of the A amino acid and the B amino acid of the dipeptide prodrug element can include: A1-B1; A1-B2; A1-B3; A1-B4; A1-B5; A1-B6; A1-B7; A1-B8; A1-B9; A1-B10; A1-B11; A1-B12; A1-B13; A1-B14; A1-B15; A1-B16; A1-B17; A1-B18; A1-B19; A1-B20; A1-B21; A1-B22; A1-B23; A1-B24; A1-B25; A1-B26; A1-B27; A1-B28; A1-B29; A1-B30; A1-B31; A1-B32; A1-B33; A1-B34; A1-B35; A1-B36; A1-B37; A1-B38; A1-B39; A1-B40; A1-B41; A1-B42; A1-B43; A1-B44; A1-B45; A1-B46; A1-B47; A1-B48; A1-B49; A1-B50; A1-B51; A1-B52; A1-B53; A1-B54; A1-B55; A1-B56; A1-B57; A1-B58; A1-B59; A1-B60; A1-B61; A1-B62; A1-B63; A1-B64; A1-B65; A1-B66; A1-B67; A1-B68; A1-B69; A1-B70; A1-B71; A1-B72; A1-B73; A1-B74; A1-B75; A1-B76; A1-B77; A1-B78; A1-B79; A1-B80; A1-B81; A1-B82; A1-B83; A1-B84; A1-B85; A1-B86; A1-B87; A1-B88; A1-B89; A1-B90; A1-B91; A1-B92; A1-B93; A1-B94; A1-B95; A1-B96; A1-B97; A1-B98; A1-B99; A1-B100; A1-B101; A1-B102; A1-B103; A1-B104; A1-B105; A1-B106; A1-B107; A1-B108; A1-B109; A1-B110; A1-B111; A1-B112; A1-B113.

In some embodiments, the dipeptide prodrug element includes the combination of any one of A1-A154 with any one of B1-B113. For example, combinations of the A amino acid and the B amino acid of the dipeptide prodrug element can include: A1-B1; A1-B2; A1-B3; A1-B4; A1-B5; A1-B6; A1-B7; A1-B8; A1-B9; A1-B10; A1-B11; A1-B12; A1-B13; A1-B14; A1-B15; A1-B16; A1-B17; A1-B18; A1-B19; A1-B20; A1-B21; A1-B22; A1-B23; A1-B24; A1-B25; A1-B26; A1-B27; A1-B28; A1-B29; A1-B30; A1-B31; A1-B32; A1-B33; A1-B34; A1-B35; A1-B36; A1-B37; A1-B38; A1-B39; A1-B40; A1-B41; A1-B42; A1-B43; A1-B44; A1-B45; A1-B46; A1-B47; A1-B48; A1-B49; A1-B50; A1-B51; A1-B52; A1-B53; A1-B54; A1-B55; A1-B56; A1-B57; A1-B58; A1-B59; A1-B60; A1-B61; A1-B62; A1-B63; A1-B64; A1-B65; A1-B66; A1-B67; A1-B68; A1-B69; A1-B70; A1-B71; A1-B72; A1-B73; A1-B74; A1-B75; A1-B76; A1-B77; A1-B78; A1-B79; A1-B80; A1-B81; A1-B82; A1-B83; A1-B84; A1-B85; A1-B86; A1-B87; A1-B88; A1-B89; A1-B90; A1-B91; A1-B92; A1-B93; A1-B94; A1-B95; A1-B96; A1-B97; A1-B98; A1-B99; A1-B100; A1-B101; A1-B102; A1-B103; A1-B104; A1-B105; A1-B106; A1-B107; A1-B108; A1-B109; A1-B110; A1-B111; A1-B112; A1-B113;
A2-B1; A2-B2; A2-B3; A2-B4; A2-B5; A2-B6; A2-B7; A2-B8; A2-B9; A2-B10; A2-B11; A2-B12; A2-B13; A2-B14; A2-B15; A2-B16; A2-B17; A2-B18; A2-B19; A2-B20; A2-B21; A2-B22; A2-B23; A2-B24; A2-B25; A2-B26; A2-B27; A2-B28; A2-B29; A2-B30; A2-B31; A2-B32; A2-B33; A2-B34; A2-B35; A2-B36; A2-B37; A2-B38; A2-B39; A2-B40; A2-B41; A2-B42; A2-B43; A2-B44; A2-B45; A2-B46; A2-B47; A2-B48; A2-B49; A2-B50; A2-B51; A2-B52; A2-B53; A2-B54; A2-B55; A2-B56; A2-B57; A2-B58; A2-B59; A2-B60; A2-B61; A2-B62; A2-B63; A2-B64; A2-B65; A2-B66; A2-B67; A2-B68; A2-B69; A2-B70; A2-B71; A2-B72; A2-B73; A2-B74; A2-B75; A2-B76; A2-B77; A2-B78; A2-B79; A2-B80; A2-B81; A2-B82; A2-B83; A2-B84; A2-B85; A2-B86; A2-B87; A2-B88; A2-B89; A2-B90; A2-B91; A2-B92; A2-B93; A2-B94; A2-B95; A2-B96; A2-B97; A2-B98; A2-B99; A2-B100; A2-B101; A2-B102; A2-B103; A2-B104; A2-B105; A2-B106; A2-B107; A2-B108; A2-B109; A2-B110; A2-B111; A2-B112; A2-B113;
A3-B1; A3-B2; A3-B3; A3-B4; A3-B5; A3-B6; A3-B7; A3-B8; A3-B9; A3-B10; A3-B11; A3-B12; A3-B13; A3-B14; A3-B15; A3-B16; A3-B17; A3-B18; A3-B19; A3-B20; A3-B21; A3-B22; A3-B23; A3-B24; A3-B25; A3-B26; A3-B27; A3-B28; A3-B29; A3-B30; A3-B31; A3-B32; A3-B33; A3-B34; A3-B35; A3-B36; A3-B37; A3-B38; A3-B39; A3-B40; A3-B41; A3-B42; A3-B43; A3-B44; A3-B45; A3-B46; A3-B47; A3-B48; A3-B49; A3-B50; A3-B51; A3-B52; A3-B53; A3-B54; A3-B55; A3-B56; A3-B57; A3-B58; A3-B59; A3-B60; A3-B61; A3-B62; A3-B63; A3-B64; A3-B65; A3-B66; A3-B67; A3-B68; A3-B69; A3-B70; A3-B71; A3-B72; A3-B73; A3-B74; A3-B75; A3-B76; A3-B77; A3-B78; A3-B79; A3-B80; A3-B81; A3-B82; A3-B83; A3-B84; A3-B85; A3-B86; A3-B87; A3-B88; A3-B89; A3-B90; A3-B91; A3-B92; A3-B93; A3-B94; A3-B95; A3-B96; A3-B97; A3-B98; A3-B99; A3-B100; A3-B101; A3-B102; A3-B103; A3-B104; A3-B105; A3-B106; A3-B107; A3-B108; A3-B109; A3-B110; A3-B111; A3-B112; A3-B113;
A4-B1; A4-B2; A4-B3; A4-B4; A4-B5; A4-B6; A4-B7; A4-B8; A4-B9; A4-B10; A4-B11; A4-B12; A4-B13; A4-B14; A4-B15; A4-B16; A4-B17; A4-B18; A4-B19; A4-B20; A4-B21; A4-B22; A4-B23; A4-B24; A4-B25; A4-B26; A4-B27; A4-B28; A4-B29; A4-B30; A4-B31; A4-B32; A4-B33; A4-B34; A4-B35; A4-B36; A4-B37; A4-B38; A4-B39; A4-B40; A4-B41; A4-B42; A4-B43; A4-B44; A4-B45; A4-B46; A4-B47; A4-B48; A4-B49; A4-B50; A4-B51; A4-B52; A4-B53; A4-B54; A4-B55; A4-B56; A4-B57; A4-B58; A4-B59; A4-B60; A4-B61; A4-B62; A4-B63; A4-B64; A4-B65; A4-B66; A4-B67;

A4-B68; A4-B69; A4-B70; A4-B71; A4-B72; A4-B73; A4-B74; A4-B75; A4-B76; A4-B77; A4-B78; A4-B79; A4-B80; A4-B81; A4-B82; A4-B83; A4-B84; A4-B85; A4-B86; A4-B87; A4-B88; A4-B89; A4-B90; A4-B91; A4-B92; A4-B93; A4-B94; A4-B95; A4-B96; A4-B97; A4-B98; A4-B99; A4-B100; A4-B101; A4-B102; A4-B103; A4-B104; A4-B105; A4-B106; A4-B107; A4-B108; A4-B109; A4-B110; A4-B111; A4-B112; A4-B113;

A5-B1; A5-B2; A5-B3; A5-B4; A5-B5; A5-B6; A5-B7; A5-B8; A5-B9; A5-B10; A5-B11; A5-B12; A5-B13; A5-B14; A5-B15; A5-B16; A5-B17; A5-B18; A5-B19; A5-B20; A5-B21; A5-B22; A5-B23; A5-B24; A5-B25; A5-B26; A5-B27; A5-B28; A5-B29; A5-B30; A5-B31; A5-B32; A5-B33; A5-B34; A5-B35; A5-B36; A5-B37; A5-B38; A5-B39; A5-B40; A5-B41; A5-B42; A5-B43; A5-B44; A5-B45; A5-B46; A5-B47; A5-B48; A5-B49; A5-B50; A5-B51; A5-B52; A5-B53; A5-B54; A5-B55; A5-B56; A5-B57; A5-B58; A5-B59; A5-B60; A5-B61; A5-B62; A5-B63; A5-B64; A5-B65; A5-B66; A5-B67; A5-B68; A5-B69; A5-B70; A5-B71; A5-B72; A5-B73; A5-B74; A5-B75; A5-B76; A5-B77; A5-B78; A5-B79; A5-B80; A5-B81; A5-B82; A5-B83; A5-B84; A5-B85; A5-B86; A5-B87; A5-B88; A5-B89; A5-B90; A5-B91; A5-B92; A5-B93; A5-B94; A5-B95; A5-B96; A5-B97; A5-B98; A5-B99; A5-B100; A5-B101; A5-B102; A5-B103; A5-B104; A5-B105; A5-B106; A5-B107; A5-B108; A5-B109; A5-B110; A5-B111; A5-B112; A5-B113;

A6-B1; A6-B2; A6-B3; A6-B4; A6-B5; A6-B6; A6-B7; A6-B8; A6-B9; A6-B10; A6-B11; A6-B12; A6-B13; A6-B14; A6-B15; A6-B16; A6-B17; A6-B18; A6-B19; A6-B20; A6-B21; A6-B22; A6-B23; A6-B24; A6-B25; A6-B26; A6-B27; A6-B28; A6-B29; A6-B30; A6-B31; A6-B32; A6-B33; A6-B34; A6-B35; A6-B36; A6-B37; A6-B38; A6-B39; A6-B40; A6-B41; A6-B42; A6-B43; A6-B44; A6-B45; A6-B46; A6-B47; A6-B48; A6-B49; A6-B50; A6-B51; A6-B52; A6-B53; A6-B54; A6-B55; A6-B56; A6-B57; A6-B58; A6-B59; A6-B60; A6-B61; A6-B62; A6-B63; A6-B64; A6-B65; A6-B66; A6-B67; A6-B68; A6-B69; A6-B70; A6-B71; A6-B72; A6-B73; A6-B74; A6-B75; A6-B76; A6-B77; A6-B78; A6-B79; A6-B80; A6-B81; A6-B82; A6-B83; A6-B84; A6-B85; A6-B86; A6-B87; A6-B88; A6-B89; A6-B90; A6-B91; A6-B92; A6-B93; A6-B94; A6-B95; A6-B96; A6-B97; A6-B98; A6-B99; A6-B100; A6-B101; A6-B102; A6-B103; A6-B104; A6-B105; A6-B106; A6-B107; A6-B108; A6-B109; A6-B110; A6-B111; A6-B112; A6-B113;

A7-B1; A7-B2; A7-B3; A7-B4; A7-B5; A7-B6; A7-B7; A7-B8; A7-B9; A7-B10; A7-B11; A7-B12; A7-B13; A7-B14; A7-B15; A7-B16; A7-B17; A7-B18; A7-B19; A7-B20; A7-B21; A7-B22; A7-B23; A7-B24; A7-B25; A7-B26; A7-B27; A7-B28; A7-B29; A7-B30; A7-B31; A7-B32; A7-B33; A7-B34; A7-B35; A7-B36; A7-B37; A7-B38; A7-B39; A7-B40; A7-B41; A7-B42; A7-B43; A7-B44; A7-B45; A7-B46; A7-B47; A7-B48; A7-B49; A7-B50; A7-B51; A7-B52; A7-B53; A7-B54; A7-B55; A7-B56; A7-B57; A7-B58; A7-B59; A7-B60; A7-B61; A7-B62; A7-B63; A7-B64; A7-B65; A7-B66; A7-B67; A7-B68; A7-B69; A7-B70; A7-B71; A7-B72; A7-B73; A7-B74; A7-B75; A7-B76; A7-B77; A7-B78; A7-B79; A7-B80; A7-B81; A7-B82; A7-B83; A7-B84; A7-B85; A7-B86; A7-B87; A7-B88; A7-B89; A7-B90; A7-B91; A7-B92; A7-B93; A7-B94; A7-B95; A7-B96; A7-B97; A7-B98; A7-B99; A7-B100; A7-B101; A7-B102; A7-B103; A7-B104; A7-B105; A7-B106; A7-B107; A7-B108; A7-B109; A7-B110; A7-B111; A7-B112; A7-B113;

A8-B1; A8-B2; A8-B3; A8-B4; A8-B5; A8-B6; A8-B7; A8-B8; A8-B9; A8-B10; A8-B11; A8-B12; A8-B13; A8-B14; A8-B15; A8-B16; A8-B17; A8-B18; A8-B19; A8-B20; A8-B21; A8-B22; A8-B23; A8-B24; A8-B25; A8-B26; A8-B27; A8-B28; A8-B29; A8-B30; A8-B31; A8-B32; A8-B33; A8-B34; A8-B35; A8-B36; A8-B37; A8-B38; A8-B39; A8-B40; A8-B41; A8-B42; A8-B43; A8-B44; A8-B45; A8-B46; A8-B47; A8-B48; A8-B49; A8-B50; A8-B51; A8-B52; A8-B53; A8-B54; A8-B55; A8-B56; A8-B57; A8-B58; A8-B59; A8-B60; A8-B61; A8-B62; A8-B63; A8-B64; A8-B65; A8-B66; A8-B67; A8-B68; A8-B69; A8-B70; A8-B71; A8-B72; A8-B73; A8-B74; A8-B75; A8-B76; A8-B77; A8-B78; A8-B79; A8-B80; A8-B81; A8-B82; A8-B83; A8-B84; A8-B85; A8-B86; A8-B87; A8-B88; A8-B89; A8-B90; A8-B91; A8-B92; A8-B93; A8-B94; A8-B95; A8-B96; A8-B97; A8-B98; A8-B99; A8-B100; A8-B101; A8-B102; A8-B103; A8-B104; A8-B105; A8-B106; A8-B107; A8-B108; A8-B109; A8-B110; A8-B111; A8-B112; A8-B113;

A9-B1; A9-B2; A9-B3; A9-B4; A9-B5; A9-B6; A9-B7; A9-B8; A9-B9; A9-B10; A9-B11; A9-B12; A9-B13; A9-B14; A9-B15; A9-B16; A9-B17; A9-B18; A9-B19; A9-B20; A9-B21; A9-B22; A9-B23; A9-B24; A9-B25; A9-B26; A9-B27; A9-B28; A9-B29; A9-B30; A9-B31; A9-B32; A9-B33; A9-B34; A9-B35; A9-B36; A9-B37; A9-B38; A9-B39; A9-B40; A9-B41; A9-B42; A9-B43; A9-B44; A9-B45; A9-B46; A9-B47; A9-B48; A9-B49; A9-B50; A9-B51; A9-B52; A9-B53; A9-B54; A9-B55; A9-B56; A9-B57; A9-B58; A9-B59; A9-B60; A9-B61; A9-B62; A9-B63; A9-B64; A9-B65; A9-B66; A9-B67; A9-B68; A9-B69; A9-B70; A9-B71; A9-B72; A9-B73; A9-B74; A9-B75; A9-B76; A9-B77; A9-B78; A9-B79; A9-B80; A9-B81; A9-B82; A9-B83; A9-B84; A9-B85; A9-B86; A9-B87; A9-B88; A9-B89; A9-B90; A9-B91; A9-B92; A9-B93; A9-B94; A9-B95; A9-B96; A9-B97; A9-B98; A9-B99; A9-B100; A9-B101; A9-B102; A9-B103; A9-B104; A9-B105; A9-B106; A9-B107; A9-B108; A9-B109; A9-B110; A9-B111; A9-B112; A9-B113;

A10-B1; A10-B2; A10-B3; A10-B4; A10-B5; A10-B6; A10-B7; A10-B8; A10-B9; A10-B10; A10-B11; A10-B12; A10-B13; A10-B14; A10-B15; A10-B16; A10-B17; A10-B18; A10-B19; A10-B20; A10-B21; A10-B22; A10-B23; A10-B24; A10-B25; A10-B26; A10-B27; A10-B28; A10-B29; A10-B30; A10-B31; A10-B32; A10-B33; A10-B34; A10-B35; A10-B36; A10-B37; A10-B38; A10-B39; A10-B40; A10-B41; A10-B42; A10-B43; A10-B44; A10-B45; A10-B46; A10-B47; A10-B48; A10-B49; A10-B50; A10-B51; A10-B52; A10-B53; A10-B54; A10-B55; A10-B56; A10-B57; A10-B58; A10-B59; A10-B60; A10-B61; A10-B62; A10-B63; A10-B64; A10-B65; A10-B66; A10-B67; A10-B68; A10-B69; A10-B70; A10-B71; A10-B72; A10-B73; A10-B74; A10-B75; A10-B76; A10-B77; A10-B78; A10-B79; A10-B80; A10-B81; A10-B82; A10-B83; A10-B84; A10-B85; A10-B86; A10-B87; A10-B88; A10-B89; A10-B90; A10-B91; A10-B92; A10-B93; A10-B94; A10-B95; A10-B96; A10-B97; A10-B98; A10-B99; A10-B100; A10-B101; A10-B102; A10-B103; A10-B104; A10-B105; A10-B106; A10-B107; A10-B108; A10-B109; A10-B110; A10-B111; A10-B112; A10-B113;

A11-B1; A11-B2; A11-B3; A11-B4; A11-B5; A11-B6; A11-B7; A11-B8; A11-B9; A11-B10; A11-B11; A11-B12; A11-B13; A11-B14; A11-B15; A11-B16; A11-B17; A11-B18; A11-B19; A11-B20; A11-B21; A11-B22; A11-B23; A11-B24; A11-B25; A11-B26; A11-B27; A11-B28; A11-B29; A11-B30; A11-B31; A11-B32; A11-B33; A11-B34; A11-B35; A11-B36; A11-B37; A11-B38; A11-B39; A11-B40; A11-B41; A11-B42; A11-B43; A11-B44; A11-B45; A11-B46; A11-B47; A11-B48; A11-B49; A11-B50; A11-B51; A11-B52; A11-B53; A11-B54; A11-B55; A11-B56;

A11-B57; A11-B58; A11-B59; A11-B60; A11-B61; A11-B62; A11-B63; A11-B64; A11-B65; A11-B66; A11-B67; A11-B68; A11-B69; A11-B70; A11-B71; A11-B72; A11-B73; A11-B74; A11-B75; A11-B76; A11-B77; A11-B78; A11-B79; A11-B80; A11-B81; A11-B82; A11-B83; A11-B84; A11-B85; A11-B86; A11-B87; A11-B88; A11-B89; A11-B90; A11-B91; A11-B92; A11-B93; A11-B94; A11-B95; A11-B96; A11-B97; A11-B98; A11-B99; A11-B100; A11-B101; A11-B102; A11-B103; A11-B104; A11-B105; A11-B106; A11-B107; A11-B108; A11-B109; A11-B110; A11-B111; A11-B112; A11-B113;

A12-B1; A12-B2; A12-B3; A12-B4; A12-B5; A12-B6; A12-B7; A12-B8; A12-B9; A12-B10; A12-B11; A12-B12; A12-B13; A12-B14; A12-B15; A12-B16; A12-B17; A12-B18; A12-B19; A12-B20; A12-B21; A12-B22; A12-B23; A12-B24; A12-B25; A12-B26; A12-B27; A12-B28; A12-B29; A12-B30; A12-B31; A12-B32; A12-B33; A12-B34; A12-B35; A12-B36; A12-B37; A12-B38; A12-B39; A12-B40; A12-B41; A12-B42; A12-B43; A12-B44; A12-B45; A12-B46; A12-B47; A12-B48; A12-B49; A12-B50; A12-B51; A12-B52; A12-B53; A12-B54; A12-B55; A12-B56; A12-B57; A12-B58; A12-B59; A12-B60; A12-B61; A12-B62; A12-B63; A12-B64; A12-B65; A12-B66; A12-B67; A12-B68; A12-B69; A12-B70; A12-B71; A12-B72; A12-B73; A12-B74; A12-B75; A12-B76; A12-B77; A12-B78; A12-B79; A12-B80; A12-B81; A12-B82; A12-B83; A12-B84; A12-B85; A12-B86; A12-B87; A12-B88; A12-B89; A12-B90; A12-B91; A12-B92; A12-B93; A12-B94; A12-B95; A12-B96; A12-B97; A12-B98; A12-B99; A12-B100; A12-B101; A12-B102; A12-B103; A12-B104; A12-B105; A12-B106; A12-B107; A12-B108; A12-B109; A12-B110; A12-B111; A12-B112; A12-B113;

A13-B1; A13-B2; A13-B3; A13-B4; A13-B5; A13-B6; A13-B7; A13-B8; A13-B9; A13-B10; A13-B11; A13-B12; A13-B13; A13-B14; A13-B15; A13-B16; A13-B17; A13-B18; A13-B19; A13-B20; A13-B21; A13-B22; A13-B23; A13-B24; A13-B25; A13-B26; A13-B27; A13-B28; A13-B29; A13-B30; A13-B31; A13-B32; A13-B33; A13-B34; A13-B35; A13-B36; A13-B37; A13-B38; A13-B39; A13-B40; A13-B41; A13-B42; A13-B43; A13-B44; A13-B45; A13-B46; A13-B47; A13-B48; A13-B49; A13-B50; A13-B51; A13-B52; A13-B53; A13-B54; A13-B55; A13-B56; A13-B57; A13-B58; A13-B59; A13-B60; A13-B61; A13-B62; A13-B63; A13-B64; A13-B65; A13-B66; A13-B67; A13-B68; A13-B69; A13-B70; A13-B71; A13-B72; A13-B73; A13-B74; A13-B75; A13-B76; A13-B77; A13-B78; A13-B79; A13-B80; A13-B81; A13-B82; A13-B83; A13-B84; A13-B85; A13-B86; A13-B87; A13-B88; A13-B89; A13-B90; A13-B91; A13-B92; A13-B93; A13-B94; A13-B95; A13-B96; A13-B97; A13-B98; A13-B99; A13-B100; A13-B101; A13-B102; A13-B103; A13-B104; A13-B105; A13-B106; A13-B107; A13-B108; A13-B109; A13-B110; A13-B111; A13-B112; A13-B113;

A14-B1; A14-B2; A14-B3; A14-B4; A14-B5; A14-B6; A14-B7; A14-B8; A14-B9; A14-B10; A14-B11; A14-B12; A14-B13; A14-B14; A14-B15; A14-B16; A14-B17; A14-B18; A14-B19; A14-B20; A14-B21; A14-B22; A14-B23; A14-B24; A14-B25; A14-B26; A14-B27; A14-B28; A14-B29; A14-B30; A14-B31; A14-B32; A14-B33; A14-B34; A14-B35; A14-B36; A14-B37; A14-B38; A14-B39; A14-B40; A14-B41; A14-B42; A14-B43; A14-B44; A14-B45; A14-B46; A14-B47; A14-B48; A14-B49; A14-B50; A14-B51; A14-B52; A14-B53; A14-B54; A14-B55; A14-B56; A14-B57; A14-B58; A14-B59; A14-B60; A14-B61; A14-B62; A14-B63; A14-B64; A14-B65; A14-B66; A14-B67; A14-B68; A14-B69; A14-B70; A14-B71; A14-B72; A14-B73; A14-B74; A14-B75; A14-B76; A14-B77; A14-B78; A14-B79; A14-B80; A14-B81; A14-B82; A14-B83; A14-B84; A14-B85; A14-B86; A14-B87; A14-B88; A14-B89; A14-B90; A14-B91; A14-B92; A14-B93; A14-B94; A14-B95; A14-B96; A14-B97; A14-B98; A14-B99; A14-B100; A14-B101; A14-B102; A14-B103; A14-B104; A14-B105; A14-B106; A14-B107; A14-B108; A14-B109; A14-B110; A14-B111; A14-B112; A14-B113;

A15-B1; A15-B2; A15-B3; A15-B4; A15-B5; A15-B6; A15-B7; A15-B8; A15-B9; A15-B10; A15-B11; A15-B12; A15-B13; A15-B14; A15-B15; A15-B16; A15-B17; A15-B18; A15-B19; A15-B20; A15-B21; A15-B22; A15-B23; A15-B24; A15-B25; A15-B26; A15-B27; A15-B28; A15-B29; A15-B30; A15-B31; A15-B32; A15-B33; A15-B34; A15-B35; A15-B36; A15-B37; A15-B38; A15-B39; A15-B40; A15-B41; A15-B42; A15-B43; A15-B44; A15-B45; A15-B46; A15-B47; A15-B48; A15-B49; A15-B50; A15-B51; A15-B52; A15-B53; A15-B54; A15-B55; A15-B56; A15-B57; A15-B58; A15-B59; A15-B60; A15-B61; A15-B62; A15-B63; A15-B64; A15-B65; A15-B66; A15-B67; A15-B68; A15-B69; A15-B70; A15-B71; A15-B72; A15-B73; A15-B74; A15-B75; A15-B76; A15-B77; A15-B78; A15-B79; A15-B80; A15-B81; A15-B82; A15-B83; A15-B84; A15-B85; A15-B86; A15-B87; A15-B88; A15-B89; A15-B90; A15-B91; A15-B92; A15-B93; A15-B94; A15-B95; A15-B96; A15-B97; A15-B98; A15-B99; A15-B100; A15-B101; A15-B102; A15-B103; A15-B104; A15-B105; A15-B106; A15-B107; A15-B108; A15-B109; A15-B110; A15-B111; A15-B112; A15-B113;

A16-B1; A16-B2; A16-B3; A16-B4; A16-B5; A16-B6; A16-B7; A16-B8; A16-B9; A16-B10; A16-B11; A16-B12; A16-B13; A16-B14; A16-B15; A16-B16; A16-B17; A16-B18; A16-B19; A16-B20; A16-B21; A16-B22; A16-B23; A16-B24; A16-B25; A16-B26; A16-B27; A16-B28; A16-B29; A16-B30; A16-B31; A16-B32; A16-B33; A16-B34; A16-B35; A16-B36; A16-B37; A16-B38; A16-B39; A16-B40; A16-B41; A16-B42; A16-B43; A16-B44; A16-B45; A16-B46; A16-B47; A16-B48; A16-B49; A16-B50; A16-B51; A16-B52; A16-B53; A16-B54; A16-B55; A16-B56; A16-B57; A16-B58; A16-B59; A16-B60; A16-B61; A16-B62; A16-B63; A16-B64; A16-B65; A16-B66; A16-B67; A16-B68; A16-B69; A16-B70; A16-B71; A16-B72; A16-B73; A16-B74; A16-B75; A16-B76; A16-B77; A16-B78; A16-B79; A16-B80; A16-B81; A16-B82; A16-B83; A16-B84; A16-B85; A16-B86; A16-B87; A16-B88; A16-B89; A16-B90; A16-B91; A16-B92; A16-B93; A16-B94; A16-B95; A16-B96; A16-B97; A16-B98; A16-B99; A16-B100; A16-B101; A16-B102; A16-B103; A16-B104; A16-B105; A16-B106; A16-B107; A16-B108; A16-B109; A16-B110; A16-B111; A16-B112; A16-B113;

A17-B1; A17-B2; A17-B3; A17-B4; A17-B5; A17-B6; A17-B7; A17-B8; A17-B9; A17-B10; A17-B11; A17-B12; A17-B13; A17-B14; A17-B15; A17-B16; A17-B17; A17-B18; A17-B19; A17-B20; A17-B21; A17-B22; A17-B23; A17-B24; A17-B25; A17-B26; A17-B27; A17-B28; A17-B29; A17-B30; A17-B31; A17-B32; A17-B33; A17-B34; A17-B35; A17-B36; A17-B37; A17-B38; A17-B39; A17-B40; A17-B41; A17-B42; A17-B43; A17-B44; A17-B45; A17-B46; A17-B47; A17-B48; A17-B49; A17-B50; A17-B51; A17-B52; A17-B53; A17-B54; A17-B55; A17-B56; A17-B57; A17-B58; A17-B59; A17-B60; A17-B61; A17-B62; A17-B63; A17-B64; A17-B65; A17-B66; A17-B67; A17-B68; A17-B69; A17-B70; A17-B71; A17-B72; A17-B73; A17-B74; A17-B75; A17-B76; A17-B77; A17-B78; A17-B79; A17-B80; A17-B81; A17-B82; A17-B83; A17-B84; A17-B85; A17-B86; A17-B87; A17-B88; A17-B89; A17-B90; A17-B91; A17-B92; A17-B93; A17-B94; A17-B95; A17-B96; A17-B97; A17-B98; A17-B99; A17-B100;

A17-B101; A17-B102; A17-B103; A17-B104; A17-B105; A17-B106; A17-B107; A17-B108; A17-B109; A17-B110; A17-B111; A17-B112; A17-B113;

A18-B1; A18-B2; A18-B3; A18-B4; A18-B5; A18-B6; A18-B7; A18-B8; A18-B9; A18-B10; A18-B11; A18-B12; A18-B13; A18-B14; A18-B15; A18-B16; A18-B17; A18-B18; A18-B19; A18-B20; A18-B21; A18-B22; A18-B23; A18-B24; A18-B25; A18-B26; A18-B27; A18-B28; A18-B29; A18-B30; A18-B31; A18-B32; A18-B33; A18-B34; A18-B35; A18-B36; A18-B37; A18-B38; A18-B39; A18-B40; A18-B41; A18-B42; A18-B43; A18-B44; A18-B45; A18-B46; A18-B47; A18-B48; A18-B49; A18-B50; A18-B51; A18-B52; A18-B53; A18-B54; A18-B55; A18-B56; A18-B57; A18-B58; A18-B59; A18-B60; A18-B61; A18-B62; A18-B63; A18-B64; A18-B65; A18-B66; A18-B67; A18-B68; A18-B69; A18-B70; A18-B71; A18-B72; A18-B73; A18-B74; A18-B75; A18-B76; A18-B77; A18-B78; A18-B79; A18-B80; A18-B81; A18-B82; A18-B83; A18-B84; A18-B85; A18-B86; A18-B87; A18-B88; A18-B89; A18-B90; A18-B91; A18-B92; A18-B93; A18-B94; A18-B95; A18-B96; A18-B97; A18-B98; A18-B99; A18-B100; A18-B101; A18-B102; A18-B103; A18-B104; A18-B105; A18-B106; A18-B107; A18-B108; A18-B109; A18-B110; A18-B111; A18-B112; A18-B113;

A19-B1; A19-B2; A19-B3; A19-B4; A19-B5; A19-B6; A19-B7; A19-B8; A19-B9; A19-B10; A19-B11; A19-B12; A19-B13; A19-B14; A19-B15; A19-B16; A19-B17; A19-B18; A19-B19; A19-B20; A19-B21; A19-B22; A19-B23; A19-B24; A19-B25; A19-B26; A19-B27; A19-B28; A19-B29; A19-B30; A19-B31; A19-B32; A19-B33; A19-B34; A19-B35; A19-B36; A19-B37; A19-B38; A19-B39; A19-B40; A19-B41; A19-B42; A19-B43; A19-B44; A19-B45; A19-B46; A19-B47; A19-B48; A19-B49; A19-B50; A19-B51; A19-B52; A19-B53; A19-B54; A19-B55; A19-B56; A19-B57; A19-B58; A19-B59; A19-B60; A19-B61; A19-B62; A19-B63; A19-B64; A19-B65; A19-B66; A19-B67; A19-B68; A19-B69; A19-B70; A19-B71; A19-B72; A19-B73; A19-B74; A19-B75; A19-B76; A19-B77; A19-B78; A19-B79; A19-B80; A19-B81; A19-B82; A19-B83; A19-B84; A19-B85; A19-B86; A19-B87; A19-B88; A19-B89; A19-B90; A19-B91; A19-B92; A19-B93; A19-B94; A19-B95; A19-B96; A19-B97; A19-B98; A19-B99; A19-B100; A19-B101; A19-B102; A19-B103; A19-B104; A19-B105; A19-B106; A19-B107; A19-B108; A19-B109; A19-B110; A19-B111; A19-B112; A19-B113;

A20-B1; A20-B2; A20-B3; A20-B4; A20-B5; A20-B6; A20-B7; A20-B8; A20-B9; A20-B10; A20-B11; A20-B12; A20-B13; A20-B14; A20-B15; A20-B16; A20-B17; A20-B18; A20-B19; A20-B20; A20-B21; A20-B22; A20-B23; A20-B24; A20-B25; A20-B26; A20-B27; A20-B28; A20-B29; A20-B30; A20-B31; A20-B32; A20-B33; A20-B34; A20-B35; A20-B36; A20-B37; A20-B38; A20-B39; A20-B40; A20-B41; A20-B42; A20-B43; A20-B44; A20-B45; A20-B46; A20-B47; A20-B48; A20-B49; A20-B50; A20-B51; A20-B52; A20-B53; A20-B54; A20-B55; A20-B56; A20-B57; A20-B58; A20-B59; A20-B60; A20-B61; A20-B62; A20-B63; A20-B64; A20-B65; A20-B66; A20-B67; A20-B68; A20-B69; A20-B70; A20-B71; A20-B72; A20-B73; A20-B74; A20-B75; A20-B76; A20-B77; A20-B78; A20-B79; A20-B80; A20-B81; A20-B82; A20-B83; A20-B84; A20-B85; A20-B86; A20-B87; A20-B88; A20-B89; A20-B90; A20-B91; A20-B92; A20-B93; A20-B94; A20-B95; A20-B96; A20-B97; A20-B98; A20-B99; A20-B100; A20-B101; A20-B102; A20-B103; A20-B104; A20-B105; A20-B106; A20-B107; A20-B108; A20-B109; A20-B110; A20-B111; A20-B112; A20-B113;

A21-B1; A21-B2; A21-B3; A21-B4; A21-B5; A21-B6; A21-B7; A21-B8; A21-B9; A21-B10; A21-B11; A21-B12; A21-B13; A21-B14; A21-B15; A21-B16; A21-B17; A21-B18; A21-B19; A21-B20; A21-B21; A21-B22; A21-B23; A21-B24; A21-B25; A21-B26; A21-B27; A21-B28; A21-B29; A21-B30; A21-B31; A21-B32; A21-B33; A21-B34; A21-B35; A21-B36; A21-B37; A21-B38; A21-B39; A21-B40; A21-B41; A21-B42; A21-B43; A21-B44; A21-B45; A21-B46; A21-B47; A21-B48; A21-B49; A21-B50; A21-B51; A21-B52; A21-B53; A21-B54; A21-B55; A21-B56; A21-B57; A21-B58; A21-B59; A21-B60; A21-B61; A21-B62; A21-B63; A21-B64; A21-B65; A21-B66; A21-B67; A21-B68; A21-B69; A21-B70; A21-B71; A21-B72; A21-B73; A21-B74; A21-B75; A21-B76; A21-B77; A21-B78; A21-B79; A21-B80; A21-B81; A21-B82; A21-B83; A21-B84; A21-B85; A21-B86; A21-B87; A21-B88; A21-B89; A21-B90; A21-B91; A21-B92; A21-B93; A21-B94; A21-B95; A21-B96; A21-B97; A21-B98; A21-B99; A21-B100; A21-B101; A21-B102; A21-B103; A21-B104; A21-B105; A21-B106; A21-B107; A21-B108; A21-B109; A21-B110; A21-B111; A21-B112; A21-B113;

A22-B1; A22-B2; A22-B3; A22-B4; A22-B5; A22-B6; A22-B7; A22-B8; A22-B9; A22-B10; A22-B11; A22-B12; A22-B13; A22-B14; A22-B15; A22-B16; A22-B17; A22-B18; A22-B19; A22-B20; A22-B21; A22-B22; A22-B23; A22-B24; A22-B25; A22-B26; A22-B27; A22-B28; A22-B29; A22-B30; A22-B31; A22-B32; A22-B33; A22-B34; A22-B35; A22-B36; A22-B37; A22-B38; A22-B39; A22-B40; A22-B41; A22-B42; A22-B43; A22-B44; A22-B45; A22-B46; A22-B47; A22-B48; A22-B49; A22-B50; A22-B51; A22-B52; A22-B53; A22-B54; A22-B55; A22-B56; A22-B57; A22-B58; A22-B59; A22-B60; A22-B61; A22-B62; A22-B63; A22-B64; A22-B65; A22-B66; A22-B67; A22-B68; A22-B69; A22-B70; A22-B71; A22-B72; A22-B73; A22-B74; A22-B75; A22-B76; A22-B77; A22-B78; A22-B79; A22-B80; A22-B81; A22-B82; A22-B83; A22-B84; A22-B85; A22-B86; A22-B87; A22-B88; A22-B89; A22-B90; A22-B91; A22-B92; A22-B93; A22-B94; A22-B95; A22-B96; A22-B97; A22-B98; A22-B99; A22-B100; A22-B101; A22-B102; A22-B103; A22-B104; A22-B105; A22-B106; A22-B107; A22-B108; A22-B109; A22-B110; A22-B111; A22-B112; A22-B113;

A23-B1; A23-B2; A23-B3; A23-B4; A23-B5; A23-B6; A23-B7; A23-B8; A23-B9; A23-B10; A23-B11; A23-B12; A23-B13; A23-B14; A23-B15; A23-B16; A23-B17; A23-B18; A23-B19; A23-B20; A23-B21; A23-B22; A23-B23; A23-B24; A23-B25; A23-B26; A23-B27; A23-B28; A23-B29; A23-B30; A23-B31; A23-B32; A23-B33; A23-B34; A23-B35; A23-B36; A23-B37; A23-B38; A23-B39; A23-B40; A23-B41; A23-B42; A23-B43; A23-B44; A23-B45; A23-B46; A23-B47; A23-B48; A23-B49; A23-B50; A23-B51; A23-B52; A23-B53; A23-B54; A23-B55; A23-B56; A23-B57; A23-B58; A23-B59; A23-B60; A23-B61; A23-B62; A23-B63; A23-B64; A23-B65; A23-B66; A23-B67; A23-B68; A23-B69; A23-B70; A23-B71; A23-B72; A23-B73; A23-B74; A23-B75; A23-B76; A23-B77; A23-B78; A23-B79; A23-B80; A23-B81; A23-B82; A23-B83; A23-B84; A23-B85; A23-B86; A23-B87; A23-B88; A23-B89; A23-B90; A23-B91; A23-B92; A23-B93; A23-B94; A23-B95; A23-B96; A23-B97; A23-B98; A23-B99; A23-B100; A23-B101; A23-B102; A23-B103; A23-B104; A23-B105; A23-B106; A23-B107; A23-B108; A23-B109; A23-B110; A23-B111; A23-B112; A23-B113;

A24-B1; A24-B2; A24-B3; A24-B4; A24-B5; A24-B6; A24-B7; A24-B8; A24-B9; A24-B10; A24-B11; A24-B12; A24-B13; A24-B14; A24-B15; A24-B16; A24-B17; A24-B18; A24-B19; A24-B20; A24-B21; A24-B22; A24-B23;

A24-B24; A24-B25; A24-B26; A24-B27; A24-B28; A24-B29; A24-B30; A24-B31; A24-B32; A24-B33; A24-B34; A24-B35; A24-B36; A24-B37; A24-B38; A24-B39; A24-B40; A24-B41; A24-B42; A24-B43; A24-B44; A24-B45; A24-B46; A24-B47; A24-B48; A24-B49; A24-B50; A24-B51; A24-B52; A24-B53; A24-B54; A24-B55; A24-B56; A24-B57; A24-B58; A24-B59; A24-B60; A24-B61; A24-B62; A24-B63; A24-B64; A24-B65; A24-B66; A24-B67; A24-B68; A24-B69; A24-B70; A24-B71; A24-B72; A24-B73; A24-B74; A24-B75; A24-B76; A24-B77; A24-B78; A24-B79; A24-B80; A24-B81; A24-B82; A24-B83; A24-B84; A24-B85; A24-B86; A24-B87; A24-B88; A24-B89; A24-B90; A24-B91; A24-B92; A24-B93; A24-B94; A24-B95; A24-B96; A24-B97; A24-B98; A24-B99; A24-B100; A24-B101; A24-B102; A24-B103; A24-B104; A24-B105; A24-B106; A24-B107; A24-B108; A24-B109; A24-B110; A24-B111; A24-B112; A24-B113;

A25-B1; A25-B2; A25-B3; A25-B4; A25-B5; A25-B6; A25-B7; A25-B8; A25-B9; A25-B10; A25-B11; A25-B12; A25-B13; A25-B14; A25-B15; A25-B16; A25-B17; A25-B18; A25-B19; A25-B20; A25-B21; A25-B22; A25-B23; A25-B24; A25-B25; A25-B26; A25-B27; A25-B28; A25-B29; A25-B30; A25-B31; A25-B32; A25-B33; A25-B34; A25-B35; A25-B36; A25-B37; A25-B38; A25-B39; A25-B40; A25-B41; A25-B42; A25-B43; A25-B44; A25-B45; A25-B46; A25-B47; A25-B48; A25-B49; A25-B50; A25-B51; A25-B52; A25-B53; A25-B54; A25-B55; A25-B56; A25-B57; A25-B58; A25-B59; A25-B60; A25-B61; A25-B62; A25-B63; A25-B64; A25-B65; A25-B66; A25-B67; A25-B68; A25-B69; A25-B70; A25-B71; A25-B72; A25-B73; A25-B74; A25-B75; A25-B76; A25-B77; A25-B78; A25-B79; A25-B80; A25-B81; A25-B82; A25-B83; A25-B84; A25-B85; A25-B86; A25-B87; A25-B88; A25-B89; A25-B90; A25-B91; A25-B92; A25-B93; A25-B94; A25-B95; A25-B96; A25-B97; A25-B98; A25-B99; A25-B100; A25-B101; A25-B102; A25-B103; A25-B104; A25-B105; A25-B106; A25-B107; A25-B108; A25-B109; A25-B110; A25-B111; A25-B112; A25-B113;

A26-B1; A26-B2; A26-B3; A26-B4; A26-B5; A26-B6; A26-B7; A26-B8; A26-B9; A26-B10; A26-B11; A26-B12; A26-B13; A26-B14; A26-B15; A26-B16; A26-B17; A26-B18; A26-B19; A26-B20; A26-B21; A26-B22; A26-B23; A26-B24; A26-B25; A26-B26; A26-B27; A26-B28; A26-B29; A26-B30; A26-B31; A26-B32; A26-B33; A26-B34; A26-B35; A26-B36; A26-B37; A26-B38; A26-B39; A26-B40; A26-B41; A26-B42; A26-B43; A26-B44; A26-B45; A26-B46; A26-B47; A26-B48; A26-B49; A26-B50; A26-B51; A26-B52; A26-B53; A26-B54; A26-B55; A26-B56; A26-B57; A26-B58; A26-B59; A26-B60; A26-B61; A26-B62; A26-B63; A26-B64; A26-B65; A26-B66; A26-B67; A26-B68; A26-B69; A26-B70; A26-B71; A26-B72; A26-B73; A26-B74; A26-B75; A26-B76; A26-B77; A26-B78; A26-B79; A26-B80; A26-B81; A26-B82; A26-B83; A26-B84; A26-B85; A26-B86; A26-B87; A26-B88; A26-B89; A26-B90; A26-B91; A26-B92; A26-B93; A26-B94; A26-B95; A26-B96; A26-B97; A26-B98; A26-B99; A26-B100; A26-B101; A26-B102; A26-B103; A26-B104; A26-B105; A26-B106; A26-B107; A26-B108; A26-B109; A26-B110; A26-B111; A26-B112; A26-B113;

A27-B1; A27-B2; A27-B3; A27-B4; A27-B5; A27-B6; A27-B7; A27-B8; A27-B9; A27-B10; A27-B11; A27-B12; A27-B13; A27-B14; A27-B15; A27-B16; A27-B17; A27-B18; A27-B19; A27-B20; A27-B21; A27-B22; A27-B23; A27-B24; A27-B25; A27-B26; A27-B27; A27-B28; A27-B29; A27-B30; A27-B31; A27-B32; A27-B33; A27-B34; A27-B35; A27-B36; A27-B37; A27-B38; A27-B39; A27-B40; A27-B41; A27-B42; A27-B43; A27-B44; A27-B45; A27-B46; A27-B47; A27-B48; A27-B49; A27-B50; A27-B51; A27-B52; A27-B53; A27-B54; A27-B55; A27-B56; A27-B57; A27-B58; A27-B59; A27-B60; A27-B61; A27-B62; A27-B63; A27-B64; A27-B65; A27-B66; A27-B67; A27-B68; A27-B69; A27-B70; A27-B71; A27-B72; A27-B73; A27-B74; A27-B75; A27-B76; A27-B77; A27-B78; A27-B79; A27-B80; A27-B81; A27-B82; A27-B83; A27-B84; A27-B85; A27-B86; A27-B87; A27-B88; A27-B89; A27-B90; A27-B91; A27-B92; A27-B93; A27-B94; A27-B95; A27-B96; A27-B97; A27-B98; A27-B99; A27-B100; A27-B101; A27-B102; A27-B103; A27-B104; A27-B105; A27-B106; A27-B107; A27-B108; A27-B109; A27-B110; A27-B111; A27-B112; A27-B113;

A28-B1; A28-B2; A28-B3; A28-B4; A28-B5; A28-B6; A28-B7; A28-B8; A28-B9; A28-B10; A28-B11; A28-B12; A28-B13; A28-B14; A28-B15; A28-B16; A28-B17; A28-B18; A28-B19; A28-B20; A28-B21; A28-B22; A28-B23; A28-B24; A28-B25; A28-B26; A28-B27; A28-B28; A28-B29; A28-B30; A28-B31; A28-B32; A28-B33; A28-B34; A28-B35; A28-B36; A28-B37; A28-B38; A28-B39; A28-B40; A28-B41; A28-B42; A28-B43; A28-B44; A28-B45; A28-B46; A28-B47; A28-B48; A28-B49; A28-B50; A28-B51; A28-B52; A28-B53; A28-B54; A28-B55; A28-B56; A28-B57; A28-B58; A28-B59; A28-B60; A28-B61; A28-B62; A28-B63; A28-B64; A28-B65; A28-B66; A28-B67; A28-B68; A28-B69; A28-B70; A28-B71; A28-B72; A28-B73; A28-B74; A28-B75; A28-B76; A28-B77; A28-B78; A28-B79; A28-B80; A28-B81; A28-B82; A28-B83; A28-B84; A28-B85; A28-B86; A28-B87; A28-B88; A28-B89; A28-B90; A28-B91; A28-B92; A28-B93; A28-B94; A28-B95; A28-B96; A28-B97; A28-B98; A28-B99; A28-B100; A28-B101; A28-B102; A28-B103; A28-B104; A28-B105; A28-B106; A28-B107; A28-B108; A28-B109; A28-B110; A28-B111; A28-B112; A28-B113;

A29-B1; A29-B2; A29-B3; A29-B4; A29-B5; A29-B6; A29-B7; A29-B8; A29-B9; A29-B10; A29-B11; A29-B12; A29-B13; A29-B14; A29-B15; A29-B16; A29-B17; A29-B18; A29-B19; A29-B20; A29-B21; A29-B22; A29-B23; A29-B24; A29-B25; A29-B26; A29-B27; A29-B28; A29-B29; A29-B30; A29-B31; A29-B32; A29-B33; A29-B34; A29-B35; A29-B36; A29-B37; A29-B38; A29-B39; A29-B40; A29-B41; A29-B42; A29-B43; A29-B44; A29-B45; A29-B46; A29-B47; A29-B48; A29-B49; A29-B50; A29-B51; A29-B52; A29-B53; A29-B54; A29-B55; A29-B56; A29-B57; A29-B58; A29-B59; A29-B60; A29-B61; A29-B62; A29-B63; A29-B64; A29-B65; A29-B66; A29-B67; A29-B68; A29-B69; A29-B70; A29-B71; A29-B72; A29-B73; A29-B74; A29-B75; A29-B76; A29-B77; A29-B78; A29-B79; A29-B80; A29-B81; A29-B82; A29-B83; A29-B84; A29-B85; A29-B86; A29-B87; A29-B88; A29-B89; A29-B90; A29-B91; A29-B92; A29-B93; A29-B94; A29-B95; A29-B96; A29-B97; A29-B98; A29-B99; A29-B100; A29-B101; A29-B102; A29-B103; A29-B104; A29-B105; A29-B106; A29-B107; A29-B108; A29-B109; A29-B110; A29-B111; A29-B112; A29-B113;

A30-B1; A30-B2; A30-B3; A30-B4; A30-B5; A30-B6; A30-B7; A30-B8; A30-B9; A30-B10; A30-B11; A30-B12; A30-B13; A30-B14; A30-B15; A30-B16; A30-B17; A30-B18; A30-B19; A30-B20; A30-B21; A30-B22; A30-B23; A30-B24; A30-B25; A30-B26; A30-B27; A30-B28; A30-B29; A30-B30; A30-B31; A30-B32; A30-B33; A30-B34; A30-B35; A30-B36; A30-B37; A30-B38; A30-B39; A30-B40; A30-B41; A30-B42; A30-B43; A30-B44; A30-B45; A30-B46; A30-B47; A30-B48; A30-B49; A30-B50; A30-B51; A30-B52; A30-B53; A30-B54; A30-B55; A30-B56; A30-B57; A30-B58; A30-B59; A30-B60; A30-B61; A30-B62; A30-B63; A30-B64; A30-B65; A30-B66; A30-B67;

A30-B68; A30-B69; A30-B70; A30-B71; A30-B72; A30-B73; A30-B74; A30-B75; A30-B76; A30-B77; A30-B78; A30-B79; A30-B80; A30-B81; A30-B82; A30-B83; A30-B84; A30-B85; A30-B86; A30-B87; A30-B88; A30-B89; A30-B90; A30-B91; A30-B92; A30-B93; A30-B94; A30-B95; A30-B96; A30-B97; A30-B98; A30-B99; A30-B100; A30-B101; A30-B102; A30-B103; A30-B104; A30-B105; A30-B106; A30-B107; A30-B108; A30-B109; A30-B110; A30-B111; A30-B112; A30-B113;

A31-B1; A31-B2; A31-B3; A31-B4; A31-B5; A31-B6; A31-B7; A31-B8; A31-B9; A31-B10; A31-B11; A31-B12; A31-B13; A31-B14; A31-B15; A31-B16; A31-B17; A31-B18; A31-B19; A31-B20; A31-B21; A31-B22; A31-B23; A31-B24; A31-B25; A31-B26; A31-B27; A31-B28; A31-B29; A31-B30; A31-B31; A31-B32; A31-B33; A31-B34; A31-B35; A31-B36; A31-B37; A31-B38; A31-B39; A31-B40; A31-B41; A31-B42; A31-B43; A31-B44; A31-B45; A31-B46; A31-B47; A31-B48; A31-B49; A31-B50; A31-B51; A31-B52; A31-B53; A31-B54; A31-B55; A31-B56; A31-B57; A31-B58; A31-B59; A31-B60; A31-B61; A31-B62; A31-B63; A31-B64; A31-B65; A31-B66; A31-B67; A31-B68; A31-B69; A31-B70; A31-B71; A31-B72; A31-B73; A31-B74; A31-B75; A31-B76; A31-B77; A31-B78; A31-B79; A31-B80; A31-B81; A31-B82; A31-B83; A31-B84; A31-B85; A31-B86; A31-B87; A31-B88; A31-B89; A31-B90; A31-B91; A31-B92; A31-B93; A31-B94; A31-B95; A31-B96; A31-B97; A31-B98; A31-B99; A31-B100; A31-B101; A31-B102; A31-B103; A31-B104; A31-B105; A31-B106; A31-B107; A31-B108; A31-B109; A31-B110; A31-B111; A31-B112; A31-B113;

A32-B1; A32-B2; A32-B3; A32-B4; A32-B5; A32-B6; A32-B7; A32-B8; A32-B9; A32-B10; A32-B11; A32-B12; A32-B13; A32-B14; A32-B15; A32-B16; A32-B17; A32-B18; A32-B19; A32-B20; A32-B21; A32-B22; A32-B23; A32-B24; A32-B25; A32-B26; A32-B27; A32-B28; A32-B29; A32-B30; A32-B31; A32-B32; A32-B33; A32-B34; A32-B35; A32-B36; A32-B37; A32-B38; A32-B39; A32-B40; A32-B41; A32-B42; A32-B43; A32-B44; A32-B45; A32-B46; A32-B47; A32-B48; A32-B49; A32-B50; A32-B51; A32-B52; A32-B53; A32-B54; A32-B55; A32-B56; A32-B57; A32-B58; A32-B59; A32-B60; A32-B61; A32-B62; A32-B63; A32-B64; A32-B65; A32-B66; A32-B67; A32-B68; A32-B69; A32-B70; A32-B71; A32-B72; A32-B73; A32-B74; A32-B75; A32-B76; A32-B77; A32-B78; A32-B79; A32-B80; A32-B81; A32-B82; A32-B83; A32-B84; A32-B85; A32-B86; A32-B87; A32-B88; A32-B89; A32-B90; A32-B91; A32-B92; A32-B93; A32-B94; A32-B95; A32-B96; A32-B97; A32-B98; A32-B99; A32-B100; A32-B101; A32-B102; A32-B103; A32-B104; A32-B105; A32-B106; A32-B107; A32-B108; A32-B109; A32-B110; A32-B111; A32-B112; A32-B113;

A33-B1; A33-B2; A33-B3; A33-B4; A33-B5; A33-B6; A33-B7; A33-B8; A33-B9; A33-B10; A33-B11; A33-B12; A33-B13; A33-B14; A33-B15; A33-B16; A33-B17; A33-B18; A33-B19; A33-B20; A33-B21; A33-B22; A33-B23; A33-B24; A33-B25; A33-B26; A33-B27; A33-B28; A33-B29; A33-B30; A33-B31; A33-B32; A33-B33; A33-B34; A33-B35; A33-B36; A33-B37; A33-B38; A33-B39; A33-B40; A33-B41; A33-B42; A33-B43; A33-B44; A33-B45; A33-B46; A33-B47; A33-B48; A33-B49; A33-B50; A33-B51; A33-B52; A33-B53; A33-B54; A33-B55; A33-B56; A33-B57; A33-B58; A33-B59; A33-B60; A33-B61; A33-B62; A33-B63; A33-B64; A33-B65; A33-B66; A33-B67; A33-B68; A33-B69; A33-B70; A33-B71; A33-B72; A33-B73; A33-B74; A33-B75; A33-B76; A33-B77; A33-B78; A33-B79; A33-B80; A33-B81; A33-B82; A33-B83; A33-B84; A33-B85; A33-B86; A33-B87; A33-B88; A33-B89; A33-B90; A33-B91; A33-B92; A33-B93; A33-B94; A33-B95; A33-B96; A33-B97; A33-B98; A33-B99; A33-B100; A33-B101; A33-B102; A33-B103; A33-B104; A33-B105; A33-B106; A33-B107; A33-B108; A33-B109; A33-B110; A33-B111; A33-B112; A33-B113;

A34-B1; A34-B2; A34-B3; A34-B4; A34-B5; A34-B6; A34-B7; A34-B8; A34-B9; A34-B10; A34-B11; A34-B12; A34-B13; A34-B14; A34-B15; A34-B16; A34-B17; A34-B18; A34-B19; A34-B20; A34-B21; A34-B22; A34-B23; A34-B24; A34-B25; A34-B26; A34-B27; A34-B28; A34-B29; A34-B30; A34-B31; A34-B32; A34-B33; A34-B34; A34-B35; A34-B36; A34-B37; A34-B38; A34-B39; A34-B40; A34-B41; A34-B42; A34-B43; A34-B44; A34-B45; A34-B46; A34-B47; A34-B48; A34-B49; A34-B50; A34-B51; A34-B52; A34-B53; A34-B54; A34-B55; A34-B56; A34-B57; A34-B58; A34-B59; A34-B60; A34-B61; A34-B62; A34-B63; A34-B64; A34-B65; A34-B66; A34-B67; A34-B68; A34-B69; A34-B70; A34-B71; A34-B72; A34-B73; A34-B74; A34-B75; A34-B76; A34-B77; A34-B78; A34-B79; A34-B80; A34-B81; A34-B82; A34-B83; A34-B84; A34-B85; A34-B86; A34-B87; A34-B88; A34-B89; A34-B90; A34-B91; A34-B92; A34-B93; A34-B94; A34-B95; A34-B96; A34-B97; A34-B98; A34-B99; A34-B100; A34-B101; A34-B102; A34-B103; A34-B104; A34-B105; A34-B106; A34-B107; A34-B108; A34-B109; A34-B110; A34-B111; A34-B112; A34-B113;

A35-B1; A35-B2; A35-B3; A35-B4; A35-B5; A35-B6; A35-B7; A35-B8; A35-B9; A35-B10; A35-B11; A35-B12; A35-B13; A35-B14; A35-B15; A35-B16; A35-B17; A35-B18; A35-B19; A35-B20; A35-B21; A35-B22; A35-B23; A35-B24; A35-B25; A35-B26; A35-B27; A35-B28; A35-B29; A35-B30; A35-B31; A35-B32; A35-B33; A35-B34; A35-B35; A35-B36; A35-B37; A35-B38; A35-B39; A35-B40; A35-B41; A35-B42; A35-B43; A35-B44; A35-B45; A35-B46; A35-B47; A35-B48; A35-B49; A35-B50; A35-B51; A35-B52; A35-B53; A35-B54; A35-B55; A35-B56; A35-B57; A35-B58; A35-B59; A35-B60; A35-B61; A35-B62; A35-B63; A35-B64; A35-B65; A35-B66; A35-B67; A35-B68; A35-B69; A35-B70; A35-B71; A35-B72; A35-B73; A35-B74; A35-B75; A35-B76; A35-B77; A35-B78; A35-B79; A35-B80; A35-B81; A35-B82; A35-B83; A35-B84; A35-B85; A35-B86; A35-B87; A35-B88; A35-B89; A35-B90; A35-B91; A35-B92; A35-B93; A35-B94; A35-B95; A35-B96; A35-B97; A35-B98; A35-B99; A35-B100; A35-B101; A35-B102; A35-B103; A35-B104; A35-B105; A35-B106; A35-B107; A35-B108; A35-B109; A35-B110; A35-B111; A35-B112; A35-B113;

A36-B1; A36-B2; A36-B3; A36-B4; A36-B5; A36-B6; A36-B7; A36-B8; A36-B9; A36-B10; A36-B11; A36-B12; A36-B13; A36-B14; A36-B15; A36-B16; A36-B17; A36-B18; A36-B19; A36-B20; A36-B21; A36-B22; A36-B23; A36-B24; A36-B25; A36-B26; A36-B27; A36-B28; A36-B29; A36-B30; A36-B31; A36-B32; A36-B33; A36-B34; A36-B35; A36-B36; A36-B37; A36-B38; A36-B39; A36-B40; A36-B41; A36-B42; A36-B43; A36-B44; A36-B45; A36-B46; A36-B47; A36-B48; A36-B49; A36-B50; A36-B51; A36-B52; A36-B53; A36-B54; A36-B55; A36-B56; A36-B57; A36-B58; A36-B59; A36-B60; A36-B61; A36-B62; A36-B63; A36-B64; A36-B65; A36-B66; A36-B67; A36-B68; A36-B69; A36-B70; A36-B71; A36-B72; A36-B73; A36-B74; A36-B75; A36-B76; A36-B77; A36-B78; A36-B79; A36-B80; A36-B81; A36-B82; A36-B83; A36-B84; A36-B85; A36-B86; A36-B87; A36-B88; A36-B89; A36-B90; A36-B91; A36-B92; A36-B93; A36-B94; A36-B95; A36-B96; A36-B97; A36-B98; A36-B99; A36-B100; A36-B101; A36-B102; A36-B103; A36-B104; A36-B105;

A36-B106; A36-B107; A36-B108; A36-B109; A36-B110; A36-B111; A36-B112; A36-B113;

A37-B1; A37-B2; A37-B3; A37-B4; A37-B5; A37-B6; A37-B7; A37-B8; A37-B9; A37-B10; A37-B11; A37-B12; A37-B13; A37-B14; A37-B15; A37-B16; A37-B17; A37-B18; A37-B19; A37-B20; A37-B21; A37-B22; A37-B23; A37-B24; A37-B25; A37-B26; A37-B27; A37-B28; A37-B29; A37-B30; A37-B31; A37-B32; A37-B33; A37-B34; A37-B35; A37-B36; A37-B37; A37-B38; A37-B39; A37-B40; A37-B41; A37-B42; A37-B43; A37-B44; A37-B45; A37-B46; A37-B47; A37-B48; A37-B49; A37-B50; A37-B51; A37-B52; A37-B53; A37-B54; A37-B55; A37-B56; A37-B57; A37-B58; A37-B59; A37-B60; A37-B61; A37-B62; A37-B63; A37-B64; A37-B65; A37-B66; A37-B67; A37-B68; A37-B69; A37-B70; A37-B71; A37-B72; A37-B73; A37-B74; A37-B75; A37-B76; A37-B77; A37-B78; A37-B79; A37-B80; A37-B81; A37-B82; A37-B83; A37-B84; A37-B85; A37-B86; A37-B87; A37-B88; A37-B89; A37-B90; A37-B91; A37-B92; A37-B93; A37-B94; A37-B95; A37-B96; A37-B97; A37-B98; A37-B99; A37-B100; A37-B101; A37-B102; A37-B103; A37-B104; A37-B105; A37-B106; A37-B107; A37-B108; A37-B109; A37-B110; A37-B111; A37-B112; A37-B113;

A38-B1; A38-B2; A38-B3; A38-B4; A38-B5; A38-B6; A38-B7; A38-B8; A38-B9; A38-B10; A38-B11; A38-B12; A38-B13; A38-B14; A38-B15; A38-B16; A38-B17; A38-B18; A38-B19; A38-B20; A38-B21; A38-B22; A38-B23; A38-B24; A38-B25; A38-B26; A38-B27; A38-B28; A38-B29; A38-B30; A38-B31; A38-B32; A38-B33; A38-B34; A38-B35; A38-B36; A38-B37; A38-B38; A38-B39; A38-B40; A38-B41; A38-B42; A38-B43; A38-B44; A38-B45; A38-B46; A38-B47; A38-B48; A38-B49; A38-B50; A38-B51; A38-B52; A38-B53; A38-B54; A38-B55; A38-B56; A38-B57; A38-B58; A38-B59; A38-B60; A38-B61; A38-B62; A38-B63; A38-B64; A38-B65; A38-B66; A38-B67; A38-B68; A38-B69; A38-B70; A38-B71; A38-B72; A38-B73; A38-B74; A38-B75; A38-B76; A38-B77; A38-B78; A38-B79; A38-B80; A38-B81; A38-B82; A38-B83; A38-B84; A38-B85; A38-B86; A38-B87; A38-B88; A38-B89; A38-B90; A38-B91; A38-B92; A38-B93; A38-B94; A38-B95; A38-B96; A38-B97; A38-B98; A38-B99; A38-B100; A38-B101; A38-B102; A38-B103; A38-B104; A38-B105; A38-B106; A38-B107; A38-B108; A38-B109; A38-B110; A38-B111; A38-B112; A38-B113;

A39-B1; A39-B2; A39-B3; A39-B4; A39-B5; A39-B6; A39-B7; A39-B8; A39-B9; A39-B10; A39-B11; A39-B12; A39-B13; A39-B14; A39-B15; A39-B16; A39-B17; A39-B18; A39-B19; A39-B20; A39-B21; A39-B22; A39-B23; A39-B24; A39-B25; A39-B26; A39-B27; A39-B28; A39-B29; A39-B30; A39-B31; A39-B32; A39-B33; A39-B34; A39-B35; A39-B36; A39-B37; A39-B38; A39-B39; A39-B40; A39-B41; A39-B42; A39-B43; A39-B44; A39-B45; A39-B46; A39-B47; A39-B48; A39-B49; A39-B50; A39-B51; A39-B52; A39-B53; A39-B54; A39-B55; A39-B56; A39-B57; A39-B58; A39-B59; A39-B60; A39-B61; A39-B62; A39-B63; A39-B64; A39-B65; A39-B66; A39-B67; A39-B68; A39-B69; A39-B70; A39-B71; A39-B72; A39-B73; A39-B74; A39-B75; A39-B76; A39-B77; A39-B78; A39-B79; A39-B80; A39-B81; A39-B82; A39-B83; A39-B84; A39-B85; A39-B86; A39-B87; A39-B88; A39-B89; A39-B90; A39-B91; A39-B92; A39-B93; A39-B94; A39-B95; A39-B96; A39-B97; A39-B98; A39-B99; A39-B100; A39-B101; A39-B102; A39-B103; A39-B104; A39-B105; A39-B106; A39-B107; A39-B108; A39-B109; A39-B110; A39-B111; A39-B112; A39-B113;

A40-B1; A40-B2; A40-B3; A40-B4; A40-B5; A40-B6; A40-B7; A40-B8; A40-B9; A40-B10; A40-B11; A40-B12; A40-B13; A40-B14; A40-B15; A40-B16; A40-B17; A40-B18; A40-B19; A40-B20; A40-B21; A40-B22; A40-B23; A40-B24; A40-B25; A40-B26; A40-B27; A40-B28; A40-B29; A40-B30; A40-B31; A40-B32; A40-B33; A40-B34; A40-B35; A40-B36; A40-B37; A40-B38; A40-B39; A40-B40; A40-B41; A40-B42; A40-B43; A40-B44; A40-B45; A40-B46; A40-B47; A40-B48; A40-B49; A40-B50; A40-B51; A40-B52; A40-B53; A40-B54; A40-B55; A40-B56; A40-B57; A40-B58; A40-B59; A40-B60; A40-B61; A40-B62; A40-B63; A40-B64; A40-B65; A40-B66; A40-B67; A40-B68; A40-B69; A40-B70; A40-B71; A40-B72; A40-B73; A40-B74; A40-B75; A40-B76; A40-B77; A40-B78; A40-B79; A40-B80; A40-B81; A40-B82; A40-B83; A40-B84; A40-B85; A40-B86; A40-B87; A40-B88; A40-B89; A40-B90; A40-B91; A40-B92; A40-B93; A40-B94; A40-B95; A40-B96; A40-B97; A40-B98; A40-B99; A40-B100; A40-B101; A40-B102; A40-B103; A40-B104; A40-B105; A40-B106; A40-B107; A40-B108; A40-B109; A40-B110; A40-B111; A40-B112; A40-B113;

A41-B1; A41-B2; A41-B3; A41-B4; A41-B5; A41-B6; A41-B7; A41-B8; A41-B9; A41-B10; A41-B11; A41-B12; A41-B13; A41-B14; A41-B15; A41-B16; A41-B17; A41-B18; A41-B19; A41-B20; A41-B21; A41-B22; A41-B23; A41-B24; A41-B25; A41-B26; A41-B27; A41-B28; A41-B29; A41-B30; A41-B31; A41-B32; A41-B33; A41-B34; A41-B35; A41-B36; A41-B37; A41-B38; A41-B39; A41-B40; A41-B41; A41-B42; A41-B43; A41-B44; A41-B45; A41-B46; A41-B47; A41-B48; A41-B49; A41-B50; A41-B51; A41-B52; A41-B53; A41-B54; A41-B55; A41-B56; A41-B57; A41-B58; A41-B59; A41-B60; A41-B61; A41-B62; A41-B63; A41-B64; A41-B65; A41-B66; A41-B67; A41-B68; A41-B69; A41-B70; A41-B71; A41-B72; A41-B73; A41-B74; A41-B75; A41-B76; A41-B77; A41-B78; A41-B79; A41-B80; A41-B81; A41-B82; A41-B83; A41-B84; A41-B85; A41-B86; A41-B87; A41-B88; A41-B89; A41-B90; A41-B91; A41-B92; A41-B93; A41-B94; A41-B95; A41-B96; A41-B97; A41-B98; A41-B99; A41-B100; A41-B101; A41-B102; A41-B103; A41-B104; A41-B105; A41-B106; A41-B107; A41-B108; A41-B109; A41-B110; A41-B111; A41-B112; A41-B113;

A42-B1; A42-B2; A42-B3; A42-B4; A42-B5; A42-B6; A42-B7; A42-B8; A42-B9; A42-B10; A42-B11; A42-B12; A42-B13; A42-B14; A42-B15; A42-B16; A42-B17; A42-B18; A42-B19; A42-B20; A42-B21; A42-B22; A42-B23; A42-B24; A42-B25; A42-B26; A42-B27; A42-B28; A42-B29; A42-B30; A42-B31; A42-B32; A42-B33; A42-B34; A42-B35; A42-B36; A42-B37; A42-B38; A42-B39; A42-B40; A42-B41; A42-B42; A42-B43; A42-B44; A42-B45; A42-B46; A42-B47; A42-B48; A42-B49; A42-B50; A42-B51; A42-B52; A42-B53; A42-B54; A42-B55; A42-B56; A42-B57; A42-B58; A42-B59; A42-B60; A42-B61; A42-B62; A42-B63; A42-B64; A42-B65; A42-B66; A42-B67; A42-B68; A42-B69; A42-B70; A42-B71; A42-B72; A42-B73; A42-B74; A42-B75; A42-B76; A42-B77; A42-B78; A42-B79; A42-B80; A42-B81; A42-B82; A42-B83; A42-B84; A42-B85; A42-B86; A42-B87; A42-B88; A42-B89; A42-B90; A42-B91; A42-B92; A42-B93; A42-B94; A42-B95; A42-B96; A42-B97; A42-B98; A42-B99; A42-B100; A42-B101; A42-B102; A42-B103; A42-B104; A42-B105; A42-B106; A42-B107; A42-B108; A42-B109; A42-B110; A42-B111; A42-B112; A42-B113;

A43-B1; A43-B2; A43-B3; A43-B4; A43-B5; A43-B6; A43-B7; A43-B8; A43-B9; A43-B10; A43-B11; A43-B12; A43-B13; A43-B14; A43-B15; A43-B16; A43-B17; A43-B18; A43-B19; A43-B20; A43-B21; A43-B22; A43-B23; A43-B24; A43-B25; A43-B26; A43-B27; A43-B28; A43-B29; A43-B30; A43-B31; A43-B32; A43-B33; A43-B34;

A43-B35; A43-B36; A43-B37; A43-B38; A43-B39; A43-B40; A43-B41; A43-B42; A43-B43; A43-B44; A43-B45; A43-B46; A43-B47; A43-B48; A43-B49; A43-B50; A43-B51; A43-B52; A43-B53; A43-B54; A43-B55; A43-B56; A43-B57; A43-B58; A43-B59; A43-B60; A43-B61; A43-B62; A43-B63; A43-B64; A43-B65; A43-B66; A43-B67; A43-B68; A43-B69; A43-B70; A43-B71; A43-B72; A43-B73; A43-B74; A43-B75; A43-B76; A43-B77; A43-B78; A43-B79; A43-B80; A43-B81; A43-B82; A43-B83; A43-B84; A43-B85; A43-B86; A43-B87; A43-B88; A43-B89; A43-B90; A43-B91; A43-B92; A43-B93; A43-B94; A43-B95; A43-B96; A43-B97; A43-B98; A43-B99; A43-B100; A43-B101; A43-B102; A43-B103; A43-B104; A43-B105; A43-B106; A43-B107; A43-B108; A43-B109; A43-B110; A43-B111; A43-B112; A43-B113;

A44-B1; A44-B2; A44-B3; A44-B4; A44-B5; A44-B6; A44-B7; A44-B8; A44-B9; A44-B10; A44-B11; A44-B12; A44-B13; A44-B14; A44-B15; A44-B16; A44-B17; A44-B18; A44-B19; A44-B20; A44-B21; A44-B22; A44-B23; A44-B24; A44-B25; A44-B26; A44-B27; A44-B28; A44-B29; A44-B30; A44-B31; A44-B32; A44-B33; A44-B34; A44-B35; A44-B36; A44-B37; A44-B38; A44-B39; A44-B40; A44-B41; A44-B42; A44-B43; A44-B44; A44-B45; A44-B46; A44-B47; A44-B48; A44-B49; A44-B50; A44-B51; A44-B52; A44-B53; A44-B54; A44-B55; A44-B56; A44-B57; A44-B58; A44-B59; A44-B60; A44-B61; A44-B62; A44-B63; A44-B64; A44-B65; A44-B66; A44-B67; A44-B68; A44-B69; A44-B70; A44-B71; A44-B72; A44-B73; A44-B74; A44-B75; A44-B76; A44-B77; A44-B78; A44-B79; A44-B80; A44-B81; A44-B82; A44-B83; A44-B84; A44-B85; A44-B86; A44-B87; A44-B88; A44-B89; A44-B90; A44-B91; A44-B92; A44-B93; A44-B94; A44-B95; A44-B96; A44-B97; A44-B98; A44-B99; A44-B100; A44-B101; A44-B102; A44-B103; A44-B104; A44-B105; A44-B106; A44-B107; A44-B108; A44-B109; A44-B110; A44-B111; A44-B112; A44-B113;

A45-B1; A45-B2; A45-B3; A45-B4; A45-B5; A45-B6; A45-B7; A45-B8; A45-B9; A45-B10; A45-B11; A45-B12; A45-B13; A45-B14; A45-B15; A45-B16; A45-B17; A45-B18; A45-B19; A45-B20; A45-B21; A45-B22; A45-B23; A45-B24; A45-B25; A45-B26; A45-B27; A45-B28; A45-B29; A45-B30; A45-B31; A45-B32; A45-B33; A45-B34; A45-B35; A45-B36; A45-B37; A45-B38; A45-B39; A45-B40; A45-B41; A45-B42; A45-B43; A45-B44; A45-B45; A45-B46; A45-B47; A45-B48; A45-B49; A45-B50; A45-B51; A45-B52; A45-B53; A45-B54; A45-B55; A45-B56; A45-B57; A45-B58; A45-B59; A45-B60; A45-B61; A45-B62; A45-B63; A45-B64; A45-B65; A45-B66; A45-B67; A45-B68; A45-B69; A45-B70; A45-B71; A45-B72; A45-B73; A45-B74; A45-B75; A45-B76; A45-B77; A45-B78; A45-B79; A45-B80; A45-B81; A45-B82; A45-B83; A45-B84; A45-B85; A45-B86; A45-B87; A45-B88; A45-B89; A45-B90; A45-B91; A45-B92; A45-B93; A45-B94; A45-B95; A45-B96; A45-B97; A45-B98; A45-B99; A45-B100; A45-B101; A45-B102; A45-B103; A45-B104; A45-B105; A45-B106; A45-B107; A45-B108; A45-B109; A45-B110; A45-B111; A45-B112; A45-B113;

A46-B1; A46-B2; A46-B3; A46-B4; A46-B5; A46-B6; A46-B7; A46-B8; A46-B9; A46-B10; A46-B11; A46-B12; A46-B13; A46-B14; A46-B15; A46-B16; A46-B17; A46-B18; A46-B19; A46-B20; A46-B21; A46-B22; A46-B23; A46-B24; A46-B25; A46-B26; A46-B27; A46-B28; A46-B29; A46-B30; A46-B31; A46-B32; A46-B33; A46-B34; A46-B35; A46-B36; A46-B37; A46-B38; A46-B39; A46-B40; A46-B41; A46-B42; A46-B43; A46-B44; A46-B45; A46-B46; A46-B47; A46-B48; A46-B49; A46-B50; A46-B51; A46-B52; A46-B53; A46-B54; A46-B55; A46-B56; A46-B57; A46-B58; A46-B59; A46-B60; A46-B61; A46-B62; A46-B63; A46-B64; A46-B65; A46-B66; A46-B67; A46-B68; A46-B69; A46-B70; A46-B71; A46-B72; A46-B73; A46-B74; A46-B75; A46-B76; A46-B77; A46-B78; A46-B79; A46-B80; A46-B81; A46-B82; A46-B83; A46-B84; A46-B85; A46-B86; A46-B87; A46-B88; A46-B89; A46-B90; A46-B91; A46-B92; A46-B93; A46-B94; A46-B95; A46-B96; A46-B97; A46-B98; A46-B99; A46-B100; A46-B101; A46-B102; A46-B103; A46-B104; A46-B105; A46-B106; A46-B107; A46-B108; A46-B109; A46-B110; A46-B111; A46-B112; A46-B113;

A47-B1; A47-B2; A47-B3; A47-B4; A47-B5; A47-B6; A47-B7; A47-B8; A47-B9; A47-B10; A47-B11; A47-B12; A47-B13; A47-B14; A47-B15; A47-B16; A47-B17; A47-B18; A47-B19; A47-B20; A47-B21; A47-B22; A47-B23; A47-B24; A47-B25; A47-B26; A47-B27; A47-B28; A47-B29; A47-B30; A47-B31; A47-B32; A47-B33; A47-B34; A47-B35; A47-B36; A47-B37; A47-B38; A47-B39; A47-B40; A47-B41; A47-B42; A47-B43; A47-B44; A47-B45; A47-B46; A47-B47; A47-B48; A47-B49; A47-B50; A47-B51; A47-B52; A47-B53; A47-B54; A47-B55; A47-B56; A47-B57; A47-B58; A47-B59; A47-B60; A47-B61; A47-B62; A47-B63; A47-B64; A47-B65; A47-B66; A47-B67; A47-B68; A47-B69; A47-B70; A47-B71; A47-B72; A47-B73; A47-B74; A47-B75; A47-B76; A47-B77; A47-B78; A47-B79; A47-B80; A47-B81; A47-B82; A47-B83; A47-B84; A47-B85; A47-B86; A47-B87; A47-B88; A47-B89; A47-B90; A47-B91; A47-B92; A47-B93; A47-B94; A47-B95; A47-B96; A47-B97; A47-B98; A47-B99; A47-B100; A47-B101; A47-B102; A47-B103; A47-B104; A47-B105; A47-B106; A47-B107; A47-B108; A47-B109; A47-B110; A47-B111; A47-B112; A47-B113;

A48-B1; A48-B2; A48-B3; A48-B4; A48-B5; A48-B6; A48-B7; A48-B8; A48-B9; A48-B10; A48-B11; A48-B12; A48-B13; A48-B14; A48-B15; A48-B16; A48-B17; A48-B18; A48-B19; A48-B20; A48-B21; A48-B22; A48-B23; A48-B24; A48-B25; A48-B26; A48-B27; A48-B28; A48-B29; A48-B30; A48-B31; A48-B32; A48-B33; A48-B34; A48-B35; A48-B36; A48-B37; A48-B38; A48-B39; A48-B40; A48-B41; A48-B42; A48-B43; A48-B44; A48-B45; A48-B46; A48-B47; A48-B48; A48-B49; A48-B50; A48-B51; A48-B52; A48-B53; A48-B54; A48-B55; A48-B56; A48-B57; A48-B58; A48-B59; A48-B60; A48-B61; A48-B62; A48-B63; A48-B64; A48-B65; A48-B66; A48-B67; A48-B68; A48-B69; A48-B70; A48-B71; A48-B72; A48-B73; A48-B74; A48-B75; A48-B76; A48-B77; A48-B78; A48-B79; A48-B80; A48-B81; A48-B82; A48-B83; A48-B84; A48-B85; A48-B86; A48-B87; A48-B88; A48-B89; A48-B90; A48-B91; A48-B92; A48-B93; A48-B94; A48-B95; A48-B96; A48-B97; A48-B98; A48-B99; A48-B100; A48-B101; A48-B102; A48-B103; A48-B104; A48-B105; A48-B106; A48-B107; A48-B108; A48-B109; A48-B110; A48-B111; A48-B112; A48-B113;

A49-B1; A49-B2; A49-B3; A49-B4; A49-B5; A49-B6; A49-B7; A49-B8; A49-B9; A49-B10; A49-B11; A49-B12; A49-B13; A49-B14; A49-B15; A49-B16; A49-B17; A49-B18; A49-B19; A49-B20; A49-B21; A49-B22; A49-B23; A49-B24; A49-B25; A49-B26; A49-B27; A49-B28; A49-B29; A49-B30; A49-B31; A49-B32; A49-B33; A49-B34; A49-B35; A49-B36; A49-B37; A49-B38; A49-B39; A49-B40; A49-B41; A49-B42; A49-B43; A49-B44; A49-B45; A49-B46; A49-B47; A49-B48; A49-B49; A49-B50; A49-B51; A49-B52; A49-B53; A49-B54; A49-B55; A49-B56; A49-B57; A49-B58; A49-B59; A49-B60; A49-B61; A49-B62; A49-B63; A49-B64; A49-B65; A49-B66; A49-B67; A49-B68; A49-B69; A49-B70; A49-B71; A49-B72; A49-B73; A49-B74; A49-B75; A49-B76; A49-B77; A49-B78;

A49-B79; A49-B80; A49-B81; A49-B82; A49-B83; A49-B84; A49-B85; A49-B86; A49-B87; A49-B88; A49-B89; A49-B90; A49-B91; A49-B92; A49-B93; A49-B94; A49-B95; A49-B96; A49-B97; A49-B98; A49-B99; A49-B100; A49-B101; A49-B102; A49-B103; A49-B104; A49-B105; A49-B106; A49-B107; A49-B108; A49-B109; A49-B110; A49-B111; A49-B112; A49-B113;

A50-B1; A50-B2; A50-B3; A50-B4; A50-B5; A50-B6; A50-B7; A50-B8; A50-B9; A50-B10; A50-B11; A50-B12; A50-B13; A50-B14; A50-B15; A50-B16; A50-B17; A50-B18; A50-B19; A50-B20; A50-B21; A50-B22; A50-B23; A50-B24; A50-B25; A50-B26; A50-B27; A50-B28; A50-B29; A50-B30; A50-B31; A50-B32; A50-B33; A50-B34; A50-B35; A50-B36; A50-B37; A50-B38; A50-B39; A50-B40; A50-B41; A50-B42; A50-B43; A50-B44; A50-B45; A50-B46; A50-B47; A50-B48; A50-B49; A50-B50; A50-B51; A50-B52; A50-B53; A50-B54; A50-B55; A50-B56; A50-B57; A50-B58; A50-B59; A50-B60; A50-B61; A50-B62; A50-B63; A50-B64; A50-B65; A50-B66; A50-B67; A50-B68; A50-B69; A50-B70; A50-B71; A50-B72; A50-B73; A50-B74; A50-B75; A50-B76; A50-B77; A50-B78; A50-B79; A50-B80; A50-B81; A50-B82; A50-B83; A50-B84; A50-B85; A50-B86; A50-B87; A50-B88; A50-B89; A50-B90; A50-B91; A50-B92; A50-B93; A50-B94; A50-B95; A50-B96; A50-B97; A50-B98; A50-B99; A50-B100; A50-B101; A50-B102; A50-B103; A50-B104; A50-B105; A50-B106; A50-B107; A50-B108; A50-B109; A50-B110; A50-B111; A50-B112; A50-B113;

A51-B1; A51-B2; A51-B3; A51-B4; A51-B5; A51-B6; A51-B7; A51-B8; A51-B9; A51-B10; A51-B11; A51-B12; A51-B13; A51-B14; A51-B15; A51-B16; A51-B17; A51-B18; A51-B19; A51-B20; A51-B21; A51-B22; A51-B23; A51-B24; A51-B25; A51-B26; A51-B27; A51-B28; A51-B29; A51-B30; A51-B31; A51-B32; A51-B33; A51-B34; A51-B35; A51-B36; A51-B37; A51-B38; A51-B39; A51-B40; A51-B41; A51-B42; A51-B43; A51-B44; A51-B45; A51-B46; A51-B47; A51-B48; A51-B49; A51-B50; A51-B51; A51-B52; A51-B53; A51-B54; A51-B55; A51-B56; A51-B57; A51-B58; A51-B59; A51-B60; A51-B61; A51-B62; A51-B63; A51-B64; A51-B65; A51-B66; A51-B67; A51-B68; A51-B69; A51-B70; A51-B71; A51-B72; A51-B73; A51-B74; A51-B75; A51-B76; A51-B77; A51-B78; A51-B79; A51-B80; A51-B81; A51-B82; A51-B83; A51-B84; A51-B85; A51-B86; A51-B87; A51-B88; A51-B89; A51-B90; A51-B91; A51-B92; A51-B93; A51-B94; A51-B95; A51-B96; A51-B97; A51-B98; A51-B99; A51-B100; A51-B101; A51-B102; A51-B103; A51-B104; A51-B105; A51-B106; A51-B107; A51-B108; A51-B109; A51-B110; A51-B111; A51-B112; A51-B113;

A52-B1; A52-B2; A52-B3; A52-B4; A52-B5; A52-B6; A52-B7; A52-B8; A52-B9; A52-B10; A52-B11; A52-B12; A52-B13; A52-B14; A52-B15; A52-B16; A52-B17; A52-B18; A52-B19; A52-B20; A52-B21; A52-B22; A52-B23; A52-B24; A52-B25; A52-B26; A52-B27; A52-B28; A52-B29; A52-B30; A52-B31; A52-B32; A52-B33; A52-B34; A52-B35; A52-B36; A52-B37; A52-B38; A52-B39; A52-B40; A52-B41; A52-B42; A52-B43; A52-B44; A52-B45; A52-B46; A52-B47; A52-B48; A52-B49; A52-B50; A52-B51; A52-B52; A52-B53; A52-B54; A52-B55; A52-B56; A52-B57; A52-B58; A52-B59; A52-B60; A52-B61; A52-B62; A52-B63; A52-B64; A52-B65; A52-B66; A52-B67; A52-B68; A52-B69; A52-B70; A52-B71; A52-B72; A52-B73; A52-B74; A52-B75; A52-B76; A52-B77; A52-B78; A52-B79; A52-B80; A52-B81; A52-B82; A52-B83; A52-B84; A52-B85; A52-B86; A52-B87; A52-B88; A52-B89; A52-B90; A52-B91; A52-B92; A52-B93; A52-B94; A52-B95; A52-B96; A52-B97; A52-B98; A52-B99; A52-B100; A52-B101; A52-B102; A52-B103; A52-B104; A52-B105; A52-B106; A52-B107; A52-B108; A52-B109; A52-B110; A52-B111; A52-B112; A52-B113;

A53-B1; A53-B2; A53-B3; A53-B4; A53-B5; A53-B6; A53-B7; A53-B8; A53-B9; A53-B10; A53-B11; A53-B12; A53-B13; A53-B14; A53-B15; A53-B16; A53-B17; A53-B18; A53-B19; A53-B20; A53-B21; A53-B22; A53-B23; A53-B24; A53-B25; A53-B26; A53-B27; A53-B28; A53-B29; A53-B30; A53-B31; A53-B32; A53-B33; A53-B34; A53-B35; A53-B36; A53-B37; A53-B38; A53-B39; A53-B40; A53-B41; A53-B42; A53-B43; A53-B44; A53-B45; A53-B46; A53-B47; A53-B48; A53-B49; A53-B50; A53-B51; A53-B52; A53-B53; A53-B54; A53-B55; A53-B56; A53-B57; A53-B58; A53-B59; A53-B60; A53-B61; A53-B62; A53-B63; A53-B64; A53-B65; A53-B66; A53-B67; A53-B68; A53-B69; A53-B70; A53-B71; A53-B72; A53-B73; A53-B74; A53-B75; A53-B76; A53-B77; A53-B78; A53-B79; A53-B80; A53-B81; A53-B82; A53-B83; A53-B84; A53-B85; A53-B86; A53-B87; A53-B88; A53-B89; A53-B90; A53-B91; A53-B92; A53-B93; A53-B94; A53-B95; A53-B96; A53-B97; A53-B98; A53-B99; A53-B100; A53-B101; A53-B102; A53-B103; A53-B104; A53-B105; A53-B106; A53-B107; A53-B108; A53-B109; A53-B110; A53-B111; A53-B112; A53-B113;

A54-B1; A54-B2; A54-B3; A54-B4; A54-B5; A54-B6; A54-B7; A54-B8; A54-B9; A54-B10; A54-B11; A54-B12; A54-B13; A54-B14; A54-B15; A54-B16; A54-B17; A54-B18; A54-B19; A54-B20; A54-B21; A54-B22; A54-B23; A54-B24; A54-B25; A54-B26; A54-B27; A54-B28; A54-B29; A54-B30; A54-B31; A54-B32; A54-B33; A54-B34; A54-B35; A54-B36; A54-B37; A54-B38; A54-B39; A54-B40; A54-B41; A54-B42; A54-B43; A54-B44; A54-B45; A54-B46; A54-B47; A54-B48; A54-B49; A54-B50; A54-B51; A54-B52; A54-B53; A54-B54; A54-B55; A54-B56; A54-B57; A54-B58; A54-B59; A54-B60; A54-B61; A54-B62; A54-B63; A54-B64; A54-B65; A54-B66; A54-B67; A54-B68; A54-B69; A54-B70; A54-B71; A54-B72; A54-B73; A54-B74; A54-B75; A54-B76; A54-B77; A54-B78; A54-B79; A54-B80; A54-B81; A54-B82; A54-B83; A54-B84; A54-B85; A54-B86; A54-B87; A54-B88; A54-B89; A54-B90; A54-B91; A54-B92; A54-B93; A54-B94; A54-B95; A54-B96; A54-B97; A54-B98; A54-B99; A54-B100; A54-B101; A54-B102; A54-B103; A54-B104; A54-B105; A54-B106; A54-B107; A54-B108; A54-B109; A54-B110; A54-B111; A54-B112; A54-B113;

A55-B1; A55-B2; A55-B3; A55-B4; A55-B5; A55-B6; A55-B7; A55-B8; A55-B9; A55-B10; A55-B11; A55-B12; A55-B13; A55-B14; A55-B15; A55-B16; A55-B17; A55-B18; A55-B19; A55-B20; A55-B21; A55-B22; A55-B23; A55-B24; A55-B25; A55-B26; A55-B27; A55-B28; A55-B29; A55-B30; A55-B31; A55-B32; A55-B33; A55-B34; A55-B35; A55-B36; A55-B37; A55-B38; A55-B39; A55-B40; A55-B41; A55-B42; A55-B43; A55-B44; A55-B45; A55-B46; A55-B47; A55-B48; A55-B49; A55-B50; A55-B51; A55-B52; A55-B53; A55-B54; A55-B55; A55-B56; A55-B57; A55-B58; A55-B59; A55-B60; A55-B61; A55-B62; A55-B63; A55-B64; A55-B65; A55-B66; A55-B67; A55-B68; A55-B69; A55-B70; A55-B71; A55-B72; A55-B73; A55-B74; A55-B75; A55-B76; A55-B77; A55-B78; A55-B79; A55-B80; A55-B81; A55-B82; A55-B83; A55-B84; A55-B85; A55-B86; A55-B87; A55-B88; A55-B89; A55-B90; A55-B91; A55-B92; A55-B93; A55-B94; A55-B95; A55-B96; A55-B97; A55-B98; A55-B99; A55-B100; A55-B101; A55-B102; A55-B103; A55-B104; A55-B105; A55-B106; A55-B107; A55-B108; A55-B109; A55-B110; A55-B111; A55-B112; A55-B113;

A56-B1; A56-B2; A56-B3; A56-B4; A56-B5; A56-B6; A56-B7; A56-B8; A56-B9; A56-B10; A56-B11; A56-B12; A56-B13; A56-B14; A56-B15; A56-B16; A56-B17; A56-B18; A56-B19; A56-B20; A56-B21; A56-B22; A56-B23; A56-B24; A56-B25; A56-B26; A56-B27; A56-B28; A56-B29; A56-B30; A56-B31; A56-B32; A56-B33; A56-B34; A56-B35; A56-B36; A56-B37; A56-B38; A56-B39; A56-B40; A56-B41; A56-B42; A56-B43; A56-B44; A56-B45; A56-B46; A56-B47; A56-B48; A56-B49; A56-B50; A56-B51; A56-B52; A56-B53; A56-B54; A56-B55; A56-B56; A56-B57; A56-B58; A56-B59; A56-B60; A56-B61; A56-B62; A56-B63; A56-B64; A56-B65; A56-B66; A56-B67; A56-B68; A56-B69; A56-B70; A56-B71; A56-B72; A56-B73; A56-B74; A56-B75; A56-B76; A56-B77; A56-B78; A56-B79; A56-B80; A56-B81; A56-B82; A56-B83; A56-B84; A56-B85; A56-B86; A56-B87; A56-B88; A56-B89; A56-B90; A56-B91; A56-B92; A56-B93; A56-B94; A56-B95; A56-B96; A56-B97; A56-B98; A56-B99; A56-B100; A56-B101; A56-B102; A56-B103; A56-B104; A56-B105; A56-B106; A56-B107; A56-B108; A56-B109; A56-B110; A56-B111; A56-B112; A56-B113;

A57-B1; A57-B2; A57-B3; A57-B4; A57-B5; A57-B6; A57-B7; A57-B8; A57-B9; A57-B10; A57-B11; A57-B12; A57-B13; A57-B14; A57-B15; A57-B16; A57-B17; A57-B18; A57-B19; A57-B20; A57-B21; A57-B22; A57-B23; A57-B24; A57-B25; A57-B26; A57-B27; A57-B28; A57-B29; A57-B30; A57-B31; A57-B32; A57-B33; A57-B34; A57-B35; A57-B36; A57-B37; A57-B38; A57-B39; A57-B40; A57-B41; A57-B42; A57-B43; A57-B44; A57-B45; A57-B46; A57-B47; A57-B48; A57-B49; A57-B50; A57-B51; A57-B52; A57-B53; A57-B54; A57-B55; A57-B56; A57-B57; A57-B58; A57-B59; A57-B60; A57-B61; A57-B62; A57-B63; A57-B64; A57-B65; A57-B66; A57-B67; A57-B68; A57-B69; A57-B70; A57-B71; A57-B72; A57-B73; A57-B74; A57-B75; A57-B76; A57-B77; A57-B78; A57-B79; A57-B80; A57-B81; A57-B82; A57-B83; A57-B84; A57-B85; A57-B86; A57-B87; A57-B88; A57-B89; A57-B90; A57-B91; A57-B92; A57-B93; A57-B94; A57-B95; A57-B96; A57-B97; A57-B98; A57-B99; A57-B100; A57-B101; A57-B102; A57-B103; A57-B104; A57-B105; A57-B106; A57-B107; A57-B108; A57-B109; A57-B110; A57-B111; A57-B112; A57-B113;

A58-B1; A58-B2; A58-B3; A58-B4; A58-B5; A58-B6; A58-B7; A58-B8; A58-B9; A58-B10; A58-B11; A58-B12; A58-B13; A58-B14; A58-B15; A58-B16; A58-B17; A58-B18; A58-B19; A58-B20; A58-B21; A58-B22; A58-B23; A58-B24; A58-B25; A58-B26; A58-B27; A58-B28; A58-B29; A58-B30; A58-B31; A58-B32; A58-B33; A58-B34; A58-B35; A58-B36; A58-B37; A58-B38; A58-B39; A58-B40; A58-B41; A58-B42; A58-B43; A58-B44; A58-B45; A58-B46; A58-B47; A58-B48; A58-B49; A58-B50; A58-B51; A58-B52; A58-B53; A58-B54; A58-B55; A58-B56; A58-B57; A58-B58; A58-B59; A58-B60; A58-B61; A58-B62; A58-B63; A58-B64; A58-B65; A58-B66; A58-B67; A58-B68; A58-B69; A58-B70; A58-B71; A58-B72; A58-B73; A58-B74; A58-B75; A58-B76; A58-B77; A58-B78; A58-B79; A58-B80; A58-B81; A58-B82; A58-B83; A58-B84; A58-B85; A58-B86; A58-B87; A58-B88; A58-B89; A58-B90; A58-B91; A58-B92; A58-B93; A58-B94; A58-B95; A58-B96; A58-B97; A58-B98; A58-B99; A58-B100; A58-B101; A58-B102; A58-B103; A58-B104; A58-B105; A58-B106; A58-B107; A58-B108; A58-B109; A58-B110; A58-B111; A58-B112; A58-B113;

A59-B1; A59-B2; A59-B3; A59-B4; A59-B5; A59-B6; A59-B7; A59-B8; A59-B9; A59-B10; A59-B11; A59-B12; A59-B13; A59-B14; A59-B15; A59-B16; A59-B17; A59-B18; A59-B19; A59-B20; A59-B21; A59-B22; A59-B23; A59-B24; A59-B25; A59-B26; A59-B27; A59-B28; A59-B29; A59-B30; A59-B31; A59-B32; A59-B33; A59-B34; A59-B35; A59-B36; A59-B37; A59-B38; A59-B39; A59-B40; A59-B41; A59-B42; A59-B43; A59-B44; A59-B45; A59-B46; A59-B47; A59-B48; A59-B49; A59-B50; A59-B51; A59-B52; A59-B53; A59-B54; A59-B55; A59-B56; A59-B57; A59-B58; A59-B59; A59-B60; A59-B61; A59-B62; A59-B63; A59-B64; A59-B65; A59-B66; A59-B67; A59-B68; A59-B69; A59-B70; A59-B71; A59-B72; A59-B73; A59-B74; A59-B75; A59-B76; A59-B77; A59-B78; A59-B79; A59-B80; A59-B81; A59-B82; A59-B83; A59-B84; A59-B85; A59-B86; A59-B87; A59-B88; A59-B89; A59-B90; A59-B91; A59-B92; A59-B93; A59-B94; A59-B95; A59-B96; A59-B97; A59-B98; A59-B99; A59-B100; A59-B101; A59-B102; A59-B103; A59-B104; A59-B105; A59-B106; A59-B107; A59-B108; A59-B109; A59-B110; A59-B111; A59-B112; A59-B113;

A60-B1; A60-B2; A60-B3; A60-B4; A60-B5; A60-B6; A60-B7; A60-B8; A60-B9; A60-B10; A60-B11; A60-B12; A60-B13; A60-B14; A60-B15; A60-B16; A60-B17; A60-B18; A60-B19; A60-B20; A60-B21; A60-B22; A60-B23; A60-B24; A60-B25; A60-B26; A60-B27; A60-B28; A60-B29; A60-B30; A60-B31; A60-B32; A60-B33; A60-B34; A60-B35; A60-B36; A60-B37; A60-B38; A60-B39; A60-B40; A60-B41; A60-B42; A60-B43; A60-B44; A60-B45; A60-B46; A60-B47; A60-B48; A60-B49; A60-B50; A60-B51; A60-B52; A60-B53; A60-B54; A60-B55; A60-B56; A60-B57; A60-B58; A60-B59; A60-B60; A60-B61; A60-B62; A60-B63; A60-B64; A60-B65; A60-B66; A60-B67; A60-B68; A60-B69; A60-B70; A60-B71; A60-B72; A60-B73; A60-B74; A60-B75; A60-B76; A60-B77; A60-B78; A60-B79; A60-B80; A60-B81; A60-B82; A60-B83; A60-B84; A60-B85; A60-B86; A60-B87; A60-B88; A60-B89; A60-B90; A60-B91; A60-B92; A60-B93; A60-B94; A60-B95; A60-B96; A60-B97; A60-B98; A60-B99; A60-B100; A60-B101; A60-B102; A60-B103; A60-B104; A60-B105; A60-B106; A60-B107; A60-B108; A60-B109; A60-B110; A60-B111; A60-B112; A60-B113;

A61-B1; A61-B2; A61-B3; A61-B4; A61-B5; A61-B6; A61-B7; A61-B8; A61-B9; A61-B10; A61-B11; A61-B12; A61-B13; A61-B14; A61-B15; A61-B16; A61-B17; A61-B18; A61-B19; A61-B20; A61-B21; A61-B22; A61-B23; A61-B24; A61-B25; A61-B26; A61-B27; A61-B28; A61-B29; A61-B30; A61-B31; A61-B32; A61-B33; A61-B34; A61-B35; A61-B36; A61-B37; A61-B38; A61-B39; A61-B40; A61-B41; A61-B42; A61-B43; A61-B44; A61-B45; A61-B46; A61-B47; A61-B48; A61-B49; A61-B50; A61-B51; A61-B52; A61-B53; A61-B54; A61-B55; A61-B56; A61-B57; A61-B58; A61-B59; A61-B60; A61-B61; A61-B62; A61-B63; A61-B64; A61-B65; A61-B66; A61-B67; A61-B68; A61-B69; A61-B70; A61-B71; A61-B72; A61-B73; A61-B74; A61-B75; A61-B76; A61-B77; A61-B78; A61-B79; A61-B80; A61-B81; A61-B82; A61-B83; A61-B84; A61-B85; A61-B86; A61-B87; A61-B88; A61-B89; A61-B90; A61-B91; A61-B92; A61-B93; A61-B94; A61-B95; A61-B96; A61-B97; A61-B98; A61-B99; A61-B100; A61-B101; A61-B102; A61-B103; A61-B104; A61-B105; A61-B106; A61-B107; A61-B108; A61-B109; A61-B110; A61-B111; A61-B112; A61-B113;

A62-B1; A62-B2; A62-B3; A62-B4; A62-B5; A62-B6; A62-B7; A62-B8; A62-B9; A62-B10; A62-B11; A62-B12; A62-B13; A62-B14; A62-B15; A62-B16; A62-B17; A62-B18; A62-B19; A62-B20; A62-B21; A62-B22; A62-B23; A62-B24; A62-B25; A62-B26; A62-B27; A62-B28; A62-B29; A62-B30; A62-B31; A62-B32; A62-B33; A62-B34; A62-B35; A62-B36; A62-B37; A62-B38; A62-B39; A62-B40; A62-B41; A62-B42; A62-B43; A62-B44; A62-B45;

A62-B46; A62-B47; A62-B48; A62-B49; A62-B50; A62-B51; A62-B52; A62-B53; A62-B54; A62-B55; A62-B56; A62-B57; A62-B58; A62-B59; A62-B60; A62-B61; A62-B62; A62-B63; A62-B64; A62-B65; A62-B66; A62-B67; A62-B68; A62-B69; A62-B70; A62-B71; A62-B72; A62-B73; A62-B74; A62-B75; A62-B76; A62-B77; A62-B78; A62-B79; A62-B80; A62-B81; A62-B82; A62-B83; A62-B84; A62-B85; A62-B86; A62-B87; A62-B88; A62-B89; A62-B90; A62-B91; A62-B92; A62-B93; A62-B94; A62-B95; A62-B96; A62-B97; A62-B98; A62-B99; A62-B100; A62-B101; A62-B102; A62-B103; A62-B104; A62-B105; A62-B106; A62-B107; A62-B108; A62-B109; A62-B110; A62-B111; A62-B112; A62-B113;

A63-B1; A63-B2; A63-B3; A63-B4; A63-B5; A63-B6; A63-B7; A63-B8; A63-B9; A63-B10; A63-B11; A63-B12; A63-B13; A63-B14; A63-B15; A63-B16; A63-B17; A63-B18; A63-B19; A63-B20; A63-B21; A63-B22; A63-B23; A63-B24; A63-B25; A63-B26; A63-B27; A63-B28; A63-B29; A63-B30; A63-B31; A63-B32; A63-B33; A63-B34; A63-B35; A63-B36; A63-B37; A63-B38; A63-B39; A63-B40; A63-B41; A63-B42; A63-B43; A63-B44; A63-B45; A63-B46; A63-B47; A63-B48; A63-B49; A63-B50; A63-B51; A63-B52; A63-B53; A63-B54; A63-B55; A63-B56; A63-B57; A63-B58; A63-B59; A63-B60; A63-B61; A63-B62; A63-B63; A63-B64; A63-B65; A63-B66; A63-B67; A63-B68; A63-B69; A63-B70; A63-B71; A63-B72; A63-B73; A63-B74; A63-B75; A63-B76; A63-B77; A63-B78; A63-B79; A63-B80; A63-B81; A63-B82; A63-B83; A63-B84; A63-B85; A63-B86; A63-B87; A63-B88; A63-B89; A63-B90; A63-B91; A63-B92; A63-B93; A63-B94; A63-B95; A63-B96; A63-B97; A63-B98; A63-B99; A63-B100; A63-B101; A63-B102; A63-B103; A63-B104; A63-B105; A63-B106; A63-B107; A63-B108; A63-B109; A63-B110; A63-B111; A63-B112; A63-B113;

A64-B1; A64-B2; A64-B3; A64-B4; A64-B5; A64-B6; A64-B7; A64-B8; A64-B9; A64-B10; A64-B11; A64-B12; A64-B13; A64-B14; A64-B15; A64-B16; A64-B17; A64-B18; A64-B19; A64-B20; A64-B21; A64-B22; A64-B23; A64-B24; A64-B25; A64-B26; A64-B27; A64-B28; A64-B29; A64-B30; A64-B31; A64-B32; A64-B33; A64-B34; A64-B35; A64-B36; A64-B37; A64-B38; A64-B39; A64-B40; A64-B41; A64-B42; A64-B43; A64-B44; A64-B45; A64-B46; A64-B47; A64-B48; A64-B49; A64-B50; A64-B51; A64-B52; A64-B53; A64-B54; A64-B55; A64-B56; A64-B57; A64-B58; A64-B59; A64-B60; A64-B61; A64-B62; A64-B63; A64-B64; A64-B65; A64-B66; A64-B67; A64-B68; A64-B69; A64-B70; A64-B71; A64-B72; A64-B73; A64-B74; A64-B75; A64-B76; A64-B77; A64-B78; A64-B79; A64-B80; A64-B81; A64-B82; A64-B83; A64-B84; A64-B85; A64-B86; A64-B87; A64-B88; A64-B89; A64-B90; A64-B91; A64-B92; A64-B93; A64-B94; A64-B95; A64-B96; A64-B97; A64-B98; A64-B99; A64-B100; A64-B101; A64-B102; A64-B103; A64-B104; A64-B105; A64-B106; A64-B107; A64-B108; A64-B109; A64-B110; A64-B111; A64-B112; A64-B113;

A65-B1; A65-B2; A65-B3; A65-B4; A65-B5; A65-B6; A65-B7; A65-B8; A65-B9; A65-B10; A65-B11; A65-B12; A65-B13; A65-B14; A65-B15; A65-B16; A65-B17; A65-B18; A65-B19; A65-B20; A65-B21; A65-B22; A65-B23; A65-B24; A65-B25; A65-B26; A65-B27; A65-B28; A65-B29; A65-B30; A65-B31; A65-B32; A65-B33; A65-B34; A65-B35; A65-B36; A65-B37; A65-B38; A65-B39; A65-B40; A65-B41; A65-B42; A65-B43; A65-B44; A65-B45; A65-B46; A65-B47; A65-B48; A65-B49; A65-B50; A65-B51; A65-B52; A65-B53; A65-B54; A65-B55; A65-B56; A65-B57; A65-B58; A65-B59; A65-B60; A65-B61; A65-B62; A65-B63; A65-B64; A65-B65; A65-B66; A65-B67; A65-B68; A65-B69; A65-B70; A65-B71; A65-B72; A65-B73; A65-B74; A65-B75; A65-B76; A65-B77; A65-B78; A65-B79; A65-B80; A65-B81; A65-B82; A65-B83; A65-B84; A65-B85; A65-B86; A65-B87; A65-B88; A65-B89; A65-B90; A65-B91; A65-B92; A65-B93; A65-B94; A65-B95; A65-B96; A65-B97; A65-B98; A65-B99; A65-B100; A65-B101; A65-B102; A65-B103; A65-B104; A65-B105; A65-B106; A65-B107; A65-B108; A65-B109; A65-B110; A65-B111; A65-B112; A65-B113;

A66-B1; A66-B2; A66-B3; A66-B4; A66-B5; A66-B6; A66-B7; A66-B8; A66-B9; A66-B10; A66-B11; A66-B12; A66-B13; A66-B14; A66-B15; A66-B16; A66-B17; A66-B18; A66-B19; A66-B20; A66-B21; A66-B22; A66-B23; A66-B24; A66-B25; A66-B26; A66-B27; A66-B28; A66-B29; A66-B30; A66-B31; A66-B32; A66-B33; A66-B34; A66-B35; A66-B36; A66-B37; A66-B38; A66-B39; A66-B40; A66-B41; A66-B42; A66-B43; A66-B44; A66-B45; A66-B46; A66-B47; A66-B48; A66-B49; A66-B50; A66-B51; A66-B52; A66-B53; A66-B54; A66-B55; A66-B56; A66-B57; A66-B58; A66-B59; A66-B60; A66-B61; A66-B62; A66-B63; A66-B64; A66-B65; A66-B66; A66-B67; A66-B68; A66-B69; A66-B70; A66-B71; A66-B72; A66-B73; A66-B74; A66-B75; A66-B76; A66-B77; A66-B78; A66-B79; A66-B80; A66-B81; A66-B82; A66-B83; A66-B84; A66-B85; A66-B86; A66-B87; A66-B88; A66-B89; A66-B90; A66-B91; A66-B92; A66-B93; A66-B94; A66-B95; A66-B96; A66-B97; A66-B98; A66-B99; A66-B100; A66-B101; A66-B102; A66-B103; A66-B104; A66-B105; A66-B106; A66-B107; A66-B108; A66-B109; A66-B110; A66-B111; A66-B112; A66-B113;

A67-B1; A67-B2; A67-B3; A67-B4; A67-B5; A67-B6; A67-B7; A67-B8; A67-B9; A67-B10; A67-B11; A67-B12; A67-B13; A67-B14; A67-B15; A67-B16; A67-B17; A67-B18; A67-B19; A67-B20; A67-B21; A67-B22; A67-B23; A67-B24; A67-B25; A67-B26; A67-B27; A67-B28; A67-B29; A67-B30; A67-B31; A67-B32; A67-B33; A67-B34; A67-B35; A67-B36; A67-B37; A67-B38; A67-B39; A67-B40; A67-B41; A67-B42; A67-B43; A67-B44; A67-B45; A67-B46; A67-B47; A67-B48; A67-B49; A67-B50; A67-B51; A67-B52; A67-B53; A67-B54; A67-B55; A67-B56; A67-B57; A67-B58; A67-B59; A67-B60; A67-B61; A67-B62; A67-B63; A67-B64; A67-B65; A67-B66; A67-B67; A67-B68; A67-B69; A67-B70; A67-B71; A67-B72; A67-B73; A67-B74; A67-B75; A67-B76; A67-B77; A67-B78; A67-B79; A67-B80; A67-B81; A67-B82; A67-B83; A67-B84; A67-B85; A67-B86; A67-B87; A67-B88; A67-B89; A67-B90; A67-B91; A67-B92; A67-B93; A67-B94; A67-B95; A67-B96; A67-B97; A67-B98; A67-B99; A67-B100; A67-B101; A67-B102; A67-B103; A67-B104; A67-B105; A67-B106; A67-B107; A67-B108; A67-B109; A67-B110; A67-B111; A67-B112; A67-B113;

A68-B1; A68-B2; A68-B3; A68-B4; A68-B5; A68-B6; A68-B7; A68-B8; A68-B9; A68-B10; A68-B11; A68-B12; A68-B13; A68-B14; A68-B15; A68-B16; A68-B17; A68-B18; A68-B19; A68-B20; A68-B21; A68-B22; A68-B23; A68-B24; A68-B25; A68-B26; A68-B27; A68-B28; A68-B29; A68-B30; A68-B31; A68-B32; A68-B33; A68-B34; A68-B35; A68-B36; A68-B37; A68-B38; A68-B39; A68-B40; A68-B41; A68-B42; A68-B43; A68-B44; A68-B45; A68-B46; A68-B47; A68-B48; A68-B49; A68-B50; A68-B51; A68-B52; A68-B53; A68-B54; A68-B55; A68-B56; A68-B57; A68-B58; A68-B59; A68-B60; A68-B61; A68-B62; A68-B63; A68-B64; A68-B65; A68-B66; A68-B67; A68-B68; A68-B69; A68-B70; A68-B71; A68-B72; A68-B73; A68-B74; A68-B75; A68-B76; A68-B77; A68-B78; A68-B79; A68-B80; A68-B81; A68-B82; A68-B83; A68-B84; A68-B85; A68-B86; A68-B87; A68-B88; A68-B89;

A68-B90; A68-B91; A68-B92; A68-B93; A68-B94; A68-B95; A68-B96; A68-B97; A68-B98; A68-B99; A68-B100; A68-B101; A68-B102; A68-B103; A68-B104; A68-B105; A68-B106; A68-B107; A68-B108; A68-B109; A68-B110; A68-B111; A68-B112; A68-B113;

A69-B1; A69-B2; A69-B3; A69-B4; A69-B5; A69-B6; A69-B7; A69-B8; A69-B9; A69-B10; A69-B11; A69-B12; A69-B13; A69-B14; A69-B15; A69-B16; A69-B17; A69-B18; A69-B19; A69-B20; A69-B21; A69-B22; A69-B23; A69-B24; A69-B25; A69-B26; A69-B27; A69-B28; A69-B29; A69-B30; A69-B31; A69-B32; A69-B33; A69-B34; A69-B35; A69-B36; A69-B37; A69-B38; A69-B39; A69-B40; A69-B41; A69-B42; A69-B43; A69-B44; A69-B45; A69-B46; A69-B47; A69-B48; A69-B49; A69-B50; A69-B51; A69-B52; A69-B53; A69-B54; A69-B55; A69-B56; A69-B57; A69-B58; A69-B59; A69-B60; A69-B61; A69-B62; A69-B63; A69-B64; A69-B65; A69-B66; A69-B67; A69-B68; A69-B69; A69-B70; A69-B71; A69-B72; A69-B73; A69-B74; A69-B75; A69-B76; A69-B77; A69-B78; A69-B79; A69-B80; A69-B81; A69-B82; A69-B83; A69-B84; A69-B85; A69-B86; A69-B87; A69-B88; A69-B89; A69-B90; A69-B91; A69-B92; A69-B93; A69-B94; A69-B95; A69-B96; A69-B97; A69-B98; A69-B99; A69-B100; A69-B101; A69-B102; A69-B103; A69-B104; A69-B105; A69-B106; A69-B107; A69-B108; A69-B109; A69-B110; A69-B111; A69-B112; A69-B113;

A70-B1; A70-B2; A70-B3; A70-B4; A70-B5; A70-B6; A70-B7; A70-B8; A70-B9; A70-B10; A70-B11; A70-B12; A70-B13; A70-B14; A70-B15; A70-B16; A70-B17; A70-B18; A70-B19; A70-B20; A70-B21; A70-B22; A70-B23; A70-B24; A70-B25; A70-B26; A70-B27; A70-B28; A70-B29; A70-B30; A70-B31; A70-B32; A70-B33; A70-B34; A70-B35; A70-B36; A70-B37; A70-B38; A70-B39; A70-B40; A70-B41; A70-B42; A70-B43; A70-B44; A70-B45; A70-B46; A70-B47; A70-B48; A70-B49; A70-B50; A70-B51; A70-B52; A70-B53; A70-B54; A70-B55; A70-B56; A70-B57; A70-B58; A70-B59; A70-B60; A70-B61; A70-B62; A70-B63; A70-B64; A70-B65; A70-B66; A70-B67; A70-B68; A70-B69; A70-B70; A70-B71; A70-B72; A70-B73; A70-B74; A70-B75; A70-B76; A70-B77; A70-B78; A70-B79; A70-B80; A70-B81; A70-B82; A70-B83; A70-B84; A70-B85; A70-B86; A70-B87; A70-B88; A70-B89; A70-B90; A70-B91; A70-B92; A70-B93; A70-B94; A70-B95; A70-B96; A70-B97; A70-B98; A70-B99; A70-B100; A70-B101; A70-B102; A70-B103; A70-B104; A70-B105; A70-B106; A70-B107; A70-B108; A70-B109; A70-B110; A70-B111; A70-B112; A70-B113;

A71-B1; A71-B2; A71-B3; A71-B4; A71-B5; A71-B6; A71-B7; A71-B8; A71-B9; A71-B10; A71-B11; A71-B12; A71-B13; A71-B14; A71-B15; A71-B16; A71-B17; A71-B18; A71-B19; A71-B20; A71-B21; A71-B22; A71-B23; A71-B24; A71-B25; A71-B26; A71-B27; A71-B28; A71-B29; A71-B30; A71-B31; A71-B32; A71-B33; A71-B34; A71-B35; A71-B36; A71-B37; A71-B38; A71-B39; A71-B40; A71-B41; A71-B42; A71-B43; A71-B44; A71-B45; A71-B46; A71-B47; A71-B48; A71-B49; A71-B50; A71-B51; A71-B52; A71-B53; A71-B54; A71-B55; A71-B56; A71-B57; A71-B58; A71-B59; A71-B60; A71-B61; A71-B62; A71-B63; A71-B64; A71-B65; A71-B66; A71-B67; A71-B68; A71-B69; A71-B70; A71-B71; A71-B72; A71-B73; A71-B74; A71-B75; A71-B76; A71-B77; A71-B78; A71-B79; A71-B80; A71-B81; A71-B82; A71-B83; A71-B84; A71-B85; A71-B86; A71-B87; A71-B88; A71-B89; A71-B90; A71-B91; A71-B92; A71-B93; A71-B94; A71-B95; A71-B96; A71-B97; A71-B98; A71-B99; A71-B100; A71-B101; A71-B102; A71-B103; A71-B104; A71-B105; A71-B106; A71-B107; A71-B108; A71-B109; A71-B110; A71-B111; A71-B112; A71-B113;

A72-B1; A72-B2; A72-B3; A72-B4; A72-B5; A72-B6; A72-B7; A72-B8; A72-B9; A72-B10; A72-B11; A72-B12; A72-B13; A72-B14; A72-B15; A72-B16; A72-B17; A72-B18; A72-B19; A72-B20; A72-B21; A72-B22; A72-B23; A72-B24; A72-B25; A72-B26; A72-B27; A72-B28; A72-B29; A72-B30; A72-B31; A72-B32; A72-B33; A72-B34; A72-B35; A72-B36; A72-B37; A72-B38; A72-B39; A72-B40; A72-B41; A72-B42; A72-B43; A72-B44; A72-B45; A72-B46; A72-B47; A72-B48; A72-B49; A72-B50; A72-B51; A72-B52; A72-B53; A72-B54; A72-B55; A72-B56; A72-B57; A72-B58; A72-B59; A72-B60; A72-B61; A72-B62; A72-B63; A72-B64; A72-B65; A72-B66; A72-B67; A72-B68; A72-B69; A72-B70; A72-B71; A72-B72; A72-B73; A72-B74; A72-B75; A72-B76; A72-B77; A72-B78; A72-B79; A72-B80; A72-B81; A72-B82; A72-B83; A72-B84; A72-B85; A72-B86; A72-B87; A72-B88; A72-B89; A72-B90; A72-B91; A72-B92; A72-B93; A72-B94; A72-B95; A72-B96; A72-B97; A72-B98; A72-B99; A72-B100; A72-B101; A72-B102; A72-B103; A72-B104; A72-B105; A72-B106; A72-B107; A72-B108; A72-B109; A72-B110; A72-B111; A72-B112; A72-B113;

A73-B1; A73-B2; A73-B3; A73-B4; A73-B5; A73-B6; A73-B7; A73-B8; A73-B9; A73-B10; A73-B11; A73-B12; A73-B13; A73-B14; A73-B15; A73-B16; A73-B17; A73-B18; A73-B19; A73-B20; A73-B21; A73-B22; A73-B23; A73-B24; A73-B25; A73-B26; A73-B27; A73-B28; A73-B29; A73-B30; A73-B31; A73-B32; A73-B33; A73-B34; A73-B35; A73-B36; A73-B37; A73-B38; A73-B39; A73-B40; A73-B41; A73-B42; A73-B43; A73-B44; A73-B45; A73-B46; A73-B47; A73-B48; A73-B49; A73-B50; A73-B51; A73-B52; A73-B53; A73-B54; A73-B55; A73-B56; A73-B57; A73-B58; A73-B59; A73-B60; A73-B61; A73-B62; A73-B63; A73-B64; A73-B65; A73-B66; A73-B67; A73-B68; A73-B69; A73-B70; A73-B71; A73-B72; A73-B73; A73-B74; A73-B75; A73-B76; A73-B77; A73-B78; A73-B79; A73-B80; A73-B81; A73-B82; A73-B83; A73-B84; A73-B85; A73-B86; A73-B87; A73-B88; A73-B89; A73-B90; A73-B91; A73-B92; A73-B93; A73-B94; A73-B95; A73-B96; A73-B97; A73-B98; A73-B99; A73-B100; A73-B101; A73-B102; A73-B103; A73-B104; A73-B105; A73-B106; A73-B107; A73-B108; A73-B109; A73-B110; A73-B111; A73-B112; A73-B113;

A74-B1; A74-B2; A74-B3; A74-B4; A74-B5; A74-B6; A74-B7; A74-B8; A74-B9; A74-B10; A74-B11; A74-B12; A74-B13; A74-B14; A74-B15; A74-B16; A74-B17; A74-B18; A74-B19; A74-B20; A74-B21; A74-B22; A74-B23; A74-B24; A74-B25; A74-B26; A74-B27; A74-B28; A74-B29; A74-B30; A74-B31; A74-B32; A74-B33; A74-B34; A74-B35; A74-B36; A74-B37; A74-B38; A74-B39; A74-B40; A74-B41; A74-B42; A74-B43; A74-B44; A74-B45; A74-B46; A74-B47; A74-B48; A74-B49; A74-B50; A74-B51; A74-B52; A74-B53; A74-B54; A74-B55; A74-B56; A74-B57; A74-B58; A74-B59; A74-B60; A74-B61; A74-B62; A74-B63; A74-B64; A74-B65; A74-B66; A74-B67; A74-B68; A74-B69; A74-B70; A74-B71; A74-B72; A74-B73; A74-B74; A74-B75; A74-B76; A74-B77; A74-B78; A74-B79; A74-B80; A74-B81; A74-B82; A74-B83; A74-B84; A74-B85; A74-B86; A74-B87; A74-B88; A74-B89; A74-B90; A74-B91; A74-B92; A74-B93; A74-B94; A74-B95; A74-B96; A74-B97; A74-B98; A74-B99; A74-B100; A74-B101; A74-B102; A74-B103; A74-B104; A74-B105; A74-B106; A74-B107; A74-B108; A74-B109; A74-B110; A74-B111; A74-B112; A74-B113;

A75-B1; A75-B2; A75-B3; A75-B4; A75-B5; A75-B6; A75-B7; A75-B8; A75-B9; A75-B10; A75-B11; A75-B12;

A75-B13; A75-B14; A75-B15; A75-B16; A75-B17; A75-B18; A75-B19; A75-B20; A75-B21; A75-B22; A75-B23; A75-B24; A75-B25; A75-B26; A75-B27; A75-B28; A75-B29; A75-B30; A75-B31; A75-B32; A75-B33; A75-B34; A75-B35; A75-B36; A75-B37; A75-B38; A75-B39; A75-B40; A75-B41; A75-B42; A75-B43; A75-B44; A75-B45; A75-B46; A75-B47; A75-B48; A75-B49; A75-B50; A75-B51; A75-B52; A75-B53; A75-B54; A75-B55; A75-B56; A75-B57; A75-B58; A75-B59; A75-B60; A75-B61; A75-B62; A75-B63; A75-B64; A75-B65; A75-B66; A75-B67; A75-B68; A75-B69; A75-B70; A75-B71; A75-B72; A75-B73; A75-B74; A75-B75; A75-B76; A75-B77; A75-B78; A75-B79; A75-B80; A75-B81; A75-B82; A75-B83; A75-B84; A75-B85; A75-B86; A75-B87; A75-B88; A75-B89; A75-B90; A75-B91; A75-B92; A75-B93; A75-B94; A75-B95; A75-B96; A75-B97; A75-B98; A75-B99; A75-B100; A75-B101; A75-B102; A75-B103; A75-B104; A75-B105; A75-B106; A75-B107; A75-B108; A75-B109; A75-B110; A75-B111; A75-B112; A75-B113;

A76-B1; A76-B2; A76-B3; A76-B4; A76-B5; A76-B6; A76-B7; A76-B8; A76-B9; A76-B10; A76-B11; A76-B12; A76-B13; A76-B14; A76-B15; A76-B16; A76-B17; A76-B18; A76-B19; A76-B20; A76-B21; A76-B22; A76-B23; A76-B24; A76-B25; A76-B26; A76-B27; A76-B28; A76-B29; A76-B30; A76-B31; A76-B32; A76-B33; A76-B34; A76-B35; A76-B36; A76-B37; A76-B38; A76-B39; A76-B40; A76-B41; A76-B42; A76-B43; A76-B44; A76-B45; A76-B46; A76-B47; A76-B48; A76-B49; A76-B50; A76-B51; A76-B52; A76-B53; A76-B54; A76-B55; A76-B56; A76-B57; A76-B58; A76-B59; A76-B60; A76-B61; A76-B62; A76-B63; A76-B64; A76-B65; A76-B66; A76-B67; A76-B68; A76-B69; A76-B70; A76-B71; A76-B72; A76-B73; A76-B74; A76-B75; A76-B76; A76-B77; A76-B78; A76-B79; A76-B80; A76-B81; A76-B82; A76-B83; A76-B84; A76-B85; A76-B86; A76-B87; A76-B88; A76-B89; A76-B90; A76-B91; A76-B92; A76-B93; A76-B94; A76-B95; A76-B96; A76-B97; A76-B98; A76-B99; A76-B100; A76-B101; A76-B102; A76-B103; A76-B104; A76-B105; A76-B106; A76-B107; A76-B108; A76-B109; A76-B110; A76-B111; A76-B112; A76-B113;

A77-B1; A77-B2; A77-B3; A77-B4; A77-B5; A77-B6; A77-B7; A77-B8; A77-B9; A77-B10; A77-B11; A77-B12; A77-B13; A77-B14; A77-B15; A77-B16; A77-B17; A77-B18; A77-B19; A77-B20; A77-B21; A77-B22; A77-B23; A77-B24; A77-B25; A77-B26; A77-B27; A77-B28; A77-B29; A77-B30; A77-B31; A77-B32; A77-B33; A77-B34; A77-B35; A77-B36; A77-B37; A77-B38; A77-B39; A77-B40; A77-B41; A77-B42; A77-B43; A77-B44; A77-B45; A77-B46; A77-B47; A77-B48; A77-B49; A77-B50; A77-B51; A77-B52; A77-B53; A77-B54; A77-B55; A77-B56; A77-B57; A77-B58; A77-B59; A77-B60; A77-B61; A77-B62; A77-B63; A77-B64; A77-B65; A77-B66; A77-B67; A77-B68; A77-B69; A77-B70; A77-B71; A77-B72; A77-B73; A77-B74; A77-B75; A77-B76; A77-B77; A77-B78; A77-B79; A77-B80; A77-B81; A77-B82; A77-B83; A77-B84; A77-B85; A77-B86; A77-B87; A77-B88; A77-B89; A77-B90; A77-B91; A77-B92; A77-B93; A77-B94; A77-B95; A77-B96; A77-B97; A77-B98; A77-B99; A77-B100; A77-B101; A77-B102; A77-B103; A77-B104; A77-B105; A77-B106; A77-B107; A77-B108; A77-B109; A77-B110; A77-B111; A77-B112; A77-B113;

A78-B1; A78-B2; A78-B3; A78-B4; A78-B5; A78-B6; A78-B7; A78-B8; A78-B9; A78-B10; A78-B11; A78-B12; A78-B13; A78-B14; A78-B15; A78-B16; A78-B17; A78-B18; A78-B19; A78-B20; A78-B21; A78-B22; A78-B23; A78-B24; A78-B25; A78-B26; A78-B27; A78-B28; A78-B29; A78-B30; A78-B31; A78-B32; A78-B33; A78-B34; A78-B35; A78-B36; A78-B37; A78-B38; A78-B39; A78-B40; A78-B41; A78-B42; A78-B43; A78-B44; A78-B45; A78-B46; A78-B47; A78-B48; A78-B49; A78-B50; A78-B51; A78-B52; A78-B53; A78-B54; A78-B55; A78-B56; A78-B57; A78-B58; A78-B59; A78-B60; A78-B61; A78-B62; A78-B63; A78-B64; A78-B65; A78-B66; A78-B67; A78-B68; A78-B69; A78-B70; A78-B71; A78-B72; A78-B73; A78-B74; A78-B75; A78-B76; A78-B77; A78-B78; A78-B79; A78-B80; A78-B81; A78-B82; A78-B83; A78-B84; A78-B85; A78-B86; A78-B87; A78-B88; A78-B89; A78-B90; A78-B91; A78-B92; A78-B93; A78-B94; A78-B95; A78-B96; A78-B97; A78-B98; A78-B99; A78-B100; A78-B101; A78-B102; A78-B103; A78-B104; A78-B105; A78-B106; A78-B107; A78-B108; A78-B109; A78-B110; A78-B111; A78-B112; A78-B113;

A79-B1; A79-B2; A79-B3; A79-B4; A79-B5; A79-B6; A79-B7; A79-B8; A79-B9; A79-B10; A79-B11; A79-B12; A79-B13; A79-B14; A79-B15; A79-B16; A79-B17; A79-B18; A79-B19; A79-B20; A79-B21; A79-B22; A79-B23; A79-B24; A79-B25; A79-B26; A79-B27; A79-B28; A79-B29; A79-B30; A79-B31; A79-B32; A79-B33; A79-B34; A79-B35; A79-B36; A79-B37; A79-B38; A79-B39; A79-B40; A79-B41; A79-B42; A79-B43; A79-B44; A79-B45; A79-B46; A79-B47; A79-B48; A79-B49; A79-B50; A79-B51; A79-B52; A79-B53; A79-B54; A79-B55; A79-B56; A79-B57; A79-B58; A79-B59; A79-B60; A79-B61; A79-B62; A79-B63; A79-B64; A79-B65; A79-B66; A79-B67; A79-B68; A79-B69; A79-B70; A79-B71; A79-B72; A79-B73; A79-B74; A79-B75; A79-B76; A79-B77; A79-B78; A79-B79; A79-B80; A79-B81; A79-B82; A79-B83; A79-B84; A79-B85; A79-B86; A79-B87; A79-B88; A79-B89; A79-B90; A79-B91; A79-B92; A79-B93; A79-B94; A79-B95; A79-B96; A79-B97; A79-B98; A79-B99; A79-B100; A79-B101; A79-B102; A79-B103; A79-B104; A79-B105; A79-B106; A79-B107; A79-B108; A79-B109; A79-B110; A79-B111; A79-B112; A79-B113;

A80-B1; A80-B2; A80-B3; A80-B4; A80-B5; A80-B6; A80-B7; A80-B8; A80-B9; A80-B10; A80-B11; A80-B12; A80-B13; A80-B14; A80-B15; A80-B16; A80-B17; A80-B18; A80-B19; A80-B20; A80-B21; A80-B22; A80-B23; A80-B24; A80-B25; A80-B26; A80-B27; A80-B28; A80-B29; A80-B30; A80-B31; A80-B32; A80-B33; A80-B34; A80-B35; A80-B36; A80-B37; A80-B38; A80-B39; A80-B40; A80-B41; A80-B42; A80-B43; A80-B44; A80-B45; A80-B46; A80-B47; A80-B48; A80-B49; A80-B50; A80-B51; A80-B52; A80-B53; A80-B54; A80-B55; A80-B56; A80-B57; A80-B58; A80-B59; A80-B60; A80-B61; A80-B62; A80-B63; A80-B64; A80-B65; A80-B66; A80-B67; A80-B68; A80-B69; A80-B70; A80-B71; A80-B72; A80-B73; A80-B74; A80-B75; A80-B76; A80-B77; A80-B78; A80-B79; A80-B80; A80-B81; A80-B82; A80-B83; A80-B84; A80-B85; A80-B86; A80-B87; A80-B88; A80-B89; A80-B90; A80-B91; A80-B92; A80-B93; A80-B94; A80-B95; A80-B96; A80-B97; A80-B98; A80-B99; A80-B100; A80-B101; A80-B102; A80-B103; A80-B104; A80-B105; A80-B106; A80-B107; A80-B108; A80-B109; A80-B110; A80-B111; A80-B112; A80-B113;

A81-B1; A81-B2; A81-B3; A81-B4; A81-B5; A81-B6; A81-B7; A81-B8; A81-B9; A81-B10; A81-B11; A81-B12; A81-B13; A81-B14; A81-B15; A81-B16; A81-B17; A81-B18; A81-B19; A81-B20; A81-B21; A81-B22; A81-B23; A81-B24; A81-B25; A81-B26; A81-B27; A81-B28; A81-B29; A81-B30; A81-B31; A81-B32; A81-B33; A81-B34; A81-B35; A81-B36; A81-B37; A81-B38; A81-B39; A81-B40; A81-B41; A81-B42; A81-B43; A81-B44; A81-B45; A81-B46; A81-B47; A81-B48; A81-B49; A81-B50; A81-B51; A81-B52; A81-B53; A81-B54; A81-B55; A81-B56;

A81-B57; A81-B58; A81-B59; A81-B60; A81-B61; A81-B62; A81-B63; A81-B64; A81-B65; A81-B66; A81-B67; A81-B68; A81-B69; A81-B70; A81-B71; A81-B72; A81-B73; A81-B74; A81-B75; A81-B76; A81-B77; A81-B78; A81-B79; A81-B80; A81-B81; A81-B82; A81-B83; A81-B84; A81-B85; A81-B86; A81-B87; A81-B88; A81-B89; A81-B90; A81-B91; A81-B92; A81-B93; A81-B94; A81-B95; A81-B96; A81-B97; A81-B98; A81-B99; A81-B100; A81-B101; A81-B102; A81-B103; A81-B104; A81-B105; A81-B106; A81-B107; A81-B108; A81-B109; A81-B110; A81-B111; A81-B112; A81-B113;

A82-B1; A82-B2; A82-B3; A82-B4; A82-B5; A82-B6; A82-B7; A82-B8; A82-B9; A82-B10; A82-B11; A82-B12; A82-B13; A82-B14; A82-B15; A82-B16; A82-B17; A82-B18; A82-B19; A82-B20; A82-B21; A82-B22; A82-B23; A82-B24; A82-B25; A82-B26; A82-B27; A82-B28; A82-B29; A82-B30; A82-B31; A82-B32; A82-B33; A82-B34; A82-B35; A82-B36; A82-B37; A82-B38; A82-B39; A82-B40; A82-B41; A82-B42; A82-B43; A82-B44; A82-B45; A82-B46; A82-B47; A82-B48; A82-B49; A82-B50; A82-B51; A82-B52; A82-B53; A82-B54; A82-B55; A82-B56; A82-B57; A82-B58; A82-B59; A82-B60; A82-B61; A82-B62; A82-B63; A82-B64; A82-B65; A82-B66; A82-B67; A82-B68; A82-B69; A82-B70; A82-B71; A82-B72; A82-B73; A82-B74; A82-B75; A82-B76; A82-B77; A82-B78; A82-B79; A82-B80; A82-B81; A82-B82; A82-B83; A82-B84; A82-B85; A82-B86; A82-B87; A82-B88; A82-B89; A82-B90; A82-B91; A82-B92; A82-B93; A82-B94; A82-B95; A82-B96; A82-B97; A82-B98; A82-B99; A82-B100; A82-B101; A82-B102; A82-B103; A82-B104; A82-B105; A82-B106; A82-B107; A82-B108; A82-B109; A82-B110; A82-B111; A82-B112; A82-B113;

A83-B1; A83-B2; A83-B3; A83-B4; A83-B5; A83-B6; A83-B7; A83-B8; A83-B9; A83-B10; A83-B11; A83-B12; A83-B13; A83-B14; A83-B15; A83-B16; A83-B17; A83-B18; A83-B19; A83-B20; A83-B21; A83-B22; A83-B23; A83-B24; A83-B25; A83-B26; A83-B27; A83-B28; A83-B29; A83-B30; A83-B31; A83-B32; A83-B33; A83-B34; A83-B35; A83-B36; A83-B37; A83-B38; A83-B39; A83-B40; A83-B41; A83-B42; A83-B43; A83-B44; A83-B45; A83-B46; A83-B47; A83-B48; A83-B49; A83-B50; A83-B51; A83-B52; A83-B53; A83-B54; A83-B55; A83-B56; A83-B57; A83-B58; A83-B59; A83-B60; A83-B61; A83-B62; A83-B63; A83-B64; A83-B65; A83-B66; A83-B67; A83-B68; A83-B69; A83-B70; A83-B71; A83-B72; A83-B73; A83-B74; A83-B75; A83-B76; A83-B77; A83-B78; A83-B79; A83-B80; A83-B81; A83-B82; A83-B83; A83-B84; A83-B85; A83-B86; A83-B87; A83-B88; A83-B89; A83-B90; A83-B91; A83-B92; A83-B93; A83-B94; A83-B95; A83-B96; A83-B97; A83-B98; A83-B99; A83-B100; A83-B101; A83-B102; A83-B103; A83-B104; A83-B105; A83-B106; A83-B107; A83-B108; A83-B109; A83-B110; A83-B111; A83-B112; A83-B113;

A84-B1; A84-B2; A84-B3; A84-B4; A84-B5; A84-B6; A84-B7; A84-B8; A84-B9; A84-B10; A84-B11; A84-B12; A84-B13; A84-B14; A84-B15; A84-B16; A84-B17; A84-B18; A84-B19; A84-B20; A84-B21; A84-B22; A84-B23; A84-B24; A84-B25; A84-B26; A84-B27; A84-B28; A84-B29; A84-B30; A84-B31; A84-B32; A84-B33; A84-B34; A84-B35; A84-B36; A84-B37; A84-B38; A84-B39; A84-B40; A84-B41; A84-B42; A84-B43; A84-B44; A84-B45; A84-B46; A84-B47; A84-B48; A84-B49; A84-B50; A84-B51; A84-B52; A84-B53; A84-B54; A84-B55; A84-B56; A84-B57; A84-B58; A84-B59; A84-B60; A84-B61; A84-B62; A84-B63; A84-B64; A84-B65; A84-B66; A84-B67; A84-B68; A84-B69; A84-B70; A84-B71; A84-B72; A84-B73; A84-B74; A84-B75; A84-B76; A84-B77; A84-B78; A84-B79; A84-B80; A84-B81; A84-B82; A84-B83; A84-B84; A84-B85; A84-B86; A84-B87; A84-B88; A84-B89; A84-B90; A84-B91; A84-B92; A84-B93; A84-B94; A84-B95; A84-B96; A84-B97; A84-B98; A84-B99; A84-B100; A84-B101; A84-B102; A84-B103; A84-B104; A84-B105; A84-B106; A84-B107; A84-B108; A84-B109; A84-B110; A84-B111; A84-B112; A84-B113;

A85-B1; A85-B2; A85-B3; A85-B4; A85-B5; A85-B6; A85-B7; A85-B8; A85-B9; A85-B10; A85-B11; A85-B12; A85-B13; A85-B14; A85-B15; A85-B16; A85-B17; A85-B18; A85-B19; A85-B20; A85-B21; A85-B22; A85-B23; A85-B24; A85-B25; A85-B26; A85-B27; A85-B28; A85-B29; A85-B30; A85-B31; A85-B32; A85-B33; A85-B34; A85-B35; A85-B36; A85-B37; A85-B38; A85-B39; A85-B40; A85-B41; A85-B42; A85-B43; A85-B44; A85-B45; A85-B46; A85-B47; A85-B48; A85-B49; A85-B50; A85-B51; A85-B52; A85-B53; A85-B54; A85-B55; A85-B56; A85-B57; A85-B58; A85-B59; A85-B60; A85-B61; A85-B62; A85-B63; A85-B64; A85-B65; A85-B66; A85-B67; A85-B68; A85-B69; A85-B70; A85-B71; A85-B72; A85-B73; A85-B74; A85-B75; A85-B76; A85-B77; A85-B78; A85-B79; A85-B80; A85-B81; A85-B82; A85-B83; A85-B84; A85-B85; A85-B86; A85-B87; A85-B88; A85-B89; A85-B90; A85-B91; A85-B92; A85-B93; A85-B94; A85-B95; A85-B96; A85-B97; A85-B98; A85-B99; A85-B100; A85-B101; A85-B102; A85-B103; A85-B104; A85-B105; A85-B106; A85-B107; A85-B108; A85-B109; A85-B110; A85-B111; A85-B112; A85-B113;

A86-B1; A86-B2; A86-B3; A86-B4; A86-B5; A86-B6; A86-B7; A86-B8; A86-B9; A86-B10; A86-B11; A86-B12; A86-B13; A86-B14; A86-B15; A86-B16; A86-B17; A86-B18; A86-B19; A86-B20; A86-B21; A86-B22; A86-B23; A86-B24; A86-B25; A86-B26; A86-B27; A86-B28; A86-B29; A86-B30; A86-B31; A86-B32; A86-B33; A86-B34; A86-B35; A86-B36; A86-B37; A86-B38; A86-B39; A86-B40; A86-B41; A86-B42; A86-B43; A86-B44; A86-B45; A86-B46; A86-B47; A86-B48; A86-B49; A86-B50; A86-B51; A86-B52; A86-B53; A86-B54; A86-B55; A86-B56; A86-B57; A86-B58; A86-B59; A86-B60; A86-B61; A86-B62; A86-B63; A86-B64; A86-B65; A86-B66; A86-B67; A86-B68; A86-B69; A86-B70; A86-B71; A86-B72; A86-B73; A86-B74; A86-B75; A86-B76; A86-B77; A86-B78; A86-B79; A86-B80; A86-B81; A86-B82; A86-B83; A86-B84; A86-B85; A86-B86; A86-B87; A86-B88; A86-B89; A86-B90; A86-B91; A86-B92; A86-B93; A86-B94; A86-B95; A86-B96; A86-B97; A86-B98; A86-B99; A86-B100; A86-B101; A86-B102; A86-B103; A86-B104; A86-B105; A86-B106; A86-B107; A86-B108; A86-B109; A86-B110; A86-B111; A86-B112; A86-B113;

A87-B1; A87-B2; A87-B3; A87-B4; A87-B5; A87-B6; A87-B7; A87-B8; A87-B9; A87-B10; A87-B11; A87-B12; A87-B13; A87-B14; A87-B15; A87-B16; A87-B17; A87-B18; A87-B19; A87-B20; A87-B21; A87-B22; A87-B23; A87-B24; A87-B25; A87-B26; A87-B27; A87-B28; A87-B29; A87-B30; A87-B31; A87-B32; A87-B33; A87-B34; A87-B35; A87-B36; A87-B37; A87-B38; A87-B39; A87-B40; A87-B41; A87-B42; A87-B43; A87-B44; A87-B45; A87-B46; A87-B47; A87-B48; A87-B49; A87-B50; A87-B51; A87-B52; A87-B53; A87-B54; A87-B55; A87-B56; A87-B57; A87-B58; A87-B59; A87-B60; A87-B61; A87-B62; A87-B63; A87-B64; A87-B65; A87-B66; A87-B67; A87-B68; A87-B69; A87-B70; A87-B71; A87-B72; A87-B73; A87-B74; A87-B75; A87-B76; A87-B77; A87-B78; A87-B79; A87-B80; A87-B81; A87-B82; A87-B83; A87-B84; A87-B85; A87-B86; A87-B87; A87-B88; A87-B89; A87-B90; A87-B91; A87-B92; A87-B93; A87-B94; A87-B95; A87-B96; A87-B97; A87-B98; A87-B99; A87-B100;

A87-B101; A87-B102; A87-B103; A87-B104; A87-B105; A87-B106; A87-B107; A87-B108; A87-B109; A87-B110; A87-B111; A87-B112; A87-B113;

A88-B1; A88-B2; A88-B3; A88-B4; A88-B5; A88-B6; A88-B7; A88-B8; A88-B9; A88-B10; A88-B11; A88-B12; A88-B13; A88-B14; A88-B15; A88-B16; A88-B17; A88-B18; A88-B19; A88-B20; A88-B21; A88-B22; A88-B23; A88-B24; A88-B25; A88-B26; A88-B27; A88-B28; A88-B29; A88-B30; A88-B31; A88-B32; A88-B33; A88-B34; A88-B35; A88-B36; A88-B37; A88-B38; A88-B39; A88-B40; A88-B41; A88-B42; A88-B43; A88-B44; A88-B45; A88-B46; A88-B47; A88-B48; A88-B49; A88-B50; A88-B51; A88-B52; A88-B53; A88-B54; A88-B55; A88-B56; A88-B57; A88-B58; A88-B59; A88-B60; A88-B61; A88-B62; A88-B63; A88-B64; A88-B65; A88-B66; A88-B67; A88-B68; A88-B69; A88-B70; A88-B71; A88-B72; A88-B73; A88-B74; A88-B75; A88-B76; A88-B77; A88-B78; A88-B79; A88-B80; A88-B81; A88-B82; A88-B83; A88-B84; A88-B85; A88-B86; A88-B87; A88-B88; A88-B89; A88-B90; A88-B91; A88-B92; A88-B93; A88-B94; A88-B95; A88-B96; A88-B97; A88-B98; A88-B99; A88-B100; A88-B101; A88-B102; A88-B103; A88-B104; A88-B105; A88-B106; A88-B107; A88-B108; A88-B109; A88-B110; A88-B111; A88-B112; A88-B113;

A89-B1; A89-B2; A89-B3; A89-B4; A89-B5; A89-B6; A89-B7; A89-B8; A89-B9; A89-B10; A89-B11; A89-B12; A89-B13; A89-B14; A89-B15; A89-B16; A89-B17; A89-B18; A89-B19; A89-B20; A89-B21; A89-B22; A89-B23; A89-B24; A89-B25; A89-B26; A89-B27; A89-B28; A89-B29; A89-B30; A89-B31; A89-B32; A89-B33; A89-B34; A89-B35; A89-B36; A89-B37; A89-B38; A89-B39; A89-B40; A89-B41; A89-B42; A89-B43; A89-B44; A89-B45; A89-B46; A89-B47; A89-B48; A89-B49; A89-B50; A89-B51; A89-B52; A89-B53; A89-B54; A89-B55; A89-B56; A89-B57; A89-B58; A89-B59; A89-B60; A89-B61; A89-B62; A89-B63; A89-B64; A89-B65; A89-B66; A89-B67; A89-B68; A89-B69; A89-B70; A89-B71; A89-B72; A89-B73; A89-B74; A89-B75; A89-B76; A89-B77; A89-B78; A89-B79; A89-B80; A89-B81; A89-B82; A89-B83; A89-B84; A89-B85; A89-B86; A89-B87; A89-B88; A89-B89; A89-B90; A89-B91; A89-B92; A89-B93; A89-B94; A89-B95; A89-B96; A89-B97; A89-B98; A89-B99; A89-B100; A89-B101; A89-B102; A89-B103; A89-B104; A89-B105; A89-B106; A89-B107; A89-B108; A89-B109; A89-B110; A89-B111; A89-B112; A89-B113;

A90-B1; A90-B2; A90-B3; A90-B4; A90-B5; A90-B6; A90-B7; A90-B8; A90-B9; A90-B10; A90-B11; A90-B12; A90-B13; A90-B14; A90-B15; A90-B16; A90-B17; A90-B18; A90-B19; A90-B20; A90-B21; A90-B22; A90-B23; A90-B24; A90-B25; A90-B26; A90-B27; A90-B28; A90-B29; A90-B30; A90-B31; A90-B32; A90-B33; A90-B34; A90-B35; A90-B36; A90-B37; A90-B38; A90-B39; A90-B40; A90-B41; A90-B42; A90-B43; A90-B44; A90-B45; A90-B46; A90-B47; A90-B48; A90-B49; A90-B50; A90-B51; A90-B52; A90-B53; A90-B54; A90-B55; A90-B56; A90-B57; A90-B58; A90-B59; A90-B60; A90-B61; A90-B62; A90-B63; A90-B64; A90-B65; A90-B66; A90-B67; A90-B68; A90-B69; A90-B70; A90-B71; A90-B72; A90-B73; A90-B74; A90-B75; A90-B76; A90-B77; A90-B78; A90-B79; A90-B80; A90-B81; A90-B82; A90-B83; A90-B84; A90-B85; A90-B86; A90-B87; A90-B88; A90-B89; A90-B90; A90-B91; A90-B92; A90-B93; A90-B94; A90-B95; A90-B96; A90-B97; A90-B98; A90-B99; A90-B100; A90-B101; A90-B102; A90-B103; A90-B104; A90-B105; A90-B106; A90-B107; A90-B108; A90-B109; A90-B110; A90-B111; A90-B112; A90-B113;

A91-B1; A91-B2; A91-B3; A91-B4; A91-B5; A91-B6; A91-B7; A91-B8; A91-B9; A91-B10; A91-B11; A91-B12; A91-B13; A91-B14; A91-B15; A91-B16; A91-B17; A91-B18; A91-B19; A91-B20; A91-B21; A91-B22; A91-B23; A91-B24; A91-B25; A91-B26; A91-B27; A91-B28; A91-B29; A91-B30; A91-B31; A91-B32; A91-B33; A91-B34; A91-B35; A91-B36; A91-B37; A91-B38; A91-B39; A91-B40; A91-B41; A91-B42; A91-B43; A91-B44; A91-B45; A91-B46; A91-B47; A91-B48; A91-B49; A91-B50; A91-B51; A91-B52; A91-B53; A91-B54; A91-B55; A91-B56; A91-B57; A91-B58; A91-B59; A91-B60; A91-B61; A91-B62; A91-B63; A91-B64; A91-B65; A91-B66; A91-B67; A91-B68; A91-B69; A91-B70; A91-B71; A91-B72; A91-B73; A91-B74; A91-B75; A91-B76; A91-B77; A91-B78; A91-B79; A91-B80; A91-B81; A91-B82; A91-B83; A91-B84; A91-B85; A91-B86; A91-B87; A91-B88; A91-B89; A91-B90; A91-B91; A91-B92; A91-B93; A91-B94; A91-B95; A91-B96; A91-B97; A91-B98; A91-B99; A91-B100; A91-B101; A91-B102; A91-B103; A91-B104; A91-B105; A91-B106; A91-B107; A91-B108; A91-B109; A91-B110; A91-B111; A91-B112; A91-B113;

A92-B1; A92-B2; A92-B3; A92-B4; A92-B5; A92-B6; A92-B7; A92-B8; A92-B9; A92-B10; A92-B11; A92-B12; A92-B13; A92-B14; A92-B15; A92-B16; A92-B17; A92-B18; A92-B19; A92-B20; A92-B21; A92-B22; A92-B23; A92-B24; A92-B25; A92-B26; A92-B27; A92-B28; A92-B29; A92-B30; A92-B31; A92-B32; A92-B33; A92-B34; A92-B35; A92-B36; A92-B37; A92-B38; A92-B39; A92-B40; A92-B41; A92-B42; A92-B43; A92-B44; A92-B45; A92-B46; A92-B47; A92-B48; A92-B49; A92-B50; A92-B51; A92-B52; A92-B53; A92-B54; A92-B55; A92-B56; A92-B57; A92-B58; A92-B59; A92-B60; A92-B61; A92-B62; A92-B63; A92-B64; A92-B65; A92-B66; A92-B67; A92-B68; A92-B69; A92-B70; A92-B71; A92-B72; A92-B73; A92-B74; A92-B75; A92-B76; A92-B77; A92-B78; A92-B79; A92-B80; A92-B81; A92-B82; A92-B83; A92-B84; A92-B85; A92-B86; A92-B87; A92-B88; A92-B89; A92-B90; A92-B91; A92-B92; A92-B93; A92-B94; A92-B95; A92-B96; A92-B97; A92-B98; A92-B99; A92-B100; A92-B101; A92-B102; A92-B103; A92-B104; A92-B105; A92-B106; A92-B107; A92-B108; A92-B109; A92-B110; A92-B111; A92-B112; A92-B113;

A93-B1; A93-B2; A93-B3; A93-B4; A93-B5; A93-B6; A93-B7; A93-B8; A93-B9; A93-B10; A93-B11; A93-B12; A93-B13; A93-B14; A93-B15; A93-B16; A93-B17; A93-B18; A93-B19; A93-B20; A93-B21; A93-B22; A93-B23; A93-B24; A93-B25; A93-B26; A93-B27; A93-B28; A93-B29; A93-B30; A93-B31; A93-B32; A93-B33; A93-B34; A93-B35; A93-B36; A93-B37; A93-B38; A93-B39; A93-B40; A93-B41; A93-B42; A93-B43; A93-B44; A93-B45; A93-B46; A93-B47; A93-B48; A93-B49; A93-B50; A93-B51; A93-B52; A93-B53; A93-B54; A93-B55; A93-B56; A93-B57; A93-B58; A93-B59; A93-B60; A93-B61; A93-B62; A93-B63; A93-B64; A93-B65; A93-B66; A93-B67; A93-B68; A93-B69; A93-B70; A93-B71; A93-B72; A93-B73; A93-B74; A93-B75; A93-B76; A93-B77; A93-B78; A93-B79; A93-B80; A93-B81; A93-B82; A93-B83; A93-B84; A93-B85; A93-B86; A93-B87; A93-B88; A93-B89; A93-B90; A93-B91; A93-B92; A93-B93; A93-B94; A93-B95; A93-B96; A93-B97; A93-B98; A93-B99; A93-B100; A93-B101; A93-B102; A93-B103; A93-B104; A93-B105; A93-B106; A93-B107; A93-B108; A93-B109; A93-B110; A93-B111; A93-B112; A93-B113;

A94-B1; A94-B2; A94-B3; A94-B4; A94-B5; A94-B6; A94-B7; A94-B8; A94-B9; A94-B10; A94-B11; A94-B12; A94-B13; A94-B14; A94-B15; A94-B16; A94-B17; A94-B18; A94-B19; A94-B20; A94-B21; A94-B22; A94-B23;

A94-B24; A94-B25; A94-B26; A94-B27; A94-B28; A94-B29; A94-B30; A94-B31; A94-B32; A94-B33; A94-B34; A94-B35; A94-B36; A94-B37; A94-B38; A94-B39; A94-B40; A94-B41; A94-B42; A94-B43; A94-B44; A94-B45; A94-B46; A94-B47; A94-B48; A94-B49; A94-B50; A94-B51; A94-B52; A94-B53; A94-B54; A94-B55; A94-B56; A94-B57; A94-B58; A94-B59; A94-B60; A94-B61; A94-B62; A94-B63; A94-B64; A94-B65; A94-B66; A94-B67; A94-B68; A94-B69; A94-B70; A94-B71; A94-B72; A94-B73; A94-B74; A94-B75; A94-B76; A94-B77; A94-B78; A94-B79; A94-B80; A94-B81; A94-B82; A94-B83; A94-B84; A94-B85; A94-B86; A94-B87; A94-B88; A94-B89; A94-B90; A94-B91; A94-B92; A94-B93; A94-B94; A94-B95; A94-B96; A94-B97; A94-B98; A94-B99; A94-B100; A94-B101; A94-B102; A94-B103; A94-B104; A94-B105; A94-B106; A94-B107; A94-B108; A94-B109; A94-B110; A94-B111; A94-B112; A94-B113;

A95-B1; A95-B2; A95-B3; A95-B4; A95-B5; A95-B6; A95-B7; A95-B8; A95-B9; A95-B10; A95-B11; A95-B12; A95-B13; A95-B14; A95-B15; A95-B16; A95-B17; A95-B18; A95-B19; A95-B20; A95-B21; A95-B22; A95-B23; A95-B24; A95-B25; A95-B26; A95-B27; A95-B28; A95-B29; A95-B30; A95-B31; A95-B32; A95-B33; A95-B34; A95-B35; A95-B36; A95-B37; A95-B38; A95-B39; A95-B40; A95-B41; A95-B42; A95-B43; A95-B44; A95-B45; A95-B46; A95-B47; A95-B48; A95-B49; A95-B50; A95-B51; A95-B52; A95-B53; A95-B54; A95-B55; A95-B56; A95-B57; A95-B58; A95-B59; A95-B60; A95-B61; A95-B62; A95-B63; A95-B64; A95-B65; A95-B66; A95-B67; A95-B68; A95-B69; A95-B70; A95-B71; A95-B72; A95-B73; A95-B74; A95-B75; A95-B76; A95-B77; A95-B78; A95-B79; A95-B80; A95-B81; A95-B82; A95-B83; A95-B84; A95-B85; A95-B86; A95-B87; A95-B88; A95-B89; A95-B90; A95-B91; A95-B92; A95-B93; A95-B94; A95-B95; A95-B96; A95-B97; A95-B98; A95-B99; A95-B100; A95-B101; A95-B102; A95-B103; A95-B104; A95-B105; A95-B106; A95-B107; A95-B108; A95-B109; A95-B110; A95-B111; A95-B112; A95-B113;

A96-B1; A96-B2; A96-B3; A96-B4; A96-B5; A96-B6; A96-B7; A96-B8; A96-B9; A96-B10; A96-B11; A96-B12; A96-B13; A96-B14; A96-B15; A96-B16; A96-B17; A96-B18; A96-B19; A96-B20; A96-B21; A96-B22; A96-B23; A96-B24; A96-B25; A96-B26; A96-B27; A96-B28; A96-B29; A96-B30; A96-B31; A96-B32; A96-B33; A96-B34; A96-B35; A96-B36; A96-B37; A96-B38; A96-B39; A96-B40; A96-B41; A96-B42; A96-B43; A96-B44; A96-B45; A96-B46; A96-B47; A96-B48; A96-B49; A96-B50; A96-B51; A96-B52; A96-B53; A96-B54; A96-B55; A96-B56; A96-B57; A96-B58; A96-B59; A96-B60; A96-B61; A96-B62; A96-B63; A96-B64; A96-B65; A96-B66; A96-B67; A96-B68; A96-B69; A96-B70; A96-B71; A96-B72; A96-B73; A96-B74; A96-B75; A96-B76; A96-B77; A96-B78; A96-B79; A96-B80; A96-B81; A96-B82; A96-B83; A96-B84; A96-B85; A96-B86; A96-B87; A96-B88; A96-B89; A96-B90; A96-B91; A96-B92; A96-B93; A96-B94; A96-B95; A96-B96; A96-B97; A96-B98; A96-B99; A96-B100; A96-B101; A96-B102; A96-B103; A96-B104; A96-B105; A96-B106; A96-B107; A96-B108; A96-B109; A96-B110; A96-B111; A96-B112; A96-B113;

A97-B1; A97-B2; A97-B3; A97-B4; A97-B5; A97-B6; A97-B7; A97-B8; A97-B9; A97-B10; A97-B11; A97-B12; A97-B13; A97-B14; A97-B15; A97-B16; A97-B17; A97-B18; A97-B19; A97-B20; A97-B21; A97-B22; A97-B23; A97-B24; A97-B25; A97-B26; A97-B27; A97-B28; A97-B29; A97-B30; A97-B31; A97-B32; A97-B33; A97-B34; A97-B35; A97-B36; A97-B37; A97-B38; A97-B39; A97-B40; A97-B41; A97-B42; A97-B43; A97-B44; A97-B45; A97-B46; A97-B47; A97-B48; A97-B49; A97-B50; A97-B51; A97-B52; A97-B53; A97-B54; A97-B55; A97-B56; A97-B57; A97-B58; A97-B59; A97-B60; A97-B61; A97-B62; A97-B63; A97-B64; A97-B65; A97-B66; A97-B67; A97-B68; A97-B69; A97-B70; A97-B71; A97-B72; A97-B73; A97-B74; A97-B75; A97-B76; A97-B77; A97-B78; A97-B79; A97-B80; A97-B81; A97-B82; A97-B83; A97-B84; A97-B85; A97-B86; A97-B87; A97-B88; A97-B89; A97-B90; A97-B91; A97-B92; A97-B93; A97-B94; A97-B95; A97-B96; A97-B97; A97-B98; A97-B99; A97-B100; A97-B101; A97-B102; A97-B103; A97-B104; A97-B105; A97-B106; A97-B107; A97-B108; A97-B109; A97-B110; A97-B111; A97-B112; A97-B113;

A98-B1; A98-B2; A98-B3; A98-B4; A98-B5; A98-B6; A98-B7; A98-B8; A98-B9; A98-B10; A98-B11; A98-B12; A98-B13; A98-B14; A98-B15; A98-B16; A98-B17; A98-B18; A98-B19; A98-B20; A98-B21; A98-B22; A98-B23; A98-B24; A98-B25; A98-B26; A98-B27; A98-B28; A98-B29; A98-B30; A98-B31; A98-B32; A98-B33; A98-B34; A98-B35; A98-B36; A98-B37; A98-B38; A98-B39; A98-B40; A98-B41; A98-B42; A98-B43; A98-B44; A98-B45; A98-B46; A98-B47; A98-B48; A98-B49; A98-B50; A98-B51; A98-B52; A98-B53; A98-B54; A98-B55; A98-B56; A98-B57; A98-B58; A98-B59; A98-B60; A98-B61; A98-B62; A98-B63; A98-B64; A98-B65; A98-B66; A98-B67; A98-B68; A98-B69; A98-B70; A98-B71; A98-B72; A98-B73; A98-B74; A98-B75; A98-B76; A98-B77; A98-B78; A98-B79; A98-B80; A98-B81; A98-B82; A98-B83; A98-B84; A98-B85; A98-B86; A98-B87; A98-B88; A98-B89; A98-B90; A98-B91; A98-B92; A98-B93; A98-B94; A98-B95; A98-B96; A98-B97; A98-B98; A98-B99; A98-B100; A98-B101; A98-B102; A98-B103; A98-B104; A98-B105; A98-B106; A98-B107; A98-B108; A98-B109; A98-B110; A98-B111; A98-B112; A98-B113;

A99-B1; A99-B2; A99-B3; A99-B4; A99-B5; A99-B6; A99-B7; A99-B8; A99-B9; A99-B10; A99-B11; A99-B12; A99-B13; A99-B14; A99-B15; A99-B16; A99-B17; A99-B18; A99-B19; A99-B20; A99-B21; A99-B22; A99-B23; A99-B24; A99-B25; A99-B26; A99-B27; A99-B28; A99-B29; A99-B30; A99-B31; A99-B32; A99-B33; A99-B34; A99-B35; A99-B36; A99-B37; A99-B38; A99-B39; A99-B40; A99-B41; A99-B42; A99-B43; A99-B44; A99-B45; A99-B46; A99-B47; A99-B48; A99-B49; A99-B50; A99-B51; A99-B52; A99-B53; A99-B54; A99-B55; A99-B56; A99-B57; A99-B58; A99-B59; A99-B60; A99-B61; A99-B62; A99-B63; A99-B64; A99-B65; A99-B66; A99-B67; A99-B68; A99-B69; A99-B70; A99-B71; A99-B72; A99-B73; A99-B74; A99-B75; A99-B76; A99-B77; A99-B78; A99-B79; A99-B80; A99-B81; A99-B82; A99-B83; A99-B84; A99-B85; A99-B86; A99-B87; A99-B88; A99-B89; A99-B90; A99-B91; A99-B92; A99-B93; A99-B94; A99-B95; A99-B96; A99-B97; A99-B98; A99-B99; A99-B100; A99-B101; A99-B102; A99-B103; A99-B104; A99-B105; A99-B106; A99-B107; A99-B108; A99-B109; A99-B110; A99-B111; A99-B112; A99-B113;

A100-B1; A100-B2; A100-B3; A100-B4; A100-B5; A100-B6; A100-B7; A100-B8; A100-B9; A100-B10; A100-B11; A100-B12; A100-B13; A100-B14; A100-B15; A100-B16; A100-B17; A100-B18; A100-B19; A100-B20; A100-B21; A100-B22; A100-B23; A100-B24; A100-B25; A100-B26; A100-B27; A100-B28; A100-B29; A100-B30; A100-B31; A100-B32; A100-B33; A100-B34; A100-B35; A100-B36; A100-B37; A100-B38; A100-B39; A100-B40; A100-B41; A100-B42; A100-B43; A100-B44; A100-B45; A100-B46; A100-B47; A100-B48; A100-B49; A100-B50; A100-B51; A100-B52; A100-B53; A100-B54; A100-B55; A100-B56; A100-B57; A100-B58; A100-B59; A100-B60; A100-

B61; A100-B62; A100-B63; A100-B64; A100-B65; A100-B66; A100-B67; A100-B68; A100-B69; A100-B70; A100-B71; A100-B72; A100-B73; A100-B74; A100-B75; A100-B76; A100-B77; A100-B78; A100-B79; A100-B80; A100-B81; A100-B82; A100-B83; A100-B84; A100-B85; A100-B86; A100-B87; A100-B88; A100-B89; A100-B90; A100-B91; A100-B92; A100-B93; A100-B94; A100-B95; A100-B96; A100-B97; A100-B98; A100-B99; A100-B100; A100-B101; A100-B102; A100-B103; A100-B104; A100-B105; A100-B106; A100-B107; A100-B108; A100-B109; A100-B110; A100-B111; A100-B112; A100-B113;

A101-B1; A101-B2; A101-B3; A101-B4; A101-B5; A101-B6; A101-B7; A101-B8; A101-B9; A101-B10; A101-B11; A101-B12; A101-B13; A101-B14; A101-B15; A101-B16; A101-B17; A101-B18; A101-B19; A101-B20; A101-B21; A101-B22; A101-B23; A101-B24; A101-B25; A101-B26; A101-B27; A101-B28; A101-B29; A101-B30; A101-B31; A101-B32; A101-B33; A101-B34; A101-B35; A101-B36; A101-B37; A101-B38; A101-B39; A101-B40; A101-B41; A101-B42; A101-B43; A101-B44; A101-B45; A101-B46; A101-B47; A101-B48; A101-B49; A101-B50; A101-B51; A101-B52; A101-B53; A101-B54; A101-B55; A101-B56; A101-B57; A101-B58; A101-B59; A101-B60; A101-B61; A101-B62; A101-B63; A101-B64; A101-B65; A101-B66; A101-B67; A101-B68; A101-B69; A101-B70; A101-B71; A101-B72; A101-B73; A101-B74; A101-B75; A101-B76; A101-B77; A101-B78; A101-B79; A101-B80; A101-B81; A101-B82; A101-B83; A101-B84; A101-B85; A101-B86; A101-B87; A101-B88; A101-B89; A101-B90; A101-B91; A101-B92; A101-B93; A101-B94; A101-B95; A101-B96; A101-B97; A101-B98; A101-B99; A101-B100; A101-B101; A101-B102; A101-B103; A101-B104; A101-B105; A101-B106; A101-B107; A101-B108; A101-B109; A101-B110; A101-B111; A101-B112; A101-B113;

A102-B1; A102-B2; A102-B3; A102-B4; A102-B5; A102-B6; A102-B7; A102-B8; A102-B9; A102-B10; A102-B11; A102-B12; A102-B13; A102-B14; A102-B15; A102-B16; A102-B17; A102-B18; A102-B19; A102-B20; A102-B21; A102-B22; A102-B23; A102-B24; A102-B25; A102-B26; A102-B27; A102-B28; A102-B29; A102-B30; A102-B31; A102-B32; A102-B33; A102-B34; A102-B35; A102-B36; A102-B37; A102-B38; A102-B39; A102-B40; A102-B41; A102-B42; A102-B43; A102-B44; A102-B45; A102-B46; A102-B47; A102-B48; A102-B49; A102-B50; A102-B51; A102-B52; A102-B53; A102-B54; A102-B55; A102-B56; A102-B57; A102-B58; A102-B59; A102-B60; A102-B61; A102-B62; A102-B63; A102-B64; A102-B65; A102-B66; A102-B67; A102-B68; A102-B69; A102-B70; A102-B71; A102-B72; A102-B73; A102-B74; A102-B75; A102-B76; A102-B77; A102-B78; A102-B79; A102-B80; A102-B81; A102-B82; A102-B83; A102-B84; A102-B85; A102-B86; A102-B87; A102-B88; A102-B89; A102-B90; A102-B91; A102-B92; A102-B93; A102-B94; A102-B95; A102-B96; A102-B97; A102-B98; A102-B99; A102-B100; A102-B101; A102-B102; A102-B103; A102-B104; A102-B105; A102-B106; A102-B107; A102-B108; A102-B109; A102-B110; A102-B111; A102-B112; A102-B113;

A103-B1; A103-B2; A103-B3; A103-B4; A103-B5; A103-B6; A103-B7; A103-B8; A103-B9; A103-B10; A103-B11; A103-B12; A103-B13; A103-B14; A103-B15; A103-B16; A103-B17; A103-B18; A103-B19; A103-B20; A103-B21; A103-B22; A103-B23; A103-B24; A103-B25; A103-B26; A103-B27; A103-B28; A103-B29; A103-B30; A103-B31; A103-B32; A103-B33; A103-B34; A103-B35; A103-B36; A103-B37; A103-B38; A103-B39; A103-B40; A103-B41; A103-B42; A103-B43; A103-B44; A103-B45; A103-B46; A103-B47; A103-B48; A103-B49; A103-B50; A103-B51; A103-B52; A103-B53; A103-B54; A103-B55; A103-B56; A103-B57; A103-B58; A103-B59; A103-B60; A103-B61; A103-B62; A103-B63; A103-B64; A103-B65; A103-B66; A103-B67; A103-B68; A103-B69; A103-B70; A103-B71; A103-B72; A103-B73; A103-B74; A103-B75; A103-B76; A103-B77; A103-B78; A103-B79; A103-B80; A103-B81; A103-B82; A103-B83; A103-B84; A103-B85; A103-B86; A103-B87; A103-B88; A103-B89; A103-B90; A103-B91; A103-B92; A103-B93; A103-B94; A103-B95; A103-B96; A103-B97; A103-B98; A103-B99; A103-B100; A103-B101; A103-B102; A103-B103; A103-B104; A103-B105; A103-B106; A103-B107; A103-B108; A103-B109; A103-B110; A103-B111; A103-B112; A103-B113;

A104-B1; A104-B2; A104-B3; A104-B4; A104-B5; A104-B6; A104-B7; A104-B8; A104-B9; A104-B10; A104-B11; A104-B12; A104-B13; A104-B14; A104-B15; A104-B16; A104-B17; A104-B18; A104-B19; A104-B20; A104-B21; A104-B22; A104-B23; A104-B24; A104-B25; A104-B26; A104-B27; A104-B28; A104-B29; A104-B30; A104-B31; A104-B32; A104-B33; A104-B34; A104-B35; A104-B36; A104-B37; A104-B38; A104-B39; A104-B40; A104-B41; A104-B42; A104-B43; A104-B44; A104-B45; A104-B46; A104-B47; A104-B48; A104-B49; A104-B50; A104-B51; A104-B52; A104-B53; A104-B54; A104-B55; A104-B56; A104-B57; A104-B58; A104-B59; A104-B60; A104-B61; A104-B62; A104-B63; A104-B64; A104-B65; A104-B66; A104-B67; A104-B68; A104-B69; A104-B70; A104-B71; A104-B72; A104-B73; A104-B74; A104-B75; A104-B76; A104-B77; A104-B78; A104-B79; A104-B80; A104-B81; A104-B82; A104-B83; A104-B84; A104-B85; A104-B86; A104-B87; A104-B88; A104-B89; A104-B90; A104-B91; A104-B92; A104-B93; A104-B94; A104-B95; A104-B96; A104-B97; A104-B98; A104-B99; A104-B100; A104-B101; A104-B102; A104-B103; A104-B104; A104-B105; A104-B106; A104-B107; A104-B108; A104-B109; A104-B110; A104-B111; A104-B112; A104-B113;

A105-B1; A105-B2; A105-B3; A105-B4; A105-B5; A105-B6; A105-B7; A105-B8; A105-B9; A105-B10; A105-B11; A105-B12; A105-B13; A105-B14; A105-B15; A105-B16; A105-B17; A105-B18; A105-B19; A105-B20; A105-B21; A105-B22; A105-B23; A105-B24; A105-B25; A105-B26; A105-B27; A105-B28; A105-B29; A105-B30; A105-B31; A105-B32; A105-B33; A105-B34; A105-B35; A105-B36; A105-B37; A105-B38; A105-B39; A105-B40; A105-B41; A105-B42; A105-B43; A105-B44; A105-B45; A105-B46; A105-B47; A105-B48; A105-B49; A105-B50; A105-B51; A105-B52; A105-B53; A105-B54; A105-B55; A105-B56; A105-B57; A105-B58; A105-B59; A105-B60; A105-B61; A105-B62; A105-B63; A105-B64; A105-B65; A105-B66; A105-B67; A105-B68; A105-B69; A105-B70; A105-B71; A105-B72; A105-B73; A105-B74; A105-B75; A105-B76; A105-B77; A105-B78; A105-B79; A105-B80; A105-B81; A105-B82; A105-B83; A105-B84; A105-B85; A105-B86; A105-B87; A105-B88; A105-B89; A105-B90; A105-B91; A105-B92; A105-B93; A105-B94; A105-B95; A105-B96; A105-B97; A105-B98; A105-B99; A105-B100; A105-B101; A105-B102; A105-B103; A105-B104; A105-B105; A105-B106; A105-B107; A105-B108; A105-B109; A105-B110; A105-B111; A105-B112; A105-B113;

A106-B1; A106-B2; A106-B3; A106-B4; A106-B5; A106-B6; A106-B7; A106-B8; A106-B9; A106-B10; A106-B11; A106-B12; A106-B13; A106-B14; A106-B15; A106-B16; A106-B17; A106-B18; A106-B19; A106-B20; A106-B21; A106-B22; A106-B23; A106-B24; A106-B25; A106-B26; A106-B27; A106-B28; A106-B29; A106-B30; A106-B31; A106-B32; A106-B33; A106-B34; A106-B35; A106-B36; A106-B37; A106-B38; A106-B39; A106-B40; A106-

B41; A106-B42; A106-B43; A106-B44; A106-B45; A106-B46; A106-B47; A106-B48; A106-B49; A106-B50; A106-B51; A106-B52; A106-B53; A106-B54; A106-B55; A106-B56; A106-B57; A106-B58; A106-B59; A106-B60; A106-B61; A106-B62; A106-B63; A106-B64; A106-B65; A106-B66; A106-B67; A106-B68; A106-B69; A106-B70; A106-B71; A106-B72; A106-B73; A106-B74; A106-B75; A106-B76; A106-B77; A106-B78; A106-B79; A106-B80; A106-B81; A106-B82; A106-B83; A106-B84; A106-B85; A106-B86; A106-B87; A106-B88; A106-B89; A106-B90; A106-B91; A106-B92; A106-B93; A106-B94; A106-B95; A106-B96; A106-B97; A106-B98; A106-B99; A106-B100; A106-B101; A106-B102; A106-B103; A106-B104; A106-B105; A106-B106; A106-B107; A106-B108; A106-B109; A106-B110; A106-B111; A106-B112; A106-B113;

A107-B1; A107-B2; A107-B3; A107-B4; A107-B5; A107-B6; A107-B7; A107-B8; A107-B9; A107-B10; A107-B11; A107-B12; A107-B13; A107-B14; A107-B15; A107-B16; A107-B17; A107-B18; A107-B19; A107-B20; A107-B21; A107-B22; A107-B23; A107-B24; A107-B25; A107-B26; A107-B27; A107-B28; A107-B29; A107-B30; A107-B31; A107-B32; A107-B33; A107-B34; A107-B35; A107-B36; A107-B37; A107-B38; A107-B39; A107-B40; A107-B41; A107-B42; A107-B43; A107-B44; A107-B45; A107-B46; A107-B47; A107-B48; A107-B49; A107-B50; A107-B51; A107-B52; A107-B53; A107-B54; A107-B55; A107-B56; A107-B57; A107-B58; A107-B59; A107-B60; A107-B61; A107-B62; A107-B63; A107-B64; A107-B65; A107-B66; A107-B67; A107-B68; A107-B69; A107-B70; A107-B71; A107-B72; A107-B73; A107-B74; A107-B75; A107-B76; A107-B77; A107-B78; A107-B79; A107-B80; A107-B81; A107-B82; A107-B83; A107-B84; A107-B85; A107-B86; A107-B87; A107-B88; A107-B89; A107-B90; A107-B91; A107-B92; A107-B93; A107-B94; A107-B95; A107-B96; A107-B97; A107-B98; A107-B99; A107-B100; A107-B101; A107-B102; A107-B103; A107-B104; A107-B105; A107-B106; A107-B107; A107-B108; A107-B109; A107-B110; A107-B111; A107-B112; A107-B113;

A108-B1; A108-B2; A108-B3; A108-B4; A108-B5; A108-B6; A108-B7; A108-B8; A108-B9; A108-B10; A108-B11; A108-B12; A108-B13; A108-B14; A108-B15; A108-B16; A108-B17; A108-B18; A108-B19; A108-B20; A108-B21; A108-B22; A108-B23; A108-B24; A108-B25; A108-B26; A108-B27; A108-B28; A108-B29; A108-B30; A108-B31; A108-B32; A108-B33; A108-B34; A108-B35; A108-B36; A108-B37; A108-B38; A108-B39; A108-B40; A108-B41; A108-B42; A108-B43; A108-B44; A108-B45; A108-B46; A108-B47; A108-B48; A108-B49; A108-B50; A108-B51; A108-B52; A108-B53; A108-B54; A108-B55; A108-B56; A108-B57; A108-B58; A108-B59; A108-B60; A108-B61; A108-B62; A108-B63; A108-B64; A108-B65; A108-B66; A108-B67; A108-B68; A108-B69; A108-B70; A108-B71; A108-B72; A108-B73; A108-B74; A108-B75; A108-B76; A108-B77; A108-B78; A108-B79; A108-B80; A108-B81; A108-B82; A108-B83; A108-B84; A108-B85; A108-B86; A108-B87; A108-B88; A108-B89; A108-B90; A108-B91; A108-B92; A108-B93; A108-B94; A108-B95; A108-B96; A108-B97; A108-B98; A108-B99; A108-B100; A108-B101; A108-B102; A108-B103; A108-B104; A108-B105; A108-B106; A108-B107; A108-B108; A108-B109; A108-B110; A108-B111; A108-B112; A108-B113;

A109-B1; A109-B2; A109-B3; A109-B4; A109-B5; A109-B6; A109-B7; A109-B8; A109-B9; A109-B10; A109-B11; A109-B12; A109-B13; A109-B14; A109-B15; A109-B16; A109-B17; A109-B18; A109-B19; A109-B20; A109-B21; A109-B22; A109-B23; A109-B24; A109-B25; A109-B26; A109-B27; A109-B28; A109-B29; A109-B30; A109-B31; A109-B32; A109-B33; A109-B34; A109-B35; A109-B36; A109-B37; A109-B38; A109-B39; A109-B40; A109-B41; A109-B42; A109-B43; A109-B44; A109-B45; A109-B46; A109-B47; A109-B48; A109-B49; A109-B50; A109-B51; A109-B52; A109-B53; A109-B54; A109-B55; A109-B56; A109-B57; A109-B58; A109-B59; A109-B60; A109-B61; A109-B62; A109-B63; A109-B64; A109-B65; A109-B66; A109-B67; A109-B68; A109-B69; A109-B70; A109-B71; A109-B72; A109-B73; A109-B74; A109-B75; A109-B76; A109-B77; A109-B78; A109-B79; A109-B80; A109-B81; A109-B82; A109-B83; A109-B84; A109-B85; A109-B86; A109-B87; A109-B88; A109-B89; A109-B90; A109-B91; A109-B92; A109-B93; A109-B94; A109-B95; A109-B96; A109-B97; A109-B98; A109-B99; A109-B100; A109-B101; A109-B102; A109-B103; A109-B104; A109-B105; A109-B106; A109-B107; A109-B108; A109-B109; A109-B110; A109-B111; A109-B112; A109-B113;

A110-B1; A110-B2; A110-B3; A110-B4; A110-B5; A110-B6; A110-B7; A110-B8; A110-B9; A110-B10; A110-B11; A110-B12; A110-B13; A110-B14; A110-B15; A110-B16; A110-B17; A110-B18; A110-B19; A110-B20; A110-B21; A110-B22; A110-B23; A110-B24; A110-B25; A110-B26; A110-B27; A110-B28; A110-B29; A110-B30; A110-B31; A110-B32; A110-B33; A110-B34; A110-B35; A110-B36; A110-B37; A110-B38; A110-B39; A110-B40; A110-B41; A110-B42; A110-B43; A110-B44; A110-B45; A110-B46; A110-B47; A110-B48; A110-B49; A110-B50; A110-B51; A110-B52; A110-B53; A110-B54; A110-B55; A110-B56; A110-B57; A110-B58; A110-B59; A110-B60; A110-B61; A110-B62; A110-B63; A110-B64; A110-B65; A110-B66; A110-B67; A110-B68; A110-B69; A110-B70; A110-B71; A110-B72; A110-B73; A110-B74; A110-B75; A110-B76; A110-B77; A110-B78; A110-B79; A110-B80; A110-B81; A110-B82; A110-B83; A110-B84; A110-B85; A110-B86; A110-B87; A110-B88; A110-B89; A110-B90; A110-B91; A110-B92; A110-B93; A110-B94; A110-B95; A110-B96; A110-B97; A110-B98; A110-B99; A110-B100; A110-B101; A110-B102; A110-B103; A110-B104; A110-B105; A110-B106; A110-B107; A110-B108; A110-B109; A110-B110; A110-B111; A110-B112; A110-B113;

A111-B1; A111-B2; A111-B3; A111-B4; A111-B5; A111-B6; A111-B7; A111-B8; A111-B9; A111-B10; A111-B11; A111-B12; A111-B13; A111-B14; A111-B15; A111-B16; A111-B17; A111-B18; A111-B19; A111-B20; A111-B21; A111-B22; A111-B23; A111-B24; A111-B25; A111-B26; A111-B27; A111-B28; A111-B29; A111-B30; A111-B31; A111-B32; A111-B33; A111-B34; A111-B35; A111-B36; A111-B37; A111-B38; A111-B39; A111-B40; A111-B41; A111-B42; A111-B43; A111-B44; A111-B45; A111-B46; A111-B47; A111-B48; A111-B49; A111-B50; A111-B51; A111-B52; A111-B53; A111-B54; A111-B55; A111-B56; A111-B57; A111-B58; A111-B59; A111-B60; A111-B61; A111-B62; A111-B63; A111-B64; A111-B65; A111-B66; A111-B67; A111-B68; A111-B69; A111-B70; A111-B71; A111-B72; A111-B73; A111-B74; A111-B75; A111-B76; A111-B77; A111-B78; A111-B79; A111-B80; A111-B81; A111-B82; A111-B83; A111-B84; A111-B85; A111-B86; A111-B87; A111-B88; A111-B89; A111-B90; A111-B91; A111-B92; A111-B93; A111-B94; A111-B95; A111-B96; A111-B97; A111-B98; A111-B99; A111-B100; A111-B101; A111-B102; A111-B103; A111-B104; A111-B105; A111-B106; A111-B107; A111-B108; A111-B109; A111-B110; A111-B111; A111-B112; A111-B113;

A112-B1; A112-B2; A112-B3; A112-B4; A112-B5; A112-B6; A112-B7; A112-B8; A112-B9; A112-B10; A112-B11; A112-B12; A112-B13; A112-B14; A112-B15; A112-B16; A112-B17; A112-B18; A112-B19; A112-B20; A112-

B21; A112-B22; A112-B23; A112-B24; A112-B25; A112-B26; A112-B27; A112-B28; A112-B29; A112-B30; A112-B31; A112-B32; A112-B33; A112-B34; A112-B35; A112-B36; A112-B37; A112-B38; A112-B39; A112-B40; A112-B41; A112-B42; A112-B43; A112-B44; A112-B45; A112-B46; A112-B47; A112-B48; A112-B49; A112-B50; A112-B51; A112-B52; A112-B53; A112-B54; A112-B55; A112-B56; A112-B57; A112-B58; A112-B59; A112-B60; A112-B61; A112-B62; A112-B63; A112-B64; A112-B65; A112-B66; A112-B67; A112-B68; A112-B69; A112-B70; A112-B71; A112-B72; A112-B73; A112-B74; A112-B75; A112-B76; A112-B77; A112-B78; A112-B79; A112-B80; A112-B81; A112-B82; A112-B83; A112-B84; A112-B85; A112-B86; A112-B87; A112-B88; A112-B89; A112-B90; A112-B91; A112-B92; A112-B93; A112-B94; A112-B95; A112-B96; A112-B97; A112-B98; A112-B99; A112-B100; A112-B101; A112-B102; A112-B103; A112-B104; A112-B105; A112-B106; A112-B107; A112-B108; A112-B109; A112-B110; A112-B111; A112-B112; A112-B113;

A113-B1; A113-B2; A113-B3; A113-B4; A113-B5; A113-B6; A113-B7; A113-B8; A113-B9; A113-B10; A113-B11; A113-B12; A113-B13; A113-B14; A113-B15; A113-B16; A113-B17; A113-B18; A113-B19; A113-B20; A113-B21; A113-B22; A113-B23; A113-B24; A113-B25; A113-B26; A113-B27; A113-B28; A113-B29; A113-B30; A113-B31; A113-B32; A113-B33; A113-B34; A113-B35; A113-B36; A113-B37; A113-B38; A113-B39; A113-B40; A113-B41; A113-B42; A113-B43; A113-B44; A113-B45; A113-B46; A113-B47; A113-B48; A113-B49; A113-B50; A113-B51; A113-B52; A113-B53; A113-B54; A113-B55; A113-B56; A113-B57; A113-B58; A113-B59; A113-B60; A113-B61; A113-B62; A113-B63; A113-B64; A113-B65; A113-B66; A113-B67; A113-B68; A113-B69; A113-B70; A113-B71; A113-B72; A113-B73; A113-B74; A113-B75; A113-B76; A113-B77; A113-B78; A113-B79; A113-B80; A113-B81; A113-B82; A113-B83; A113-B84; A113-B85; A113-B86; A113-B87; A113-B88; A113-B89; A113-B90; A113-B91; A113-B92; A113-B93; A113-B94; A113-B95; A113-B96; A113-B97; A113-B98; A113-B99; A113-B100; A113-B101; A113-B102; A113-B103; A113-B104; A113-B105; A113-B106; A113-B107; A113-B108; A113-B109; A113-B110; A113-B111; A113-B112; A113-B113;

A114-B1; A114-B2; A114-B3; A114-B4; A114-B5; A114-B6; A114-B7; A114-B8; A114-B9; A114-B10; A114-B11; A114-B12; A114-B13; A114-B14; A114-B15; A114-B16; A114-B17; A114-B18; A114-B19; A114-B20; A114-B21; A114-B22; A114-B23; A114-B24; A114-B25; A114-B26; A114-B27; A114-B28; A114-B29; A114-B30; A114-B31; A114-B32; A114-B33; A114-B34; A114-B35; A114-B36; A114-B37; A114-B38; A114-B39; A114-B40; A114-B41; A114-B42; A114-B43; A114-B44; A114-B45; A114-B46; A114-B47; A114-B48; A114-B49; A114-B50; A114-B51; A114-B52; A114-B53; A114-B54; A114-B55; A114-B56; A114-B57; A114-B58; A114-B59; A114-B60; A114-B61; A114-B62; A114-B63; A114-B64; A114-B65; A114-B66; A114-B67; A114-B68; A114-B69; A114-B70; A114-B71; A114-B72; A114-B73; A114-B74; A114-B75; A114-B76; A114-B77; A114-B78; A114-B79; A114-B80; A114-B81; A114-B82; A114-B83; A114-B84; A114-B85; A114-B86; A114-B87; A114-B88; A114-B89; A114-B90; A114-B91; A114-B92; A114-B93; A114-B94; A114-B95; A114-B96; A114-B97; A114-B98; A114-B99; A114-B100; A114-B101; A114-B102; A114-B103; A114-B104; A114-B105; A114-B106; A114-B107; A114-B108; A114-B109; A114-B110; A114-B111; A114-B112; A114-B113;

A115-B1; A115-B2; A115-B3; A115-B4; A115-B5; A115-B6; A115-B7; A115-B8; A115-B9; A115-B10; A115-B11; A115-B12; A115-B13; A115-B14; A115-B15; A115-B16; A115-B17; A115-B18; A115-B19; A115-B20; A115-B21; A115-B22; A115-B23; A115-B24; A115-B25; A115-B26; A115-B27; A115-B28; A115-B29; A115-B30; A115-B31; A115-B32; A115-B33; A115-B34; A115-B35; A115-B36; A115-B37; A115-B38; A115-B39; A115-B40; A115-B41; A115-B42; A115-B43; A115-B44; A115-B45; A115-B46; A115-B47; A115-B48; A115-B49; A115-B50; A115-B51; A115-B52; A115-B53; A115-B54; A115-B55; A115-B56; A115-B57; A115-B58; A115-B59; A115-B60; A115-B61; A115-B62; A115-B63; A115-B64; A115-B65; A115-B66; A115-B67; A115-B68; A115-B69; A115-B70; A115-B71; A115-B72; A115-B73; A115-B74; A115-B75; A115-B76; A115-B77; A115-B78; A115-B79; A115-B80; A115-B81; A115-B82; A115-B83; A115-B84; A115-B85; A115-B86; A115-B87; A115-B88; A115-B89; A115-B90; A115-B91; A115-B92; A115-B93; A115-B94; A115-B95; A115-B96; A115-B97; A115-B98; A115-B99; A115-B100; A115-B101; A115-B102; A115-B103; A115-B104; A115-B105; A115-B106; A115-B107; A115-B108; A115-B109; A115-B110; A115-B111; A115-B112; A115-B113;

A116-B1; A116-B2; A116-B3; A116-B4; A116-B5; A116-B6; A116-B7; A116-B8; A116-B9; A116-B10; A116-B11; A116-B12; A116-B13; A116-B14; A116-B15; A116-B16; A116-B17; A116-B18; A116-B19; A116-B20; A116-B21; A116-B22; A116-B23; A116-B24; A116-B25; A116-B26; A116-B27; A116-B28; A116-B29; A116-B30; A116-B31; A116-B32; A116-B33; A116-B34; A116-B35; A116-B36; A116-B37; A116-B38; A116-B39; A116-B40; A116-B41; A116-B42; A116-B43; A116-B44; A116-B45; A116-B46; A116-B47; A116-B48; A116-B49; A116-B50; A116-B51; A116-B52; A116-B53; A116-B54; A116-B55; A116-B56; A116-B57; A116-B58; A116-B59; A116-B60; A116-B61; A116-B62; A116-B63; A116-B64; A116-B65; A116-B66; A116-B67; A116-B68; A116-B69; A116-B70; A116-B71; A116-B72; A116-B73; A116-B74; A116-B75; A116-B76; A116-B77; A116-B78; A116-B79; A116-B80; A116-B81; A116-B82; A116-B83; A116-B84; A116-B85; A116-B86; A116-B87; A116-B88; A116-B89; A116-B90; A116-B91; A116-B92; A116-B93; A116-B94; A116-B95; A116-B96; A116-B97; A116-B98; A116-B99; A116-B100; A116-B101; A116-B102; A116-B103; A116-B104; A116-B105; A116-B106; A116-B107; A116-B108; A116-B109; A116-B110; A116-B111; A116-B112; A116-B113;

A117-B1; A117-B2; A117-B3; A117-B4; A117-B5; A117-B6; A117-B7; A117-B8; A117-B9; A117-B10; A117-B11; A117-B12; A117-B13; A117-B14; A117-B15; A117-B16; A117-B17; A117-B18; A117-B19; A117-B20; A117-B21; A117-B22; A117-B23; A117-B24; A117-B25; A117-B26; A117-B27; A117-B28; A117-B29; A117-B30; A117-B31; A117-B32; A117-B33; A117-B34; A117-B35; A117-B36; A117-B37; A117-B38; A117-B39; A117-B40; A117-B41; A117-B42; A117-B43; A117-B44; A117-B45; A117-B46; A117-B47; A117-B48; A117-B49; A117-B50; A117-B51; A117-B52; A117-B53; A117-B54; A117-B55; A117-B56; A117-B57; A117-B58; A117-B59; A117-B60; A117-B61; A117-B62; A117-B63; A117-B64; A117-B65; A117-B66; A117-B67; A117-B68; A117-B69; A117-B70; A117-B71; A117-B72; A117-B73; A117-B74; A117-B75; A117-B76; A117-B77; A117-B78; A117-B79; A117-B80; A117-B81; A117-B82; A117-B83; A117-B84; A117-B85; A117-B86; A117-B87; A117-B88; A117-B89; A117-B90; A117-B91; A117-B92; A117-B93; A117-B94; A117-B95; A117-B96; A117-B97; A117-B98; A117-B99; A117-B100; A117-B101; A117-B102; A117-B103; A117-B104; A117-B105; A117-B106; A117-B107; A117-B108; A117-B109; A117-B110; A117-B111; A117-B112; A117-B113;

A118-B1; A118-B2; A118-B3; A118-B4; A118-B5; A118-B6; A118-B7; A118-B8; A118-B9; A118-B10; A118-B11; A118-B12; A118-B13; A118-B14; A118-B15; A118-B16; A118-B17; A118-B18; A118-B19; A118-B20; A118-B21; A118-B22; A118-B23; A118-B24; A118-B25; A118-B26; A118-B27; A118-B28; A118-B29; A118-B30; A118-B31; A118-B32; A118-B33; A118-B34; A118-B35; A118-B36; A118-B37; A118-B38; A118-B39; A118-B40; A118-B41; A118-B42; A118-B43; A118-B44; A118-B45; A118-B46; A118-B47; A118-B48; A118-B49; A118-B50; A118-B51; A118-B52; A118-B53; A118-B54; A118-B55; A118-B56; A118-B57; A118-B58; A118-B59; A118-B60; A118-B61; A118-B62; A118-B63; A118-B64; A118-B65; A118-B66; A118-B67; A118-B68; A118-B69; A118-B70; A118-B71; A118-B72; A118-B73; A118-B74; A118-B75; A118-B76; A118-B77; A118-B78; A118-B79; A118-B80; A118-B81; A118-B82; A118-B83; A118-B84; A118-B85; A118-B86; A118-B87; A118-B88; A118-B89; A118-B90; A118-B91; A118-B92; A118-B93; A118-B94; A118-B95; A118-B96; A118-B97; A118-B98; A118-B99; A118-B100; A118-B101; A118-B102; A118-B103; A118-B104; A118-B105; A118-B106; A118-B107; A118-B108; A118-B109; A118-B110; A118-B111; A118-B112; A118-B113;

A119-B1; A119-B2; A119-B3; A119-B4; A119-B5; A119-B6; A119-B7; A119-B8; A119-B9; A119-B10; A119-B11; A119-B12; A119-B13; A119-B14; A119-B15; A119-B16; A119-B17; A119-B18; A119-B19; A119-B20; A119-B21; A119-B22; A119-B23; A119-B24; A119-B25; A119-B26; A119-B27; A119-B28; A119-B29; A119-B30; A119-B31; A119-B32; A119-B33; A119-B34; A119-B35; A119-B36; A119-B37; A119-B38; A119-B39; A119-B40; A119-B41; A119-B42; A119-B43; A119-B44; A119-B45; A119-B46; A119-B47; A119-B48; A119-B49; A119-B50; A119-B51; A119-B52; A119-B53; A119-B54; A119-B55; A119-B56; A119-B57; A119-B58; A119-B59; A119-B60; A119-B61; A119-B62; A119-B63; A119-B64; A119-B65; A119-B66; A119-B67; A119-B68; A119-B69; A119-B70; A119-B71; A119-B72; A119-B73; A119-B74; A119-B75; A119-B76; A119-B77; A119-B78; A119-B79; A119-B80; A119-B81; A119-B82; A119-B83; A119-B84; A119-B85; A119-B86; A119-B87; A119-B88; A119-B89; A119-B90; A119-B91; A119-B92; A119-B93; A119-B94; A119-B95; A119-B96; A119-B97; A119-B98; A119-B99; A119-B100; A119-B101; A119-B102; A119-B103; A119-B104; A119-B105; A119-B106; A119-B107; A119-B108; A119-B109; A119-B110; A119-B111; A119-B112; A119-B113;

A120-B1; A120-B2; A120-B3; A120-B4; A120-B5; A120-B6; A120-B7; A120-B8; A120-B9; A120-B10; A120-B11; A120-B12; A120-B13; A120-B14; A120-B15; A120-B16; A120-B17; A120-B18; A120-B19; A120-B20; A120-B21; A120-B22; A120-B23; A120-B24; A120-B25; A120-B26; A120-B27; A120-B28; A120-B29; A120-B30; A120-B31; A120-B32; A120-B33; A120-B34; A120-B35; A120-B36; A120-B37; A120-B38; A120-B39; A120-B40; A120-B41; A120-B42; A120-B43; A120-B44; A120-B45; A120-B46; A120-B47; A120-B48; A120-B49; A120-B50; A120-B51; A120-B52; A120-B53; A120-B54; A120-B55; A120-B56; A120-B57; A120-B58; A120-B59; A120-B60; A120-B61; A120-B62; A120-B63; A120-B64; A120-B65; A120-B66; A120-B67; A120-B68; A120-B69; A120-B70; A120-B71; A120-B72; A120-B73; A120-B74; A120-B75; A120-B76; A120-B77; A120-B78; A120-B79; A120-B80; A120-B81; A120-B82; A120-B83; A120-B84; A120-B85; A120-B86; A120-B87; A120-B88; A120-B89; A120-B90; A120-B91; A120-B92; A120-B93; A120-B94; A120-B95; A120-B96; A120-B97; A120-B98; A120-B99; A120-B100; A120-B101; A120-B102; A120-B103; A120-B104; A120-B105; A120-B106; A120-B107; A120-B108; A120-B109; A120-B110; A120-B111; A120-B112; A120-B113;

A121-B1; A121-B2; A121-B3; A121-B4; A121-B5; A121-B6; A121-B7; A121-B8; A121-B9; A121-B10; A121-B11; A121-B12; A121-B13; A121-B14; A121-B15; A121-B16; A121-B17; A121-B18; A121-B19; A121-B20; A121-B21; A121-B22; A121-B23; A121-B24; A121-B25; A121-B26; A121-B27; A121-B28; A121-B29; A121-B30; A121-B31; A121-B32; A121-B33; A121-B34; A121-B35; A121-B36; A121-B37; A121-B38; A121-B39; A121-B40; A121-B41; A121-B42; A121-B43; A121-B44; A121-B45; A121-B46; A121-B47; A121-B48; A121-B49; A121-B50; A121-B51; A121-B52; A121-B53; A121-B54; A121-B55; A121-B56; A121-B57; A121-B58; A121-B59; A121-B60; A121-B61; A121-B62; A121-B63; A121-B64; A121-B65; A121-B66; A121-B67; A121-B68; A121-B69; A121-B70; A121-B71; A121-B72; A121-B73; A121-B74; A121-B75; A121-B76; A121-B77; A121-B78; A121-B79; A121-B80; A121-B81; A121-B82; A121-B83; A121-B84; A121-B85; A121-B86; A121-B87; A121-B88; A121-B89; A121-B90; A121-B91; A121-B92; A121-B93; A121-B94; A121-B95; A121-B96; A121-B97; A121-B98; A121-B99; A121-B100; A121-B101; A121-B102; A121-B103; A121-B104; A121-B105; A121-B106; A121-B107; A121-B108; A121-B109; A121-B110; A121-B111; A121-B112; A121-B113;

A122-B1; A122-B2; A122-B3; A122-B4; A122-B5; A122-B6; A122-B7; A122-B8; A122-B9; A122-B10; A122-B11; A122-B12; A122-B13; A122-B14; A122-B15; A122-B16; A122-B17; A122-B18; A122-B19; A122-B20; A122-B21; A122-B22; A122-B23; A122-B24; A122-B25; A122-B26; A122-B27; A122-B28; A122-B29; A122-B30; A122-B31; A122-B32; A122-B33; A122-B34; A122-B35; A122-B36; A122-B37; A122-B38; A122-B39; A122-B40; A122-B41; A122-B42; A122-B43; A122-B44; A122-B45; A122-B46; A122-B47; A122-B48; A122-B49; A122-B50; A122-B51; A122-B52; A122-B53; A122-B54; A122-B55; A122-B56; A122-B57; A122-B58; A122-B59; A122-B60; A122-B61; A122-B62; A122-B63; A122-B64; A122-B65; A122-B66; A122-B67; A122-B68; A122-B69; A122-B70; A122-B71; A122-B72; A122-B73; A122-B74; A122-B75; A122-B76; A122-B77; A122-B78; A122-B79; A122-B80; A122-B81; A122-B82; A122-B83; A122-B84; A122-B85; A122-B86; A122-B87; A122-B88; A122-B89; A122-B90; A122-B91; A122-B92; A122-B93; A122-B94; A122-B95; A122-B96; A122-B97; A122-B98; A122-B99; A122-B100; A122-B101; A122-B102; A122-B103; A122-B104; A122-B105; A122-B106; A122-B107; A122-B108; A122-B109; A122-B110; A122-B111; A122-B112; A122-B113;

A123-B1; A123-B2; A123-B3; A123-B4; A123-B5; A123-B6; A123-B7; A123-B8; A123-B9; A123-B10; A123-B11; A123-B12; A123-B13; A123-B14; A123-B15; A123-B16; A123-B17; A123-B18; A123-B19; A123-B20; A123-B21; A123-B22; A123-B23; A123-B24; A123-B25; A123-B26; A123-B27; A123-B28; A123-B29; A123-B30; A123-B31; A123-B32; A123-B33; A123-B34; A123-B35; A123-B36; A123-B37; A123-B38; A123-B39; A123-B40; A123-B41; A123-B42; A123-B43; A123-B44; A123-B45; A123-B46; A123-B47; A123-B48; A123-B49; A123-B50; A123-B51; A123-B52; A123-B53; A123-B54; A123-B55; A123-B56; A123-B57; A123-B58; A123-B59; A123-B60; A123-B61; A123-B62; A123-B63; A123-B64; A123-B65; A123-B66; A123-B67; A123-B68; A123-B69; A123-B70; A123-B71; A123-B72; A123-B73; A123-B74; A123-B75; A123-B76; A123-B77; A123-B78; A123-B79; A123-B80; A123-B81; A123-B82; A123-B83; A123-B84; A123-B85; A123-B86; A123-B87; A123-B88; A123-B89; A123-B90; A123-B91; A123-B92; A123-B93; A123-B94; A123-B95; A123-

B96; A123-B97; A123-B98; A123-B99; A123-B100; A123-B101; A123-B102; A123-B103; A123-B104; A123-B105; A123-B106; A123-B107; A123-B108; A123-B109; A123-B110; A123-B111; A123-B112; A123-B113;

A124-B1; A124-B2; A124-B3; A124-B4; A124-B5; A124-B6; A124-B7; A124-B8; A124-B9; A124-B10; A124-B11; A124-B12; A124-B13; A124-B14; A124-B15; A124-B16; A124-B17; A124-B18; A124-B19; A124-B20; A124-B21; A124-B22; A124-B23; A124-B24; A124-B25; A124-B26; A124-B27; A124-B28; A124-B29; A124-B30; A124-B31; A124-B32; A124-B33; A124-B34; A124-B35; A124-B36; A124-B37; A124-B38; A124-B39; A124-B40; A124-B41; A124-B42; A124-B43; A124-B44; A124-B45; A124-B46; A124-B47; A124-B48; A124-B49; A124-B50; A124-B51; A124-B52; A124-B53; A124-B54; A124-B55; A124-B56; A124-B57; A124-B58; A124-B59; A124-B60; A124-B61; A124-B62; A124-B63; A124-B64; A124-B65; A124-B66; A124-B67; A124-B68; A124-B69; A124-B70; A124-B71; A124-B72; A124-B73; A124-B74; A124-B75; A124-B76; A124-B77; A124-B78; A124-B79; A124-B80; A124-B81; A124-B82; A124-B83; A124-B84; A124-B85; A124-B86; A124-B87; A124-B88; A124-B89; A124-B90; A124-B91; A124-B92; A124-B93; A124-B94; A124-B95; A124-B96; A124-B97; A124-B98; A124-B99; A124-B100; A124-B101; A124-B102; A124-B103; A124-B104; A124-B105; A124-B106; A124-B107; A124-B108; A124-B109; A124-B110; A124-B111; A124-B112; A124-B113;

A125-B1; A125-B2; A125-B3; A125-B4; A125-B5; A125-B6; A125-B7; A125-B8; A125-B9; A125-B10; A125-B11; A125-B12; A125-B13; A125-B14; A125-B15; A125-B16; A125-B17; A125-B18; A125-B19; A125-B20; A125-B21; A125-B22; A125-B23; A125-B24; A125-B25; A125-B26; A125-B27; A125-B28; A125-B29; A125-B30; A125-B31; A125-B32; A125-B33; A125-B34; A125-B35; A125-B36; A125-B37; A125-B38; A125-B39; A125-B40; A125-B41; A125-B42; A125-B43; A125-B44; A125-B45; A125-B46; A125-B47; A125-B48; A125-B49; A125-B50; A125-B51; A125-B52; A125-B53; A125-B54; A125-B55; A125-B56; A125-B57; A125-B58; A125-B59; A125-B60; A125-B61; A125-B62; A125-B63; A125-B64; A125-B65; A125-B66; A125-B67; A125-B68; A125-B69; A125-B70; A125-B71; A125-B72; A125-B73; A125-B74; A125-B75; A125-B76; A125-B77; A125-B78; A125-B79; A125-B80; A125-B81; A125-B82; A125-B83; A125-B84; A125-B85; A125-B86; A125-B87; A125-B88; A125-B89; A125-B90; A125-B91; A125-B92; A125-B93; A125-B94; A125-B95; A125-B96; A125-B97; A125-B98; A125-B99; A125-B100; A125-B101; A125-B102; A125-B103; A125-B104; A125-B105; A125-B106; A125-B107; A125-B108; A125-B109; A125-B110; A125-B111; A125-B112; A125-B113;

A126-B1; A126-B2; A126-B3; A126-B4; A126-B5; A126-B6; A126-B7; A126-B8; A126-B9; A126-B10; A126-B11; A126-B12; A126-B13; A126-B14; A126-B15; A126-B16; A126-B17; A126-B18; A126-B19; A126-B20; A126-B21; A126-B22; A126-B23; A126-B24; A126-B25; A126-B26; A126-B27; A126-B28; A126-B29; A126-B30; A126-B31; A126-B32; A126-B33; A126-B34; A126-B35; A126-B36; A126-B37; A126-B38; A126-B39; A126-B40; A126-B41; A126-B42; A126-B43; A126-B44; A126-B45; A126-B46; A126-B47; A126-B48; A126-B49; A126-B50; A126-B51; A126-B52; A126-B53; A126-B54; A126-B55; A126-B56; A126-B57; A126-B58; A126-B59; A126-B60; A126-B61; A126-B62; A126-B63; A126-B64; A126-B65; A126-B66; A126-B67; A126-B68; A126-B69; A126-B70; A126-B71; A126-B72; A126-B73; A126-B74; A126-B75; A126-B76; A126-B77; A126-B78; A126-B79; A126-B80; A126-B81; A126-B82; A126-B83; A126-B84; A126-B85; A126-B86; A126-B87; A126-B88; A126-B89; A126-B90; A126-B91; A126-B92; A126-B93; A126-B94; A126-B95; A126-B96; A126-B97; A126-B98; A126-B99; A126-B100; A126-B101; A126-B102; A126-B103; A126-B104; A126-B105; A126-B106; A126-B107; A126-B108; A126-B109; A126-B110; A126-B111; A126-B112; A126-B113;

A127-B1; A127-B2; A127-B3; A127-B4; A127-B5; A127-B6; A127-B7; A127-B8; A127-B9; A127-B10; A127-B11; A127-B12; A127-B13; A127-B14; A127-B15; A127-B16; A127-B17; A127-B18; A127-B19; A127-B20; A127-B21; A127-B22; A127-B23; A127-B24; A127-B25; A127-B26; A127-B27; A127-B28; A127-B29; A127-B30; A127-B31; A127-B32; A127-B33; A127-B34; A127-B35; A127-B36; A127-B37; A127-B38; A127-B39; A127-B40; A127-B41; A127-B42; A127-B43; A127-B44; A127-B45; A127-B46; A127-B47; A127-B48; A127-B49; A127-B50; A127-B51; A127-B52; A127-B53; A127-B54; A127-B55; A127-B56; A127-B57; A127-B58; A127-B59; A127-B60; A127-B61; A127-B62; A127-B63; A127-B64; A127-B65; A127-B66; A127-B67; A127-B68; A127-B69; A127-B70; A127-B71; A127-B72; A127-B73; A127-B74; A127-B75; A127-B76; A127-B77; A127-B78; A127-B79; A127-B80; A127-B81; A127-B82; A127-B83; A127-B84; A127-B85; A127-B86; A127-B87; A127-B88; A127-B89; A127-B90; A127-B91; A127-B92; A127-B93; A127-B94; A127-B95; A127-B96; A127-B97; A127-B98; A127-B99; A127-B100; A127-B101; A127-B102; A127-B103; A127-B104; A127-B105; A127-B106; A127-B107; A127-B108; A127-B109; A127-B110; A127-B111; A127-B112; A127-B113;

A128-B1; A128-B2; A128-B3; A128-B4; A128-B5; A128-B6; A128-B7; A128-B8; A128-B9; A128-B10; A128-B11; A128-B12; A128-B13; A128-B14; A128-B15; A128-B16; A128-B17; A128-B18; A128-B19; A128-B20; A128-B21; A128-B22; A128-B23; A128-B24; A128-B25; A128-B26; A128-B27; A128-B28; A128-B29; A128-B30; A128-B31; A128-B32; A128-B33; A128-B34; A128-B35; A128-B36; A128-B37; A128-B38; A128-B39; A128-B40; A128-B41; A128-B42; A128-B43; A128-B44; A128-B45; A128-B46; A128-B47; A128-B48; A128-B49; A128-B50; A128-B51; A128-B52; A128-B53; A128-B54; A128-B55; A128-B56; A128-B57; A128-B58; A128-B59; A128-B60; A128-B61; A128-B62; A128-B63; A128-B64; A128-B65; A128-B66; A128-B67; A128-B68; A128-B69; A128-B70; A128-B71; A128-B72; A128-B73; A128-B74; A128-B75; A128-B76; A128-B77; A128-B78; A128-B79; A128-B80; A128-B81; A128-B82; A128-B83; A128-B84; A128-B85; A128-B86; A128-B87; A128-B88; A128-B89; A128-B90; A128-B91; A128-B92; A128-B93; A128-B94; A128-B95; A128-B96; A128-B97; A128-B98; A128-B99; A128-B100; A128-B101; A128-B102; A128-B103; A128-B104; A128-B105; A128-B106; A128-B107; A128-B108; A128-B109; A128-B110; A128-B111; A128-B112; A128-B113;

A129-B1; A129-B2; A129-B3; A129-B4; A129-B5; A129-B6; A129-B7; A129-B8; A129-B9; A129-B10; A129-B11; A129-B12; A129-B13; A129-B14; A129-B15; A129-B16; A129-B17; A129-B18; A129-B19; A129-B20; A129-B21; A129-B22; A129-B23; A129-B24; A129-B25; A129-B26; A129-B27; A129-B28; A129-B29; A129-B30; A129-B31; A129-B32; A129-B33; A129-B34; A129-B35; A129-B36; A129-B37; A129-B38; A129-B39; A129-B40; A129-B41; A129-B42; A129-B43; A129-B44; A129-B45; A129-B46; A129-B47; A129-B48; A129-B49; A129-B50; A129-B51; A129-B52; A129-B53; A129-B54; A129-B55; A129-B56; A129-B57; A129-B58; A129-B59; A129-B60; A129-B61; A129-B62; A129-B63; A129-B64; A129-B65; A129-B66; A129-B67; A129-B68; A129-B69; A129-B70; A129-B71; A129-B72; A129-B73; A129-B74; A129-B75; A129-

B76; A129-B77; A129-B78; A129-B79; A129-B80; A129-B81; A129-B82; A129-B83; A129-B84; A129-B85; A129-B86; A129-B87; A129-B88; A129-B89; A129-B90; A129-B91; A129-B92; A129-B93; A129-B94; A129-B95; A129-B96; A129-B97; A129-B98; A129-B99; A129-B100; A129-B101; A129-B102; A129-B103; A129-B104; A129-B105; A129-B106; A129-B107; A129-B108; A129-B109; A129-B110; A129-B111; A129-B112; A129-B113;

A130-B1; A130-B2; A130-B3; A130-B4; A130-B5; A130-B6; A130-B7; A130-B8; A130-B9; A130-B10; A130-B11; A130-B12; A130-B13; A130-B14; A130-B15; A130-B16; A130-B17; A130-B18; A130-B19; A130-B20; A130-B21; A130-B22; A130-B23; A130-B24; A130-B25; A130-B26; A130-B27; A130-B28; A130-B29; A130-B30; A130-B31; A130-B32; A130-B33; A130-B34; A130-B35; A130-B36; A130-B37; A130-B38; A130-B39; A130-B40; A130-B41; A130-B42; A130-B43; A130-B44; A130-B45; A130-B46; A130-B47; A130-B48; A130-B49; A130-B50; A130-B51; A130-B52; A130-B53; A130-B54; A130-B55; A130-B56; A130-B57; A130-B58; A130-B59; A130-B60; A130-B61; A130-B62; A130-B63; A130-B64; A130-B65; A130-B66; A130-B67; A130-B68; A130-B69; A130-B70; A130-B71; A130-B72; A130-B73; A130-B74; A130-B75; A130-B76; A130-B77; A130-B78; A130-B79; A130-B80; A130-B81; A130-B82; A130-B83; A130-B84; A130-B85; A130-B86; A130-B87; A130-B88; A130-B89; A130-B90; A130-B91; A130-B92; A130-B93; A130-B94; A130-B95; A130-B96; A130-B97; A130-B98; A130-B99; A130-B100; A130-B101; A130-B102; A130-B103; A130-B104; A130-B105; A130-B106; A130-B107; A130-B108; A130-B109; A130-B110; A130-B111; A130-B112; A130-B113;

A131-B1; A131-B2; A131-B3; A131-B4; A131-B5; A131-B6; A131-B7; A131-B8; A131-B9; A131-B10; A131-B11; A131-B12; A131-B13; A131-B14; A131-B15; A131-B16; A131-B17; A131-B18; A131-B19; A131-B20; A131-B21; A131-B22; A131-B23; A131-B24; A131-B25; A131-B26; A131-B27; A131-B28; A131-B29; A131-B30; A131-B31; A131-B32; A131-B33; A131-B34; A131-B35; A131-B36; A131-B37; A131-B38; A131-B39; A131-B40; A131-B41; A131-B42; A131-B43; A131-B44; A131-B45; A131-B46; A131-B47; A131-B48; A131-B49; A131-B50; A131-B51; A131-B52; A131-B53; A131-B54; A131-B55; A131-B56; A131-B57; A131-B58; A131-B59; A131-B60; A131-B61; A131-B62; A131-B63; A131-B64; A131-B65; A131-B66; A131-B67; A131-B68; A131-B69; A131-B70; A131-B71; A131-B72; A131-B73; A131-B74; A131-B75; A131-B76; A131-B77; A131-B78; A131-B79; A131-B80; A131-B81; A131-B82; A131-B83; A131-B84; A131-B85; A131-B86; A131-B87; A131-B88; A131-B89; A131-B90; A131-B91; A131-B92; A131-B93; A131-B94; A131-B95; A131-B96; A131-B97; A131-B98; A131-B99; A131-B100; A131-B101; A131-B102; A131-B103; A131-B104; A131-B105; A131-B106; A131-B107; A131-B108; A131-B109; A131-B110; A131-B111; A131-B112; A131-B113;

A132-B1; A132-B2; A132-B3; A132-B4; A132-B5; A132-B6; A132-B7; A132-B8; A132-B9; A132-B10; A132-B11; A132-B12; A132-B13; A132-B14; A132-B15; A132-B16; A132-B17; A132-B18; A132-B19; A132-B20; A132-B21; A132-B22; A132-B23; A132-B24; A132-B25; A132-B26; A132-B27; A132-B28; A132-B29; A132-B30; A132-B31; A132-B32; A132-B33; A132-B34; A132-B35; A132-B36; A132-B37; A132-B38; A132-B39; A132-B40; A132-B41; A132-B42; A132-B43; A132-B44; A132-B45; A132-B46; A132-B47; A132-B48; A132-B49; A132-B50; A132-B51; A132-B52; A132-B53; A132-B54; A132-B55; A132-B56; A132-B57; A132-B58; A132-B59; A132-B60; A132-B61; A132-B62; A132-B63; A132-B64; A132-B65; A132-B66; A132-B67; A132-B68; A132-B69; A132-B70; A132-B71; A132-B72; A132-B73; A132-B74; A132-B75; A132-B76; A132-B77; A132-B78; A132-B79; A132-B80; A132-B81; A132-B82; A132-B83; A132-B84; A132-B85; A132-B86; A132-B87; A132-B88; A132-B89; A132-B90; A132-B91; A132-B92; A132-B93; A132-B94; A132-B95; A132-B96; A132-B97; A132-B98; A132-B99; A132-B100; A132-B101; A132-B102; A132-B103; A132-B104; A132-B105; A132-B106; A132-B107; A132-B108; A132-B109; A132-B110; A132-B111; A132-B112; A132-B113;

A133-B1; A133-B2; A133-B3; A133-B4; A133-B5; A133-B6; A133-B7; A133-B8; A133-B9; A133-B10; A133-B11; A133-B12; A133-B13; A133-B14; A133-B15; A133-B16; A133-B17; A133-B18; A133-B19; A133-B20; A133-B21; A133-B22; A133-B23; A133-B24; A133-B25; A133-B26; A133-B27; A133-B28; A133-B29; A133-B30; A133-B31; A133-B32; A133-B33; A133-B34; A133-B35; A133-B36; A133-B37; A133-B38; A133-B39; A133-B40; A133-B41; A133-B42; A133-B43; A133-B44; A133-B45; A133-B46; A133-B47; A133-B48; A133-B49; A133-B50; A133-B51; A133-B52; A133-B53; A133-B54; A133-B55; A133-B56; A133-B57; A133-B58; A133-B59; A133-B60; A133-B61; A133-B62; A133-B63; A133-B64; A133-B65; A133-B66; A133-B67; A133-B68; A133-B69; A133-B70; A133-B71; A133-B72; A133-B73; A133-B74; A133-B75; A133-B76; A133-B77; A133-B78; A133-B79; A133-B80; A133-B81; A133-B82; A133-B83; A133-B84; A133-B85; A133-B86; A133-B87; A133-B88; A133-B89; A133-B90; A133-B91; A133-B92; A133-B93; A133-B94; A133-B95; A133-B96; A133-B97; A133-B98; A133-B99; A133-B100; A133-B101; A133-B102; A133-B103; A133-B104; A133-B105; A133-B106; A133-B107; A133-B108; A133-B109; A133-B110; A133-B111; A133-B112; A133-B113;

A134-B1; A134-B2; A134-B3; A134-B4; A134-B5; A134-B6; A134-B7; A134-B8; A134-B9; A134-B10; A134-B11; A134-B12; A134-B13; A134-B14; A134-B15; A134-B16; A134-B17; A134-B18; A134-B19; A134-B20; A134-B21; A134-B22; A134-B23; A134-B24; A134-B25; A134-B26; A134-B27; A134-B28; A134-B29; A134-B30; A134-B31; A134-B32; A134-B33; A134-B34; A134-B35; A134-B36; A134-B37; A134-B38; A134-B39; A134-B40; A134-B41; A134-B42; A134-B43; A134-B44; A134-B45; A134-B46; A134-B47; A134-B48; A134-B49; A134-B50; A134-B51; A134-B52; A134-B53; A134-B54; A134-B55; A134-B56; A134-B57; A134-B58; A134-B59; A134-B60; A134-B61; A134-B62; A134-B63; A134-B64; A134-B65; A134-B66; A134-B67; A134-B68; A134-B69; A134-B70; A134-B71; A134-B72; A134-B73; A134-B74; A134-B75; A134-B76; A134-B77; A134-B78; A134-B79; A134-B80; A134-B81; A134-B82; A134-B83; A134-B84; A134-B85; A134-B86; A134-B87; A134-B88; A134-B89; A134-B90; A134-B91; A134-B92; A134-B93; A134-B94; A134-B95; A134-B96; A134-B97; A134-B98; A134-B99; A134-B100; A134-B101; A134-B102; A134-B103; A134-B104; A134-B105; A134-B106; A134-B107; A134-B108; A134-B109; A134-B110; A134-B111; A134-B112; A134-B113;

A135-B1; A135-B2; A135-B3; A135-B4; A135-B5; A135-B6; A135-B7; A135-B8; A135-B9; A135-B10; A135-B11; A135-B12; A135-B13; A135-B14; A135-B15; A135-B16; A135-B17; A135-B18; A135-B19; A135-B20; A135-B21; A135-B22; A135-B23; A135-B24; A135-B25; A135-B26; A135-B27; A135-B28; A135-B29; A135-B30; A135-B31; A135-B32; A135-B33; A135-B34; A135-B35; A135-B36; A135-B37; A135-B38; A135-B39; A135-B40; A135-B41; A135-B42; A135-B43; A135-B44; A135-B45; A135-B46; A135-B47; A135-B48; A135-B49; A135-B50; A135-B51; A135-B52; A135-B53; A135-B54; A135-B55; A135-

B56; A135-B57; A135-B58; A135-B59; A135-B60; A135-B61; A135-B62; A135-B63; A135-B64; A135-B65; A135-B66; A135-B67; A135-B68; A135-B69; A135-B70; A135-B71; A135-B72; A135-B73; A135-B74; A135-B75; A135-B76; A135-B77; A135-B78; A135-B79; A135-B80; A135-B81; A135-B82; A135-B83; A135-B84; A135-B85; A135-B86; A135-B87; A135-B88; A135-B89; A135-B90; A135-B91; A135-B92; A135-B93; A135-B94; A135-B95; A135-B96; A135-B97; A135-B98; A135-B99; A135-B100; A135-B101; A135-B102; A135-B103; A135-B104; A135-B105; A135-B106; A135-B107; A135-B108; A135-B109; A135-B110; A135-B111; A135-B112; A135-B113;

A136-B1; A136-B2; A136-B3; A136-B4; A136-B5; A136-B6; A136-B7; A136-B8; A136-B9; A136-B10; A136-B11; A136-B12; A136-B13; A136-B14; A136-B15; A136-B16; A136-B17; A136-B18; A136-B19; A136-B20; A136-B21; A136-B22; A136-B23; A136-B24; A136-B25; A136-B26; A136-B27; A136-B28; A136-B29; A136-B30; A136-B31; A136-B32; A136-B33; A136-B34; A136-B35; A136-B36; A136-B37; A136-B38; A136-B39; A136-B40; A136-B41; A136-B42; A136-B43; A136-B44; A136-B45; A136-B46; A136-B47; A136-B48; A136-B49; A136-B50; A136-B51; A136-B52; A136-B53; A136-B54; A136-B55; A136-B56; A136-B57; A136-B58; A136-B59; A136-B60; A136-B61; A136-B62; A136-B63; A136-B64; A136-B65; A136-B66; A136-B67; A136-B68; A136-B69; A136-B70; A136-B71; A136-B72; A136-B73; A136-B74; A136-B75; A136-B76; A136-B77; A136-B78; A136-B79; A136-B80; A136-B81; A136-B82; A136-B83; A136-B84; A136-B85; A136-B86; A136-B87; A136-B88; A136-B89; A136-B90; A136-B91; A136-B92; A136-B93; A136-B94; A136-B95; A136-B96; A136-B97; A136-B98; A136-B99; A136-B100; A136-B101; A136-B102; A136-B103; A136-B104; A136-B105; A136-B106; A136-B107; A136-B108; A136-B109; A136-B110; A136-B111; A136-B112; A136-B113;

A137-B1; A137-B2; A137-B3; A137-B4; A137-B5; A137-B6; A137-B7; A137-B8; A137-B9; A137-B10; A137-B11; A137-B12; A137-B13; A137-B14; A137-B15; A137-B16; A137-B17; A137-B18; A137-B19; A137-B20; A137-B21; A137-B22; A137-B23; A137-B24; A137-B25; A137-B26; A137-B27; A137-B28; A137-B29; A137-B30; A137-B31; A137-B32; A137-B33; A137-B34; A137-B35; A137-B36; A137-B37; A137-B38; A137-B39; A137-B40; A137-B41; A137-B42; A137-B43; A137-B44; A137-B45; A137-B46; A137-B47; A137-B48; A137-B49; A137-B50; A137-B51; A137-B52; A137-B53; A137-B54; A137-B55; A137-B56; A137-B57; A137-B58; A137-B59; A137-B60; A137-B61; A137-B62; A137-B63; A137-B64; A137-B65; A137-B66; A137-B67; A137-B68; A137-B69; A137-B70; A137-B71; A137-B72; A137-B73; A137-B74; A137-B75; A137-B76; A137-B77; A137-B78; A137-B79; A137-B80; A137-B81; A137-B82; A137-B83; A137-B84; A137-B85; A137-B86; A137-B87; A137-B88; A137-B89; A137-B90; A137-B91; A137-B92; A137-B93; A137-B94; A137-B95; A137-B96; A137-B97; A137-B98; A137-B99; A137-B100; A137-B101; A137-B102; A137-B103; A137-B104; A137-B105; A137-B106; A137-B107; A137-B108; A137-B109; A137-B110; A137-B111; A137-B112; A137-B113;

A138-B1; A138-B2; A138-B3; A138-B4; A138-B5; A138-B6; A138-B7; A138-B8; A138-B9; A138-B10; A138-B11; A138-B12; A138-B13; A138-B14; A138-B15; A138-B16; A138-B17; A138-B18; A138-B19; A138-B20; A138-B21; A138-B22; A138-B23; A138-B24; A138-B25; A138-B26; A138-B27; A138-B28; A138-B29; A138-B30; A138-B31; A138-B32; A138-B33; A138-B34; A138-B35; A138-B36; A138-B37; A138-B38; A138-B39; A138-B40; A138-B41; A138-B42; A138-B43; A138-B44; A138-B45; A138-B46; A138-B47; A138-B48; A138-B49; A138-B50; A138-B51; A138-B52; A138-B53; A138-B54; A138-B55; A138-B56; A138-B57; A138-B58; A138-B59; A138-B60; A138-B61; A138-B62; A138-B63; A138-B64; A138-B65; A138-B66; A138-B67; A138-B68; A138-B69; A138-B70; A138-B71; A138-B72; A138-B73; A138-B74; A138-B75; A138-B76; A138-B77; A138-B78; A138-B79; A138-B80; A138-B81; A138-B82; A138-B83; A138-B84; A138-B85; A138-B86; A138-B87; A138-B88; A138-B89; A138-B90; A138-B91; A138-B92; A138-B93; A138-B94; A138-B95; A138-B96; A138-B97; A138-B98; A138-B99; A138-B100; A138-B101; A138-B102; A138-B103; A138-B104; A138-B105; A138-B106; A138-B107; A138-B108; A138-B109; A138-B110; A138-B111; A138-B112; A138-B113;

A139-B1; A139-B2; A139-B3; A139-B4; A139-B5; A139-B6; A139-B7; A139-B8; A139-B9; A139-B10; A139-B11; A139-B12; A139-B13; A139-B14; A139-B15; A139-B16; A139-B17; A139-B18; A139-B19; A139-B20; A139-B21; A139-B22; A139-B23; A139-B24; A139-B25; A139-B26; A139-B27; A139-B28; A139-B29; A139-B30; A139-B31; A139-B32; A139-B33; A139-B34; A139-B35; A139-B36; A139-B37; A139-B38; A139-B39; A139-B40; A139-B41; A139-B42; A139-B43; A139-B44; A139-B45; A139-B46; A139-B47; A139-B48; A139-B49; A139-B50; A139-B51; A139-B52; A139-B53; A139-B54; A139-B55; A139-B56; A139-B57; A139-B58; A139-B59; A139-B60; A139-B61; A139-B62; A139-B63; A139-B64; A139-B65; A139-B66; A139-B67; A139-B68; A139-B69; A139-B70; A139-B71; A139-B72; A139-B73; A139-B74; A139-B75; A139-B76; A139-B77; A139-B78; A139-B79; A139-B80; A139-B81; A139-B82; A139-B83; A139-B84; A139-B85; A139-B86; A139-B87; A139-B88; A139-B89; A139-B90; A139-B91; A139-B92; A139-B93; A139-B94; A139-B95; A139-B96; A139-B97; A139-B98; A139-B99; A139-B100; A139-B101; A139-B102; A139-B103; A139-B104; A139-B105; A139-B106; A139-B107; A139-B108; A139-B109; A139-B110; A139-B111; A139-B112; A139-B113;

A140-B1; A140-B2; A140-B3; A140-B4; A140-B5; A140-B6; A140-B7; A140-B8; A140-B9; A140-B10; A140-B11; A140-B12; A140-B13; A140-B14; A140-B15; A140-B16; A140-B17; A140-B18; A140-B19; A140-B20; A140-B21; A140-B22; A140-B23; A140-B24; A140-B25; A140-B26; A140-B27; A140-B28; A140-B29; A140-B30; A140-B31; A140-B32; A140-B33; A140-B34; A140-B35; A140-B36; A140-B37; A140-B38; A140-B39; A140-B40; A140-B41; A140-B42; A140-B43; A140-B44; A140-B45; A140-B46; A140-B47; A140-B48; A140-B49; A140-B50; A140-B51; A140-B52; A140-B53; A140-B54; A140-B55; A140-B56; A140-B57; A140-B58; A140-B59; A140-B60; A140-B61; A140-B62; A140-B63; A140-B64; A140-B65; A140-B66; A140-B67; A140-B68; A140-B69; A140-B70; A140-B71; A140-B72; A140-B73; A140-B74; A140-B75; A140-B76; A140-B77; A140-B78; A140-B79; A140-B80; A140-B81; A140-B82; A140-B83; A140-B84; A140-B85; A140-B86; A140-B87; A140-B88; A140-B89; A140-B90; A140-B91; A140-B92; A140-B93; A140-B94; A140-B95; A140-B96; A140-B97; A140-B98; A140-B99; A140-B100; A140-B101; A140-B102; A140-B103; A140-B104; A140-B105; A140-B106; A140-B107; A140-B108; A140-B109; A140-B110; A140-B111; A140-B112; A140-B113;

A141-B1; A141-B2; A141-B3; A141-B4; A141-B5; A141-B6; A141-B7; A141-B8; A141-B9; A141-B10; A141-B11; A141-B12; A141-B13; A141-B14; A141-B15; A141-B16; A141-B17; A141-B18; A141-B19; A141-B20; A141-B21; A141-B22; A141-B23; A141-B24; A141-B25; A141-B26; A141-B27; A141-B28; A141-B29; A141-B30; A141-B31; A141-B32; A141-B33; A141-B34; A141-B35; A141-

B36; A141-B37; A141-B38; A141-B39; A141-B40; A141-B41; A141-B42; A141-B43; A141-B44; A141-B45; A141-B46; A141-B47; A141-B48; A141-B49; A141-B50; A141-B51; A141-B52; A141-B53; A141-B54; A141-B55; A141-B56; A141-B57; A141-B58; A141-B59; A141-B60; A141-B61; A141-B62; A141-B63; A141-B64; A141-B65; A141-B66; A141-B67; A141-B68; A141-B69; A141-B70; A141-B71; A141-B72; A141-B73; A141-B74; A141-B75; A141-B76; A141-B77; A141-B78; A141-B79; A141-B80; A141-B81; A141-B82; A141-B83; A141-B84; A141-B85; A141-B86; A141-B87; A141-B88; A141-B89; A141-B90; A141-B91; A141-B92; A141-B93; A141-B94; A141-B95; A141-B96; A141-B97; A141-B98; A141-B99; A141-B100; A141-B101; A141-B102; A141-B103; A141-B104; A141-B105; A141-B106; A141-B107; A141-B108; A141-B109; A141-B110; A141-B111; A141-B112; A141-B113;

A142-B1; A142-B2; A142-B3; A142-B4; A142-B5; A142-B6; A142-B7; A142-B8; A142-B9; A142-B10; A142-B11; A142-B12; A142-B13; A142-B14; A142-B15; A142-B16; A142-B17; A142-B18; A142-B19; A142-B20; A142-B21; A142-B22; A142-B23; A142-B24; A142-B25; A142-B26; A142-B27; A142-B28; A142-B29; A142-B30; A142-B31; A142-B32; A142-B33; A142-B34; A142-B35; A142-B36; A142-B37; A142-B38; A142-B39; A142-B40; A142-B41; A142-B42; A142-B43; A142-B44; A142-B45; A142-B46; A142-B47; A142-B48; A142-B49; A142-B50; A142-B51; A142-B52; A142-B53; A142-B54; A142-B55; A142-B56; A142-B57; A142-B58; A142-B59; A142-B60; A142-B61; A142-B62; A142-B63; A142-B64; A142-B65; A142-B66; A142-B67; A142-B68; A142-B69; A142-B70; A142-B71; A142-B72; A142-B73; A142-B74; A142-B75; A142-B76; A142-B77; A142-B78; A142-B79; A142-B80; A142-B81; A142-B82; A142-B83; A142-B84; A142-B85; A142-B86; A142-B87; A142-B88; A142-B89; A142-B90; A142-B91; A142-B92; A142-B93; A142-B94; A142-B95; A142-B96; A142-B97; A142-B98; A142-B99; A142-B100; A142-B101; A142-B102; A142-B103; A142-B104; A142-B105; A142-B106; A142-B107; A142-B108; A142-B109; A142-B110; A142-B111; A142-B112; A142-B113;

A143-B1; A143-B2; A143-B3; A143-B4; A143-B5; A143-B6; A143-B7; A143-B8; A143-B9; A143-B10; A143-B11; A143-B12; A143-B13; A143-B14; A143-B15; A143-B16; A143-B17; A143-B18; A143-B19; A143-B20; A143-B21; A143-B22; A143-B23; A143-B24; A143-B25; A143-B26; A143-B27; A143-B28; A143-B29; A143-B30; A143-B31; A143-B32; A143-B33; A143-B34; A143-B35; A143-B36; A143-B37; A143-B38; A143-B39; A143-B40; A143-B41; A143-B42; A143-B43; A143-B44; A143-B45; A143-B46; A143-B47; A143-B48; A143-B49; A143-B50; A143-B51; A143-B52; A143-B53; A143-B54; A143-B55; A143-B56; A143-B57; A143-B58; A143-B59; A143-B60; A143-B61; A143-B62; A143-B63; A143-B64; A143-B65; A143-B66; A143-B67; A143-B68; A143-B69; A143-B70; A143-B71; A143-B72; A143-B73; A143-B74; A143-B75; A143-B76; A143-B77; A143-B78; A143-B79; A143-B80; A143-B81; A143-B82; A143-B83; A143-B84; A143-B85; A143-B86; A143-B87; A143-B88; A143-B89; A143-B90; A143-B91; A143-B92; A143-B93; A143-B94; A143-B95; A143-B96; A143-B97; A143-B98; A143-B99; A143-B100; A143-B101; A143-B102; A143-B103; A143-B104; A143-B105; A143-B106; A143-B107; A143-B108; A143-B109; A143-B110; A143-B111; A143-B112; A143-B113;

A144-B1; A144-B2; A144-B3; A144-B4; A144-B5; A144-B6; A144-B7; A144-B8; A144-B9; A144-B10; A144-B11; A144-B12; A144-B13; A144-B14; A144-B15; A144-B16; A144-B17; A144-B18; A144-B19; A144-B20; A144-B21; A144-B22; A144-B23; A144-B24; A144-B25; A144-B26; A144-B27; A144-B28; A144-B29; A144-B30; A144-B31; A144-B32; A144-B33; A144-B34; A144-B35; A144-B36; A144-B37; A144-B38; A144-B39; A144-B40; A144-B41; A144-B42; A144-B43; A144-B44; A144-B45; A144-B46; A144-B47; A144-B48; A144-B49; A144-B50; A144-B51; A144-B52; A144-B53; A144-B54; A144-B55; A144-B56; A144-B57; A144-B58; A144-B59; A144-B60; A144-B61; A144-B62; A144-B63; A144-B64; A144-B65; A144-B66; A144-B67; A144-B68; A144-B69; A144-B70; A144-B71; A144-B72; A144-B73; A144-B74; A144-B75; A144-B76; A144-B77; A144-B78; A144-B79; A144-B80; A144-B81; A144-B82; A144-B83; A144-B84; A144-B85; A144-B86; A144-B87; A144-B88; A144-B89; A144-B90; A144-B91; A144-B92; A144-B93; A144-B94; A144-B95; A144-B96; A144-B97; A144-B98; A144-B99; A144-B100; A144-B101; A144-B102; A144-B103; A144-B104; A144-B105; A144-B106; A144-B107; A144-B108; A144-B109; A144-B110; A144-B111; A144-B112; A144-B113;

A145-B1; A145-B2; A145-B3; A145-B4; A145-B5; A145-B6; A145-B7; A145-B8; A145-B9; A145-B10; A145-B11; A145-B12; A145-B13; A145-B14; A145-B15; A145-B16; A145-B17; A145-B18; A145-B19; A145-B20; A145-B21; A145-B22; A145-B23; A145-B24; A145-B25; A145-B26; A145-B27; A145-B28; A145-B29; A145-B30; A145-B31; A145-B32; A145-B33; A145-B34; A145-B35; A145-B36; A145-B37; A145-B38; A145-B39; A145-B40; A145-B41; A145-B42; A145-B43; A145-B44; A145-B45; A145-B46; A145-B47; A145-B48; A145-B49; A145-B50; A145-B51; A145-B52; A145-B53; A145-B54; A145-B55; A145-B56; A145-B57; A145-B58; A145-B59; A145-B60; A145-B61; A145-B62; A145-B63; A145-B64; A145-B65; A145-B66; A145-B67; A145-B68; A145-B69; A145-B70; A145-B71; A145-B72; A145-B73; A145-B74; A145-B75; A145-B76; A145-B77; A145-B78; A145-B79; A145-B80; A145-B81; A145-B82; A145-B83; A145-B84; A145-B85; A145-B86; A145-B87; A145-B88; A145-B89; A145-B90; A145-B91; A145-B92; A145-B93; A145-B94; A145-B95; A145-B96; A145-B97; A145-B98; A145-B99; A145-B100; A145-B101; A145-B102; A145-B103; A145-B104; A145-B105; A145-B106; A145-B107; A145-B108; A145-B109; A145-B110; A145-B111; A145-B112; A145-B113;

A146-B1; A146-B2; A146-B3; A146-B4; A146-B5; A146-B6; A146-B7; A146-B8; A146-B9; A146-B10; A146-B11; A146-B12; A146-B13; A146-B14; A146-B15; A146-B16; A146-B17; A146-B18; A146-B19; A146-B20; A146-B21; A146-B22; A146-B23; A146-B24; A146-B25; A146-B26; A146-B27; A146-B28; A146-B29; A146-B30; A146-B31; A146-B32; A146-B33; A146-B34; A146-B35; A146-B36; A146-B37; A146-B38; A146-B39; A146-B40; A146-B41; A146-B42; A146-B43; A146-B44; A146-B45; A146-B46; A146-B47; A146-B48; A146-B49; A146-B50; A146-B51; A146-B52; A146-B53; A146-B54; A146-B55; A146-B56; A146-B57; A146-B58; A146-B59; A146-B60; A146-B61; A146-B62; A146-B63; A146-B64; A146-B65; A146-B66; A146-B67; A146-B68; A146-B69; A146-B70; A146-B71; A146-B72; A146-B73; A146-B74; A146-B75; A146-B76; A146-B77; A146-B78; A146-B79; A146-B80; A146-B81; A146-B82; A146-B83; A146-B84; A146-B85; A146-B86; A146-B87; A146-B88; A146-B89; A146-B90; A146-B91; A146-B92; A146-B93; A146-B94; A146-B95; A146-B96; A146-B97; A146-B98; A146-B99; A146-B100; A146-B101; A146-B102; A146-B103; A146-B104; A146-B105; A146-B106; A146-B107; A146-B108; A146-B109; A146-B110; A146-B111; A146-B112; A146-B113;

A147-B1; A147-B2; A147-B3; A147-B4; A147-B5; A147-B6; A147-B7; A147-B8; A147-B9; A147-B10; A147-B11; A147-B12; A147-B13; A147-B14; A147-B15; A147-

B16; A147-B17; A147-B18; A147-B19; A147-B20; A147-B21; A147-B22; A147-B23; A147-B24; A147-B25; A147-B26; A147-B27; A147-B28; A147-B29; A147-B30; A147-B31; A147-B32; A147-B33; A147-B34; A147-B35; A147-B36; A147-B37; A147-B38; A147-B39; A147-B40; A147-B41; A147-B42; A147-B43; A147-B44; A147-B45; A147-B46; A147-B47; A147-B48; A147-B49; A147-B50; A147-B51; A147-B52; A147-B53; A147-B54; A147-B55; A147-B56; A147-B57; A147-B58; A147-B59; A147-B60; A147-B61; A147-B62; A147-B63; A147-B64; A147-B65; A147-B66; A147-B67; A147-B68; A147-B69; A147-B70; A147-B71; A147-B72; A147-B73; A147-B74; A147-B75; A147-B76; A147-B77; A147-B78; A147-B79; A147-B80; A147-B81; A147-B82; A147-B83; A147-B84; A147-B85; A147-B86; A147-B87; A147-B88; A147-B89; A147-B90; A147-B91; A147-B92; A147-B93; A147-B94; A147-B95; A147-B96; A147-B97; A147-B98; A147-B99; A147-B100; A147-B101; A147-B102; A147-B103; A147-B104; A147-B105; A147-B106; A147-B107; A147-B108; A147-B109; A147-B110; A147-B111; A147-B112; A147-B113;

A148-B1; A148-B2; A148-B3; A148-B4; A148-B5; A148-B6; A148-B7; A148-B8; A148-B9; A148-B10; A148-B11; A148-B12; A148-B13; A148-B14; A148-B15; A148-B16; A148-B17; A148-B18; A148-B19; A148-B20; A148-B21; A148-B22; A148-B23; A148-B24; A148-B25; A148-B26; A148-B27; A148-B28; A148-B29; A148-B30; A148-B31; A148-B32; A148-B33; A148-B34; A148-B35; A148-B36; A148-B37; A148-B38; A148-B39; A148-B40; A148-B41; A148-B42; A148-B43; A148-B44; A148-B45; A148-B46; A148-B47; A148-B48; A148-B49; A148-B50; A148-B51; A148-B52; A148-B53; A148-B54; A148-B55; A148-B56; A148-B57; A148-B58; A148-B59; A148-B60; A148-B61; A148-B62; A148-B63; A148-B64; A148-B65; A148-B66; A148-B67; A148-B68; A148-B69; A148-B70; A148-B71; A148-B72; A148-B73; A148-B74; A148-B75; A148-B76; A148-B77; A148-B78; A148-B79; A148-B80; A148-B81; A148-B82; A148-B83; A148-B84; A148-B85; A148-B86; A148-B87; A148-B88; A148-B89; A148-B90; A148-B91; A148-B92; A148-B93; A148-B94; A148-B95; A148-B96; A148-B97; A148-B98; A148-B99; A148-B100; A148-B101; A148-B102; A148-B103; A148-B104; A148-B105; A148-B106; A148-B107; A148-B108; A148-B109; A148-B110; A148-B111; A148-B112; A148-B113;

A149-B1; A149-B2; A149-B3; A149-B4; A149-B5; A149-B6; A149-B7; A149-B8; A149-B9; A149-B10; A149-B11; A149-B12; A149-B13; A149-B14; A149-B15; A149-B16; A149-B17; A149-B18; A149-B19; A149-B20; A149-B21; A149-B22; A149-B23; A149-B24; A149-B25; A149-B26; A149-B27; A149-B28; A149-B29; A149-B30; A149-B31; A149-B32; A149-B33; A149-B34; A149-B35; A149-B36; A149-B37; A149-B38; A149-B39; A149-B40; A149-B41; A149-B42; A149-B43; A149-B44; A149-B45; A149-B46; A149-B47; A149-B48; A149-B49; A149-B50; A149-B51; A149-B52; A149-B53; A149-B54; A149-B55; A149-B56; A149-B57; A149-B58; A149-B59; A149-B60; A149-B61; A149-B62; A149-B63; A149-B64; A149-B65; A149-B66; A149-B67; A149-B68; A149-B69; A149-B70; A149-B71; A149-B72; A149-B73; A149-B74; A149-B75; A149-B76; A149-B77; A149-B78; A149-B79; A149-B80; A149-B81; A149-B82; A149-B83; A149-B84; A149-B85; A149-B86; A149-B87; A149-B88; A149-B89; A149-B90; A149-B91; A149-B92; A149-B93; A149-B94; A149-B95; A149-B96; A149-B97; A149-B98; A149-B99; A149-B100; A149-B101; A149-B102; A149-B103; A149-B104; A149-B105; A149-B106; A149-B107; A149-B108; A149-B109; A149-B110; A149-B111; A149-B112; A149-B113;

A150-B1; A150-B2; A150-B3; A150-B4; A150-B5; A150-B6; A150-B7; A150-B8; A150-B9; A150-B10; A150-B11; A150-B12; A150-B13; A150-B14; A150-B15; A150-B16; A150-B17; A150-B18; A150-B19; A150-B20; A150-B21; A150-B22; A150-B23; A150-B24; A150-B25; A150-B26; A150-B27; A150-B28; A150-B29; A150-B30; A150-B31; A150-B32; A150-B33; A150-B34; A150-B35; A150-B36; A150-B37; A150-B38; A150-B39; A150-B40; A150-B41; A150-B42; A150-B43; A150-B44; A150-B45; A150-B46; A150-B47; A150-B48; A150-B49; A150-B50; A150-B51; A150-B52; A150-B53; A150-B54; A150-B55; A150-B56; A150-B57; A150-B58; A150-B59; A150-B60; A150-B61; A150-B62; A150-B63; A150-B64; A150-B65; A150-B66; A150-B67; A150-B68; A150-B69; A150-B70; A150-B71; A150-B72; A150-B73; A150-B74; A150-B75; A150-B76; A150-B77; A150-B78; A150-B79; A150-B80; A150-B81; A150-B82; A150-B83; A150-B84; A150-B85; A150-B86; A150-B87; A150-B88; A150-B89; A150-B90; A150-B91; A150-B92; A150-B93; A150-B94; A150-B95; A150-B96; A150-B97; A150-B98; A150-B99; A150-B100; A150-B101; A150-B102; A150-B103; A150-B104; A150-B105; A150-B106; A150-B107; A150-B108; A150-B109; A150-B110; A150-B111; A150-B112; A150-B113;

A151-B1; A151-B2; A151-B3; A151-B4; A151-B5; A151-B6; A151-B7; A151-B8; A151-B9; A151-B10; A151-B11; A151-B12; A151-B13; A151-B14; A151-B15; A151-B16; A151-B17; A151-B18; A151-B19; A151-B20; A151-B21; A151-B22; A151-B23; A151-B24; A151-B25; A151-B26; A151-B27; A151-B28; A151-B29; A151-B30; A151-B31; A151-B32; A151-B33; A151-B34; A151-B35; A151-B36; A151-B37; A151-B38; A151-B39; A151-B40; A151-B41; A151-B42; A151-B43; A151-B44; A151-B45; A151-B46; A151-B47; A151-B48; A151-B49; A151-B50; A151-B51; A151-B52; A151-B53; A151-B54; A151-B55; A151-B56; A151-B57; A151-B58; A151-B59; A151-B60; A151-B61; A151-B62; A151-B63; A151-B64; A151-B65; A151-B66; A151-B67; A151-B68; A151-B69; A151-B70; A151-B71; A151-B72; A151-B73; A151-B74; A151-B75; A151-B76; A151-B77; A151-B78; A151-B79; A151-B80; A151-B81; A151-B82; A151-B83; A151-B84; A151-B85; A151-B86; A151-B87; A151-B88; A151-B89; A151-B90; A151-B91; A151-B92; A151-B93; A151-B94; A151-B95; A151-B96; A151-B97; A151-B98; A151-B99; A151-B100; A151-B101; A151-B102; A151-B103; A151-B104; A151-B105; A151-B106; A151-B107; A151-B108; A151-B109; A151-B110; A151-B111; A151-B112; A151-B113;

A152-B1; A152-B2; A152-B3; A152-B4; A152-B5; A152-B6; A152-B7; A152-B8; A152-B9; A152-B10; A152-B11; A152-B12; A152-B13; A152-B14; A152-B15; A152-B16; A152-B17; A152-B18; A152-B19; A152-B20; A152-B21; A152-B22; A152-B23; A152-B24; A152-B25; A152-B26; A152-B27; A152-B28; A152-B29; A152-B30; A152-B31; A152-B32; A152-B33; A152-B34; A152-B35; A152-B36; A152-B37; A152-B38; A152-B39; A152-B40; A152-B41; A152-B42; A152-B43; A152-B44; A152-B45; A152-B46; A152-B47; A152-B48; A152-B49; A152-B50; A152-B51; A152-B52; A152-B53; A152-B54; A152-B55; A152-B56; A152-B57; A152-B58; A152-B59; A152-B60; A152-B61; A152-B62; A152-B63; A152-B64; A152-B65; A152-B66; A152-B67; A152-B68; A152-B69; A152-B70; A152-B71; A152-B72; A152-B73; A152-B74; A152-B75; A152-B76; A152-B77; A152-B78; A152-B79; A152-B80; A152-B81; A152-B82; A152-B83; A152-B84; A152-B85; A152-B86; A152-B87; A152-B88; A152-B89; A152-B90; A152-B91; A152-B92; A152-B93; A152-B94; A152-B95; A152-B96; A152-B97; A152-B98; A152-B99; A152-B100; A152-B101; A152-B102; A152-B103; A152-B104; A152-B105;

A152-B106; A152-B107; A152-B108; A152-B109; A152-B110; A152-B111; A152-B112; A152-B113;

A153-B1; A153-B2; A153-B3; A153-B4; A153-B5; A153-B6; A153-B7; A153-B8; A153-B9; A153-B10; A153-B11; A153-B12; A153-B13; A153-B14; A153-B15; A153-B16; A153-B17; A153-B18; A153-B19; A153-B20; A153-B21; A153-B22; A153-B23; A153-B24; A153-B25; A153-B26; A153-B27; A153-B28; A153-B29; A153-B30; A153-B31; A153-B32; A153-B33; A153-B34; A153-B35; A153-B36; A153-B37; A153-B38; A153-B39; A153-B40; A153-B41; A153-B42; A153-B43; A153-B44; A153-B45; A153-B46; A153-B47; A153-B48; A153-B49; A153-B50; A153-B51; A153-B52; A153-B53; A153-B54; A153-B55; A153-B56; A153-B57; A153-B58; A153-B59; A153-B60; A153-B61; A153-B62; A153-B63; A153-B64; A153-B65; A153-B66; A153-B67; A153-B68; A153-B69; A153-B70; A153-B71; A153-B72; A153-B73; A153-B74; A153-B75; A153-B76; A153-B77; A153-B78; A153-B79; A153-B80; A153-B81; A153-B82; A153-B83; A153-B84; A153-B85; A153-B86; A153-B87; A153-B88; A153-B89; A153-B90; A153-B91; A153-B92; A153-B93; A153-B94; A153-B95; A153-B96; A153-B97; A153-B98; A153-B99; A153-B100; A153-B101; A153-B102; A153-B103; A153-B104; A153-B105; A153-B106; A153-B107; A153-B108; A153-B109; A153-B110; A153-B111; A153-B112; A153-B113;

A154-B1; A154-B2; A154-B3; A154-B4; A154-B5; A154-B6; A154-B7; A154-B8; A154-B9; A154-B10; A154-B11; A154-B12; A154-B13; A154-B14; A154-B15; A154-B16; A154-B17; A154-B18; A154-B19; A154-B20; A154-B21; A154-B22; A154-B23; A154-B24; A154-B25; A154-B26; A154-B27; A154-B28; A154-B29; A154-B30; A154-B31; A154-B32; A154-B33; A154-B34; A154-B35; A154-B36; A154-B37; A154-B38; A154-B39; A154-B40; A154-B41; A154-B42; A154-B43; A154-B44; A154-B45; A154-B46; A154-B47; A154-B48; A154-B49; A154-B50; A154-B51; A154-B52; A154-B53; A154-B54; A154-B55; A154-B56; A154-B57; A154-B58; A154-B59; A154-B60; A154-B61; A154-B62; A154-B63; A154-B64; A154-B65; A154-B66; A154-B67; A154-B68; A154-B69; A154-B70; A154-B71; A154-B72; A154-B73; A154-B74; A154-B75; A154-B76; A154-B77; A154-B78; A154-B79; A154-B80; A154-B81; A154-B82; A154-B83; A154-B84; A154-B85; A154-B86; A154-B87; A154-B88; A154-B89; A154-B90; A154-B91; A154-B92; A154-B93; A154-B94; A154-B95; A154-B96; A154-B97; A154-B98; A154-B99; A154-B100; A154-B101; A154-B102; A154-B103; A154-B104; A154-B105; A154-B106; A154-B107; A154-B108; A154-B109; A154-B110; A154-B111; A154-B112; A154-B113;

Sub-Category IA: Amino Acid B of the Dipeptide Prodrug Element is N-Alkylated Glycine In some embodiments, the B amino acid of the dipeptide prodrug element is N-alkylated glycine. Nonlimiting examples of dipeptide prodrug elements having N-alkylated glycine as the B amino acid are shown in the below Table.

| Dipeptide Prodrug Element # | Amino Acid 'A' | Amino Acid 'B' |
|---|---|---|
| 1 | Aib | Gly(N-$C_1$-$C_8$alkyl) |
| 2 | d-Ala | Gly(N-$C_1$-$C_8$alkyl) |
| 3 | d-Lys | Gly(N-$C_1$-$C_8$alkyl) |
| 4 | d-Cys | Gly(N-$C_1$-$C_8$alkyl) |
| 5 | Aib | Gly(N-methyl) |
| 6 | d-Ala | Gly(N-methyl) |
| 7 | d-Lys | Gly(N-methyl) |
| 8 | d-Cys | Gly(N-methyl) |
| 9 | Aib | Gly(N-hexyl) |
| 10 | d-Ala | Gly(N-hexyl) |
| 11 | d-Lys | Gly(N-hexyl) |
| 12 | d-Cys | Gly(N-hexyl) |

Sub-Category IB: Amino Acid B of the Dipeptide Prodrug Element is Unsubstituted or Monosubstituted at the Beta Position In some embodiments, the B amino acid of the dipeptide prodrug element is unsubstituted or monosubstituted at the beta position and has a relatively non-bulky side chain. Non-limiting examples of dipeptide prodrug elements having a B amino acid that is unsubstituted or monosubstituted at the beta position and a relatively non-bulky side chain are shown in the below Table.

| Dipeptide Prodrug Element # | Amino Acid 'A' | Amino Acid 'B' |
|---|---|---|
| 13 | Aib | Ala(N-$C_1$-$C_8$alkyl) |
| 14 | d-Ala | Ala(N-$C_1$-$C_8$alkyl) |
| 15 | d-Lys | Ala(N-$C_1$-$C_8$alkyl) |
| 16 | d-Cys | Ala(N-$C_1$-$C_8$alkyl) |
| 17 | Aib | Leu(N-$C_1$-$C_8$alkyl) |
| 18 | d-Ala | Leu(N-$C_1$-$C_8$alkyl) |
| 19 | d-Lys | Leu(N-$C_1$-$C_8$alkyl) |
| 20 | d-Cys | Leu(N-$C_1$-$C_8$alkyl) |
| 21 | Aib | Met(N-$C_1$-$C_8$alkyl) |
| 22 | d-Ala | Met(N-$C_1$-$C_8$alkyl) |
| 23 | d-Lys | Met(N-$C_1$-$C_8$alkyl) |
| 24 | d-Cys | Met(N-$C_1$-$C_8$alkyl) |
| 25 | Aib | Asn(N-$C_1$-$C_8$alkyl) |
| 26 | d-Ala | Asn(N-$C_1$-$C_8$alkyl) |
| 27 | d-Lys | Asn(N-$C_1$-$C_8$alkyl) |
| 28 | d-Cys | Asn(N-$C_1$-$C_8$alkyl) |
| 29 | Aib | Glu(N-$C_1$-$C_8$alkyl) |
| 30 | d-Ala | Glu(N-$C_1$-$C_8$alkyl) |
| 31 | d-Lys | Glu(N-$C_1$-$C_8$alkyl) |
| 32 | d-Cys | Glu(N-$C_1$-$C_8$alkyl) |
| 33 | Aib | Asp(N-$C_1$-$C_8$alkyl) |
| 34 | d-Ala | Asp(N-$C_1$-$C_8$alkyl) |
| 35 | d-Lys | Asp(N-$C_1$-$C_8$alkyl) |
| 36 | d-Cys | Asp(N-$C_1$-$C_8$alkyl) |
| 37 | Aib | Gln(N-$C_1$-$C_8$alkyl) |
| 38 | d-Ala | Gln(N-$C_1$-$C_8$alkyl) |
| 39 | d-Lys | Gln(N-$C_1$-$C_8$alkyl) |
| 40 | d-Cys | Gln(N-$C_1$-$C_8$alkyl) |
| 41 | Aib | His(N-$C_1$-$C_8$alkyl) |
| 42 | d-Ala | His(N-$C_1$-$C_8$alkyl) |
| 43 | d-Lys | His(N-$C_1$-$C_8$alkyl) |
| 44 | d-Cys | His(N-$C_1$-$C_8$alkyl) |
| 45 | Aib | Lys(N-$C_1$-$C_8$alkyl) |
| 46 | d-Ala | Lys(N-$C_1$-$C_8$alkyl) |
| 47 | d-Lys | Lys(N-$C_1$-$C_8$alkyl) |
| 48 | d-Cys | Lys(N-$C_1$-$C_8$alkyl) |
| 49 | Aib | Arg(N-d-$C_8$alkyl) |
| 50 | d-Ala | Arg(N-$C_1$-$C_8$alkyl) |
| 51 | d-Lys | Arg(N-$C_1$-$C_8$alkyl) |
| 52 | d-Cys | Arg(N-$C_1$-$C_8$alkyl) |
| 53 | Aib | Ser(N-$C_1$-$C_8$alkyl) |
| 54 | d-Ala | Ser(N-$C_1$-$C_8$alkyl) |
| 55 | d-Lys | Ser(N-$C_1$-$C_8$alkyl) |
| 56 | d-Cys | Ser(N-$C_1$-$C_8$alkyl) |
| 57 | Aib | Cys(N-$C_1$-$C_8$alkyl) |
| 58 | d-Ala | Cys(N-$C_1$-$C_8$alkyl) |
| 59 | d-Lys | Cys(N-$C_1$-$C_8$alkyl) |
| 60 | d-Cys | Cys(N-$C_1$-$C_8$alkyl) |
| 61 | Aib | Pro |
| 62 | d-Ala | Pro |
| 63 | d-Lys | Pro |
| 64 | d-Cys | Pro |
| 65 | Aib | Ala(N-methyl) |
| 66 | d-Ala | Ala(N-methyl) |

| Dipeptide Prodrug Element # | Amino Acid 'A' | Amino Acid 'B' |
|---|---|---|
| 67 | d-Lys | Ala(N-methyl) |
| 68 | d-Cys | Ala(N-methyl) |
| 69 | Aib | Leu(N-methyl) |
| 70 | d-Ala | Leu(N-methyl) |
| 71 | d-Lys | Leu(N-methyl) |
| 72 | d-Cys | Leu(N-methyl) |
| 73 | Aib | Met(N-methyl) |
| 74 | d-Ala | Met(N-methyl) |
| 75 | d-Lys | Met(N-methyl) |
| 76 | d-Cys | Met(N-methyl) |
| 77 | Aib | Asn(N-methyl) |
| 78 | d-Ala | Asn(N-methyl) |
| 79 | d-Lys | Asn(N-methyl) |
| 80 | d-Cys | Asn(N-methyl) |
| 81 | Aib | Glu(N-methyl) |
| 82 | d-Ala | Glu(N-methyl) |
| 83 | d-Lys | Glu(N-methyl) |
| 84 | d-Cys | Glu(N-methyl) |
| 85 | Aib | Asp(N-methyl) |
| 86 | d-Ala | Asp(N-methyl) |
| 87 | d-Lys | Asp(N-methyl) |
| 88 | d-Cys | Asp(N-methyl) |
| 89 | Aib | Gln(N-methyl) |
| 90 | d-Ala | Gln(N-methyl) |
| 91 | d-Lys | Gln(N-methyl) |
| 92 | d-Cys | Gln(N-methyl) |
| 93 | Aib | His(N-methyl) |
| 94 | d-Ala | His(N-methyl) |
| 95 | d-Lys | His(N-methyl) |
| 96 | d-Cys | His(N-methyl) |
| 97 | Aib | Lys(N-methyl) |
| 98 | d-Ala | Lys(N-methyl) |
| 99 | d-Lys | Lys(N-methyl) |
| 100 | d-Cys | Lys(N-methyl) |
| 101 | Aib | Arg(N-methyl) |
| 102 | d-Ala | Arg(N-methyl) |
| 103 | d-Lys | Arg(N-methyl) |
| 104 | d-Cys | Arg(N-methyl) |
| 105 | Aib | Ser(N-methyl) |
| 106 | d-Ala | Ser(N-methyl) |
| 107 | d-Lys | Ser(N-methyl) |
| 108 | d-Cys | Ser(N-methyl) |
| 109 | Aib | Cys(N-methyl) |
| 110 | d-Ala | Cys(N-methyl) |
| 111 | d-Lys | Cys(N-methyl) |
| 112 | d-Cys | Cys(N-methyl) |
| 113 | Aib | Ala(N-hexyl) |
| 114 | d-Ala | Ala(N-hexyl) |
| 115 | d-Lys | Ala(N-hexyl) |
| 116 | d-Cys | Ala(N-hexyl) |
| 117 | Aib | Leu(N-hexyl) |
| 118 | d-Ala | Leu(N-hexyl) |
| 119 | d-Lys | Leu(N-hexyl) |
| 120 | d-Cys | Leu(N-hexyl) |
| 121 | Aib | Met(N-hexyl) |
| 122 | d-Ala | Met(N-hexyl) |
| 123 | d-Lys | Met(N-hexyl) |
| 124 | d-Cys | Met(N-hexyl) |
| 125 | Aib | Asn(N-hexyl) |
| 126 | d-Ala | Asn(N-hexyl) |
| 127 | d-Lys | Asn(N-hexyl) |
| 128 | d-Cys | Asn(N-hexyl) |
| 129 | Aib | Glu(N-hexyl) |
| 130 | d-Ala | Glu(N-hexyl) |
| 131 | d-Lys | Glu(N-hexyl) |
| 132 | d-Cys | Glu(N-hexyl) |
| 133 | Aib | Asp(N-hexyl) |
| 134 | d-Ala | Asp(N-hexyl) |
| 135 | d-Lys | Asp(N-hexyl) |
| 136 | d-Cys | Asp(N-hexyl) |
| 137 | Aib | Gln(N-hexyl) |
| 138 | d-Ala | Gln(N-hexyl) |
| 139 | d-Lys | Gln(N-hexyl) |
| 140 | d-Cys | Gln(N-hexyl) |
| 141 | Aib | His(N-hexyl) |
| 142 | d-Ala | His(N-hexyl) |
| 143 | d-Lys | His(N-hexyl) |
| 144 | d-Cys | His(N-hexyl) |
| 145 | Aib | Lys(N-hexyl) |
| 146 | d-Ala | Lys(N-hexyl) |
| 147 | d-Lys | Lys(N-hexyl) |
| 148 | d-Cys | Lys(N-hexyl) |
| 149 | Aib | Arg(N-hexyl) |
| 150 | d-Ala | Arg(N-hexyl) |
| 151 | d-Lys | Arg(N-hexyl) |
| 152 | d-Cys | Arg(N-hexyl) |
| 153 | Aib | Ser(N-hexyl) |
| 154 | d-Ala | Ser(N-hexyl) |
| 155 | d-Lys | Ser(N-hexyl) |
| 156 | d-Cys | Ser(N-hexyl) |
| 157 | Aib | Cys(N-hexyl) |
| 158 | d-Ala | Cys(N-hexyl) |
| 159 | d-Lys | Cys(N-hexyl) |
| 160 | d-Cys | Cys(N-hexyl) |

In some embodiments, the B amino acid of the dipeptide prodrug element is monosubstituted at the beta position and has a relatively bulky side chain, as shown in the below Table.

| Dipeptide Prodrug Element # | Amino Acid 'A' | Amino Acid 'B' |
|---|---|---|
| 161 | Aib | Phe(N-$C_1$-$C_8$alkyl) |
| 162 | d-Ala | Phe(N-$C_1$-$C_8$alkyl) |
| 163 | d-Lys | Phe(N-$C_1$-$C_8$alkyl) |
| 164 | d-Cys | Phe(N-$C_1$-$C_8$alkyl) |
| 165 | Aib | Tyr(N-$C_1$-$C_8$alkyl) |
| 166 | d-Ala | Tyr(N-$C_1$-$C_8$alkyl) |
| 167 | d-Lys | Tyr(N-$C_1$-$C_8$alkyl) |
| 168 | d-Cys | Tyr(N-$C_1$-$C_8$alkyl) |
| 169 | Aib | Trp(N-$C_1$-$C_8$alkyl) |
| 170 | d-Ala | Trp(N-$C_1$-$C_8$alkyl) |
| 171 | d-Lys | Trp(N-$C_1$-$C_8$alkyl) |
| 172 | d-Cys | Trp(N-$C_1$-$C_8$alkyl) |
| 173 | Aib | Phe(N-methyl) |
| 174 | d-Ala | Phe(N-methyl) |
| 175 | d-Lys | Phe(N-methyl) |
| 176 | d-Cys | Phe(N-methyl) |
| 177 | Aib | Tyr(N-methyl) |
| 178 | d-Ala | Tyr(N-methyl) |
| 179 | d-Lys | Tyr(N-methyl) |
| 180 | d-Cys | Tyr(N-methyl) |
| 181 | Aib | Trp(N-methyl) |
| 182 | d-Ala | Trp(N-methyl) |
| 183 | d-Lys | Trp(N-methyl) |
| 184 | d-Cys | Trp(N-methyl) |
| 185 | Aib | Phe(N-hexyl) |
| 186 | d-Ala | Phe(N-hexyl) |
| 187 | d-Lys | Phe(N-hexyl) |
| 188 | d-Cys | Phe(N-hexyl) |
| 189 | Aib | Tyr(N-hexyl) |
| 190 | d-Ala | Tyr(N-hexyl) |
| 191 | d-Lys | Tyr(N-hexyl) |
| 192 | d-Cys | Tyr(N-hexyl) |
| 193 | Aib | Trp(N-hexyl) |
| 194 | d-Ala | Trp(N-hexyl) |
| 195 | d-Lys | Trp(N-hexyl) |
| 196 | d-Cys | Trp(N-hexyl) |

Sub-Category IC: Amino Acid B of the Dipeptide Prodrug Element Disubstituted at the Beta Position In some embodiments, the B amino acid of the dipeptide prodrug element is disubstituted at the beta position. Nonlimiting examples of dipeptide prodrug elements having a B amino acid that is disubstituted at the beta position are shown in the below Table.

| Dipeptide Prodrug Element # | Amino Acid 'A' | Amino Acid 'B' |
|---|---|---|
| 197 | Aib | Ile(N-$C_1$-$C_8$alkyl) |
| 198 | d-Ala | Ile(N-$C_1$-$C_8$alkyl) |
| 199 | d-Lys | Ile(N-$C_1$-$C_8$alkyl) |
| 200 | d-Cys | Ile(N-$C_1$-$C_8$alkyl)) |
| 201 | Aib | Val(N-$C_1$-$C_8$alkyl) |
| 202 | d-Ala | Val(N-$C_1$-$C_8$alkyl) |
| 203 | d-Lys | Val(N-$C_1$-$C_8$alkyl) |
| 204 | d-Cys | Val(N-$C_1$-$C_8$alkyl) |
| 205 | Aib | Thr(N-$C_1$-$C_8$alkyl) |
| 206 | d-Ala | Thr(N-$C_1$-$C_8$alkyl) |
| 207 | d-Lys | Thr(N-$C_1$-$C_8$alkyl) |
| 208 | d-Cys | Thr(N-$C_1$-$C_8$alkyl) |
| 209 | Aib | Ile(N-methyl) |
| 210 | d-Ala | Ile(N-methyl) |
| 211 | d-Lys | Ile(N-methyl) |
| 212 | d-Cys | Ile(N-methyl)) |
| 213 | Aib | Val(N-methyl) |
| 214 | d-Ala | Val(N-methyl) |
| 215 | d-Lys | Val(N-methyl) |
| 216 | d-Cys | Val(N-methyl) |
| 217 | Aib | Thr(N-methyl) |
| 218 | d-Ala | Thr(N-methyl) |
| 219 | d-Lys | Thr(N-methyl) |
| 220 | d-Cys | Thr(N-methyl) |
| 221 | Aib | Ile(N-hexyl) |
| 222 | d-Ala | Ile(N-hexyl) |
| 223 | d-Lys | Ile(N-hexyl) |
| 224 | d-Cys | Ile(N-hexyl) |
| 225 | Aib | Val(N-hexyl) |
| 226 | d-Ala | Val(N-hexyl) |
| 227 | d-Lys | Val(N-hexyl) |
| 228 | d-Cys | Val(N-hexyl) |
| 229 | Aib | Thr(N-hexyl) |
| 230 | d-Ala | Thr(N-hexyl) |
| 231 | d-Lys | Thr(N-hexyl) |
| 232 | d-Cys | Thr(N-hexyl)) |

In some exemplary embodiments, Aib-Gly(N-Hexyl), dLys-Gly(N-Hexyl), dCys-Gly(N-Hexyl), dAla-Gly(N-Hexyl), Aib-Gly(N-Methyl), dLys-Gly(N-Methyl), dCys-Gly(N-Methyl), dAla-Gly(N-Hexyl), Aib-Phe(N-Methyl), dLys-Phe(N-Methyl), dCys-Phe(N-Methyl), or dAla-Phe(N-Methyl) is conjugated to the N-terminal alpha amino group of a peptide drug.

In accordance with one embodiment the dipeptide element comprises one of three amino acids at the B of the A-B dipeptide: Gly(N-Hexyl), Gly(N-Methyl) or Phe(N-Methyl). Dipeptides selected from one of these three groups of dipeptides have relative cleavage rates wherein Gly(N-Hexyl)>Gly(N-Methyl)>Phe(N-Methyl) all other factors being equal. In one embodiment Cys or Lys is provided in the first position (i.e., the A amino acid) to provides a location for acylation or pegylation. Ala is used as the A amino acid in one embodiment where no acylation or pegylation is desired.

In one embodiment an Aib in first position (i.e., the A amino acid) increases speed of cleavage relative to natural amino acids such as Ala, Cys, & Lys.
Exemplary dipeptides include:
dAla-Phe(N-Methyl)
dCys-Phe(N-Methyl)
dLys-Phe(N-Methyl)
Aib-Phe(N-Methyl)
dAla-Gly(N-Methyl)
dCys-Gly(N-Methyl)
dLys-Gly(N-Methyl)
Aib-Gly(N-Methyl)
dAla-Gly(N-Hexyl)
dCys-Gly(N-Hexyl)
dLys-Gly(N-Hexyl)
Aib-Gly(N-Hexyl)

In accordance with one embodiment a pharmaceutical composition is provided comprising any of the novel insulin prodrug analogs disclosed herein, preferably at a purity level of at least 90%, 91%, 92%, 93%, 94%, 95%, 96%, 97%, 98% or 99%, and a pharmaceutically acceptable diluent, carrier or excipient. Such compositions may contain an A19 insulin analog as disclosed herein at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored contained within various package containers. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

In one embodiment, a composition is provided comprising a mixture of a first and second insulin prodrug analog, wherein the first and second insulin prodrug analogs differ from one another based on the structure of the prodrug element. More particularly, the first insulin prodrug analog may comprise a dipeptide prodrug element that has a half life substantially different from the dipeptide prodrug element of the second insulin prodrug analog. Accordingly, selection of different combinations of substituents on the dipeptide element will allow for the preparation of compositions that comprise a mixture of insulin prodrug analogs that are activated in a controlled manner over a desired time frame and at specific time intervals. For example, the compositions can be formulated to release active insulin at mealtimes followed by a subsequent activation of insulin during nighttime with suitable dosages being released based on time of activation. In another embodiment the pharmaceutical composition comprises a mixture of an insulin prodrug analog disclosed herein and native insulin, or a known bioactive derivative of insulin.

The disclosed insulin prodrug analogs are believed to be suitable for any use that has previously been described for insulin peptides. Accordingly, the insulin prodrug analogs described herein can be used to treat hyperglycemia, or treat other metabolic diseases that result from high blood glucose levels. Accordingly, the present invention encompasses pharmaceutical compositions comprising an insulin prodrug analog of the present disclosure, and a pharmaceutically acceptable carrier for use in treating a patient suffering from high blood glucose levels. In accordance with one embodiment the patient to be treated using the insulin prodrug analogs disclosed herein is a domesticated animal, and in another embodiment the patient to be treated is a human.

One method of treating hyperglycemia in accordance with the present disclosure comprises the steps of administering the presently disclosed insulin prodrug analog to a patient using any standard route of administration, including parenterally, such as intravenously, intraperitoneally, subcutaneously or intramuscularly, intrathecally, transdermally, rectally, orally, nasally or by inhalation. In one embodiment the composition is administered subcutaneously or intramuscularly. In one embodiment, the composition is administered parenterally and the insulin prodrug analog composition is prepackaged in a syringe.

The insulin prodrug analogs of the invention may be administered alone or in combination with other anti-diabetic agents. Anti-diabetic agents known in the art or under investigation include native insulin, native glucagon and functional derivatives thereof, sulfonylureas, such as tolbutamide (Orinase), acetohexamide (Dymelor), tolazamide (Tolinase), chlorpropamide (Diabinese), glipizide (Glucotrol), glyburide (Diabeta, Micronase, Glynase), glimepiride (Amaryl), or gliclazide (Diamicron); meglitinides, such as repaglinide (Prandin) or nateglinide (Starlix); biguanides such as metformin (Glucophage) or phenformin; thiazolidinediones such as rosiglitazone (Avandia), pioglitazone (Actos), or troglitazone (Rezulin), or other PPARγ inhibitors; alpha glucosidase inhibitors that inhibit carbohydrate digestion, such as miglitol (Glyset), acarbose (Precose/Glucobay); exenatide (Byetta) or pramlintide; Dipeptidyl peptidase-4 (DPP-4) inhibitors such as vildagliptin or sitagliptin; SGLT (sodium-dependent glucose transporter 1) inhibitors; or FBPase (fructose 1,6-bis-phosphatase) inhibitors.

Pharmaceutical compositions comprising the insulin prodrug analogs disclosed herein can be formulated and administered to patients using standard pharmaceutically acceptable carriers and routes of administration known to those skilled in the art. Accordingly, the present disclosure also encompasses pharmaceutical compositions comprising one or more of the insulin prodrug analogs disclosed herein, or a pharmaceutically acceptable salt thereof, in combination with a pharmaceutically acceptable carrier. In one embodiment the pharmaceutical composition comprises a 1 mg/ml concentration of the insulin prodrug analog at pH of about 4.0 to about 7.0 in a phosphate buffer system. The pharmaceutical compositions may comprise the insulin prodrug analog as the sole pharmaceutically active component, or the insulin prodrug analog can be combined with one or more additional active agents. In accordance with one embodiment a pharmaceutical composition is provided comprising one of the insulin prodrug analogs disclosed herein, preferably sterile and preferably at a purity level of at least 90%, 91%, 92%, 93%, 94%, 95%, 96%, 97%, 98% or 99%, and a pharmaceutically acceptable diluent, carrier or excipient. Such compositions may contain an insulin prodrug analog wherein the resulting active peptide is present at a concentration of at least 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml or higher. In one embodiment the pharmaceutical compositions comprise aqueous solutions that are sterilized and optionally stored within various containers. The compounds of the present invention can be used in accordance with one embodiment to prepare pre-formulated solutions ready for injection. In other embodiments the pharmaceutical compositions comprise a lyophilized powder. The pharmaceutical compositions can be further packaged as part of a kit that includes a disposable device for administering the composition to a patient. The containers or kits may be labeled for storage at ambient room temperature or at refrigerated temperature.

All therapeutic methods, pharmaceutical compositions, kits and other similar embodiments described herein contemplate that insulin prodrug analogs include all pharmaceutically acceptable salts thereof.

In one embodiment the kit is provided with a device for administering the insulin prodrug analog composition to a patient. The kit may further include a variety of containers, e.g., vials, tubes, bottles, and the like. Preferably, the kits will also include instructions for use. In accordance with one embodiment the device of the kit is an aerosol dispensing device, wherein the composition is prepackaged within the aerosol device. In another embodiment the kit comprises a syringe and a needle, and in one embodiment the insulin analog composition is prepackaged within the syringe.

The compounds of this invention may be prepared by standard synthetic methods, recombinant DNA techniques, or any other methods of preparing peptides and fusion proteins. Although certain non-natural amino acids cannot be expressed by standard recombinant DNA techniques, techniques for their preparation are known in the art. Compounds of this invention that encompass non-peptide portions may be synthesized by standard organic chemistry reactions, in addition to standard peptide chemistry reactions when applicable.

Example 1

Synthesis of Insulin A & B Chains

Insulin A & B chains were synthesized on 4-methylbenzhyryl amine (MBHA) resin or 4-Hydroxymethyl-phenylacetamidomethyl (PAM) resin using Boc chemistry. The peptides were cleaved from the resin using HF/p-cresol 95:5 for 1 hour at 0° C. Following HF removal and ether precipitation, peptides were dissolved into 50% aqueous acetic acid and lyophilized. Alternatively, peptides were synthesized using Fmoc chemistry. The peptides were cleaved from the resin using Trifluoroacetic acid (TFA)/Triisopropylsilane (TIS)/$H_2O$ (95:2.5:2.5), for 2 hour at room temperature. The peptide was precipitated through the addition of an excessive amount of diethyl ether and the pellet solubilized in aqueous acidic buffer. The quality of peptides were monitored by RP-HPLC and confirmed by Mass Spectrometry (ESI or MALDI).

Insulin A chains were synthesized with a single free cysteine at amino acid 7 and all other cysteines protected as acetamidomethyl A-$(SH)^7(Acm)^{6,11,20}$ Insulin B chains were synthesized with a single free cysteine at position 7 and the other cysteine protected as acetamidomethyl B-$(SH)^7(Acm)^{19}$. The crude peptides were purified by conventional RP-HPLC.

The synthesized A and B chains were linked to one another through their native disulfide bond linkage in accordance with the general procedure outlined in FIG. 1. The respective B chain was activated to the $Cys^7$-Npys derivative through dissolution in DMF or DMSO and reacted with 2,2'-Dithiobis (5-nitropyridine) (Npys) at a 1:1 molar ratio, at room temperature. The activation was monitored by RP-HPLC and the product was confirmed by ESI-MS.

Figure 2:
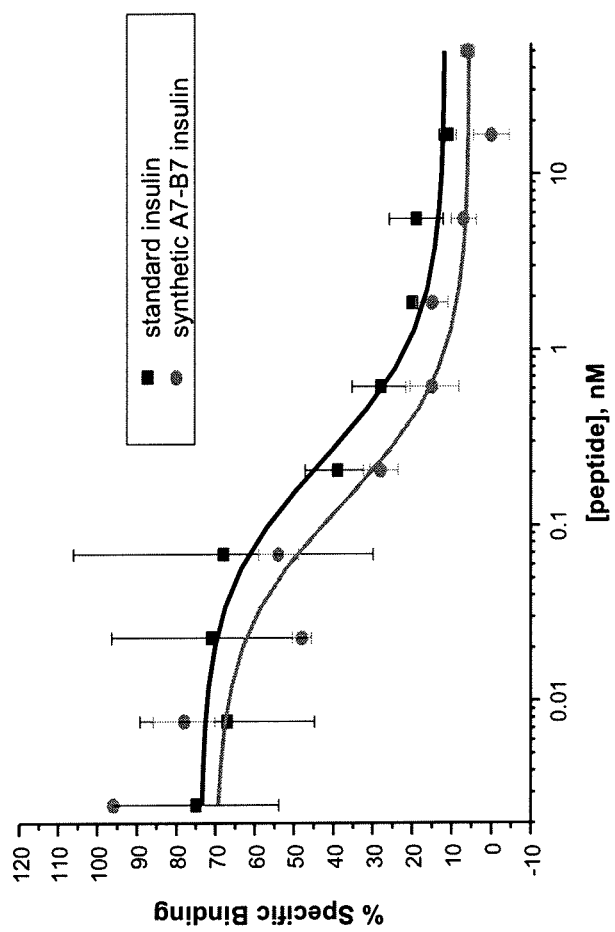
FIG. 2 is a graph comparing insulin receptor specific binding of synthetic human insulin relative to purified native insulin. As indicated by the data presented in the graph, the two molecules have similar binding activities.

The first B7-A7 disulfide bond was formed by dissolution of the respective A-$(SH)^7(Acm)^{6,11,20}$ and B-$(Npys)^7$ $(Acm)^{19}$ at 1:1 molar ratio to a total peptide concentration of 10 mg/ml. When the chain combination reaction was complete the mixture was diluted to a concentration of 50% aqueous acetic acid. The last two disulfide bonds were formed simultaneously through the addition of iodine. A 40 fold molar excess of iodine was added to the solution and the mixture was stirred at room temperature for an additional hour. The reaction was terminated by the addition of an aqueous ascorbic acid solution. The mixture was purified by RP-HPLC and the final compound was confirmed by MALDI-MS. As shown in FIG. 2 and the data in Table 1, the synthetic insulin prepared in accordance with this procedure compares well with purified insulin for insulin receptor binding.

Insulin peptides comprising a modified amino acid (such as 4-amino phenylalanine at position A19) can also be synthesized in vivo using a system that allows for incorporation of non-coded amino acids into proteins, including for example, the system taught in U.S. Pat. Nos. 7,045,337 and 7,083,970.

TABLE 1

Activity of synthesized insulin relative to native insulin

|  | Insulin Standard | | A7-B7 Insulin | |
|---|---|---|---|---|
|  | AVER. | STDEV | AVER. | STDEV |
| $IC_{50}$(nM) | 0.24 | 0.07 | 0.13 | 0.08 |
| % of Insulin Activity | 100 | | 176.9 | |

Example 2

Pegylation of Amine Groups (N-Terminus and Lysine) by Reductive Alkylation a. Synthesis Insulin (or an insulin analog), mPEG20k-Aldyhyde, and $NaBH_3CN$, in a molar ratio of 1:2:30, were dissolved in acetic acid buffer at a pH of 4.1-4.4. The reaction solution was composed of 0.1 N NaCl, 0.2 N acetic acid and 0.1 N $Na_2CO_3$. The insulin peptide concentration was approximately 0.5 mg/ml. The reaction occurs over six hours at room temperature. The degree of reaction was monitored by RP-HPLC and the yield of the reaction was approximately 50%.

b. Purification

The reaction mixture was diluted 2-5 fold with 0.1% TFA and applied to a preparative RP-HPLC column. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was eluted at approximately 35% buffer B. The desired compounds were verified by MALDI-TOF, following chemical modification through sulftolysis or trypsin degradation.

Pegylation of Amine Groups (N-Terminus and Lysine) by N-Hydroxysuccinimide Acylation.

a. Synthesis

Insulin (or an insulin analog) along with mPEG20k-NHS were dissolved in 0.1 N Bicine buffer (pH 8.0) at a molar ratio of 1:1. The insulin peptide concentration was approximately 0.5 mg/ml. Reaction progress was monitored by HPLC. The yield of the reaction is approximately 90% after 2 hours at room temperature.

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin or analogues was collected at approximately 35% B. The desired compounds were verified by MAIDI-TOF, following chemical modification through sulftolysis or trypsin degradation.

Reductive Aminated Pegylation of Acetyl Group on the Aromatic Ring of the Phenylalanine a. Synthesis Insulin (or an insulin analogue), mPEG20k-Hydrazide, and $NaBH_3CN$ in a molar ratio of 1:2:20 were dissolved in acetic acid buffer (pH of 4.1 to 4.4). The reaction solution was composed of 0.1 N NaCl, 0.2 N acetic acid and 0.1 N $Na_2CO_3$. Insulin or insulin analogue concentration was approximately 0.5 mg/ml. at room temperature for 24 h. The reaction process was monitored by HPLC. The conversion of the reaction was approximately 50%. (calculated by HPLC)

b. Purification

The reaction mixture was diluted 2-5 fold and loaded to RP-HPLC. HPLC condition: C4 column; flow rate 10 ml/min; A buffer 10% ACN and 0.1% TFA in water; B buffer 0.1% TFA in ACN; A linear gradient B % from 0-40% (0-80 min); PEG-insulin, or the PEG-insulin analogue was collected at approximately 35% B. The desired compounds were verified by MAIDI-TOF, following chemical modification through sulftolysis or trypsin degradation.

Example 3

Insulin Receptor Binding Assay

The affinity of each peptide for the insulin or IGF-1 receptor was measured in a competition binding assay utilizing scintillation proximity technology. Serial 3-fold dilutions of the peptides were made in Tris-Cl buffer (0.05 M Tris-HCl, pH 7.5, 0.15 M NaCl, 0.1% w/v bovine serum albumin) and mixed in 96 well plates (Corning Inc., Acton, Mass.) with 0.05 nM (3-[125I]-iodotyrosyl) A TyrA14 insulin or (3-[125I]-iodotyrosyl) IGF-1 (Amersham Biosciences, Piscataway, N.J.). An aliquot of 1-6 micrograms of plasma membrane fragments prepared from cells over-expressing the human insulin or IGF-1 receptors were present in each well and 0.25 mg/well polyethylene imine-treated wheat germ agglutinin type A scintillation proximity assay beads (Amersham Biosciences, Piscataway, N.J.) were added. After five minutes of shaking at 800 rpm the plate was incubated for 12 h at room temperature and radioactivity was measured with MicroBeta1450 liquid scintillation counter (Perkin-Elmer, Wellesley, Mass.). Non-specifically bound (NSB) radioactivity was measured in the wells with a four-fold concentration excess of "cold" native ligand than the highest concentration in test samples. Total bound radioactivity was detected in the wells with no competitor. Percent specific binding was calculated as following: % Specific Binding=(Bound-NSB/Total bound-NSB)×100. IC50 values were determined by using Origin software (OriginLab, Northampton, Mass.).

Example 4

Insulin Receptor Phosphorylation Assay

To measure receptor phosphorylation of insulin or insulin analog, receptor transfected HEK293 cells were plated in 96 well tissue culture plates (Costar #3596, Cambridge, Mass.) and cultured in Dulbecco's modified Eagle medium (DMEM) supplemented with 100 IU/ml penicillin, 100 µg/ml streptomycin, 10 mM HEPES and 0.25% bovine growth serum (HyClone SH30541, Logan, Utah) for 16-20 hrs at 37° C., 5% $CO_2$ and 90% humidity. Serial dilutions of insulin or insulin analogs were prepared in DMEM supplemented with 0.5% bovine serum albumin (Roche Applied Science #100350, Indianapolis, Ind.) and added to the wells with adhered cells. After 15 min incubation at 37° C. in humidified atmosphere with 5% $CO_2$ the cells were fixed with 5% paraformaldehyde for 20 min at room temperature, washed twice with phosphate buffered saline pH 7.4 and blocked with 2% bovine serum albumin in PBS for 1 hr. The plate was then washed three times and filled with horseradish peroxidase-conjugated antibody against phosphotyrosine (Upstate biotechnology #16-105, Temecula, Calif.) reconstituted in PBS with 2% bovine serum albumin per manufacturer's recommendation. After 3 hrs incubation at room temperature the plate was washed 4 times and 0.1 ml of TMB single solution substrate (Invitrogen, #00-2023, Carlsbad, Calif.) was added to each well. Color development was stopped 5 min later by adding 0.05 ml 1 N HCl. Absorbance at 450 nm was measured on Titertek Multiscan MCC340 (ThermoFisher, Pittsburgh, Pa.). Absorbance vs. peptide concentration dose response curves were plotted and $EC_{50}$ values were determined by using Origin software (OriginLab, Northampton, Mass.).

Example 5

Determination of Rate of Model Dipeptide Cleavage (in PBS)

A specific hexapeptide (HSRGTF-NH$_2$; SEQ ID NO: 59) was used as a model peptide upon which the rate of cleavage of dipeptide N-terminal extensions could be studied. The dipeptide-extended model peptides were prepared Boc-protected sarcosine and lysine were successively added to the model peptide-bound resin to produce peptide A (Lys-Sar-HSRGTF-NH$_2$; SEQ ID NO: 60). Peptide A was cleaved by HF and purified by preparative HPLC.

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half lives for cleavage of the various prodrugs were calculated by using the formula $t_{1/2}=0.693/k$. The half life of the Lys-Sar extension to this model peptide HSRGTF-NH$_2$ (SEQ ID NO: 59) was determined to be 14.0 h.

Example 6

Rate of Dipeptide Cleavage Half Time in Plasma as Determined with an all d-Isoform Model Peptide An additional model hexapeptide (dHdTdRGdTdF-NH$_2$ SEQ ID NO: 63) was used to determine the rate of dipeptide cleavage in plasma. The d-isomer of each amino acid was used to prevent enzymatic cleavage of the model peptide, with the exception of the prodrug extension. This model d-isomer hexapeptide was synthesized in an analogous fashion to the 1-isomer. The sarcosine and lysine were successively added to the N-terminus as reported previously for peptide A to prepare peptide B (dLys-dSar-dHdTdRGdTdF-NH$_2$ SEQ ID NO: 64)

The rate of cleavage was determined for the respective propeptides. The concentrations of the propeptides and the model parent peptide were determined by their respective peak areas. The first order dissociation rate constants of the prodrugs were determined by plotting the logarithm of the concentration of the prodrug at various time intervals. The slope of this plot provides the rate constant 'k'. The half life of the Lys-Sar extension to this model peptide dHdT-dRGdTdF-NH$_2$ (SEQ ID NO: 63) was determined to be 18.6 h.

Example 7

The rate of cleavage for additional dipeptides linked to the model hexapeptide (HSRGTF-NH$_2$; SEQ ID NO: 59) were determined using the procedures described in Example 5. The results generated in these experiments are presented in Tables 2 and 3.

TABLE 2

Cleavage of the Dipeptides O-U that are linked to the side chain of an N-terminal para-amino-Phe from the Model Hexapeptide (HSRGTF-NH$_2$; SEQ ID NO: 59) in PBS

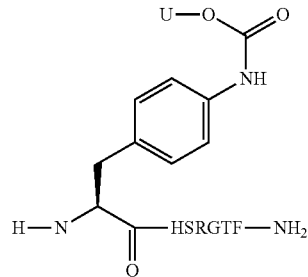

| Compounds | U (amino acid) | O (amino acid) | $t_{1/2}$ |
|---|---|---|---|
| 1 | F | P | 58 h |
| 2 | Hydroxyl-F | P | 327 h |
| 3 | d-F | P | 20 h |
| 4 | d-F | d-P | 39 h |
| 5 | G | P | 72 h |
| 6 | Hydroxyl-G | P | 603 h |
| 7 | L | P | 62 h |
| 8 | tert-L | P | 200 h |
| 9 | S | P | 34 h |
| 10 | P | P | 97 h |
| 11 | K | P | 33 h |
| 12 | dK | P | 11 h |
| 13 | E | P | 85 h |
| 14 | Sar | P | ≈1000 h |
| 15 | Aib | P | 69 min |
| 16 | Hydroxyl-Aib | P | 33 h |
| 17 | cyclohexane | P | 6 min |
| 18 | G | G | No cleavage |

TABLE 2-continued

Cleavage of the Dipeptides O-U that are linked to the side chain of an N-terminal para-amino-Phe from the Model Hexapeptide (HSRGTF-NH₂; SEQ ID NO: 59) in PBS

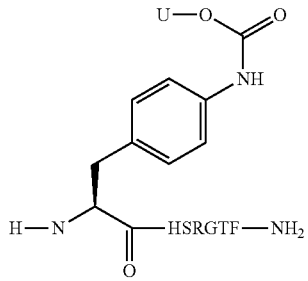

| Compounds | U (amino acid) | O (amino acid) | $t_{1/2}$ |
|---|---|---|---|
| 19 | Hydroxyl-G | G | No cleavage |
| 20 | S | N-Methyl-Gly | 4.3 h |
| 21 | K | N-Methyl-Gly | 5.2 h |
| 22 | Aib | N-Methyl-Gly | 7.1 min |
| 23 | Hydroxyl-Aib | N-Methyl-Gly | 1.0 h |

TABLE 3

Cleavage of the Dipeptides U-O linked to histidine (or histidine derivative) at position 1 (X) from the Model Hexapeptide (XSRGTF-NH₂; SEQ ID NO: 59) in PBS
NH₂-U-O-XSRGTF-NH₂

| Cmp | U (amino acid) | O (amino acid) | X (amino acid) | $t_{1/2}$ |
|---|---|---|---|---|
| 1 | F | P | H | No cleavage |
| 2 | Hydroxyl-F | P | H | No cleavage |
| 3 | G | P | H | No cleavage |
| 4 | Hydroxyl-G | P | H | No cleavage |
| 5 | A | P | H | No cleavage |
| 6 | C | P | H | No cleavage |
| 7 | S | P | H | No cleavage |
| 8 | P | P | H | No cleavage |
| 9 | K | P | H | No cleavage |
| 10 | E | P | H | No cleavage |
| 11 | Dehydro V | P | H | No cleavage |
| 12 | P | d-P | H | No cleavage |
| 13 | d-P | P | H | No cleavage |
| 14 | Aib | P | H | 32 h |
| 15 | Aib | d-P | H | 20 h |
| 16 | Aib | P | d-H | 16 h |
| 17 | Cyclohexyl- | P | H | 5 h |
| 18 | Cyclopropyl- | P | H | 10 h |
| 19 | N—Me-Aib | P | H | >500 h |
| 20 | α,α-diethyl-Gly | P | H | 46 h |
| 21 | Hydroxyl-Aib | P | H | 61 |
| 22 | Aib | P | A | 58 |
| 23 | Aib | P | N-Methyl-His | 30 h |
| 24 | Aib | N-Methyl-Gly | H | 49 min |
| 25 | Aib | N-Hexyl-Gly | H | 10 min |
| 26 | Aib | Azetidine-2-carboxylic acid | H | >500 h |
| 27 | G | N-Methyl-Gly | H | 104 h |
| 28 | Hydroxyl-G | N-Methyl-Gly | H | 149 h |
| 29 | G | N-Hexyl-Gly | H | 70 h |
| 30 | dK | N-Methyl-Gly | H | 27 h |
| 31 | dK | N-Methyl-Ala | H | 14 h |
| 32 | dK | N-Methyl-Phe | H | 57 h |
| 33 | K | N-Methyl-Gly | H | 14 h |
| 34 | F | N-Methyl-Gly | H | 29 h |
| 35 | S | N-Methyl-Gly | H | 17 h |
| 36 | P | N-Methyl-Gly | H | 181 h |

In addition various prodrug derivatives of IGF1YL insulin analogs have been prepared wherein a dipeptide element has been linked via an amide bond through the 4-amino-phenylalanine residue present at A19 of the IGF1YL. The in vitro analysis of these compounds using the procedures of Example 5 reveals that the activity of these compounds increases with time incubated in either a PBS buffer or in 20% plasma. See FIGS. 8-11. In addition, the in vitro activity of the IGF analog prodrug MIU30: A1(aF19-dLys(Ac),Sar) (dipeptide linked through and amide bond to the A19 4-aminoPhe) was measured for insulin receptor binding relative to native insulin over time (1 hour, 3 hours, 6 hours, 9 hours and 10.5 hours) incubated in 20% plasma. Table 3A compares the relative insulin receptor binding of over time incubated in 20% plasma/PBS at 37° C. As indicated by the data presented in an in vitro binding assay, see Table 3A and an in vitro phosphorylation assay, see Table 3B, increased activity is recovered from the A19 IGF prodrug derivative sample over time, as the prodrug form is converted to the active IGF1YL peptide.

TABLE 3A

| Time (hr) | % Activity of Insulin |
|---|---|
| 0 | 34.44% |
| 9 | 100.09% |
| 95 | 115.42% |

TABLE 3B

| Time (hr) | % Activity of Insulin |
|---|---|
| 1 | 23.0 |
| 3 | 26.8 |
| 6 | 32.5 |
| 9 | 41.1 |
| 10.5 | 43.2 |

Figure 20A:
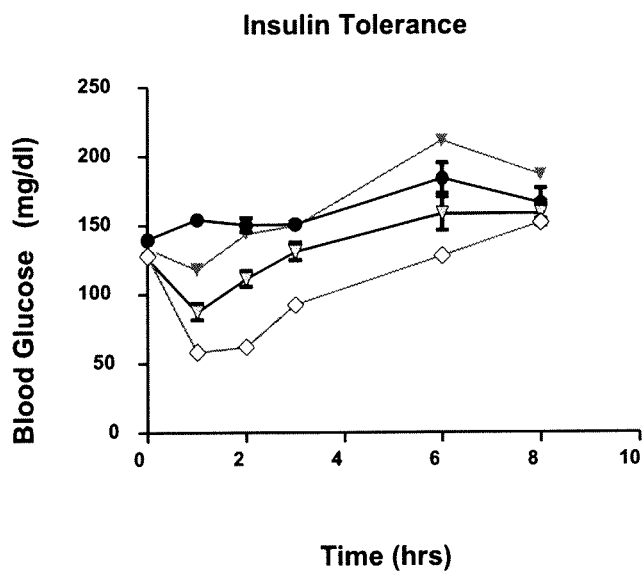
FIGS. 20A & 20B represents the results obtained from a comparative insulin tolerance test for insulin prodrug analog MIU-30a: $B^1$(Y16,L17,Y25)29a: $A^1$(dLys(Ac),Sar-aF19)
Figure 20B:
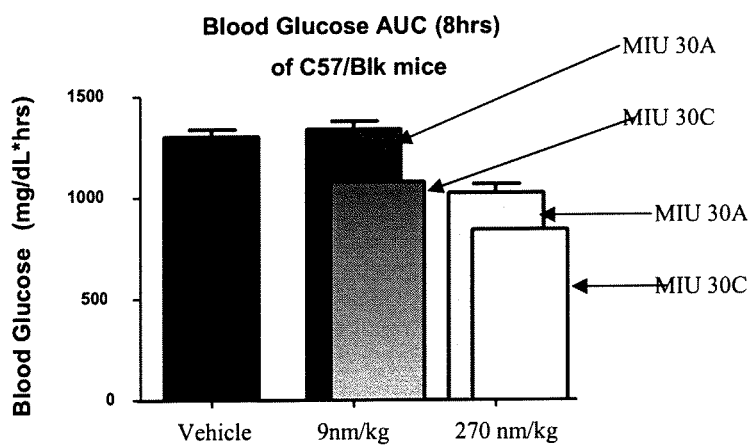

In vivo glucose tolerance tests using C57/Blk mice administered insulin analog MIU-30a: B$^1$(Y16,L17,Y25)29a: A$^1$(dLys(Ac),Sar-aF19) (dipeptide linked through and amide bond to the A19 4-aminoPhe), MIU 30 dissolved in PBS (pH 7.4) with 20% plasma and incubated for 48 hours at 37° C. (generating "MIU-30c"). Samples incubated for 0 hr (MIU 30a) and 48 hr (MIU 30c) were withdrawn and injected to C57 black mice at 90 nmol/kg and 270 nmol/kg to measure glucose lowering (insulin tolerance test). In FIG. 20A the glucose lowering profile of MIU 30a and MIU 30c at various times through 8 hr are shown. The parent compound has low potency, but after incubation in 20% plasma for 48 hours (generating "MIU-30c") potency is increased (See FIG. 20A). In FIG. 20B total blood glucose of MIU 30a and MIU 30c as compared to vehicle is reported as differential area under curve (AUC). At 90 nmol/kg, MIU 30a indicates little change in glucose, while MIU 30c causes a sizable decrease. At 270 nmol/kg, both MIU 30a and MIU 30c demonstrate glucose lowering, but the latter sample possesses significantly more hypoglycemic potency. In summary, the prodrug form of the insulin analog MIU30 shows appreciably lesser glucose lowering potency when injected prior to ex vivo conversion under physiological conditions to the parent insulin analog. These in vivo results are consistent with the in vitro analysis. The half life of the prodrug is estimated to be approximately 20 hours.

Example 8

Identification of an Insulin Analog with Structure Suitable for Prodrug Construction Position 19 of the A chain is known to be an important site for insulin activity. Modification at this site to allow the attachment of a prodrug element is therefore desirable. Specific analogs of insulin at A19 have been synthesized and characterized for their activity at the insulin receptors. Two highly active structural analogs have been identified at A19, wherein comparable structural changes at a second active site aromatic residue (B24) were not successful in identification of similarly full activity insulin analogs.

Tables 4 and 5 illustrate the high structural conservation at position A19 for full activity at the insulin receptor (receptor binding determined using the assay described in Example 3). Table 4 demonstrates that only two insulin analogs with modifications at A19 have receptor binding activities similar to native insulin. For the 4-amino insulin analog, data from three separate experiments is provided. The column labeled "Activity (in test)" compares the percent binding of the insulin analog relative to native insulin for two separate experiments conducted simultaneously. The column labeled "Activity (0.60 nM)" is the relative percent binding of the insulin analog relative to the historical average value obtained for insulin binding using this assay. Under either analysis, two A19 insulin analogs (4-amino phenylalanine and 4-methoxy phenylalanine) demonstrate receptor binding approximately equivalent to native insulin. FIG. 3 represents a graph demonstrating the respective specific binding of native insulin and the A19 insulin analog to the insulin receptor. Table 5 presents data showing that the two A19 insulin analogs (4-amino and 4-methoxy) that demonstrate equivalent binding activities as native insulin also demonstrate equivalent activity at the insulin receptor (receptor activity determined using the assay described in Example 4).

TABLE 4

Insulin Receptor Binding Activity of A19 Insulin Analogs

| | Insulin Receptor | | | |
|---|---|---|---|---|
| Analogue | $IC_{50}$ | STDev | % native ligand Activity (in test) | % native ligand Activity (0.60 nM) |
| 4-OH (native insulin) | 0.64 | 0.15 | 100.0 | 100.0 |
| 4-COCH$_3$ | 31.9 | 9.47 | 0.6 | 1.9 |

TABLE 4-continued

Insulin Receptor Binding Activity of A19 Insulin Analogs

| | Insulin Receptor | | | |
|---|---|---|---|---|
| Analogue | $IC_{50}$ | STDev | % native ligand Activity (in test) | % native ligand Activity (0.60 nM) |
| 4-NH$_2$ | 0.31 | 0.12 | 203.0 | 193.5 |
| | 0.83 | 0.15 | 103.0 | 72.3 |
| | 0.8 | 0.1 | 94.0 | 75.0 |
| 4-NO$_2$ | 215.7 | 108.01 | 0.3 | 1.3 |
| 3,4,5-3F | 123.29 | 31.10 | 0.5 | 0.5 |
| 4-OCH$_3$ | 0.5 | 0.50 | 173.0 | 120.0 |
| 3-OCH$_3$ | 4.74 | 1.09 | 28.0 | 12.7 |
| | 5.16 | 3.88 | 18.0 | 11.6 |
| 4-OH, 3,5-2Br | 1807.17 | 849.72 | 0.0 | 0.0 |
| 4-OH, 3,5-2 NO$_2$ | 2346.2 | 338.93 | 0.0 | 0.0 |

TABLE 5

Insulin Receptor Phosphorylation Activity of A19 Insulin Analogs

| | Insulin Receptor | | |
|---|---|---|---|
| Analogue | $EC_{50}$ | STDev | % native ligand Activity (in test) |
| 4-OH (native insulin) | 1.22 | 0.4 | 100.0 |
| 4-NH$_2$ | 0.31 | 0.14 | 393.5 |
| 4-OCH$_3$ | 0.94 | 0.34 | 129.8 |

Example 9

Insulin Like Growth Factor (IGF) Analog

Figure 4:
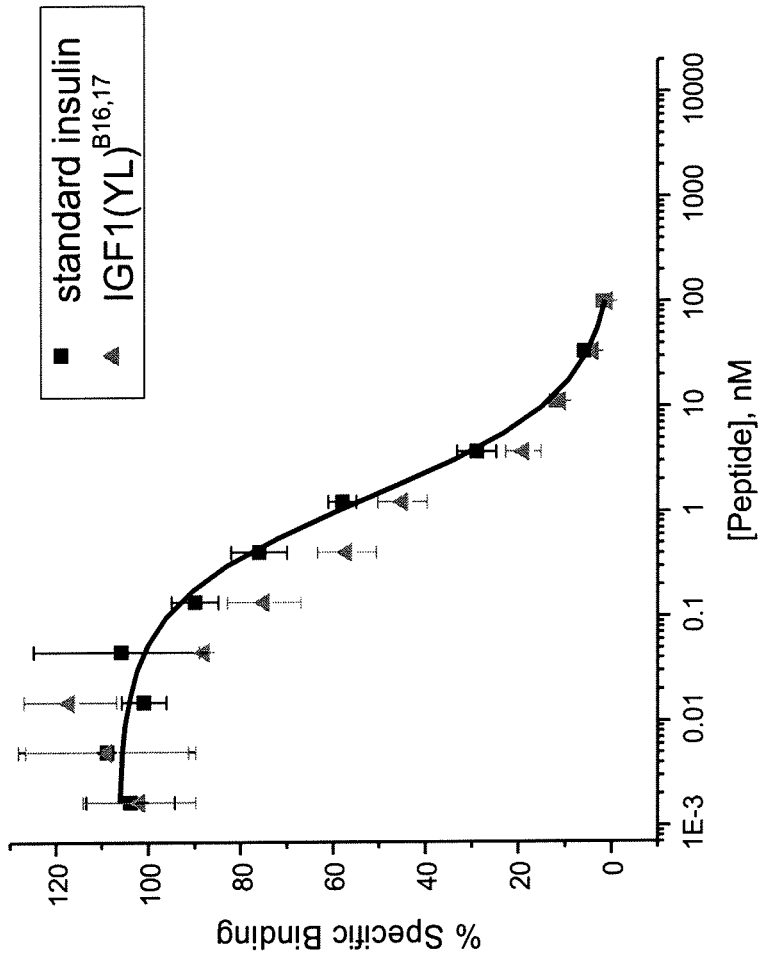
FIG. 4 is a graph comparing relative insulin receptor binding of native insulin and the IGF1(YL)$^{B16B17}$ analog. As indicated by the data presented in the graph, the two molecules have similar binding activities.

Typical purification schemes for isolating the insulin A-chain use an NH$_4$HCO$_3$ buffer (pH=7.8). Under these conditions the dipeptide prodrug element is rapidly cleaved from the A-chain. To simplify purification of prodrugs to investigate their activities at the insulin receptor, applicants conducted such studies using an IGF analog that demonstrates similar activity at the insulin receptor as native insulin. More particularly, the IGF analog (IGF1 ($Y^{B16}L^{B17}$) comprises the native IGF A and B chain (SEQ ID NO: 61 and SEQ ID NO: 62, respectively), wherein the native glutamine and phenylalanine at positions 15 and 16 of the native IGF B-chain (corresponding to positions 16 and 17 of native insulin B-chain, respectively) have been replaced with tyrosine and leucine residues, respectively. As shown in FIG. 4 and Table 6 below the binding activities of IGF1 ($Y^{B16}L^{B17}$) demonstrate the compound is a highly potent insulin analog.

TABLE 6

| | Insulin Standard | | IGF1($Y^{B16}L^{B17}$) | |
|---|---|---|---|---|
| | AVER. | STDEV | AVER. | STDEV |
| $IC_{50}$(nM) | 1.32 | 0.19 | 0.51 | 0.18 |
| % of Insulin Activity | 100 | | 262 | |

Example 10

IGF Prodrug Derivatives

Based on the activity of the A19 insulin analog (see Example 5), a similar modification was made to the IGF1

Figure 5:
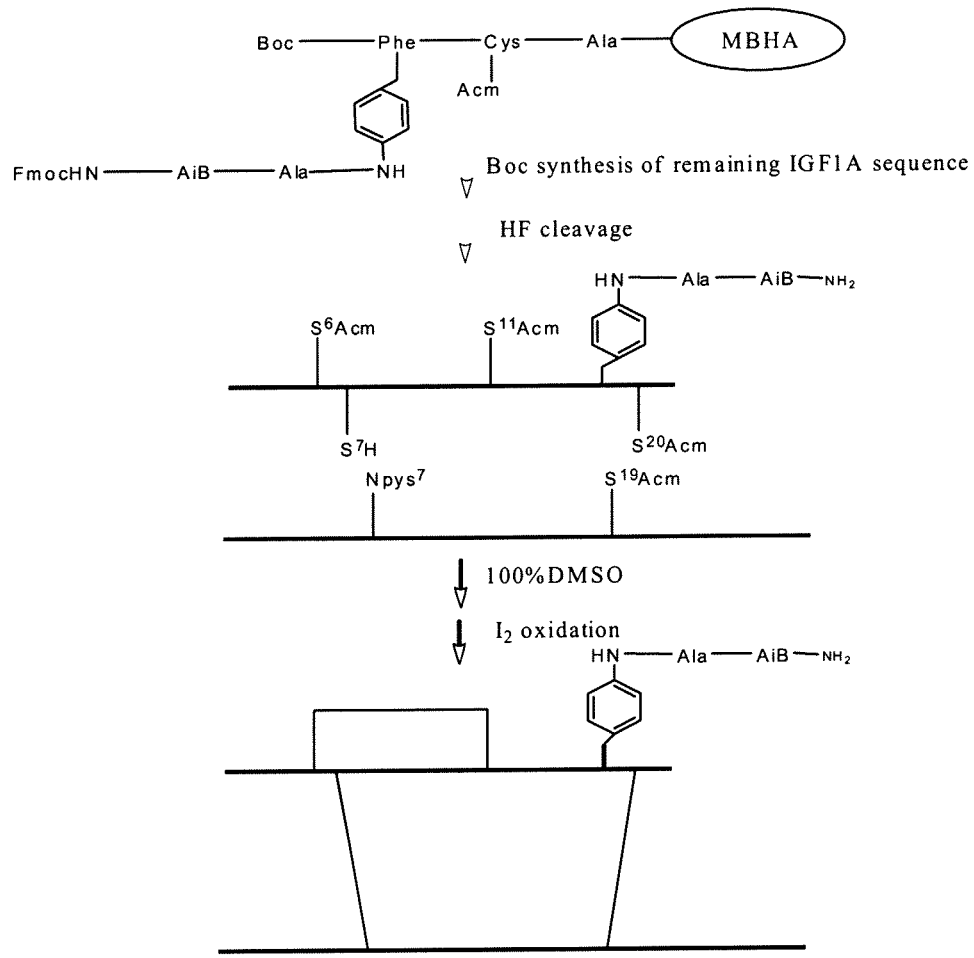
FIG. 5 is a schematic drawing of the synthetic scheme used to prepare the IGF1($Y^{B16}L^{B17}$)(p-$NH_2$—F)$^{419}$ analog.
Figure 6:
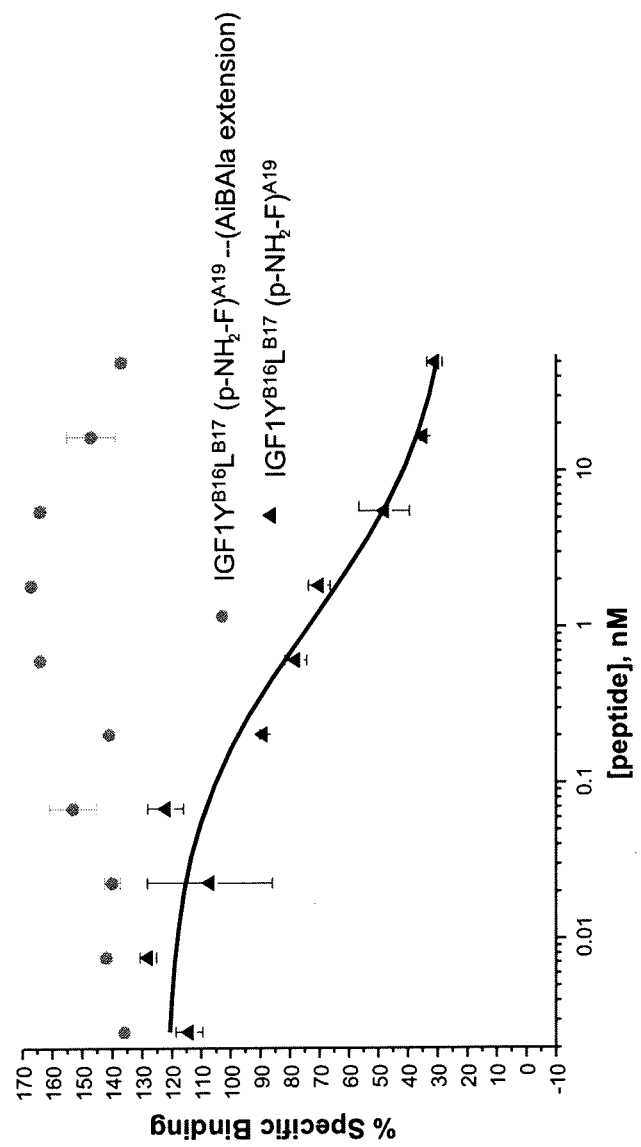
FIG. 6 is a graph comparing relative insulin receptor binding of IGF1($Y^{B16}L^{B17}$)(p-$NH_2$—F)$^{419}$ and the dipeptide extended form of IGF1($Y^{B16}L^{B17}$)(p-$NH_2$—F)$^{419}$, wherein the dipeptide AibAla is bound at position A19 (i.e. IGF1($Y^{B16}L^{B17}$)$^{419}$-AibAla).
Figure 7A:
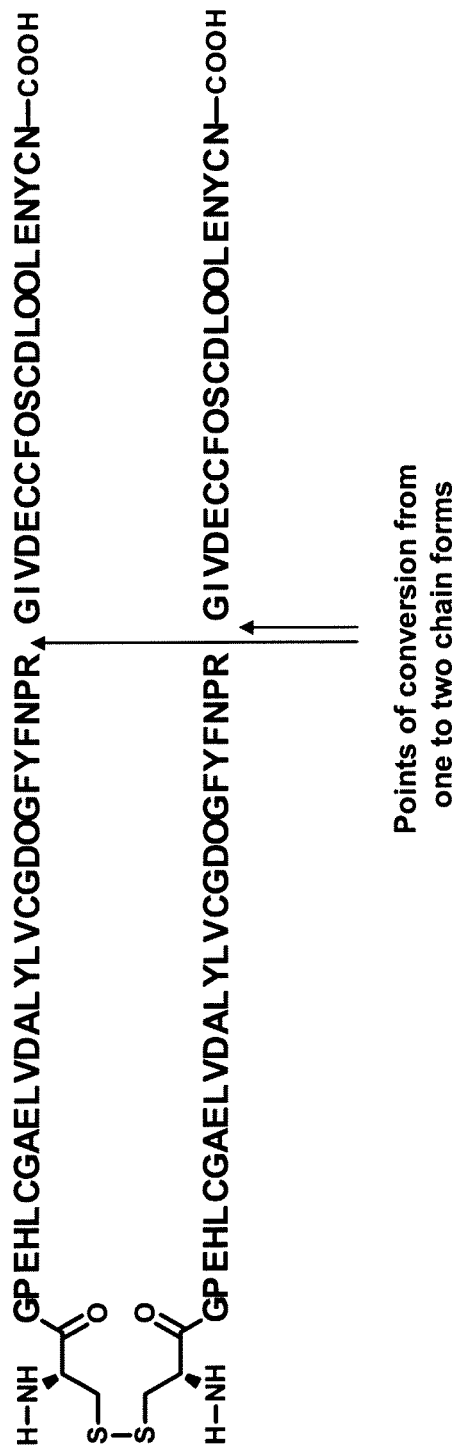

A:B($Y^{B16}L^{B17}$) analog and its ability to bind and stimulate insulin receptor activity was investigated. FIG. 5 provides the general synthetic scheme for preparing IGF1 A:B($Y^{B16}L^{B17}$) wherein the native tyrosine is replace with a 4-amino phenylalanine [IGF1 A:B($Y^{B16}L^{B17}$)(p-NH$_2$—F)$^{419}$amide] as well as the preparation of its dipeptide extended derivative [IGF1 A:B($Y^{B16}L^{B17}$)$^{419}$-AibAla amide], wherein a dipeptide comprising Aib and Ala are linked to the peptide through an amide linkage to the A19 4-amino phenylalanine. As shown in FIG. 6 and Table 7, the IGF analog, IGF1 ($Y^{B16}L^{B17}$) A(p-NH$_2$—F)$^{19}$ specifically binds to the insulin receptor wherein the dipeptide extended derivative of that analog fails to specifically bind the insulin receptor. Note the dipeptide extension lacks the proper structure to allow for spontaneous cleavage of the dipeptide (absence of an N-alkylated amino acid at the second position of the dipeptide) and therefore there is no restoration of insulin receptor binding.

TABLE 7

| | Insulin Standard | | IGF1($Y^{B16}L^{B17}$) (p-NH$_2$—F)$^{419}$amide | | IGF1($Y^{B16}L^{B17}$) (AibAla)$^{419}$amide | |
|---|---|---|---|---|---|---|
| | AVER. | STDEV | AVER. | STDEV. | AVER. | STDEV |
| IC$_{50}$ (nM) | 0.24 | 0.07 | 1.08 | .075 | No Activity | |
| % of Insulin Activity | 100 | | 22 | | | |

A further prodrug derivative of an IGF$^{B16B17}$ derivative peptide was prepared wherein the dipeptide prodrug element (alanine-proline) was linked via an amide bond to the amino terminus of the A chain (IGF1($Y^{B16}L^{B17}$) (AlaPro)$^{A-1,0}$). As shown in Table 8, the IGF1($Y^{B16}L^{B17}$)(AlaPro)$^{A-1,0}$ has substantially reduced affinity for the insulin receptor. Note, based on the data of Table 3, the dipeptide prodrug element lacks the proper structure to allow for spontaneous cleavage of the dipeptide prodrug element, and therefore the detected insulin receptor binding is not the result of cleavage of the prodrug element.

TABLE 8

| | Insulin Standard | | IGF1(YL)$_{4,1,0}^{B16,17}$(AlaPro) | |
|---|---|---|---|---|
| | AVER. | STDEV. | AVER. | STDEV. |
| IC$_{50}$(nM) | 0.72 | 0.09 | 1.93 | .96 |
| % of Insulin Activity | 100 | | 37.12 | |

Example 11

Additional IGF Insulin Analogs

Further modifications of the IGF1 ($Y^{B16}L^{B17}$)(YL)B$^{16}$B$^{17}$ peptide sequence reveal additional IGF insulin analogs that vary in their potency at the insulin and IGF-1 receptor. Binding data is presented in Table 9 for each of these analogs (using the assay of Example 3), wherein the position of the modification is designated based on the corresponding position in the native insulin peptide (DPI=des B26-30). For example, a reference herein to "position B28" absent any further elaboration would mean the corresponding position B27 of the B chain of an insulin analog in which the first amino acid of SEQ ID NO: 2 has been deleted. Thus a generic reference to "B(Y16)" refers to a substitution of a tyrosine residue at position 15 of the B chain of the native IGF-1 sequence. Data regarding the relative receptor binding of insulin and IGF analogs is provided in Table 9, and data regarding IGF analog stimulated phosphorylation (using the assay of Example 4) is provided in Table 10.

TABLE 9

Receptor Binding Affinity of Insulin and IGF Analogues

| | Insulin Receptor | | | | | IGF-1 Receptor | | | | | |
|---|---|---|---|---|---|---|---|---|---|---|---|
| | nM | | | % insulin (in test) | % native insulin activity (0.6 nM) | | | | % IGF-1 (in test) | % native IGF-1 activity (0.55 nM) | |
| Analogue | IC$_{50}$: | STDev | Date | | | IC$_{50}$: | STDev | Date | | | Ratio |
| IGF-1 A:B | 10.41 | 1.65 | Sep. 4, 2007 | 5.8 | 5.8 | | | | | | |
| IGF-1 A:B(E10Y16L17) | 0.66 | 0.36 | May 22, 2007 | 58.7 | 90.9 | 7.85 | 1.98 | Jun. 4, 2007 | 6.8 | 7.0 | 11.9 |
| | 0.51 | 0.18 | May 29, 2007 | 98.8 | 117.6 | 12.19 | 2.17 | Sep. 18, 2007 | 5.0 | 4.5 | |
| IGF-1 A:B(E10 Y16L17)-E31E32B-COOH | 1.22 | 0.30 | Mar. 20, 2008 | 36.5 | 50.0 | 17.50 | 2.25 | Apr. 4, 2007 | 3.0 | 3.1 | 14.3 |
| IGF-1 A:B(D10Y16L17) DPI A-COOH | 0.26 | 0.02 | Nov. 9, 2007 | 301.0 | 231.0 | 6.79 | 1.50 | Apr. 4, 2008 | 7.7 | 8.1 | |
| | 0.2 | 0.02 | Dec. 4, 2007 | 380.1 | 300.0 | | | | | | |
| | 0.42 | 0.06 | Jun. 5, 2008 | 174.1 | 144.1 | | | | | | |
| IGF-1 A:B (E10Y16L17) DPI | 0.38 | 0.08 | Aug. 10, 2007 | 51.1 | 157.9 | 22.89 | 5.26 | Sep. 18, 2007 | 3.3 | 2.4 | 60.2 |
| IGF-1 A:B (H5D10Y16L17) DPI | 0.16 | 0.07 | Nov. 9, 2007 | 479.0 | | 4.66 | 0.77 | Apr. 4, 2008 | 11.2 | 11.8 | 29.1 |
| IGF-1 A:B (S=O)DPI | 0.25 | 0.04 | Nov. 9, 2007 | 316.0 | | | | | | | |
| IGF-1 A (H8 A9 N21):B (H5D10Y16L17) DPI A-COOH | 0.05 | 0.01 | Dec. 4, 2007 | 1576.7 | | 4.03 | 0.50 | Apr. 4, 2008 | 12.9 | 13.6 | 80.6 |
| | 0.09 | 0.02 | Dec. 14, 2007 | 1667.0 | | | | | | | |
| IGF-1 A (H8 A9 N21):B (H5D10Y16L17 A22) DPI A-COOH | 0.12 | 0.02 | Dec. 14, 2007 | 1171.4 | | 22.83 | 3.53 | Apr. 4, 2008 | 2.3 | 2.4 | 190.3 |

TABLE 9-continued

Receptor Binding Affinity of Insulin and IGF Analogues

| | Insulin Receptor | | | | | IGF-1 Receptor | | | | | |
|---|---|---|---|---|---|---|---|---|---|---|---|
| | nM | | | % insulin (in test) | % native insulin activity (0.6 nM) | | | | % IGF-1 (in test) | % native IGF-1 activity (0.55 nM) | |
| Analogue | $IC_{50}$: | STDev | Date | | | $IC_{50}$: | STDev | Date | | | Ratio |
| IGF-1 A (H8 A9 N21):B (H5D10Y16L17A22) (S=O) DPI A-COOH | 0.36 | 0.10 | Dec. 14, 2007 | 400.7 | | | | | | | |
| IGF-1 A:IGF-1 B(1-8)-In (9-17)-IGF-1 B (18-30) | 1.59 | 0.62 | May 22, 2007 | 19.1 | 37.7 | 131.30 | 58.05 | Jun. 4, 2007 | 0.3 | 0.4 | 82.6 |
| IGF-1 A:In (1-17)-IGF-1 B (18-30) | 2.77 | 1.19 | May 22, 2007 | 14.0 | 21.7 | 62.50 | 30.28 | Jun. 4, 2007 | 0.9 | 0.9 | 22.6 |
| | 2.67 | 0.67 | May 18, 2007 | 11.3 | 22.5 | | | | | | |
| | 2.48 | 1.35 | May 29, 2007 | 20.1 | 24.2 | | | | | | |
| IGF-1 A:In B(1-5)-IGF-1 B(YL) (6-30) | 0.31 | 0.19 | Aug. 10, 2007 | 62.4 | 193.5 | 27.54 | 6.57 | Sep. 25, 2007 | 3.6 | 2 | 88.8 |
| IGF-2 native | | | | | | 13.33 | 1.85 | Sep. 25, 2007 | 7.5 | 4.5 | |
| IGF-2 AB | | | | | | | | | | | |
| IGF-2 AB(YL) | 6.81 | 3.81 | Oct. 10, 2007 | 8.4 | 8.8 | | | | | | |
| In A:IGF-1 B(YL) | 82.62 | 31.75 | Sep. 4, 2007 | 0.9 | 0.7 | | | | | | |
| | 107.24 | 65.38 | Sep. 4, 2007 | 0.7 | 0.6 | | | | | | |
| In A-IGF-2 D:In B-IGF-2 C | 0.53 | 0.11 | Sep. 4, 2007 | 141.0 | 113.0 | 1.59 | 0.34 | Sep. 18, 2007 | 47.6 | 34.6 | |
| | 0.37 | 0.05 | Oct. 13, 2007 | 179.1 | 162.2 | 14.69 | 3.02 | Sep. 25, 2007 | 6.8 | 3.7 | 39.7 |

**All C terminals are amides (DPI) unless specified otherwise

TABLE 10

Total Phosphorylation by IGF-1 & IGF-2 Analogues

| | Insulin Receptor | | | | IGF-1 Receptor | | | | Selective |
|---|---|---|---|---|---|---|---|---|---|
| Analogue | EC50: | STDev | Date | % Insulin | EC50: | STDev | Date | % IGF | Ratio |
| Insulin | 1.26 | 0.098 | Dec. 14, 2007 | | 114.88 | 46.66 | Jan. 23, 2008 | | 90.89 |
| | 1.43 | 0.72 | Apr. 1, 2008 | | 86.02 | 29.35 | May 20, 2008 | | |
| | 1.12 | 0.11 | Mar. 31, 2008 | | | | | | |
| | 1.53 | 0.13 | Apr. 11, 2008 | | | | | | |
| | 2.70 | 0.71 | Apr. 16, 2008 | | | | | | |
| | 1.22 | 0.40 | May 20, 2008 | | | | | | |
| IGF-1 | 54.39 | 21.102 | Dec. 14, 2007 | 2.3 | 0.87 | 0.16 | Jan. 23, 2008 | 100 | 0.02 |
| | | | | | 0.49 | 0.13 | May 20, 2008 | | |
| | | | | | 0.97 | 0.48 | Jul. 23, 2008 | | |
| IGF-1 AB | | | | | | | | | |
| IGF-1 A:B(E10Y16L17) | 2.57 | 0.59 | Mar. 31, 2008 | 49.2 | 7.42 | 5.59 | Jul. 23, 2008 | 13 | |
| IGF-1 A:B(E10 Y16L17)-E31E32B-COOH | 7.00 | 2.82 | Mar. 31, 2008 | 18.1 | | | | | |
| | 8.52 | 4.34 | Apr. 16, 2008 | 31.7 | | | | | |
| IGF-1 AB(D10Y16L17) DPI A-COOH | 0.08 | 0.006 | Dec. 14, 2007 | 1575 | 0.78 | 0.17 | Jan. 23, 2008 | 111.538 | 9.75 |
| | 4.38 | 2.98 | Apr. 16, 2008 | ?? | | | | | |
| IGF-1 AB (E10Y16L17) DPI | | | | | | | | | |
| IGF-1 AB (H5D10Y16L17) DPI | | | | | 12.22 | 5.46 | Jan. 23, 2008 | 7.1 | |
| IGF-1 AB (H5D10Y16L17) (S=O)DPI | | | | | | | | | |
| IGF-1 A (H8 A9 N21) B (H5D10Y16L17) DPI A-COOH | 0.15 | 0.054 | Dec. 14, 2007 | 840 | 0.43 | 0.44 | Jan. 23, 2008 | 181.395 | 2.81 |
| | 0.25 | 0.2 | Apr. 16, 2008 | 1080 | | | | | |
| IGF-1 A (H8 A9 N21) B(H5D10Y16L17A22) DPI A-COOH | 0.35 | 0.064 | Dec. 14, 2007 | 360 | 11.26 | 2.55 | Jan. 23, 2008 | 7.7 | 32.54 |
| | 0.44 | 0.17 | Apr. 16, 2008 | 614 | | | | | |
| IGF-1 A (H8 A9 N21) B(H5D10Y16L17A22) (S=O) DPI A-COOH | 0.72 | 0.098 | Dec. 14, 2007 | | | | | | |

*All C-terminals are amides unless specified otherwise.

Example 12

Dipeptide Cleavage from Prodrug forms of IGFB16B17 Derivative Peptides

The cleavage of an (pNH2-Phe) amide linked dipeptide AibPro from various IGF-1 peptides was measured to determine the impact of the peptide sequence or heteroduplex on the dipeptide cleavage. Results for the tested peptides is shown in Table 11 and the data reveals that the IGF1-A chain alone represents a good model for the study of prodrug half life for IGF1 B:A $(YL)^{B16,17}$ peptides.

TABLE 11

| Parent Peptide | Half Life (hr) |
| --- | --- |
| IGF1A(Ala)[6, 11, 20](pNH$_2$-Phe)[A19] | 2.2 |
| IGF1A(Acm)[6, 11, 20](pNH$_2$-Phe)[A19] | 1.8 |
| IGF1 B:A(S-S)[A7, B7](Acm)[A6, 11, 20, B19](pNH$_2$-Phe)[A19] | 1.8 |
| IGF1 B:A(pNH$_2$-Phe)[A19] | 1.6 |

Comparison of prodrug derivatives of the IGF A-chain relative to the disulfide bound A chain and B chain construct (IGF1 A:B($Y^{B16}L^{B17}$)) revealed the two compounds had similar half lives for the prodrug form. Accordingly, the IGF1A chain alone was determined to be a good model for the study of pro-drug half life on IGF1 B:A ($Y^{B16}L^{B17}$). Note the AibAla derivative does not cleave and thus is not a prodrug, but serves to show the modification can inactivate the insulin analog IGF1 A:B($Y^{B16}L^{B17}$)(p-NH$_2$—F)[A19]amide. For simplicity, prodrug half lives were determined using only the IGF1 A chain in the absence of the B chain. The half lives of each propeptide was determined as described in Example 5. The data is presented in Table 12:

TABLE 12

Dipeptide half life on IGF1 dipeptide extended (p-NH$_2$—F)[A19] amide

| Dipeptide | | Half Life (hr) |
| --- | --- | --- |
| Aib | Pro | 2.2 |
| AibOH | Pro | 165.0 |
| Aib | dPro | 1.9 |
| AibOH | Sar | 2.3 |
| dK(acetyl) | Sar | 16.3 |
| K | Sar | 21.8 |
| K(acetyl) | N-methyl Ala | 23.6 |
| dK(acetyl) | N-methyl Ala | 35.3 |

The data shows that by altering the substituents on the dipeptide prodrug element that the half life of prodrug can be varied from 2 hrs to >100 hrs.

Additional prodrug derivative peptides were prepared using an IGF1-A(pNH2-F)[19] base peptide and altering the amino acid composition of the dipeptide prodrug element linked through the 4-amino phenylalanine at position A19. Dipeptide half lives were measured for different constructs both in PBS and in 20% plasma/PBS (i.e. in the presence of serum enzymes. The results are provided in Table 13. The results indicate that three of the four peptides tested were not impacted by serum enzymes.

TABLE 13

Dipeptide half life on IGF1-A(pNH2—F)[19]

| | | Half Life (hr) | |
| --- | --- | --- | --- |
| | | PBS | 20% Plasma/PBS |
| Aib | Pro | 2.2 | 2.1 |
| Aib | dPro | 2.1 | 2.2 |
| AibOH | Sar | 2.3 | |
| dK | N-isobutyl Gly | 4.4 | 4.1 |
| dK | N-hexyl Gly | 10.6 | |
| dK(acetyl) | Sar | 17.2 | |
| K | Sar | 21.8 | 5.9 |
| K(acetyl) | N-methyl Ala | 23.6 | |
| dK(acetyl) | N-methyl Ala | 35.3 | |
| AibOH | Pro | 165.0 | |
| K(acetyl) | Azetidine-2-carboxylic acid | Not cleavable | |
| dK(acetyl) | Azetidine-2-carboxylic acid | Not cleavable | |

Example 13

Receptor Binding of IGF$^{B16B17}$ Derivative Peptides Over Time

Prodrug formulations of IGF$^{B16B17}$ Derivative Peptides were prepared and their degredation over time was measured using the insulin receptor binding assay of Example 3. Peptides used in the assay were prepared as follows:

Dipeptide-IGF1A Analogs

If not specified, Boc-chemistry was applied in the synthesis of designed peptide analogs. Selected dipeptide H$_2$N-AA1-AA2-COOH was added to (pNH$_2$-Phe)[19] on IGF1A (Ala)[6,7,11,20]. The IGF-1 A chain C-terminal tripeptide Boc (Fmoc-pNH-Phe)-Ala-Ala was synthesized on MBHA resin. After removal of Fmoc by the treatment with 20% piperidine/DMF at room temperature for 30 minutes, Fmoc-AA2 was coupled to the p-amino benzyl side chain at A19 by using a threefold excess of amino acid, PyBop, DIEA and catalytic amount of pyridine. The Boc-synthesis of the remaining IGF-1 A chain (Ala)[6,7,11,20] sequence was completed using an Applied Biosystems 430A Peptide Synthesizer, yielding IGF-1 A chain (Boc)[0](ma)[6,7,11,20](Fmoc-AA2-pNH-Phe)[19]-MBHA. After the Fmoc group was removed from the N-terminus of AA2, Boc-AA1 was then coupled to the amine using threefold excess of amino acid, DEPBT and DIEA. Removal of the two Boc groups remaining on the A chain by TFA was followed by HF cleavage, yielding IGF-1 A-chain (Ala)[6,7,11,20](H$_2$N-AA1-AA2-pNH-Phe)[19]amide. In the case of AA1 being d-lysine, acetylation on the ε-amine was performed prior to Boc removal. Dipeptide-IGF-1 A chain analogs were purified by semi-preparative RP-HPLC and characterized by analytical RP-HPLC and MALDI mass spectrometry.

Dipeptide-IGF-1 (YL) Analogs

A selected dipeptide H$_2$N-AA1-AA2-COOH was added to (pNH$_2$-Phe)[19] on IGF-1 A chain (Acm)[6,11,20] as described immediately above except PAM resin was used for the synthesis of IGF-1 A chain to yield a C terminal acid upon HF-cleavage. IGF-1 B chain (YL)[16,17](Acm) 19 was synthesized on MBHA resin to yield a C terminal amide. The free thiol on Cys$^{B7}$ was modified by Npys through reaction with DTNP at a 1:1 molar ratio in 100% DMSO. Purified dipeptide-IGF-1 A chain and IGF-1 B chain (YL)[16,17] derivatives were assembled using the "1+2" two step chain combination strategy illustrated in Scheme 1. Intermediate and final purifications were performed on semi-preparative RP-HPLC and characterized by analytical RP-HPLC and MALDI mass spectrometry.

Figures 8A, 8B, 8C:
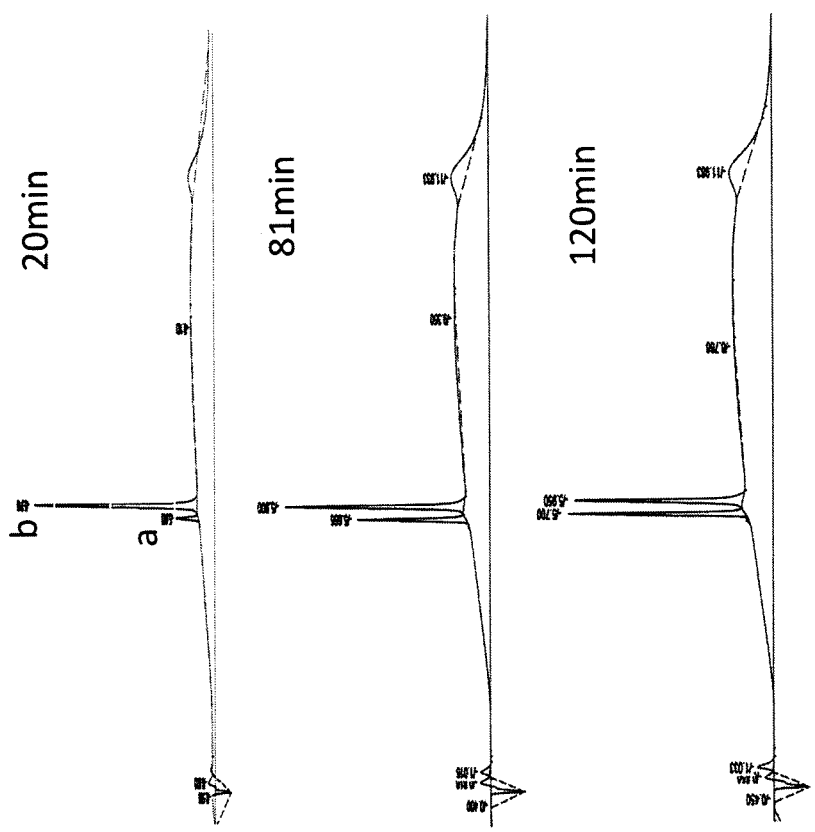
FIG. 8A-8C shows the degradation of a prodrug form of an IGF$^{B16B17}$ derivative peptide: (Aib-Pro on (p$NH_2$—F)$^{19}$ of IGF1A(Ala)$^{6,7,11,20}$ amide. The dipeptide was incubated in PBS, pH 7.4 at 37° C. for predetermined lengths of time. Aliquots were taken at 20 minutes (FIG. 8A), 81 minutes (FIG. 8B) and 120 minutes (FIG. 8C) after beginning the incubation, were quenched with 0.1% TFA and tested by analytical HPLC. Peak a (IGF1A(Ala)$^{6,7,11,20}$(pNH$_2$—F)$^1$amide) and b (IGF1A(Ala)$^{6,7,11,20}$(Aib Pro-pNH—F)$^{19}$amide) were identified with LC-MS and quantified by integration of peak area. The data indicate the spontaneous, non-enzymatic conversion of IGF1A(Ala)$^{6,7,11,20}$(Aib-Pro-pNH—F)$^{19}$amide to IGF1A(Ala)$^{6,7,11,20}$(pNH$^2$—F)$^1$amide over time.

The IGF$^{B16B17}$ derivative peptide prodrugs were incubated in PBS, pH 7.4 at 37° C. and at predetermined time intervals an aliquot was taken and further degredation was quenched with 0.1% TFA and the aliquot was subjected to analytical HPLC analysis. Peaks a and b, representing the prodrug and active forms of the IGF$^{B16B17}$ derivative peptide were identified with LC-MS and quantified by integration of peak area an HPLC. FIGS. 8A-8C show the output of an HPLC analysis of the degredation of the IGF$^{B16B17}$ derivative peptide prodrug: IGF1A(Ala)$^{6,7,11,20}$(Aib-Pro-pNH—F)$^{19}$. Aliquots were taken at 20 minutes (FIG. 8A), 81 minutes (FIG. 8B) and 120 minutes (FIG. 8C) after beginning the incubation of the prodrug in PBS. The data indicate the spontaneous, non-enzymatic conversion of IGF1A(Ala)$^{6,7,11,20}$(Aib-Pro-pNH—F)$^{19}$amide to IGF1A(Ala)$^{6,7,11,20}$(pNH$_2$—F)$^1$amide over time.

Figure 9A:
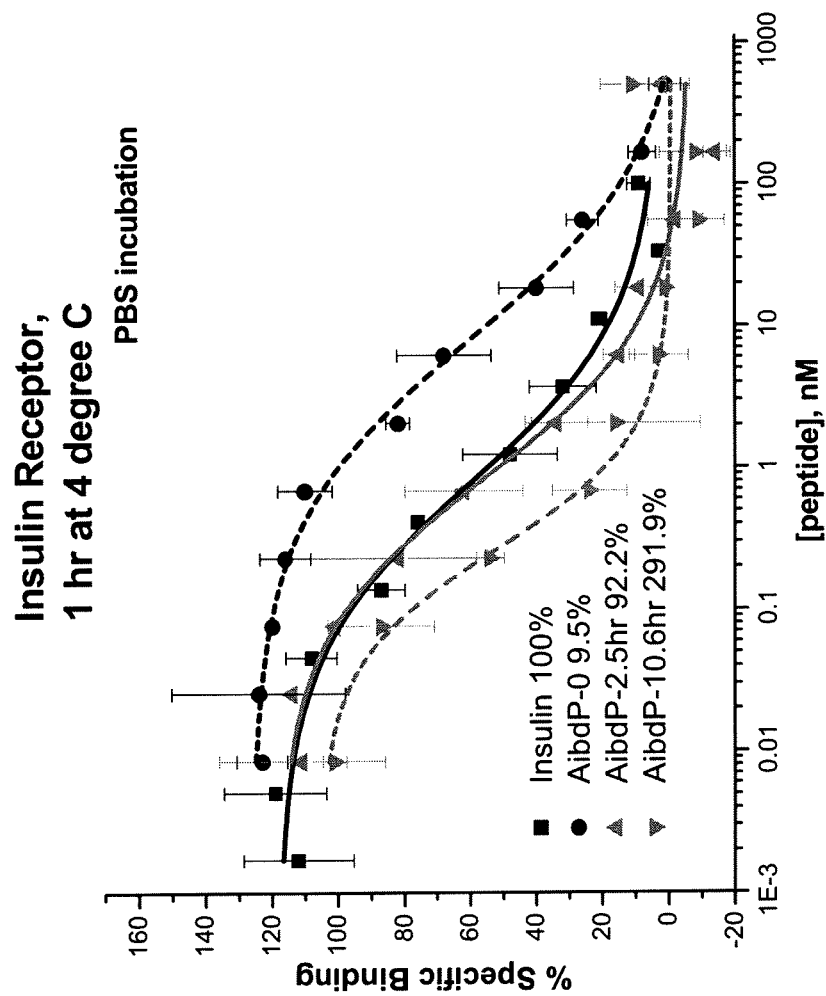
FIGS. 9A & 9B are graphs depicting the in vitro activity of the prodrug Aib,dPro-IGF1YL (dipeptide linked through the A19 4-aminoPhe).
Figure 9B:
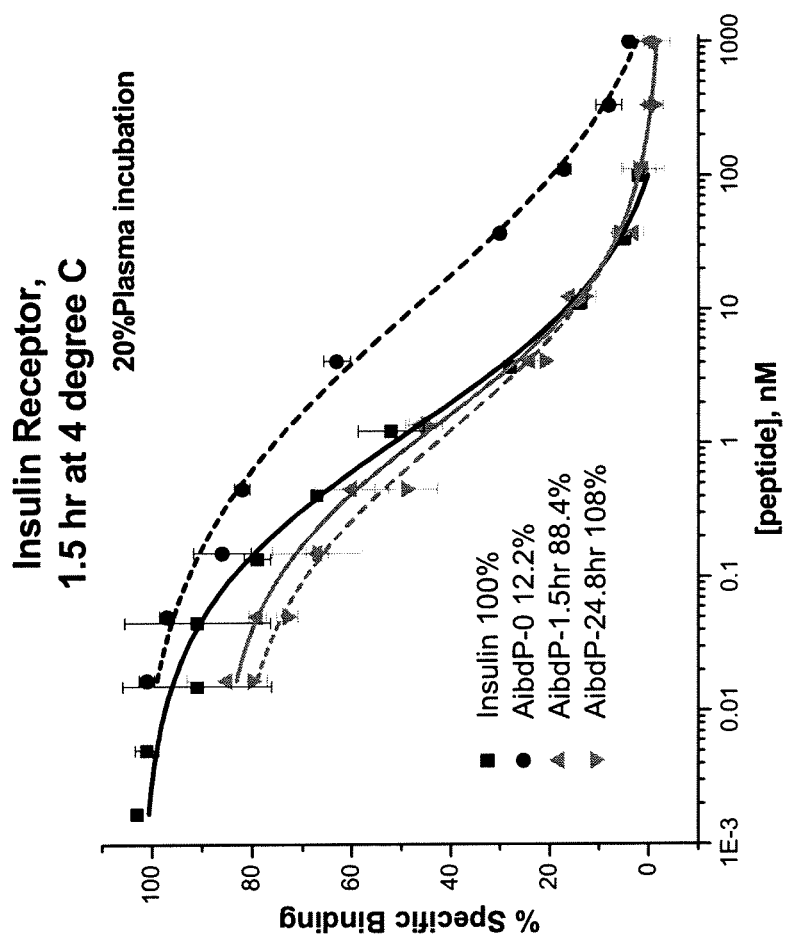

The degredation of the prodrug forms of IGF$^{B16B17}$ derivative peptides to there active from was also measured based on the compounds ability to bind to the insulin receptor as measured using the in vitro assay of Example 3. FIGS. 9A & 9B are graphs depicting the in vitro activity of the prodrug Aib, dPro-IGF1YL (dipeptide linked through the A19 4-aminoPhe). FIG. 9A is a graph comparing relative insulin receptor binding of native insulin (measured at 1 hour at 4° C.) and the A19 IGF prodrug analog (Aib,dPro-IGF1YL) over time (0 hours, 2.5 hours and 10.6 hours) incubated in PBS. FIG. 9B is a graph comparing relative insulin receptor binding of native insulin (measured at 1.5 hour at 4° C.) and the A19 IGF prodrug analog (Aib,dPro-IGF1YL) over time (0 hours, 1.5 hours and 24.8 hours) incubated in 20% plasma/PBS. As indicated by the data presented in the graph, increased activity is recovered form the A19 IGF prodrug analog sample as the prodrug form is converted to the active IGF1YL peptide. The activity of the IGF$^{B16B17}$ derivative peptides was measured relative to insulin receptor binding, and since the underlying IGF$^{B16B17}$ derivative peptides have more activity than native insulin, activity of greater than 100% relative to insulin is possible.

Figure 10A:
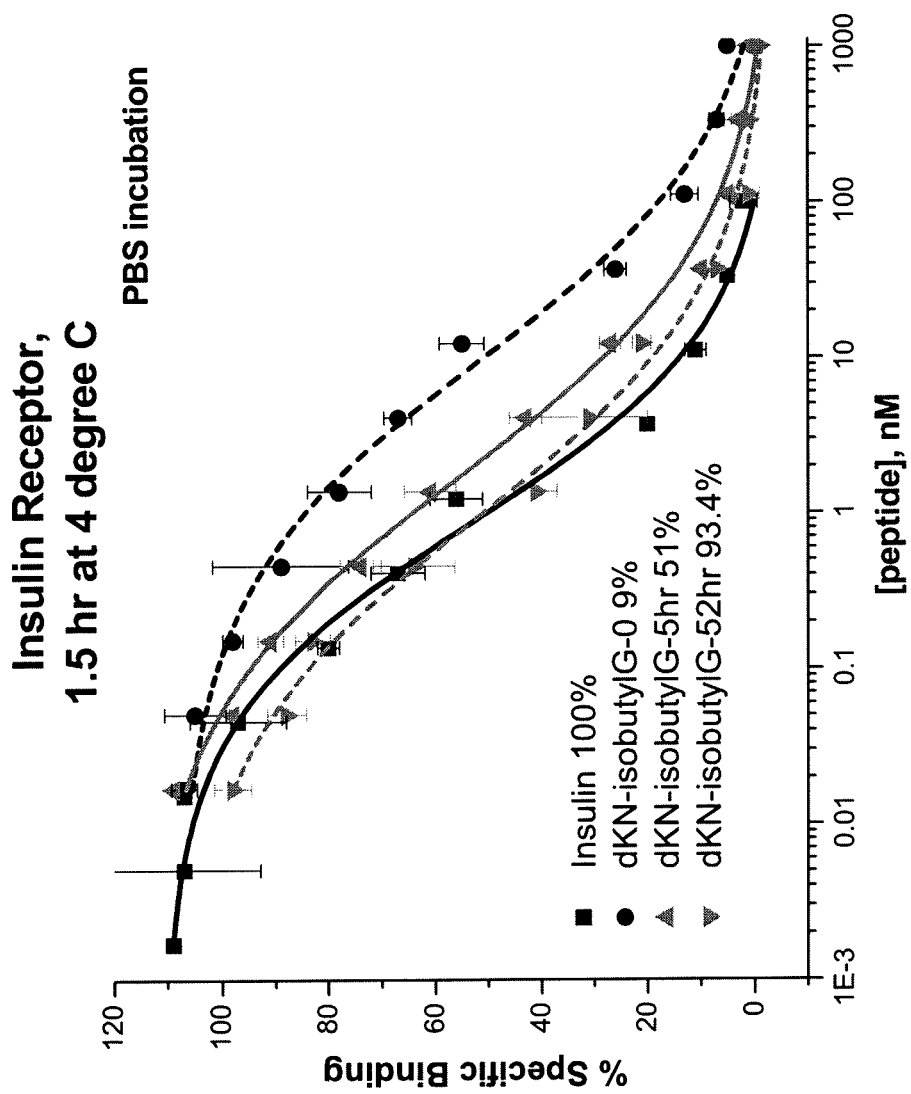
FIGS. 10A & 10B are graphs depicting the in vitro activity of the prodrug dK,(N-isobutylG)-IGF1YL (wherein the dipeptide dK,(N-isobutylG) is linked via an amide bond to the insulin analog through the A19 4-aminoPhe).
Figure 10B:
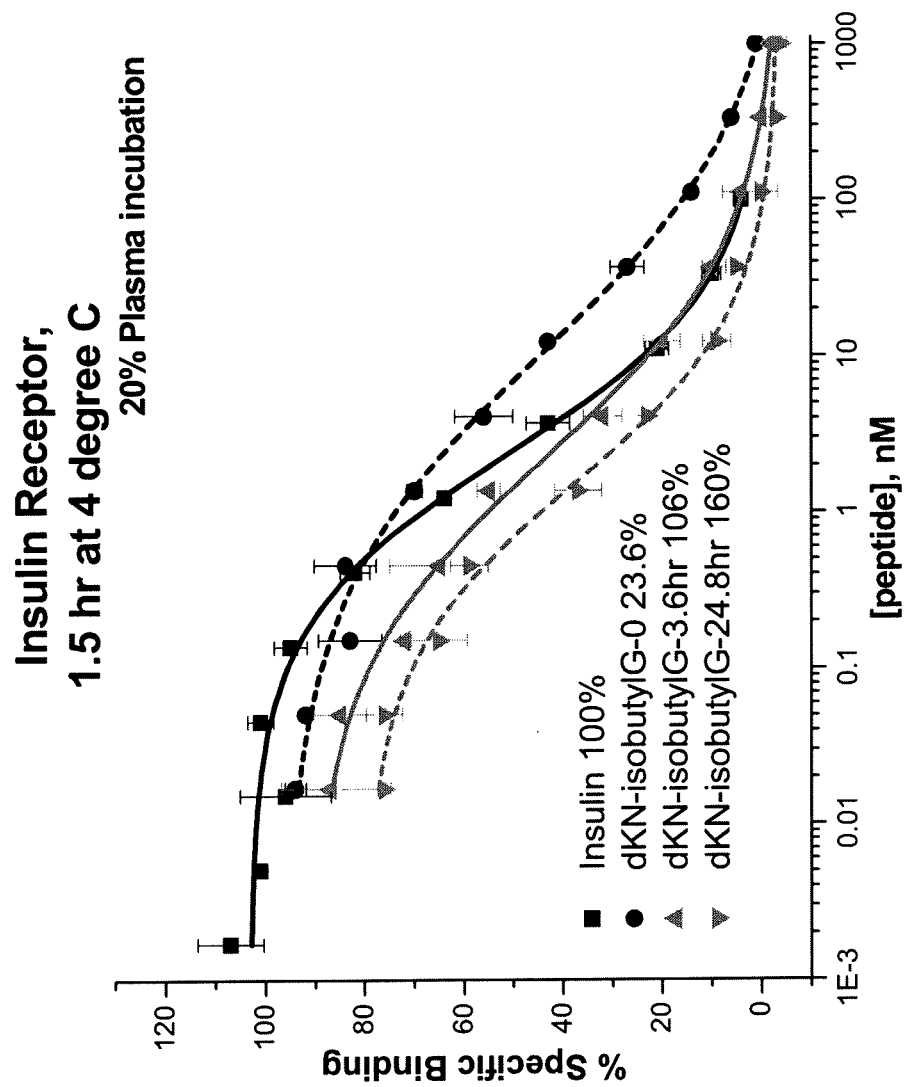

FIGS. 10A & 10B are graphs depicting the in vitro activity of the prodrug dK,(N-isobutylG)-IGF1YL (dipeptide linked through the A19 4-aminoPhe). FIG. 10A is a graph comparing relative insulin receptor binding of native insulin (measured at 1 hour at 4° C.) and the A19 IGF prodrug analog (IGF1YL: dK,(N-isobutylG) over time (0 hours, 5 hours and 52 hours) incubated in PBS. FIG. 10B is a graph comparing relative insulin receptor binding of native insulin (measured at 1.5 hour at 4° C.) and the A19 IGF prodrug analog (IGF1YL: dK,(N-isobutylG) over time (0 hours, 3.6 hours and 24.8 hours) incubated in 20% plasma/PBS. As indicated by the data presented in the graph, increased activity is recovered form the A19 IGF prodrug analog sample as the prodrug form is converted to the active IGF1YL peptide.

Figure 11A:
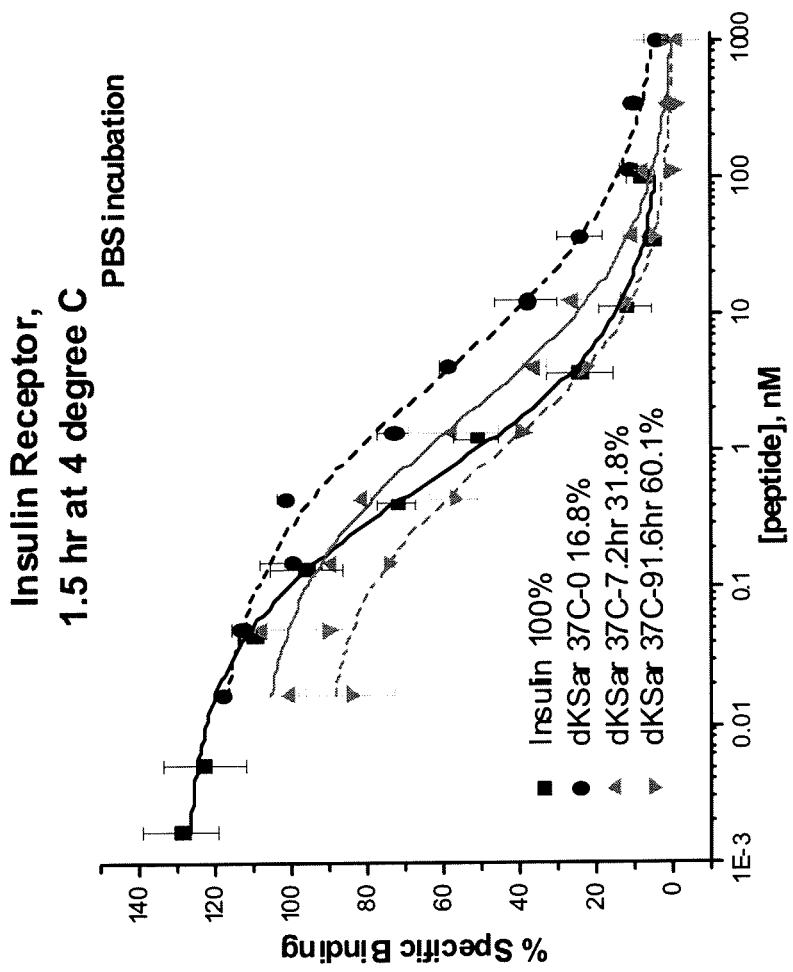
FIGS. 11A & 11B are graphs depicting the in vitro activity of the prodrug dK(e-acetyl),Sar)-IGF1YL (wherein the acylated dipeptide dK(e-acetyl),Sar) is linked via an amide bond to the insulin analog through the A19 4-aminoPhe).
Figure 11B:
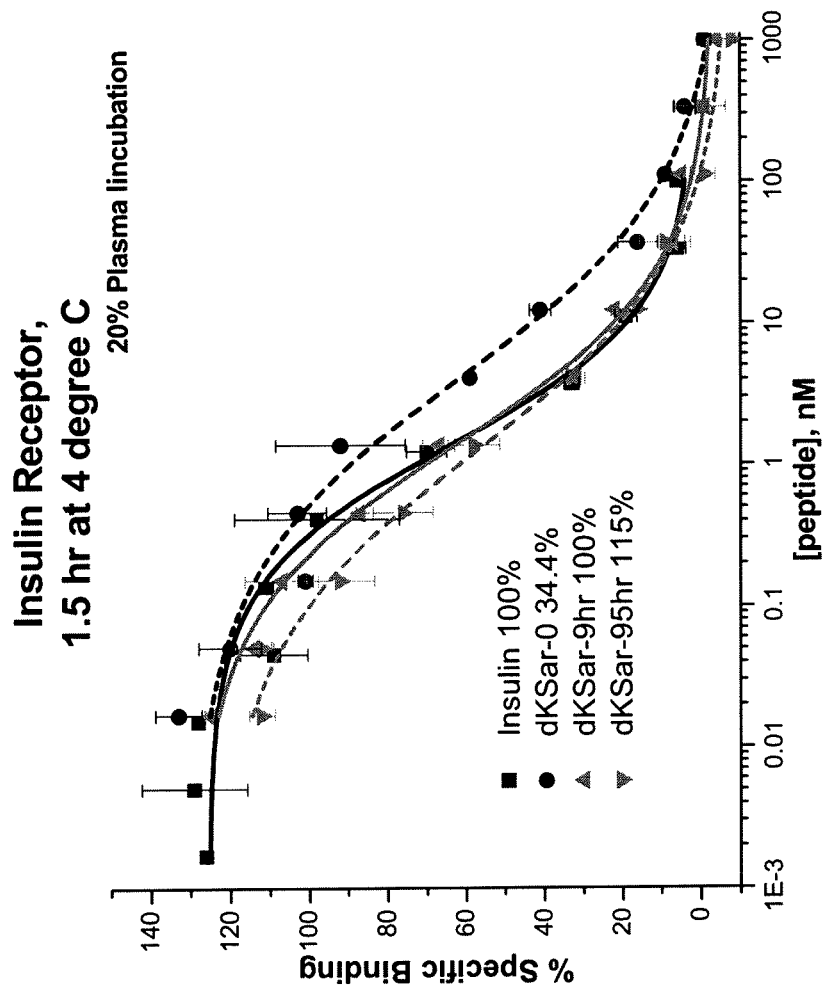
Figure 12:
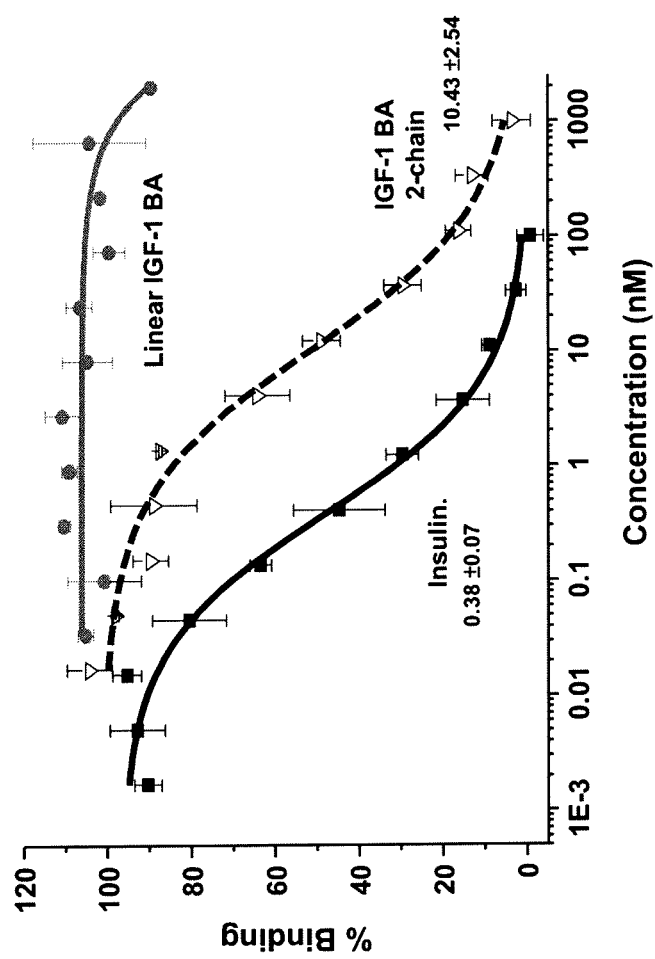
FIG. 12 is a graph comparing relative insulin receptor binding of native insulin heteroduplex and the IGF-1 A and B chain heteroduplex and a single chain IGF-1 analog wherein the carboxy terminus of the B chain is directly linked to the N-terminus of the IGF-1 A chain.
Figure 13:
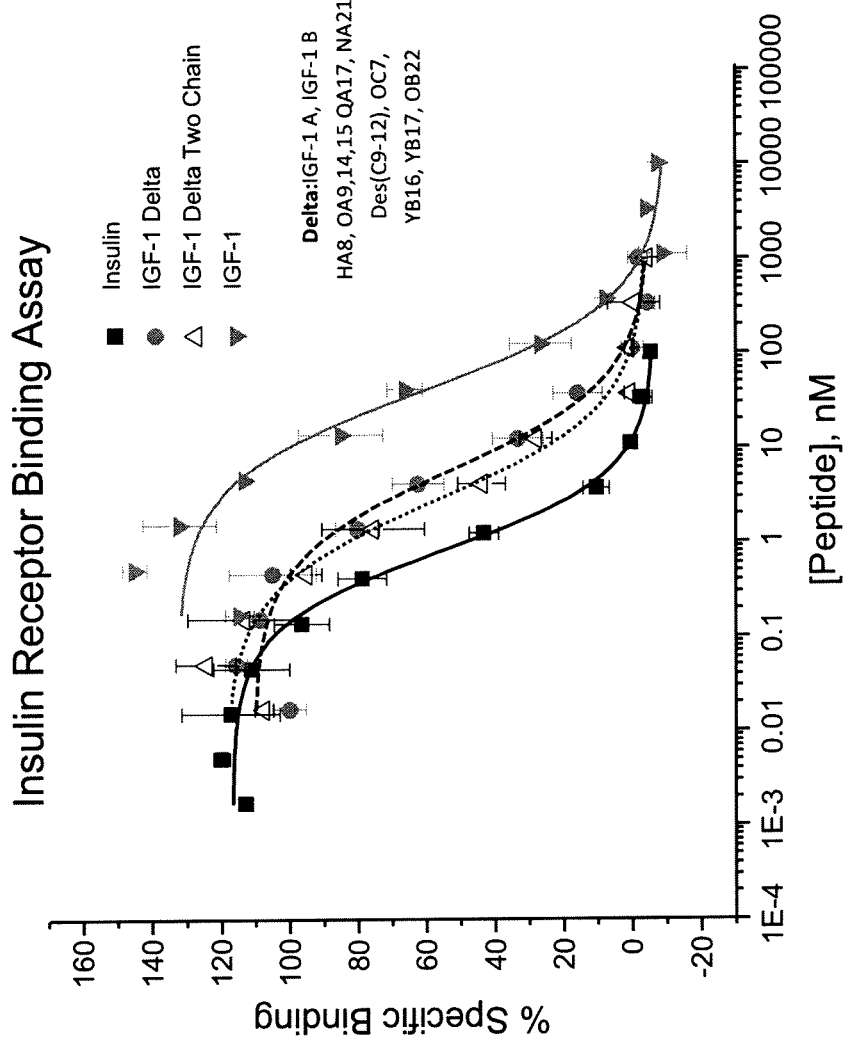
FIG. 13 is a graph comparing relative insulin receptor binding of native insulin heteroduplex, IGF-1, the IGF-1 delta heteroduplex and a single chain IGF-1 delta single chain analog wherein the carboxy terminus of the B chain is linked to the N-terminus of the IGF-1 A chain through a peptide linker consisting of the sequence GYGSSSOR (SEQ ID NO: 69), wherein the IGF-1 delta analog comprises the native IGF-1 sequence with the following amino acid substitutions: HA8, OA9, OA14, OA15, QA17, NA21, YB16, LB17, OB22.
Figure 14:
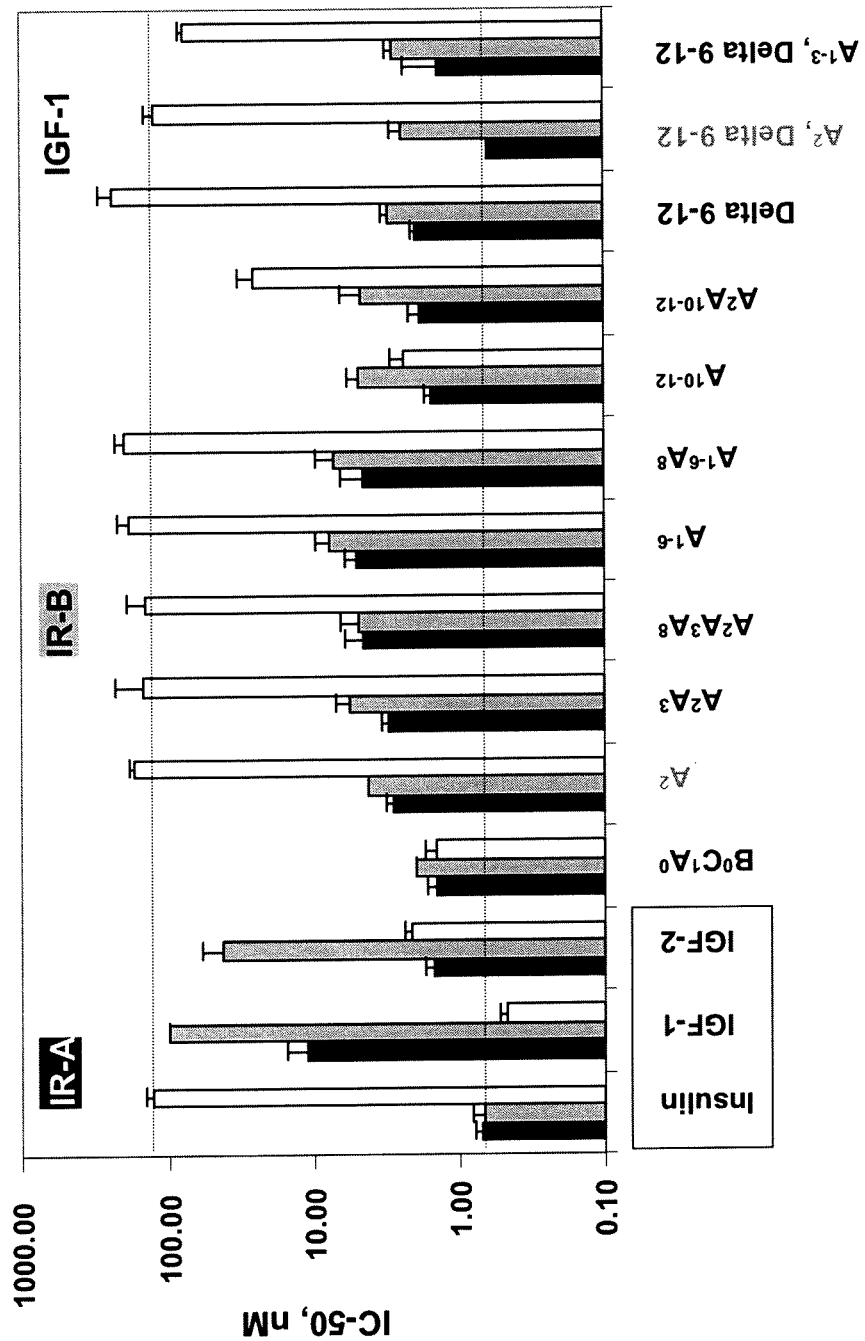
FIG. 14 is a bar graph depicting the relative in vitro binding activity of single chain insulin analogs at the IGF-1 receptor or the A or B subtype insulin receptors wherein the carboxy terminus of the native insulin B chain is linked to the amino terminus of the native insulin A chain via the IGF-1 C peptide or various derivative of the IGF-1 C peptide. In the $B^0C^1A^0$ insulin analog nomenclature, the $B^0$ and $A^0$ designations refer to the insulin sequences of the A and B chain, while $C^1$ designates the IGF-1 C peptide. As shown by the data a single chain insulin analog that links the B chain to the A chain via the IGF-1 C peptide is a potent insulin agonist. Furthermore, modifications of position 2 (e.g., substituting alanine for native tyrosine), or alternatively deleting the last four amino acids of the IGF-1 C linking peptide, generates a high potency, insulin selective single chain insulin analog.

FIGS. 11A & 11B are graphs depicting the in vitro activity of the prodrug dK(e-acetyl),Sar)-IGF1YL (dipeptide linked through the A19 4-aminoPhe). FIG. 11A is a graph comparing relative insulin receptor binding of native insulin (measured at 1 hour at 4° C.) and the A19 IGF prodrug analog (IGF1YL: dK(e-acetyl),Sar) over time (0 hours, 7.2 hours and 91.6 hours) incubated in PBS. FIG. 11B is a graph comparing relative insulin receptor binding of native insulin (measured at 1.5 hour at 4° C.) and the A19 IGF prodrug analog (IGF1YL: dK(e-acetyl),Sar) over time (0 hours, 9 hours and 95 hours) incubated in 20% plasma/PBS. As indicated by the data presented in the graph, increased activity is recovered form the A19 IGF prodrug analog sample as the prodrug form is converted to the active IGF1YL peptide.

Example 14

Comparative Insulin Tolerance for Insulin Prodrug Analogs

Figure 19A:
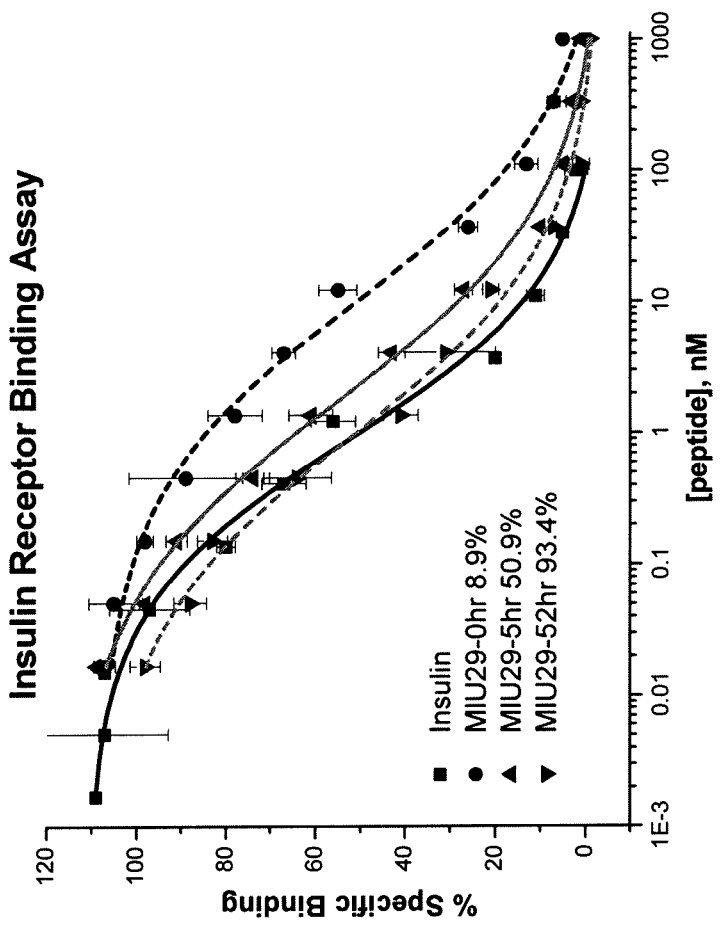
FIG. 19A-19B show the activity of prodrug MIU-29: $B^1$(Y16,L17,Y25)29a: $A^1$(aF19-dLys(Ac),NLeu).
Figure 19B:
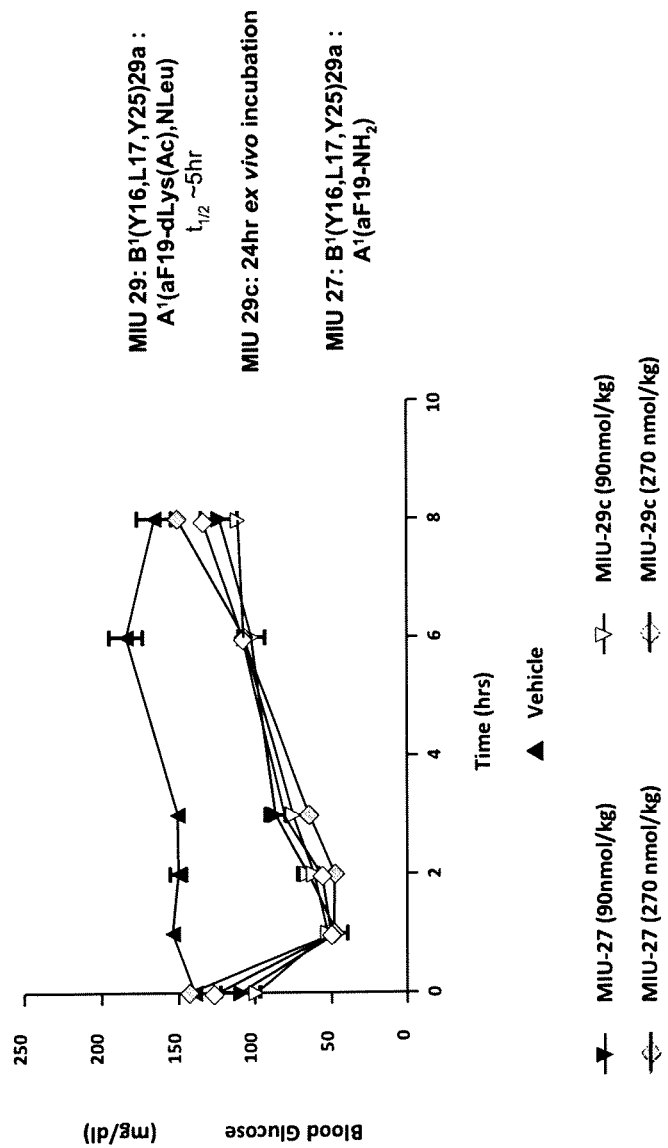

Normal mice were administered either an insulin heterodimer analog [B$^1$(Y16,L17,Y25)29a: A$^1$(aF19-NH2)], or a prodrug derivative thereof. The prodrug derivative MIU-29: [B$^1$(Y16,L17,Y25)29a: A$^1$(aF19-dLys(Ac),NLeu)] comprises a 4-amino-phenylalanine substitution at position A19 wherein a dipeptide dLys(Ac),NLeu have been covalently linked at the 4-amino position of the A19 residue. This dipeptide will auto-cleave under physiological conditions with a half life of approximately 4.4 hours (see FIG. 19A). After incubating the prodrug derivative [B$^1$(Y16,L17,Y25)29a: A$^1$(aF19-dLys(Ac),NLeu)] for 24 hours ex vivo, the resultant compound was administered to mice and its ability to lower blood glucose was compared to parent compound. As shown in FIG. 19B the two compounds performed almost identically.

Figure 21:
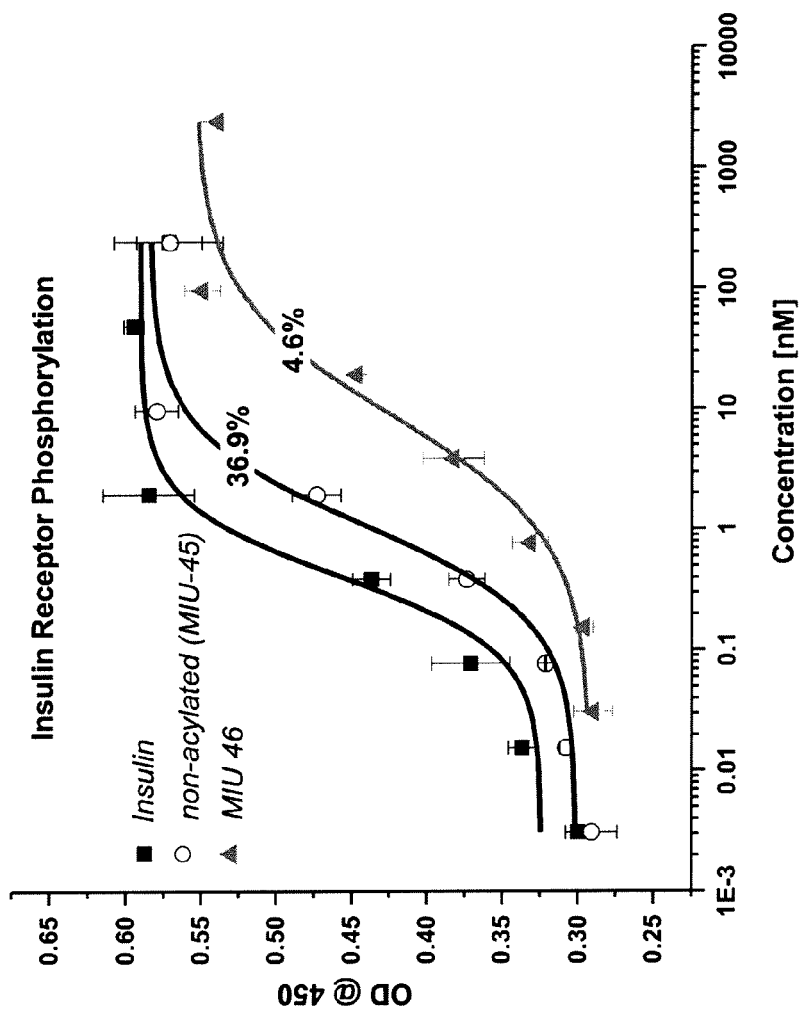
FIG. 21 is a graph depicting the in vitro activity of the acylated insulin analog MIU 46: $B^1$(H5,10 Y16,L17,Y25, K29-C14)28a: $A^1$(N18,21, aF19NH2) relative to its non-acylated counterpart (MIU-45) and to native insulin. The acylated insulin comprises a 4-amino-phenylalanine substitution at position A19 and a lysine substitution at B29, wherein the side chain of the B29 lysine has been acylated with a C14 fatty acid. The acylated analog has reduced potency relative to the parent compound.
Figure 22:
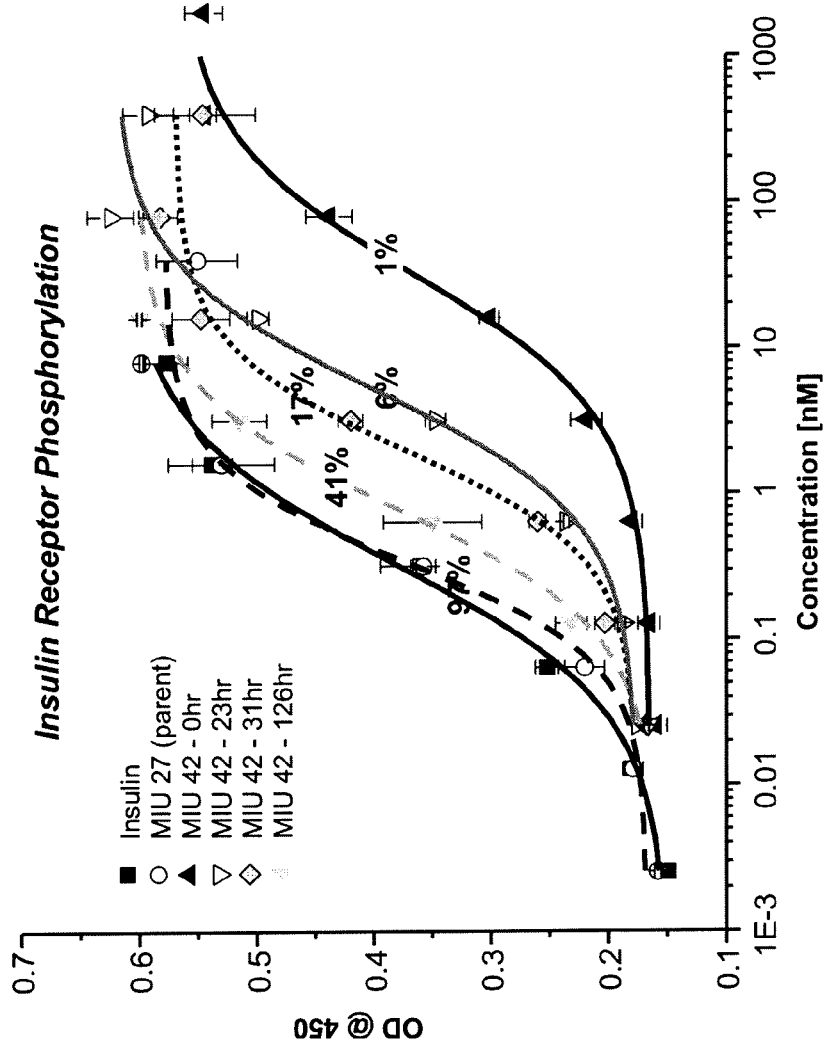
FIG. 22 is a graph depicting the in vitro activity of the acylated prodrug MIU 42: $B^1$(Y16,L17,Y25)29a: $A^1$(dLys(rE-C14),Sar-aF19) (wherein an amino acid of the dipeptide prodrug element is acylated, linked at the gamma position "rE" of a glutamic acid linker) relative to time incubated ex vivo in 30% ACN/PBS at pH 7.4 and 37° C. As shown by the data, activity is restored to parent compound MIU 42 with increased time incubated ex vivo.
Figure 23A:
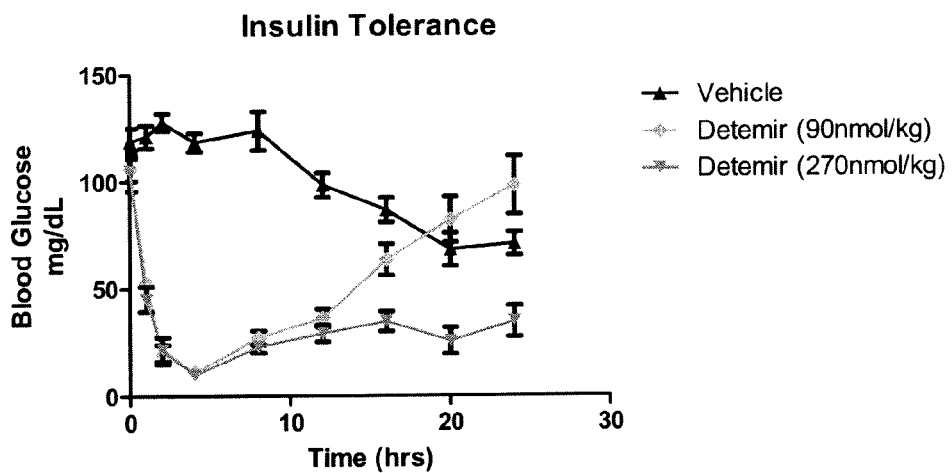
FIGS. 23A-23D provide data from a comparative insulin tolerance test for Detemir and acylated insulin analog MIU-46 using C57/Blk mice. The acylated derivative MIU 46: $B^1$(H5,10 Y16,L17,Y25, K29-C14)28a: $A^1$(N18,21, aF19NH2) comprises a lysine substitution at position 29 that has been acylated with a C14 fatty acid through a gamma glutamic acid spacer.
Figure 23B:
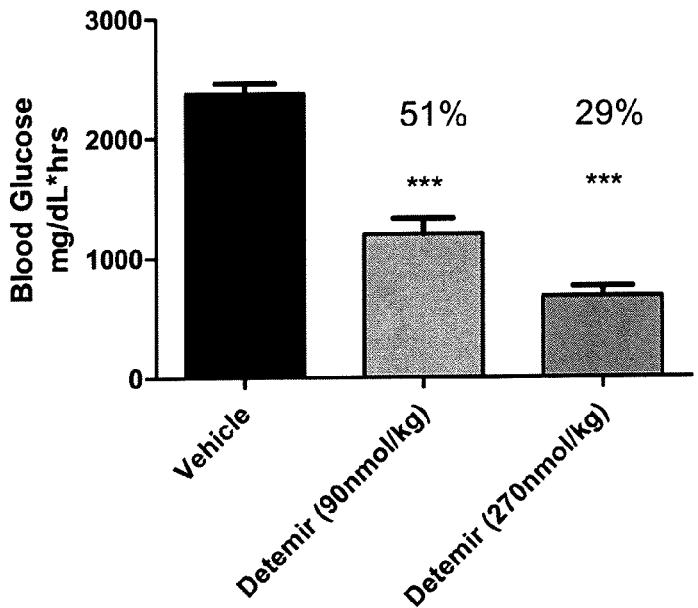
Figure 23C:
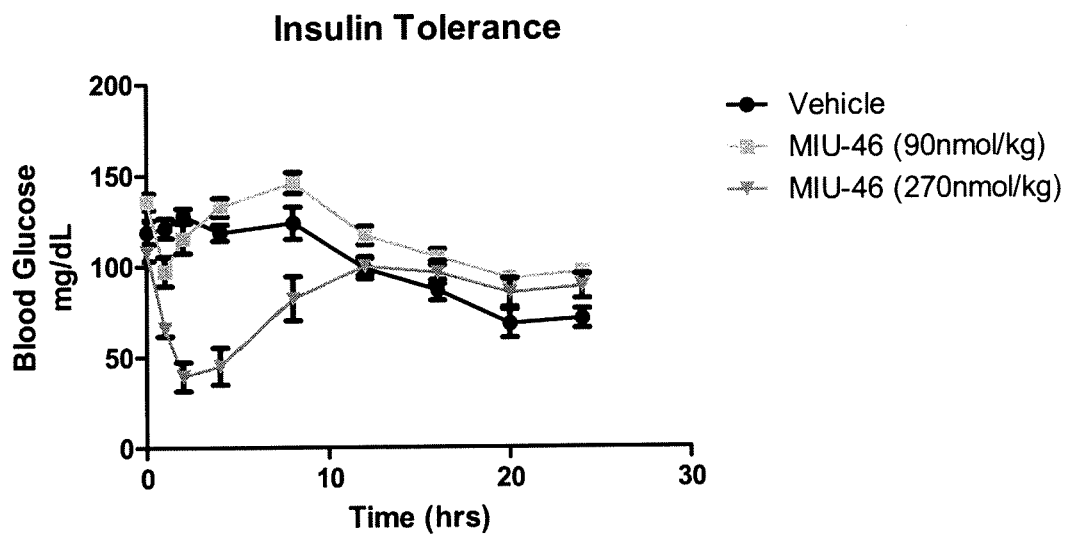
Figure 23D:
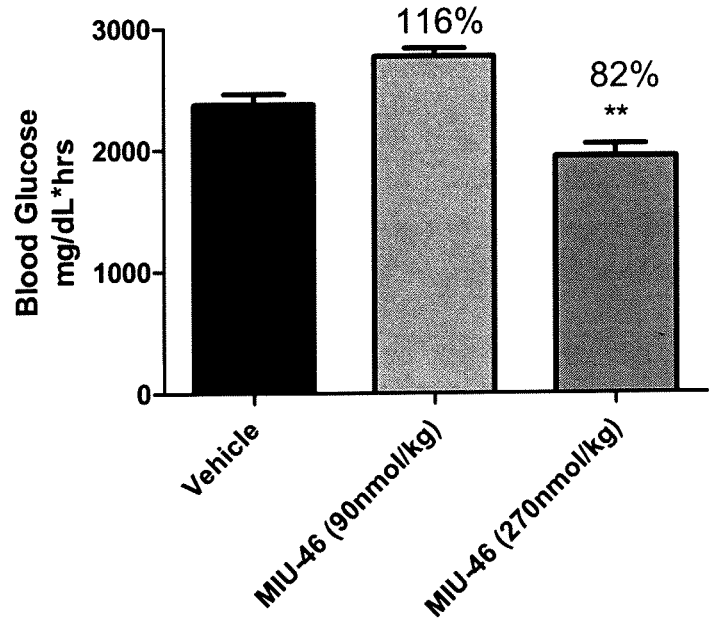

Acylation of the insulin prodrug analogs was investigated to determine if retention times in vivo could be enhanced. The in vitro activity of MIU 42 [B$^1$(Y16,L17,Y25)29a: A$^1$(dLys(rE-C14),Sar-aF19)], having an acylated dipeptide prodrug element, increases with time incubated ex vivo in 30% ACN/PBS @ pH7.4 37° C. (providing time for prodrug conversion) relative to the non-acylated prodrug (see FIG. 21). Comparative insulin potency tests conducted using the MIU 42 prodrug (FIG. 22) administered without a pre-incubation step show that the prodrug is not very potent relative to the non-prodrug parent compound (MIU-27). This was also found to be true for an acylated insulin analog MIU-46 [B$^1$(H5,10 Y16,L17,Y25, K29-C14)28a: A$^1$(N18,21, aF19NH2)] having acylation at the B29 position. The compound did not exhibit a desired in vivo potency or a basal profile when tested in vivo in mice (FIG. 23C). Accordingly, at least in mice the acylation does not produce the desired profile.

Example 15

Biosynthesis and Purification of Pegylated Insulin Prodrug Analogs

IGF1 B chain (2-25) H$^{5,10}$ Y$^{16}$ L$^{17}$ SH$^7$ H ACM$^{19}$ amide was synthesized on an MBHA resin using solid phase Boc-chemistry. After cleavage of the peptide from the resin with simultaneous removal of amino acid side chain protection, crude B chain was mixed with 2,2'-dithiobis(5-nitropyridine) in DMSO to yield a cysteine-NpyS derivative at Cys$^7$. Addition of Boc-aminooxyacetyl (Aoa) to the N-terminal of B chain was achieved through reaction between B chain and Boc-Aoa-OSu. Purified IGF1 B chain (2-25)(BocAoa)$^0$ H$^{5,10}$ Y$^{16}$ L$^{17}$ SH7 Acm$^{19}$ amide was combined with IGF1 A chain Acm$^{6,7,11}$ N$^{18,21}$ (aa1aa2)-pNH-F$^{19}$ acid using the "1+2" method described herein (see FIG. 1) to generate the insulin analog with Boc-Aoa at the N terminal of B chain. Boc was removed by treatment of the peptide with brief treatment with 6N HCl in the presence of O-(Carboxymethyl)hydroxylamine hemihydrochloride as scavenger. After Boc removal and purification, the peptide was dissolved in 1% aniline/30% ACN/0.2M NaOAc (pH4.6) at the concentration of 3 mg/ml. Two-fold excess amount of 20 KD PEG-propionic aldehyde was added to the solution, the reaction was conducted with stirring for one hour at room temperature, followed by the final purification to yield the pegylated insulin analog.

Figure 24:
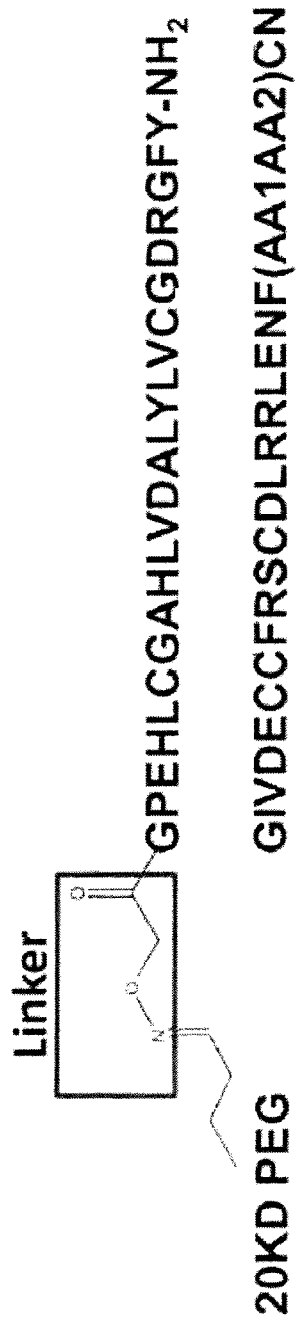
FIG. 24 is a generalized structure of one pegylated insulin prodrug embodiment wherein a 20 kDa PEG is linked to the N-terminal alpha amine of the B chain through a linker and the a chain comprises a 4-amino phenylalanine substitution at position A19, wherein a dipeptide (AA1, AA2) is linked to the 4-amino group of 4-amino phenylalanine via an amide bond. In one embodiment the dipeptide (AA1, AA2) is Norleucine, dlysine (acylated).
Figure 25:
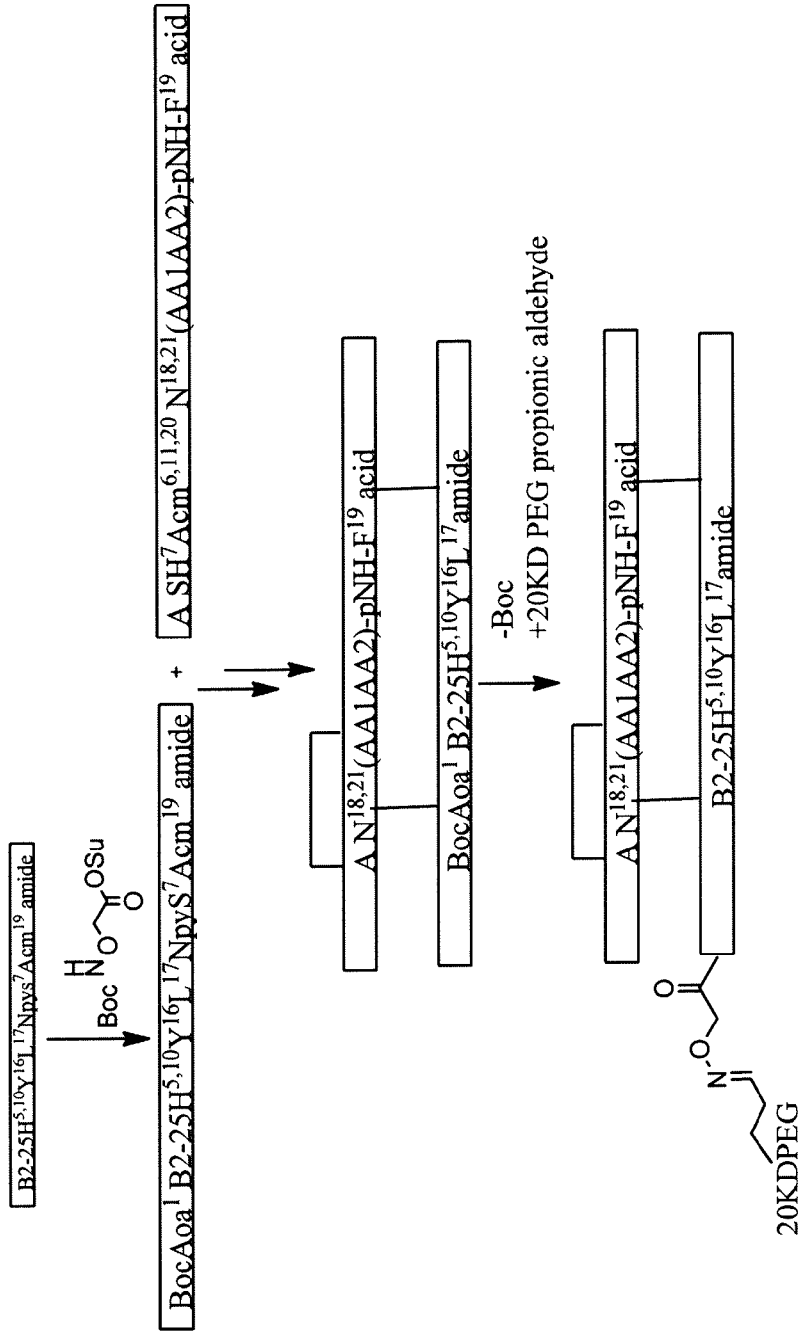
FIG. 25 is a is a schematic drawing of the synthetic scheme used to prepare the generalized structure of FIG. 24. A more detailed description of the synthesis is provided in Example 15.
Figure 26:
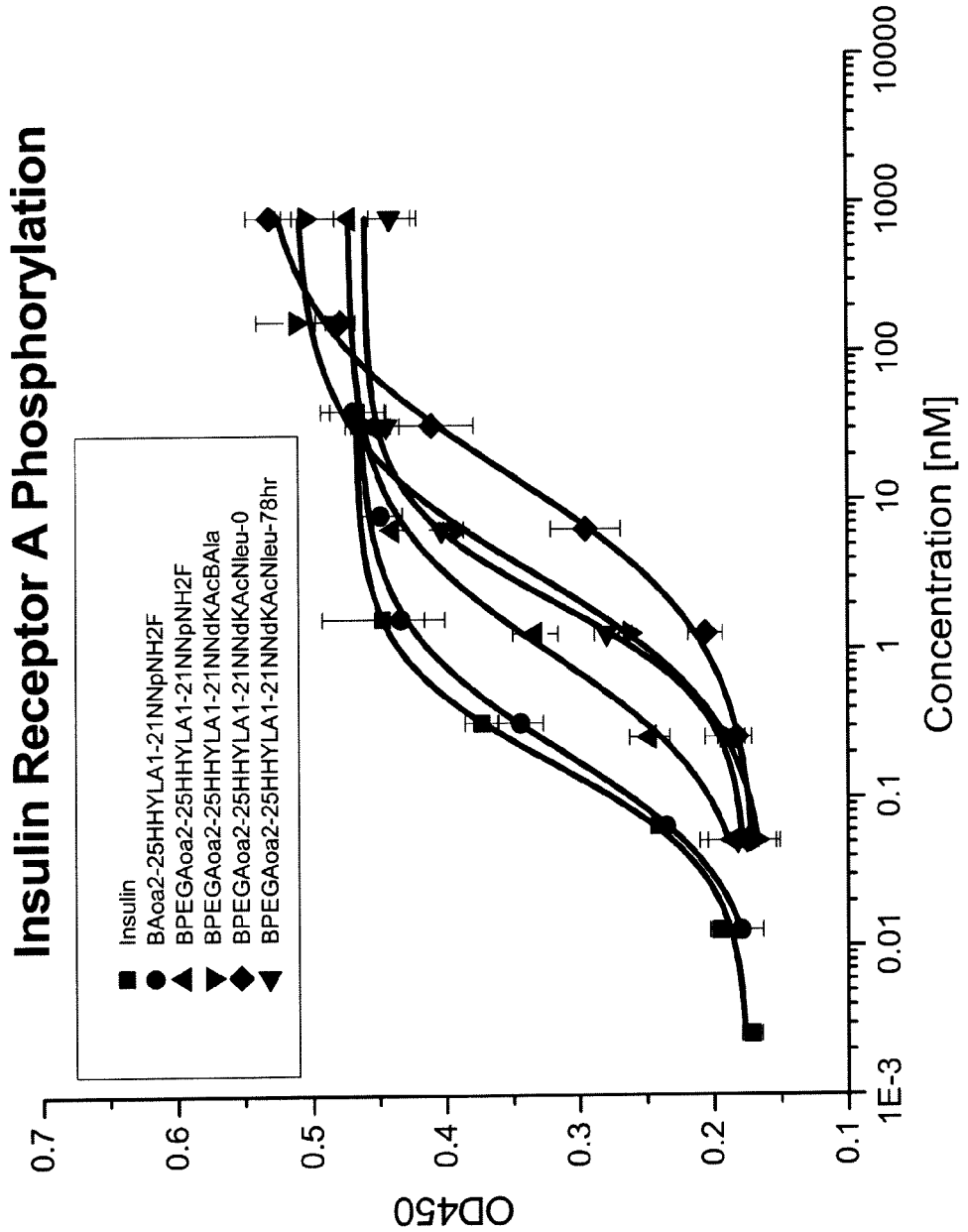
FIGS. 26 & 27 are graphs demonstrating the in vitro activity of various prodrug compounds (having the general structure of FIG. 24) at insulin A subtype receptor (FIG. 26) and B subtype receptor (FIG. 27) receptors based on a phosphorylation assay. Compounds tested were native insulin (■), $B^1$Aoa2(H5, H10,Y16,L17)25a: $A^1$(pNH$_2$—F19, N18, N21 (●, having the aminooxyacetyl (Aoa) linker but no PEG, and not dipeptide at A19), $B^1$PEG-Aoa2(H5, H10,Y16,L17)25a: $A^1$(pNH$_2$—F19dLys(rE-C14),Sar-aF19, N18, N21 (▲, having an N-terminal 20 kDa PEG but no dipeptide at A19), $B^1$PEGAoa2(H5, H10,Y16,L17)25a: $A^1$(dLys(rE-C14), βAla-aF19, N18, N21 (▼, having an N-terminal 20 kDa PEG and a poorly cleavable dipeptide (dLys(rE-C14),βAla) at A19), $B^1$PEGAoa2(H5, H10,Y16,L17)25a: $A^1$(dLys(rE-C14),Nleu-aF19, N18, N21 (◆, having an N-terminal 20 kDa PEG and a self cleaving dipeptide (dLys(rE-C14),Nleu) at A19, administered without an incubation step), and $B^1$PEGAoa2(H5, H10,Y16,L17)25a: $A^1$(dLys(rE-C14), Nleu-aF19, N18, N21 (◀, having an N-terminal 20 kDa PEG and a self cleaving dipeptide (dLys(rE-C14),Nleu) at A19, administered after incubation in PBS for 78 hours). As noted in FIGS. 19A & 19B the dipeptide dLys(rE-C14),Nleu will auto-cleave under physiological conditions with a half life of approximately 4.4 hours.
Figure 27:
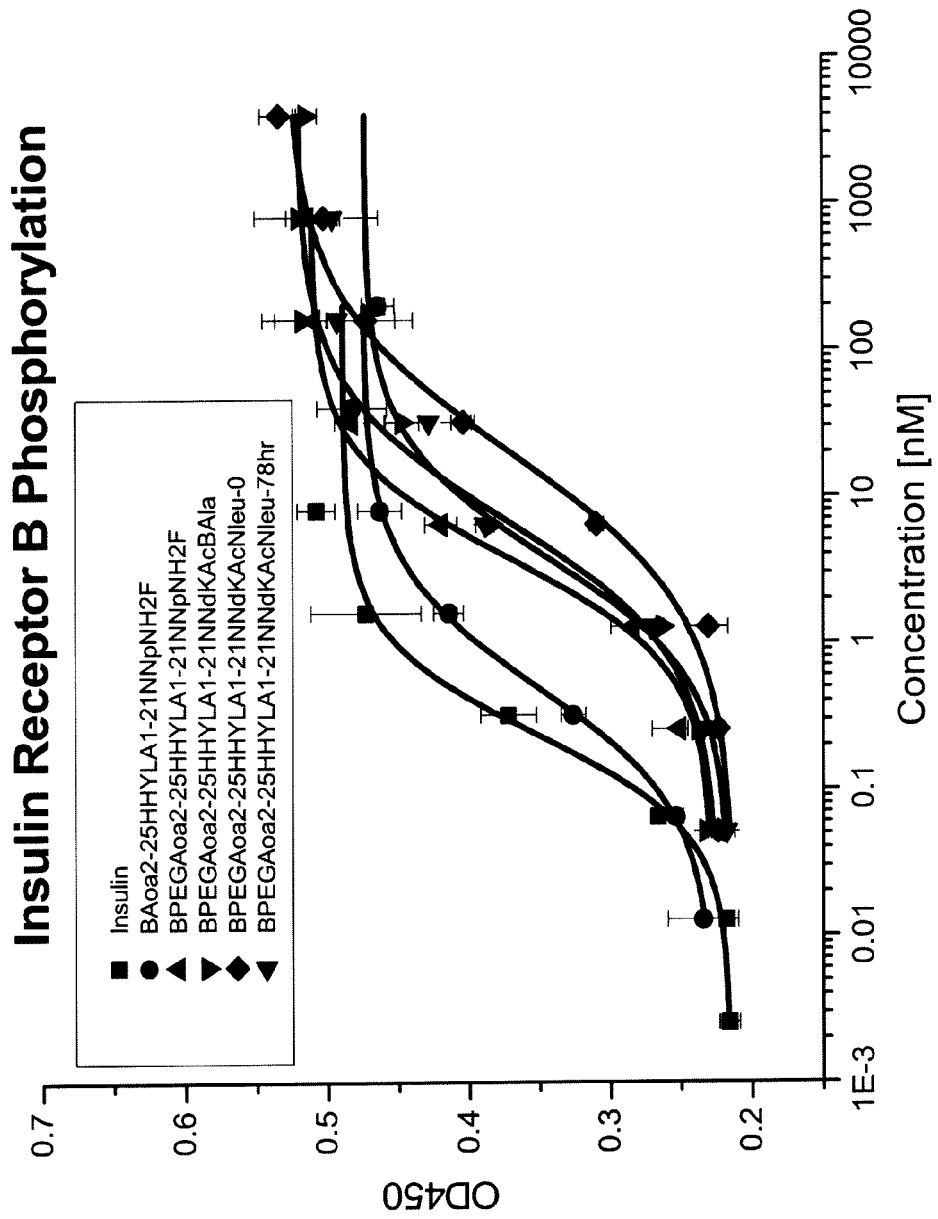

As shown in FIGS. 26 & 27 the addition of a 20 kDa PEG to the amino terminus of a two chain insulin analog (FIG. 24) reduces the potency of the insulin analog (comparing non pegylated parent compound, ●, with the pegylated compound, ▲). The addition of an auto-cleavable dipeptide prodrug element (dLys(rE-C14),Nleu) at position A19 further reduces the potency of the compound by approximately 100 fold (see FIG. 26 and FIG. 27, ♦). However preincubation of the prodrug in PBS at 37° C. for 78 hours (the dipeptide has a half life of approximately 4.4 hours) restores the potency to a value close to the parent pegylated compound. See Table 14 which lists the EC50 of the analogs at the insulin receptor A and b subtypes as measured in an in vitro phosphorylation assay.

TABLE 14

Activity of Pegylated Insulin Prodrug

| | | Insulin | Unpegylated $pNH_2F$ | PEG-$pNH_2F$ | PEG-dKAcNleu 0 h | PEG-dKAcNleu 78 h |
|---|---|---|---|---|---|---|
| IR-A | EC50 | 0.17 | 0.21 | 0.94 | 15.49 | 2.06 |
| | % | | 81% | 18% | 1.1% | 8.3% |
| IR-B | EC50 | 0.24 | 0.50 | 3.72 | 20.0 | 3.8 |
| | % | | 48% | 6.5% | 1.2% | 6.3% |

Example 16

Biosynthesis and Purification of Single Chain Insulin Analogs

An insulin-IGF-1 minigene comprising a native insulin B and A chain linked via the IGF-I C chain)($B^0$-$C^1$-$A^0$) was cloned into expression vector pGAPZα A (purchased from Invitrogen) under GAP promoter (promoter of the glyceraldehyde-3-phosphate dehydrogenase (GAPDH)) for constitutive expression and purification of recombinant protein in yeast *Pichia pastoris*. The minigene was fused to an N-terminal peptide encoding *Saccharomyces cerevisiae* α-mating factor leader signal for secretion of the recombinant protein into the medium. A Kex2 cleavage site between the minigene and the leading α-mating factor sequence was used to cleave the leader sequence for secretion of the minigene with native amino termini. Single-site alanine mutations were introduced into C peptide at positions 1 (G1A), 2 (Y2A), 3 (G3A), 4 (S4A), 5 (S5A), 6 (S6A), 7 (R7A), 8 (R8A), 10 (P10A), 11 (Q11A), and 12 (T12A) of the $B^0$-$C^1$-$A^0$ minigene.

The minigenes including $B^0$-$C^1$-$A^0$, eleven alanine mutants, and other select derivatives were transformed into yeast *Pichia pastoris* by electroporation. Positive transformants were selected on minimal methanol plates and a genomic preparation of each *Pichia* isolate was performed and integration of the constructs into the yeast genome was confirmed by PCR. An 833 base pair PCR product was visualized on an agarose DNA gel. The insulin analogs were produced by fermentation of a corresponding yeast line. The yeast cells were pelleted by centrifugation at 5 K for 20 minutes in 500 ml Beckman centrifuge tubes and the media was kept for subsequent protein purification.

Growth media supernatants were filtered through 0.2 μm Millipore filter. Acetonitrile (ACN) was added to the supernatant to a final volume of 20%. The supernatant was purified over a Amberlite XAD7HP resin from Sigma, pre-equilibrated with 20% aqueous ACN. The resin was then rinsed twice with 30 ml of 20% aqueous ACN and contaminants were removed with 30% aqueous ACN containing 0.1% TFA. Partially purified insulin analogs were eluted from the column with 54% aqueous ACN containing 0.1% TFA and lyophilized. Lyophilized samples were re-suspended in 0.025M $NH_3HCO_3$ pH 8 and purified on a Luna C18 column (10 μm particle size, 300A° pore size). Protein was eluted from the column using a linear gradient of 20-60% aqueous ACN. MALDI-MS positive fractions were pooled and transferred to a disposable scintillation vial for subsequent lyophilization. Lyophilized samples were then resuspended in 20% aqueous ACN containing 0.1% TFA, and purified on a Luna C18 column (10 μm particle size, 300A° pore size). The protein was eluted from the column using a linear gradient of 18-54% aqueous ACN with 0.1% TFA. Protein elution was monitored at an absorbance 280 nm MALDI-TOF MS positive fractions were analyzed via a C8 analytical column to insure purity.

FIG. 14 illustrates the potency of the single-chain insulin analogs. The $B^0$-$C^1$-$A^0$ analog demonstrated potency that was equally effective at both insulin receptor isoforms and the IGF-1 receptor. Mutation of the tyrosine at position 2 to alanine or the shortening of the C-peptide to eight amino acids through deletion of C9-12 provided a selective enhancement in the specificity of insulin action by significant reduction in the IGF-1 receptor activity. See also the data provided in Tables 14A and 14B:

TABLE 14A

Insulin Binding & Phosphorylation Analysis ($B^0C^1A^0$)

| | Insulin Binding | | Insulin Phosphorylation | |
|---|---|---|---|---|
| Peptide | $IC_{50}$, nM | n | $EC_{50}$, nM | n |
| Insulin | 0.54 ± 0.02 | 4 | 1.67 ± 0.13 | 1 |
| IGF-1 | 18.81 ± 1.77 | 3 | 29.20 ± 8.41 | 1 |
| 010 ($B^0C^1A^0$) | 2.83 ± 0.52 | 2 | 1.93 ± 0.43 | 1 |
| G1A | 1.21 ± 0.15 | 1 | 2.4 ± 0.24 | 1 |
| Y2A | 1.95 ± 0.28 | 3 | 1.86 ± 0.42 | 1 |
| G3A | 1.41 ± 0.05 | 2 | 2.13 ± 0.02 | 1 |
| S4A | 0.84 ± 0.47 | 2 | 0.76 ± 0.35 | 1 |
| S5A | 0.93 ± 0.44 | 1 | 2.23 ± 1.27 | 1 |
| S6A | 1.15 ± 0.24 | 1 | 2.33 ± 1.65 | 2 |
| R7A | 6.04 ± 0.82 | 1 | 5.21 ± 4.14 | 1 |
| R8A | 0.63 ± 0.09 | 1 | 2.03 ± 0.06 | 2 |
| P10A | 2.86 ± 0.93 | 1 | 2.59 ± 1.2 | 1 |
| Q11A | 1.79 ± 0.47 | 1 | 2.58 ± 0.83 | 1 |
| T12A | 1.2 ± 0.18 | 1 | 2.83 ± 1.31 | 1 |

TABLE 14B

IGF-1 Binding & Phosphorylation Analysis ($B^0C^1A^0$)

| | IGF-1 Binding | | IGF-1 Phosphorylation | |
|---|---|---|---|---|
| Peptide | $IC_{50}$, nM | n | $EC_{50}$, nM | n |
| Insulin | 60.63 ± 4.43 | 1 | 48.66 ± 1.59 | 1 |
| IGF-1 | 0.38 ± 0.07 | 1 | 0.88 ± 0.41 | 1 |
| 010 ($B^0C^1A^0$) | 4.49 ± 1.04 | 1 | 1.29 ± 2.28 | 1 |
| G1A | 42.36 ± 16.24 | 1 | 1.4 ± 0.62 | 1 |
| Y2A | 257.9 ± 29.59 | 1 | 35.6 ± 14.55 | 1 |
| G3A | 34.02 ± 16.09 | 1 | 7.85 ± 0.78 | 1 |
| S4A | 15.30 ± 3.10 | 1 | 1.64 ± 1.65 | 1 |
| S5A | 13.06 ± 3.01 | 1 | 2.63 ± 1.88 | 1 |
| S6A | 2.44 ± 0.79 | 1 | 1.54 ± 0.62 | 2 |
| R7 | 43.86 ± 8.72 | 1 | 1.26 ± 1.55 | 1 |
| R8 | 10.85 ± 1.47 | 1 | 0.50 ± 0.23 | 2 |
| P10A | 6.42 ± 0.47 | 1 | 2.79 ± 1.12 | 1 |

TABLE 14B-continued IGF-1 Binding & Phosphorylation Analysis
($B^0C^1A^0$)

| Peptide | IGF-1 Binding | | IGF-1 Phosphorylation | |
|---|---|---|---|---|
| | $IC_{50}$, nM | n | $EC_{50}$, nM | n |
| Q11A | 4.23 ± 0.43 | 1 | 0.41 ± 0.69 | 1 |
| T12A | 9.15 ± 0.83 | 1 | 1.44 ± 1.36 | 1 |

Figure 15:
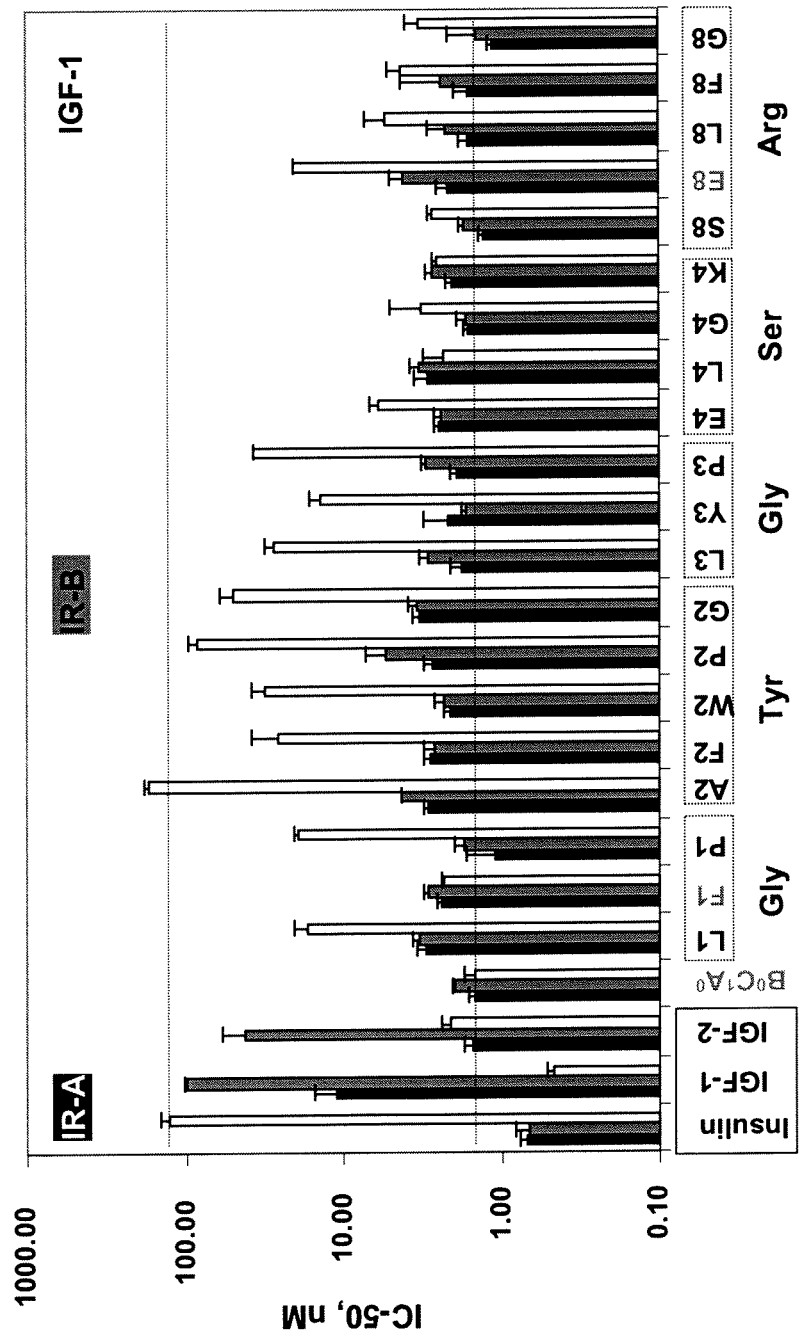
FIG. 15 is a bar graph depicting the relative in vitro binding activity of single
chain insulin analogs of the formula $B^0C^1A^0$ at the IGF-1 receptor or the A or B subtype insulin receptors wherein the native sequence of the linking IGF-1 C peptide has been modified by the indicated amino acid substitutions at position 1, 2, 3, 4 or 8. In the $B^0C^1A^0$ insulin analog nomenclature, the $B^0$ and $A^0$ designations refer to the insulin sequences of the A and B chain, while $C^1$ designates the IGF-1 C peptide.
Figure 16:
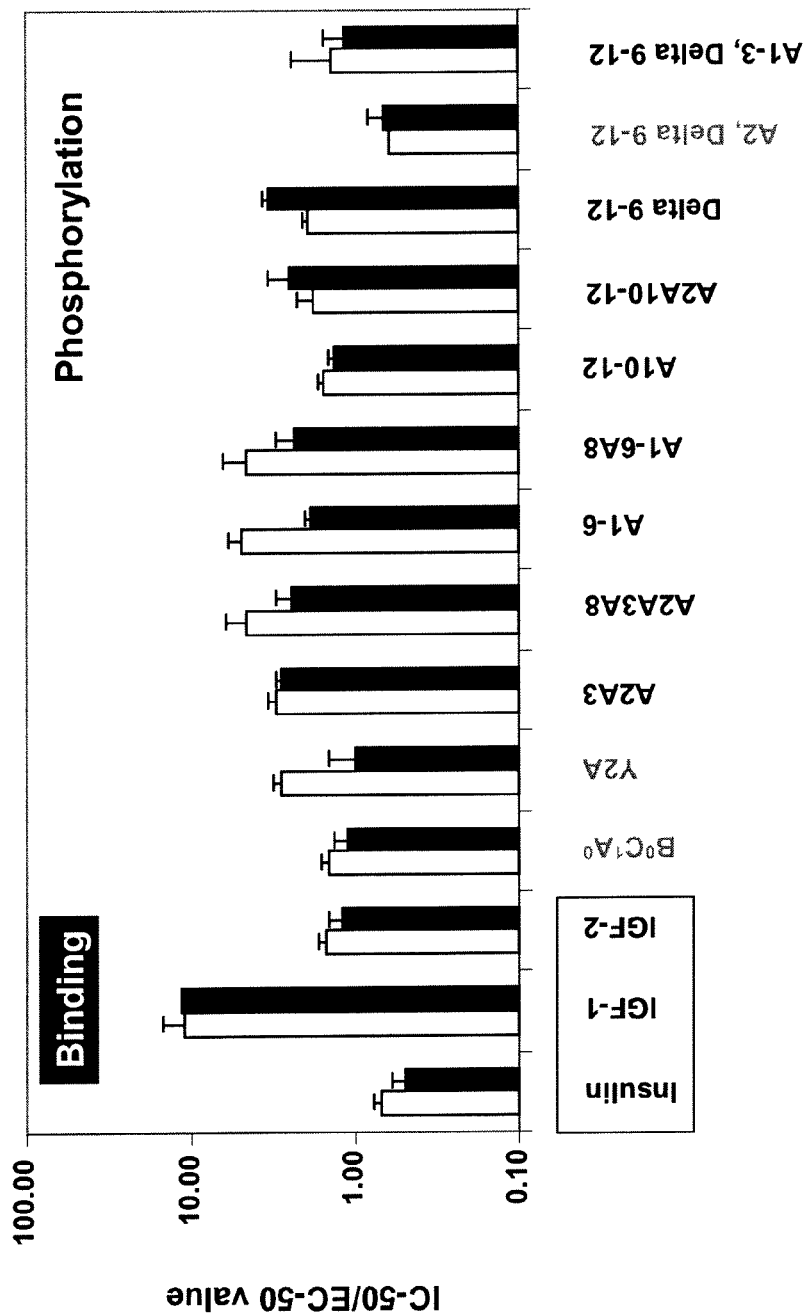
FIG. 16 is a bar graph depicting the relative in vitro binding activity and phosphorylation activity of single chain $B^0C^1A^0$ insulin analogs at the A subtype insulin receptor. The activity of the native IGF-1 C peptide (010) relative to various amino acid substitutions or deletions was compared. In the $B^0C^1A^0$ insulin analog nomenclature, the $B^0$ and $A^0$ designations refer to the insulin sequences of the A and B chain, while $C^1$ designates the IGF-1 C peptide.
Figure 17:
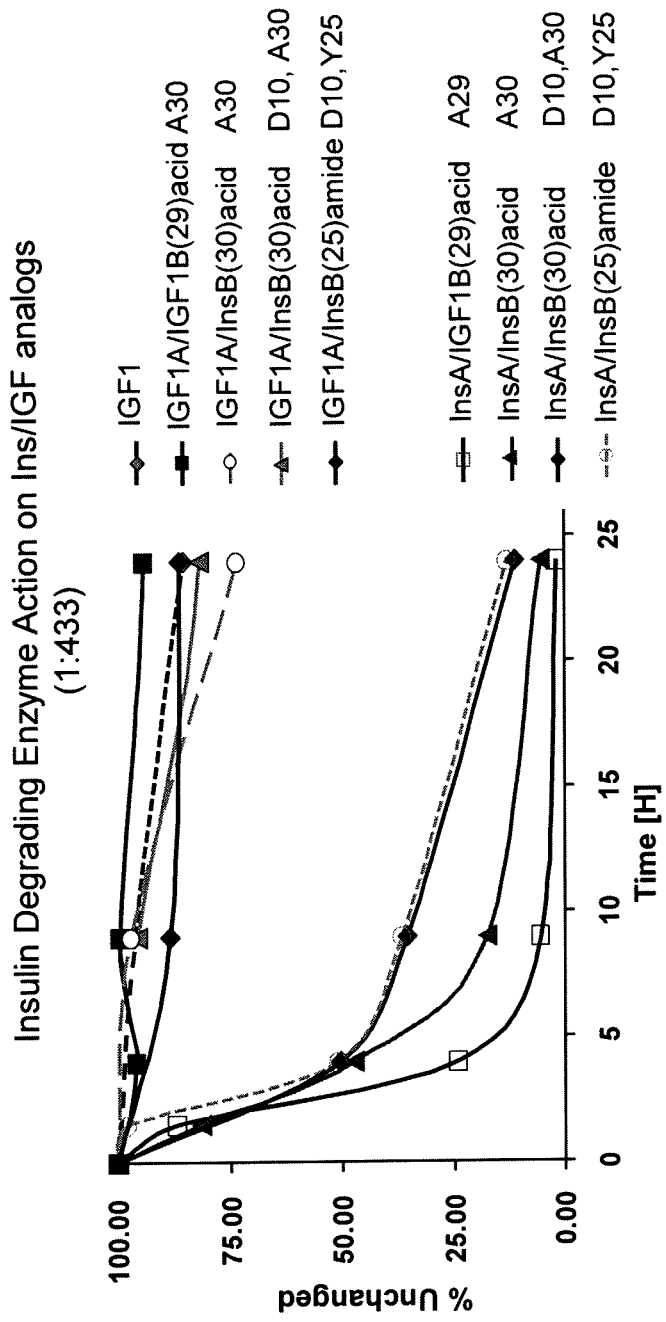
FIG. 17 is a graph demonstrating that insulin analogs comprising an IGF-1 A chain have enhanced resistance to degradation by the specific insulin degrading enzyme (IDE) relative to insulin analogs comprising an insulin A chain.
Figure 18:
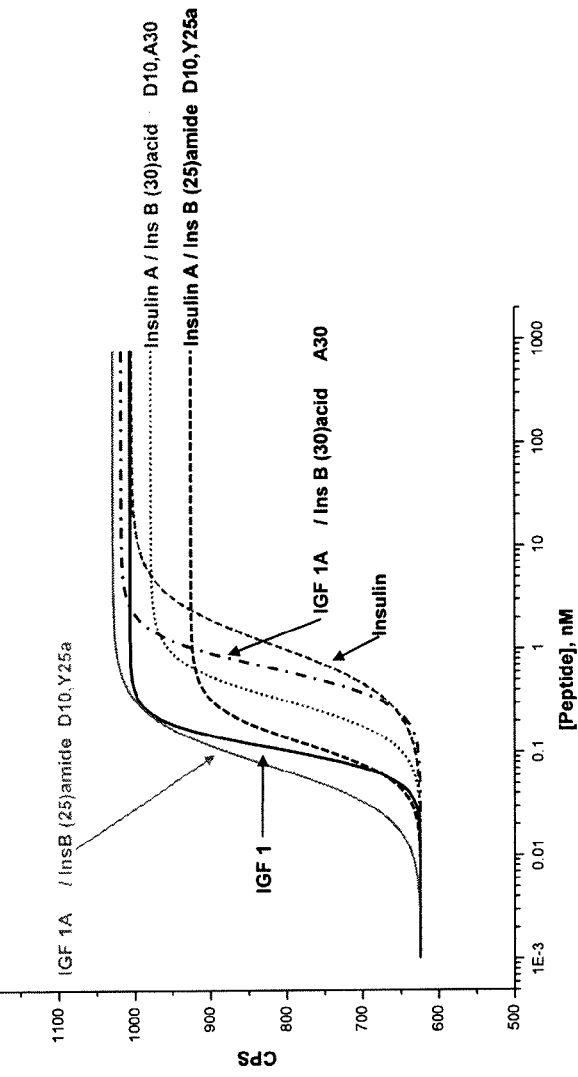
FIG. 18 is a graph demonstrating the relative activity of IGF-1, insulin and insulin/IGF chimera to induce in vitro cellular proliferation. The results indicate that the insulin activity associated with the IGF-1 single chain insulin analogs does not correlate with the proliferation activity associated with native IGF-1.

FIG. 15 demonstrates that position 2 and 3 in the C-peptide are most sensitive to modification at the IGF-1 receptor with the insulin receptor proving to be relatively immune to modification. Finally, FIG. 16 present the in vitro analysis of the single-chain insulin mutants as a ratio of binding affinity (IC50) and biochemical signaling through tyrosine phosphorylation (EC50). The two independent measurements demonstrate great consistency thereby validating this in vitro approach to structure-function analysis. All of the analogs maintained single unit nanomolar activity with certain specific analogs proving to be slightly enhanced in potency (low single unit nanomolar). The most insulin selective analogs were those that we missing the last four residues of the C-peptide, had an alanine mutation at position two of the C-peptide, or a combination of the two changes.

The stability of insulin/IGF chimeras was investigated by exposing insulin analogs to insulin-specific degrading enzyme (IDE) and assaying for activity.

Insulin Degradation assays: rDNA rat IDE was obtained from EMD Chemicals Inc. Peptides were prepared as 15 mM aliquots in ammonium bicarbonate buffer. Initial concentration was estimated based on UV absorbance at 276 nm, and further confirmed by HPLC analyze with internal standard. The pH of the solution was kept between 7.8-8.4. The IDE was added and digestion was conducted at 37° C. over time (12 to 48H). Ratio 1:350-450 (enzyme:substrate) was used depending on experiment. Aliquots were withdraw over time intervals into TFA buffered solution with internal reference peptide for the HPLC analysis. Additional aliquots were withdraw into DMEM assay medium for activity evaluation. All aliquots were immediately frozen on dry ice and kept at −55° C. until analyzed.

HPLC assay: Degradation profile of investigated peptides was evaluated in an HPLC assay. The two runs on an Agilant Zorbax C8 column attached to a Beckman-Coulter system using TFA buffer were performed for each aliquot (gradient 20 to 60% B in 10 min, where B=90% AcN).

Bioactivity: The residual potency of analogs after incubation with IDE was determined as a half maximal effective concentration (EC50) in an insulin receptor phosphorylation ELISA assay. When peptides prepared during enzymatic degradation were subjected to bioactivity assay by insulin receptor phosphorylation, we observed that all insulin and IGF-2 A-chain analogs lose substantially all activity while, all IGF-1 A-chain analogs retain it. Particularly, as shown in FIG. 17 the cleavage of insulin analogs by the insulin-specific degrading enzyme (IDE) is extremely robust and easily detected in those insulin analogs where the A-chain is derived from the native insulin sequence. In contrast those analogs where the A-chain is derived from the sequence of IGF-1 appear to be extremely resistant to proteolysis.

The prospect that the increased stability might engender increased mitogenicity was explored and the results are reported in FIG. 18. There did not appear to be a correlation of the higher insulin potency analogs with increased proliferation. Furthermore, and of specific importance to proteolytic stability, the analogs that were more resistant to IDE did not appear to be of any greater mitogenic potential.

A set of insulin analogs were subjected to in vivo testing in normal mice (Melior Research Labs). All peptides of interest demonstrated similar or enhanced glucose lowering potency when compared to standard insulin treatment. However, when analogs with insulin A vs. IGF1 A-chain with the same B-chains were compared, no significant difference in potency was observed. This supports a conclusion that IDE degradation and clearance of insulin is not a primary or physiologically relevant mechanism.

What is claimed:

1. An insulin analog comprising the structure:

X—Y—Z;

wherein Z is an insulin peptide comprising an A chain and a B chain wherein the A chain comprises the sequence GIVEQCCX$_1$SICSLYQLENX$_2$CX$_3$ (SEQ ID NO: 3), or an analog thereof comprising a sequence that differs from SEQ ID NO: 3 by 1 to 3 amino acid modifications, selected from positions A5, A8, A9, A10, A14, A15, A17, A18 and the B chain comprises the sequence of X$_{14}$-X$_4$LCGX$_5$X$_6$LVEALX$_7$LVCGERGFX$_8$ (SEQ ID NO: 14), or an analog thereof comprising a sequence that differs from SEQ ID NO: 14 sequence by 1 to 3 amino acid modifications, selected from positions B5, B13, B14, B17, B20, B22, and B23, said B chain being linked to said A chain through intermolecular disulfide linkages and optionally through an amide bond linkage between the carboxy terminus of the B chain and the amino terminus of the A chain to form a single chain polypeptide; and X—Y is a dipeptide linked via an amide bond to the N-terminal amino group of the A chain or B chain or to an amino group on a side chain of an amino acid of said A chain or B chain wherein $X_{14}$ is a bond, or a 1 to 4 amino acid sequence selected from the group consisting of a FVNQ (SEQ ID NO: 11), VNQ, NQ and Q;

$X_1$ is selected from the group consisting of threonine and histidine;

$X_2$ is an amino acid of the general structure

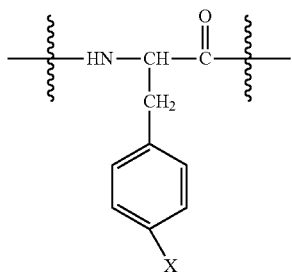

wherein X is selected from the group consisting of OH, $NH_2$, $NHR_{10}$ and $OCH_3$, wherein $R_{10}$ is a dipeptide of the general structure X—Y;

$X_3$ is selected from the group consisting of asparagine, ornithine, glycine, alanine, threonine, and serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is an amino acid of the general structure

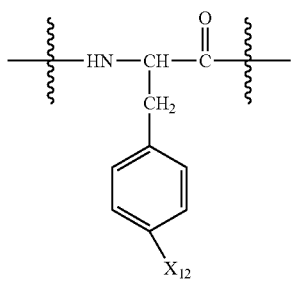

wherein $X_{12}$ is selected from the group consisting of OH, $NH_2$, $NHR_{11}$ and $OCH_3$, wherein $R_{11}$ is a dipeptide of the general structure X—Y;

$X_8$ is histidine, asparagine or an amino acid of the general structure

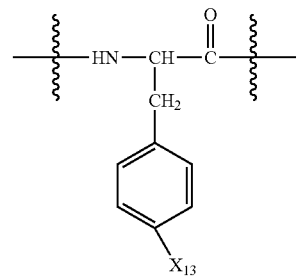

wherein $X_{13}$ is selected from the group consisting of H, OH, $NH_2$, $NHR_{12}$ and $OCH_3$, wherein $R_{12}$ is a dipeptide of the general structure X—Y;

wherein X—Y comprises a dipeptide structure:

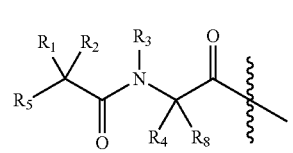

I wherein
  $R_1$ and $R_2$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)$SCH_3$, ($C_1$-$C_4$ alkyl)$CONH_2$, ($C_1$-$C_4$ alkyl)COOH, ($C_1$-$C_4$ alkyl)$NH_2$, ($C_1$-$C_4$ alkyl)NHC($NH_2^+$)$NH_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)$R_7$, ($C_1$-$C_4$ alkyl)($C_3$-$C_9$ heteroaryl), and $C_1$-$C_{12}$ alkyl($W_1$)$C_1$-$C_{12}$ alkyl, wherein $W_1$ is a heteroatom selected from the group consisting of N, S and O, or $R_1$ and $R_2$ together with the atoms to which they are attached form a $C_3$-$C_{12}$ cycloalkyl;
  $R_3$ is $C_1$-$C_{18}$ alkyl;
  $R_4$ is selected from the group consisting of $CH_3$, $CH_2$($C_1$-$C_{10}$ alkyl), $CH_2$($C_2$-$C_{10}$ alkenyl), $CH_2$($C_0$-$C_{10}$ alkyl)OH, $CH_2$($C_0$-$C_{10}$ alkyl)SH, $CH_2$($C_0$-$C_3$ alkyl)$SCH_3$, $CH_2$($C_0$-$C_3$ alkyl)$CONH_2$, $CH_2$($C_0$-$C_3$ alkyl)COOH, $CH_2$($C_0$-$C_3$ alkyl)$NH_2$, $CH_2$($C_0$-$C_3$ alkyl)NHC($NH_2^+$)$NH_2$, $CH_2$($C_0$-$C_3$ alkyl)($C_3$-$C_6$ cycloalkyl), $CH_2$($C_0$-$C_3$ alkyl)($C_2$-$C_5$ heterocyclic), $CH_2$($C_0$-$C_3$ alkyl)($C_6$-$C_{10}$ aryl)$R_7$, $CH_2$($C_1$-$C_3$ alkyl)($C_3$-$C_9$ heteroaryl), and $CH_2$($C_0$-$C_{12}$ alkyl)($W_1$)$C_1$-$C_{12}$ alkyl, wherein $W_1$ is a heteroatom selected from the group consisting of N, S and O, or $R_4$ and $R_3$ together with the atoms to which they are attached form a pyrrolidine ring;
  $R_8$ is H;
  $R_5$ is $NHR_6$, or OH;
  $R_6$ is H or $C_1$-$C_4$ alkyl; and,
  $R_7$ is selected from the group consisting of H, OH, halo, ($C_1$-$C_7$ alkyl), ($C_2$-$C_7$ alkenyl), $OCF_3$, $NO_2$, CN, NC, O($C_1$-$C_7$ alkyl), $CO_2H$, $CO_2$($C_1$-$C_7$ alkyl), $NHR_6$, aryl, and heteroaryl, wherein chemical cleavage half-life ($t_{1/2}$) of X—Y from Z is at least about 1 hour to about 1 week in PBS under physiological conditions.

2. The insulin analog of claim 1,
wherein
  $R_1$ is selected from the group consisting of H and $C_1$-$C_4$ alkyl;

$R_2$ is selected from the group consisting of H, $C_1$-$C_6$ alkyl, $C_2$-$C_8$ alkenyl, ($C_1$-$C_4$ alkyl)OH, ($C_1$-$C_4$ alkyl)NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl) or $R_2$ and $R_6$ together with the atoms to which they are attached form a 5 member heterocyclic ring;

$R_3$ is $C_1$-$C_6$ alkyl;

$R_4$ is selected from the group consisting of H and $C_1$-$C_4$ alkyl; and $R_8$ is H.

3. The insulin analog of claim 2, wherein Y is selected from the group consisting of alanine(N—$C_1$-$C_{10}$alkyl), leucine (N—$C_1$-$C_{10}$alkyl), methionine(N—$C_1$-$C_{10}$alkyl), asparagine (N—$C_1$-$C_{10}$alkyl), glutamic acid(N—$C_1$-$C_{10}$alkyl), aspartic acid(N—$C_1$-$C_{10}$alkyl), glutamine(N—$C_1$-$C_{10}$alkyl), histidine(N—$C_1$-$C_{10}$alkyl), lysine(N—$C_1$-$C_{10}$alkyl), arginine (N—$C_1$-$C_{10}$alkyl), serine(N—$C_1$-$C_{10}$alkyl), and cysteine (N—$C_1$-$C_{10}$alkyl).

4. The insulin analog of claim 3, wherein Y is selected from the group consisting of phenylalanine(N-methyl), tyrosine (N-methyl), and tryptophan(N-methyl).

5. The insulin analog of claim 1, further comprising a polyethylene glycol chain covalently linked to the dipeptide of the general structure X—Y.

6. The insulin analog of claim 1, further comprising an acyl group or alkyl group covalently linked to the dipeptide of the general structure X—Y.

7. A pharmaceutical composition comprising the insulin analog of claim 1, and a pharmaceutically acceptable carrier.

8. A method of treating diabetes, said method comprising administering an effective amount of a pharmaceutical composition of claim 7.

9. An insulin analog comprising an A chain, wherein said A chain comprises the sequence GIVEQCCX$_1$SICSLYQLENX$_2$CX$_3$ (SEQ ID NO: 3);

a B chain, wherein said B chain comprises the sequence X$_9$VNQX$_4$LCGX$_5$X$_6$LVEALX$_7$LVCGERGFX$_8$YTPKT (SEQ ID NO: 15) or X$_9$VNQX$_4$LCGX$_5$X$_6$LVEALX$_7$LVCGERGFX$_8$YTKPT (SEQ ID NO: 16); and a dipeptide comprising the general structure of X—Y linked to an amino group on a side chain of an amino acid of said A chain or B chain via an amide bond, wherein $X_1$ is selected from the group consisting of threonine, histidine, arginine and lysine;

$X_2$ is an amino acid of the general structure

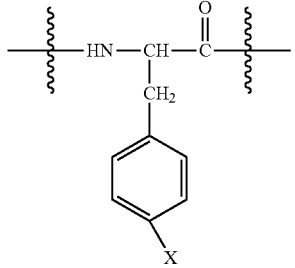

wherein X is selected from the group consisting of OH, NH$_2$, NHR$_{10}$ and OCH$_3$, wherein R$_{10}$ is a dipeptide of the general structure X—Y;

$X_3$ is asparagine, glycine, alanine, threonine, or serine;

$X_4$ is selected from the group consisting of histidine and threonine;

$X_5$ is selected from the group consisting of alanine, glycine and serine;

$X_6$ is selected from the group consisting of histidine, aspartic acid, glutamic acid, homocysteic acid and cysteic acid;

$X_7$ is an amino acid of the general structure

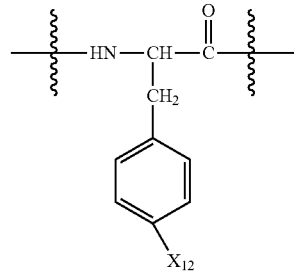

wherein $X_{12}$ is selected from the group consisting of OH, NH$_2$, NHR$_{11}$ and OCH$_3$, wherein R$_{11}$ is a dipeptide of the general structure X—Y;

$X_8$ is an amino acid of the general structure

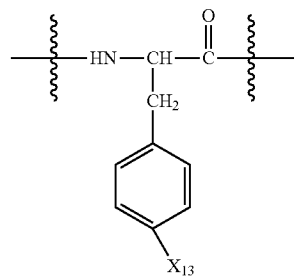

wherein $X_{13}$ is selected from the group consisting of H, OH, NH$_2$, NHR$_{12}$ and OCH$_3$, wherein R$_{12}$ is a dipeptide of the general structure X—Y;

$X_9$ is selected from the group consisting of phenylalanine and desamino-phenylalanine;

X—Y has the general structure of Formula I:

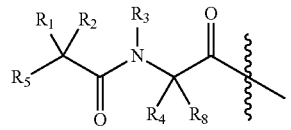

wherein $R_1$, $R_2$, $R_4$ and $R_8$ are independently selected from the group consisting of H, $C_1$-$C_{18}$ alkyl, $C_2$-$C_{18}$ alkenyl, ($C_1$-$C_{18}$ alkyl)OH, ($C_1$-$C_{18}$ alkyl)SH, ($C_2$-$C_3$ alkyl)SCH$_3$, ($C_1$-$C_4$ alkyl)CONH$_2$, ($C_1$-$C_4$ alkyl)COOH, ($C_1$-$C_4$ alkyl)NH$_2$, ($C_1$-$C_4$ alkyl)NHC(NH$_2^+$)NH$_2$, ($C_0$-$C_4$ alkyl)($C_3$-$C_6$ cycloalkyl), ($C_0$-$C_4$ alkyl)($C_2$-$C_5$ heterocyclic), ($C_0$-$C_4$ alkyl)($C_6$-$C_{10}$ aryl)R$_7$, ($C_1$-$C_4$ alkyl)($C_3$-$C_9$ heteroaryl), and $C_1$-$C_{12}$ alkyl(W$_1$)$C_1$-$C_{12}$ alkyl, wherein W$_1$ is a heteroatom selected from the group consisting of N, S and O, or $R_1$ and $R_2$ together with the atoms to which they are attached form a $C_3$-$C_{12}$ cycloalkyl; or $R_4$ and $R_8$ together with the atoms to which they are attached form a $C_3$-$C_6$ cycloalkyl;

$R_3$ is selected from the group consisting of $C_1$-$C_{18}$ alkyl, ($C_1$-$C_{18}$ alkyl)OH, ($C_1$-$C_{18}$ alkyl)NH$_2$, ($C_1$-$C_{18}$ alkyl)SH, ($C_0$-$C_4$ alkyl)($C_3$-$C_6$)cycloalkyl, ($C_0$-$C_4$ alkyl)($C_2$-$C_5$ heterocyclic), ($C_0$-$C_4$ alkyl)($C_6$-$C_{10}$ aryl)$R_7$, and ($C_1$-$C_4$ alkyl)($C_3$-$C_9$ heteroaryl) or $R_4$ and $R_3$ together with the atoms to which they are attached form a pyrrolidine ring;

$R_5$ is NHR$_6$ or OH:

$R_6$ is H $C_1$-$C_8$ alkyl or $R_6$ and $R_1$ together with the atoms to which they are attached form a 4, 5 or 6 member heterocyclic ring; and $R_7$ is selected from the group consisting of hydrogen, $C_1$-$C_{18}$ alkyl, $C_2$-$C_{18}$ alkenyl, ($C_0$-$C_4$ alkyl)CONH$_2$, ($C_0$-$C_4$ alkyl)COOH, ($C_0$-$C_4$ alkyl)NH$_2$, ($C_0$-$C_4$ alkyl)OH, and halo.

10. The insulin analog of claim 9 wherein the dipeptide is linked to the side chain amine of a lysine present at position B28 or at position B29 of the B chain.

11. The insulin analog of claim 10 wherein
$R_1$ is selected from the group consisting of H and $C_1$-$C_4$ alkyl;
$R_2$ is selected from the group consisting of H, $C_1$-$C_6$ alkyl, $C_2$-$C_8$ alkenyl, ($C_1$-$C_4$ alkyl)OH, ($C_1$-$C_4$ alkyl)NH$_2$, ($C_0$-$C_4$ alkyl)($C_3$-$C_6$ cycloalkyl), ($C_0$-$C_4$ alkyl)($C_6$-$C_{10}$ aryl)$R_7$, and CH$_2$($C_5$-$C_9$ heteroaryl) or $R_2$ and $R_6$ together with the atoms to which they are attached form a 5 member heterocyclic ring;
$R_3$ is $C_1$-$C_6$ alkyl;
$R_4$ is selected from the group consisting of H and $C_1$-$C_4$ alkyl; and
$R_8$ is H.

12. The insulin analog of claim 10 wherein
said A chain comprises the sequence GIVEQCCTSICSLYQLENYCN (SEQ ID NO: 1);
said B chain comprises a sequence selected from the group consisting of FVNQHLCGSHLVEALYLVCGERGFFYTPKT (SEQ ID NO: 8) and FVNQHLCGSHLVEALYLVCGERGFFYTKPT (SEQ ID NO: 9); and
said dipeptide is linked to the side chain amine of a lysine at position B28 of (SEQ ID NO: 8) or at position B29 of (SEQ ID NO: 9).

13. The insulin analog of claim 9 wherein X and/or Y is an amino acid in the D stereoisomer configuration.

14. The insulin analog of claim 9 wherein X is aminoisobutyric acid or an amino acid in the D stereoisomer configuration.

15. An insulin analog comprising the structure:

X—Y—Z:

wherein Z is an insulin peptide comprising an A chain and a B chain wherein the A chain comprises the sequence GIVEQCCX$_1$SICSLYQLENX$_2$CX$_3$ (SEQ ID NO: 3), or an analog thereof comprising a sequence that differs from SEQ ID NO: 3 by 1 to 3 amino acid modifications, selected from positions A5, A8, A9, A10, A14, A15, A17, A18 and the B chain comprises the sequence of X$_{14}$-X$_4$LCGX$_5$X$_6$LVEALX$_7$LVCGERGFX$_8$ (SEQ ID NO: 14), or an analog thereof comprising a sequence that differs from SEQ ID NO: 14 sequence by 1 to 3 amino acid modifications, selected from positions B5, B13, B14, B17, B20, B22, and B23, said B chain being linked to said A chain through intermolecular disulfide linkages; and X—Y is a dipeptide linked to an amino group on a side chain of an amino acid of said A chain or B chain via an amide bond, said X—Y dipeptide comprising the general structure:

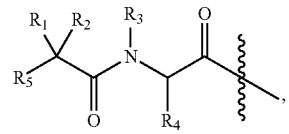

wherein
$R_2$ comprises ($C_1$-$C_4$ alkyl)NH$_2$ that is acylated at the amino group of $R_2$ with an acyl group of sufficient size to bind serum albumin;
$R_1$ and $R_4$ are each hydrogen;
$R_3$ is CH$_3$; and
$R_5$ is NH$_2$.

16. The insulin analog of claim 15 wherein the lysine of the X—Y dipeptide is in the D-stereochemical configuration and said acyl group is covalently linked to the amino group of the X—Y dipeptide lysine side chain.

17. The insulin analog of claim 16 wherein said X—Y dipeptide is acylated with an acyl group comprising 16 to 30 carbon atoms.

18. A pharmaceutical composition comprising the insulin analog of claim 9, and a pharmaceutically acceptable carrier.

19. The insulin analog of claim 15 wherein
said A chain comprises the sequence GIVEQCCTSICSLYQLENYCN (SEQ ID NO: 1);
said B chain comprises a sequence selected from the group consisting of FVNQHLCGSHLVEALYLVCGERGFFYTPKT (SEQ ID NO: 8) and FVNQHLCGSHLVEALYLVCGERGFFYTKPT (SEQ ID NO: 9); and
said dipeptide is linked to the side chain amine of a lysine at position B28 of (SEQ ID NO: 8) or at position B29 of (SEQ ID NO: 9).

20. The insulin analog of claim 15 wherein said B chain is further linked to said A chain through an amide bond linkage between the carboxy terminus of the B chain and the amino terminus of the A chain to form a single chain polypeptide.

21. The insulin analog of claim 1, wherein
$R_3$ is $C_1$ alkyl or $C_6$ alkyl.

22. The insulin analog of claim 21, wherein
$R_1$ is H; and
$R_2$ comprises ($C_3$-$C_4$)NH$_2$.

23. The insulin analog of claim 1 wherein the dipeptide comprises the general structure:

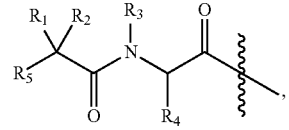

wherein
$R_2$ comprises ($C_1$-$C_4$ alkyl)NH$_2$ that is acylated at the amino group of $R_2$ with an acyl group of sufficient size to bind serum albumin;
$R_1$ and $R_4$ are each hydrogen;
$R_3$ is CH$_3$; and
$R_5$ is NH$_2$.

* * * * *

UNITED STATES PATENT AND TRADEMARK OFFICE
CERTIFICATE OF CORRECTION

| | |
|---|---|
| PATENT NO. | : 8,946,147 B2 |
| APPLICATION NO. | : 13/702197 |
| DATED | : February 3, 2015 |
| INVENTOR(S) | : DiMarchi et al. |

It is certified that error appears in the above-identified patent and that said Letters Patent is hereby corrected as shown below:

In the Claims,

In Claim 9, Column 198, line 22, please delete "OH, $NH_2$, $NHR_1$ 1 and $OCH_3$" and insert -- OH, $NH_2$, $NHR_{11}$ and $OCH_3$ -- therefor.

Signed and Sealed this
Sixteenth Day of June, 2015

Michelle K. Lee
*Director of the United States Patent and Trademark Office*